(12) United States Patent
Fantl et al.

(10) Patent No.: US 9,182,385 B2
(45) Date of Patent: Nov. 10, 2015

(54) METHODS FOR DIAGNOSIS, PROGNOSIS AND METHODS OF TREATMENT

(75) Inventors: Wendy J. Fantl, San Francisco, CA (US); Santosh K. Putta, Foster City, CA (US); Omar D. Perez, San Francisco, CA (US); Helen L. Francis-Lang, San Francisco, CA (US); Aileen C. Cohen, Palo Alto, CA (US)

(73) Assignee: NODALITY, INC., South San Francisco, CA (US)

( * ) Notice: Subject to any disclaimer, the term of this patent is extended or adjusted under 35 U.S.C. 154(b) by 0 days.

(21) Appl. No.: 13/493,857

(22) Filed: Jun. 11, 2012

(65) Prior Publication Data

US 2012/0309029 A1     Dec. 6, 2012

Related U.S. Application Data

(63) Continuation of application No. 12/229,476, filed on Aug. 21, 2008, now abandoned.

(60) Provisional application No. 60/957,160, filed on Aug. 21, 2007, provisional application No. 61/048,920, filed on Apr. 29, 2008.

(51) Int. Cl.
  *C12Q 1/02* (2006.01)
  *G01N 33/50* (2006.01)
  *G01N 33/574* (2006.01)

(52) U.S. Cl.
  CPC ........ *G01N 33/5041* (2013.01); *G01N 33/5047* (2013.01); *G01N 33/57426* (2013.01)

(58) Field of Classification Search
  CPC ....................................................... C12Q 1/02
  See application file for complete search history.

(56) References Cited

U.S. PATENT DOCUMENTS

| | | | |
|---|---|---|---|
| 5,234,816 | A | 8/1993 | Terstappen |
| 5,605,805 | A | 2/1997 | Verwer et al. |
| 5,968,738 | A | 10/1999 | Anderson et al. |
| 6,008,052 | A | 12/1999 | Davis et al. |
| 6,232,299 | B1 | 5/2001 | Jirousek et al. |
| 6,455,263 | B2 | 9/2002 | Payan |
| 6,495,333 | B1 | 12/2002 | Willmann et al. |
| 6,506,551 | B1 | 1/2003 | Chiorazzi et al. |
| 6,733,743 | B2 | 5/2004 | Jordan |
| 6,821,740 | B2 | 11/2004 | Darzynkiewicz et al. |
| 6,897,954 | B2 | 5/2005 | Bishop et al. |
| 7,316,906 | B2 | 1/2008 | Chiorazzi et al. |
| 7,329,502 | B2 | 2/2008 | Staudt et al. |
| 7,381,535 | B2 | 6/2008 | Perez et al. |
| 7,393,656 | B2 | 7/2008 | Perez et al. |
| 7,563,584 | B2 | 7/2009 | Perez et al. |
| 7,695,924 | B2 | 4/2010 | Perez et al. |
| 7,695,926 | B2 | 4/2010 | Perez et al. |
| 7,939,278 | B2 | 5/2011 | Perez et al. |
| 8,148,094 | B2 | 4/2012 | Nolan et al. |
| 8,187,885 | B2 | 5/2012 | Purvis, Jr. |
| 8,198,037 | B2 | 6/2012 | Perez et al. |
| 8,206,939 | B2 | 6/2012 | Perez et al. |
| 8,214,157 | B2 | 7/2012 | Moser et al. |
| 8,227,202 | B2 | 7/2012 | Fantl et al. |
| 8,242,248 | B2 | 8/2012 | Soper et al. |
| 8,273,544 | B2 | 9/2012 | Fantl et al. |
| 8,309,306 | B2 | 11/2012 | Nolan et al. |
| 8,309,316 | B2 | 11/2012 | Perez et al. |
| 8,394,599 | B2 | 3/2013 | Perez et al. |
| 8,399,206 | B2 | 3/2013 | Fantl et al. |
| 8,778,620 | B2 | 7/2014 | Fantl et al. |
| 2004/0076984 | A1 | 4/2004 | Eils |
| 2004/0106156 | A1 | 6/2004 | Perez et al. |
| 2005/0112700 | A1 | 5/2005 | Perez et al. |
| 2006/0046272 | A1 | 3/2006 | Chow et al. |
| 2006/0073474 | A1 | 4/2006 | Perez et al. |

(Continued)

FOREIGN PATENT DOCUMENTS

| | | |
|---|---|---|
| WO | WO 03/067210 A2 | 8/2003 |
| WO | WO 03/067210 A3 | 12/2003 |

(Continued)

OTHER PUBLICATIONS

Kawauchi et al. Activation of Extracellular Signal-Regulated Kinase through B-Cell Antigen Receptor in B-Cell Chronic Lymphocytic Leukemia. International Journal of Hematology. (2002) 75:508-513.*
Chinese office action dated Jul. 17, 2012 for CN 200880107737.6. (In Chinese with English translation).
Chinese office action dated Sep. 21, 2011 for CN 200880107737.6. (In Chinese with English translation).
Chinese office action dated Feb. 1, 2013 for CN 200880107737.6. (In Chinese with English translation).
European office action dated Jan. 23, 2013 for EP Application No. 08795509.2.
European office action dated Dec. 21, 2011 for EP Application No. 08795509.2.

(Continued)

*Primary Examiner* — Karen Chochrane Carlson
*Assistant Examiner* — Natalie Moss
(74) *Attorney, Agent, or Firm* — Wilson Sonsini Goodrich & Rosati

(57) ABSTRACT

This invention is directed to methods and compositions for diagnosis, prognosis and for determining methods of treatment. The physiological status of cells present in a sample (e.g. clinical sample) can be used in diagnosis or prognosis of a condition (e.g. Chronic Lymphocytic Leukemia), in patient selection for therapy, to monitor treatment and to modify or optimize therapeutic regimens. The physiological status of a cell can be determined by comparing the intracellular status of one or more activation elements (e.g. the phosphorylation status of a signaling molecule) in a cell (e.g. a cancer cell) to that of another cell (e.g. a normal cell). The physiological status of a cell can be further classified by adding one or more modulators (e.g. an inhibitor or activator) to the cell in question. In some embodiments, the invention is directed to methods of determining a phenotypic profile of a population of cells.

18 Claims, 28 Drawing Sheets

(56) References Cited

U.S. PATENT DOCUMENTS

| | | |
|---|---|---|
| 2007/0009923 A1 | 1/2007 | Nolan et al. |
| 2007/0105165 A1 | 5/2007 | Goolsby et al. |
| 2007/0172847 A1 | 7/2007 | Bonavida et al. |
| 2007/0196868 A1 | 8/2007 | Perez et al. |
| 2007/0196869 A1 | 8/2007 | Perez et al. |
| 2007/0196870 A1 | 8/2007 | Perez et al. |
| 2008/0026383 A1 | 1/2008 | Pepper et al. |
| 2008/0182262 A1 | 7/2008 | Perez et al. |
| 2008/0254489 A1 | 10/2008 | Perez et al. |
| 2008/0260754 A1 | 10/2008 | Li et al. |
| 2009/0068681 A1 | 3/2009 | Perez et al. |
| 2009/0081699 A1 | 3/2009 | Perez et al. |
| 2009/0098594 A1 | 4/2009 | Fantl et al. |
| 2009/0269773 A1 | 10/2009 | Fantl et al. |
| 2009/0269800 A1 | 10/2009 | Covey et al. |
| 2009/0291458 A1 | 11/2009 | Cohen et al. |
| 2009/0307248 A1 | 12/2009 | Moser et al. |
| 2010/0009364 A1 | 1/2010 | Fantl et al. |
| 2010/0014741 A1 | 1/2010 | Banville et al. |
| 2010/0030719 A1 | 2/2010 | Covey et al. |
| 2010/0042351 A1 | 2/2010 | Covey et al. |
| 2010/0086951 A1 | 4/2010 | Hedley et al. |
| 2010/0099109 A1 | 4/2010 | Fantl et al. |
| 2010/0105074 A1 | 4/2010 | Covey et al. |
| 2010/0151472 A1 | 6/2010 | Nolan et al. |
| 2010/0184092 A1 | 7/2010 | Perez et al. |
| 2010/0197512 A1 | 8/2010 | Trinkle et al. |
| 2010/0204973 A1 | 8/2010 | Parkinson et al. |
| 2010/0209929 A1 | 8/2010 | Fantl et al. |
| 2010/0215644 A1 | 8/2010 | Fantl et al. |
| 2010/0221750 A1 | 9/2010 | Perez et al. |
| 2010/0233733 A1 | 9/2010 | Fantl |
| 2010/0240542 A1 | 9/2010 | Soper et al. |
| 2010/0285594 A1 | 11/2010 | Purvis, Jr. |
| 2010/0297676 A1 | 11/2010 | Fantl et al. |
| 2011/0020839 A1 | 1/2011 | Perez et al. |
| 2011/0059861 A1 | 3/2011 | Nolan et al. |
| 2011/0104717 A1 | 5/2011 | Fantl et al. |
| 2011/0201018 A1 | 8/2011 | Perez et al. |
| 2011/0201019 A1 | 8/2011 | Perez et al. |
| 2011/0207145 A1 | 8/2011 | Perez et al. |
| 2011/0207146 A1 | 8/2011 | Perez et al. |
| 2011/0207149 A1 | 8/2011 | Perez et al. |
| 2011/0250614 A1 | 10/2011 | Perez et al. |
| 2011/0262468 A1 | 10/2011 | Fantl et al. |
| 2011/0269154 A1 | 11/2011 | Fantl et al. |
| 2011/0269634 A1 | 11/2011 | Perez et al. |
| 2012/0070849 A1 | 3/2012 | Perez et al. |
| 2012/0157340 A1 | 6/2012 | Cesano et al. |
| 2012/0215487 A1 | 8/2012 | Banville et al. |
| 2012/0276558 A1 | 11/2012 | Soper et al. |
| 2013/0024177 A1 | 1/2013 | Nolan |
| 2013/0034862 A1 | 2/2013 | Fantl et al. |
| 2013/0035253 A1 | 2/2013 | Rosen et al. |
| 2013/0071860 A1 | 3/2013 | Hale et al. |
| 2013/0078621 A1 | 3/2013 | Nolan et al. |
| 2013/0096948 A1 | 4/2013 | Parkinson et al. |
| 2013/0109050 A1 | 5/2013 | Purvis, Jr. |
| 2013/0123131 A1 | 5/2013 | Purvis et al. |
| 2013/0124522 A1 | 5/2013 | Moser et al. |
| 2013/0129681 A1 | 5/2013 | Covey et al. |
| 2013/0130279 A1 | 5/2013 | Fantl et al. |
| 2013/0177970 A1 | 7/2013 | Perez et al. |
| 2013/0218474 A1 | 8/2013 | Longo |
| 2014/0011222 A1 | 1/2014 | Fantl |
| 2014/0017678 A1 | 1/2014 | Cesano et al. |
| 2014/0031308 A1 | 1/2014 | Diane et al. |
| 2014/0040265 A1 | 2/2014 | Moser et al. |
| 2014/0057865 A1 | 2/2014 | Fantl et al. |
| 2014/0065633 A1 | 3/2014 | Fantl et al. |
| 2014/0093903 A1 | 4/2014 | Ptacek et al. |
| 2014/0120122 A1 | 5/2014 | Fantl et al. |
| 2014/0127716 A1 | 5/2014 | Longo |
| 2014/0134648 A1 | 5/2014 | Fantl et al. |
| 2014/0134650 A1 | 5/2014 | Hawtin et al. |
| 2014/0147857 A1 | 5/2014 | Fantl et al. |
| 2014/0170698 A1 | 6/2014 | Purvis, Jr. |
| 2014/0199273 A1 | 7/2014 | Cesano et al. |
| 2014/0255393 A1 | 9/2014 | Ptacek et al. |
| 2015/0017119 A1 | 1/2015 | Fantl et al. |
| 2015/0110736 A1 | 4/2015 | Fantl et al. |
| 2015/0118247 A1 | 4/2015 | Hotson et al. |
| 2015/0119288 A1 | 4/2015 | Soper et al. |

FOREIGN PATENT DOCUMENTS

| | | |
|---|---|---|
| WO | WO 2006/012507 A2 | 2/2006 |
| WO | WO 2006/050333 A2 | 5/2006 |
| WO | WO 2006/079092 A2 | 7/2006 |
| WO | WO 2006/086111 A2 | 8/2006 |
| WO | WO 2006/012507 A3 | 10/2006 |
| WO | WO 2006/050333 A3 | 10/2006 |
| WO | WO 2007/015886 A2 | 2/2007 |
| WO | WO 2007/027906 A2 | 3/2007 |
| WO | WO 2007/027957 A2 | 3/2007 |
| WO | WO 2007/056192 A2 | 5/2007 |
| WO | WO 2007/056192 A3 | 7/2007 |
| WO | WO 2007/117423 A2 | 10/2007 |
| WO | WO 2007/127335 A2 | 11/2007 |
| WO | WO 2007/140316 A1 | 12/2007 |
| WO | WO 2008/009004 A2 | 1/2008 |
| WO | WO 2007/127335 A3 | 6/2008 |
| WO | WO 2008/088857 A2 | 7/2008 |
| WO | WO 2007/015886 A3 | 10/2008 |
| WO | WO 2008/009004 A3 | 10/2008 |
| WO | WO 2007/027957 A3 | 1/2009 |
| WO | WO 2009/025847 A2 | 2/2009 |
| WO | WO 2006/086111 A3 | 4/2009 |
| WO | WO 2009/025847 A3 | 6/2009 |
| WO | WO 2009/134944 A2 | 11/2009 |
| WO | WO 2010/006291 A1 | 1/2010 |
| WO | WO 2010/006303 A2 | 1/2010 |
| WO | WO 2009/134944 A3 | 2/2010 |
| WO | WO 2010/028277 A1 | 3/2010 |
| WO | WO 2010/045651 A1 | 4/2010 |
| WO | WO 2007/027906 A3 | 11/2010 |
| WO | WO 2010/135608 A1 | 11/2010 |
| WO | WO 2011/031803 A1 | 3/2011 |
| WO | WO 2011/106558 A1 | 9/2011 |
| WO | WO 2011/119868 A2 | 9/2011 |
| WO | WO 2011/156654 A2 | 12/2011 |
| WO | WO 2012/024546 A2 | 2/2012 |
| WO | WO 2012/033537 A1 | 3/2012 |
| WO | WO 2012/083274 A2 | 6/2012 |
| WO | WO 2013/112948 A1 | 8/2013 |
| WO | WO 2013/188469 A2 | 12/2013 |
| WO | WO 2014/074646 A2 | 5/2014 |
| WO | WO 2014/081987 A1 | 5/2014 |
| WO | WO 2014/134570 A1 | 9/2014 |

OTHER PUBLICATIONS

International preliminary report on patentability dated Nov. 22, 2011 for PCT/US2010/035690.
U.S. Appl. No. 13/384,181, filed Jan. 13, 2012, Cesano et al.
U.S. Appl. No. 61/048,657, filed Apr. 29, 2008, Convey et al.
U.S. Appl. No. 61/048,886, filed Apr. 29, 2008, Fantl et al.
U.S. Appl. No. 61/048,920, filed Apr. 29, 2008, Fantl et al.
U.S. Appl. No. 61/055,362, filed May 22, 2008, Cohen et al.
U.S. Appl. No. 61/079,537, filed Jul. 10, 2008, Putta.
U.S. Appl. No. 61/079,551, filed Jul. 10, 2008, Putta.
U.S. Appl. No. 61/079,579, filed Jul. 10, 2008, Banville et al.
U.S. Appl. No. 61/079,766, filed Jul. 10, 2008, Fantl et al.
U.S. Appl. No. 61/085,789, filed Apr. 1, 2008, Fantl et al.
U.S. Appl. No. 61/087,555, filed Apr. 8, 2008, Covey et al.
Benekli, et al. Signal transducer and activator of transcription proteins in leukemias. Blood. Apr. 15, 2003;101(8):2940-54.
Bienz. APC: the plot thickens. Curr Opin Genet Dev. 1999; 9(5): 595-603.
Birkenkamp, et al. Regulation of constitutive STAT5 phosphorylation in acute myeloid leukemia blasts. Leukemia. 2001; 15(12):1923-31.

(56) References Cited

OTHER PUBLICATIONS

Chen, et al. Down-regulation of the c-Jun N-terminal kinase (JNK) phosphatase M3/6 and activation of JNK by hydrogen peroxide and pyrrolidine dithiocarbamate. Oncogene. 2001. 20(3):367-74.
Chow, et al. Constitutive phosphorylation of the S6 ribosomal protein via mTOR and ERK signaling in the peripheral blasts of acute leukemia patients. Experimental hematology. 2006; 34(9):1182-1190.
Chow, et al. Measurement of MAP kinase activation by flow cytometry using phospho-specific antibodies to MEK and ERK: potential for pharmacodynamic monitoring of signal transduction inhibitors. Cytometry. Apr. 15, 2001;46(2):72-8.
Crans-Vargas, et al. CREB as a prognostic marker in acute leukemia. Abstract. Blood. 2001; 98(11), part 1, p. 316a.
European search report and search opinion dated Feb. 22, 2011 for Application No. 10180167.8.
European Search Report dated Nov. 2, 2010 for EP Application No. EP08795509.
Fantl et al. High Level phosphatas activity revealed in chronic lymphocytic leukemia cells that use mutated ommunoglobulin heavy chain variable region genes and lack high-level expression of the zeta-assocaited protein(ZAP-70). Blood. 2007. 110(11): Part 1 pp. 228A-229A (Abstracts).
International preliminary report on patentabiliby dated Mar. 4, 2010 for PCT Application No. US2008-009975.
International search report dated Mar. 20, 2009 for PCT Application No. US2008-009975.
International search report dated Sep. 21, 2010 for PCT Application No. PCT/US2010/35690.
Irish, et al. Mapping normal and cancer cell signalling networks: towards single-cell proteomics. Nat. Rev. Cancer. 2006. 6:146-155.
Irish, et al. Single cell profiling of potentiated phospho-protein networks in cancer cells. Cell. 2004. 118: 217-28.
Irish, et al. Altered B-cell receptor signaling kinetics distinguish human follicular lymphoma B cells from tumor-infiltrating nonmalignant B cells. Blood. Nov. 1, 2006;108(9):3135-42.
Irish, et al. Flt3 Y591 duplication and Bcl-2 overexpression are detected in acute myeloid leukemia cells with high levels of phosphorylated wild-type p53. Blood. 2007. 109(6):2589-96.
Irish, et al. Kinetics of B cell receptor signaling in human B cell subsets mapped by phosphospecific flow cytometry. J Immunol. Aug. 1, 2006;177(3):1581-9.
Kindler, et al. Indentification of a novel activating mutation (Y842C) within the activation loop of FLT3 in a patient with AML. Abstract 4681. Blood. 2003; 102(11):239B-240B and 45th Annual Meeting of the American Society of Hematology. San Diego, CA, USA. Dec. 6-9, 2003.
Kornblau, et al. Dynamic single-cell network profiles in acute myelogenous leukemia are associated with patient response to standard induction therapy. Clin Cancer Res. Jul. 15, 2010;16(14):3721-33. (abstract).
Krutzik, et al. High-content single-cell drug screening with phosphospecific flow cytometry. Natural Chemical Biology. 2008. 4(2):132-42.
Krutzik, et al. Intracellular phospho-protein staining techniques for flow cytometry: monitoring single cell signaling events. Cytometry A. 2003; 55(2): 61-70.
Krutzik, et al. Analysis of protein phosphorylation and cellular signaling events by flow cytometry: techniques and clinical applications. Clin Immunol Mar. 2004;110(3):206-21.
Krutzik, et al. Coordinate analysis of murine immune cell surface markers and intracellular phosphoproteins by flow cytometry. J Immunol 2005. 175(4):2357-65.
Krutzik. Characterization of the murine immunological signaling network with phosphospecific flow cytometry. J Immunol. 2005. 175(4): 2366-73.
Mahmoud,et al. Induction of CD45 expression and proliferation in U-266 myeloma cell line by interleukin-6. Blood. 1998. 92(10):3887-97.

Marvin et al. Normal bone marrow signal transduction profiles: a requisite for enhanced detection of signaling dysregulations in AML. Blood. Jan. 13, 2011. doi:10.1182/blood-2010-10-316026 [Epub ahead of print].
Menard, et al. Biologic and therapeutic role of HER2 in cancer. Oncogene. 2003. 22(42): 6570-8.
Monroe. Ligand-independent tonic signaling in B-cell receptor function. Current opinion in Immunology. 2004; 16:288-295.
Perez, et al. LFA-1 signaling through p44/42 is coupled to perforin degranulation in CD56+CD8+ natural killer cells. Blood. Aug. 15, 2004;104(4):1083-93.
Perez, et al. Simultaneous measurement of multiple active kinase states using polychromatic flow cytometry. Nat Biotechnol. 2002; 20: 155-62.
Rosen, et al. Functional characterization of FLT3 receptor signaling deregulation in acute myeloid leukemia by single cell network profiling (SCNP). PLoS One. Oct. 27, 2010;5(10):e13543.
Schaefer, et al. IGF-I and Prostate Cancer. Science. 1998; 282:199a.
Schulz. Single-cell phospho-protein analysis by flow cytometry. Curr Protoc Immunol 2007; Chapter 8:Unit 8.17.
Shankar, et al. CREB is amplified in AML blasts and is associated with an increased risk of relapse and decreased event-free survival. Abstract. Blood. 2004; 104(11), Part 1, p. 166A.
Shankar, et al. Role of cyclic AMP response element binding protein in human leukemias. Cancer. Nov. 1, 2005;104(9):1819-24.
Shankar, et al. The role of CREB as a proto-oncogene in hematopoiesis and in acute myeloid leukemia. Cancer Cell. Apr. 2005;7(4):351-62.
Spiekermann, et al. Overexpression and constitutive activation of FLT3 induces STAT5 activation in primary acute myeloid leukemia blast cells. Clinical Cancer Research. Jun. 2003; 9:2140-2150.
Stelzer, et al. Immunophenotyping. New York, NY: Wiley-Liss, 2000.
Thomas, et al. Spontaneous activation and signaling by overexpressed epidermal growth factor receptors in glioblastoma cells. Int J Cancer. 2003; 104(1): 19-27.
UK office action and search report dated Feb. 22, 2011 for GB Application No. 1017857.2.
Van Meter, et al. K-RasG12D expression induces hyperproliferation and aberrant signaling in primary hematopoietic stem/progenitor cells. Blood. May 1, 2007;109(9):3945-52.
Walter, et al. Tyrosine phosphorylation enhances ITIM-dependent internalization of CD33, the target for the anti-AML imunnoconjugate, gentuzumab ozogamicin. Part 1 2006. 108(11):Abstract 729A.
Whang, et al. Inactivation of the tumor suppressor PTEN/MMAC1 in advanced human prostate cancer through loss of expression. Proc Natl Acad Sci USA. 1998; 95(9): 5246-50.
Wienands, et al. Evidence for a preformed transducer complex organized by the B cell antigen receptor. Proc. Natl. Acad. Sci. USA. 1996; 93:7865-7870.
Zheng, et al. Regulation of STAT3 and STAT5 in the differentiation of FLT3/ITD expressing 32Dc13 cells induced by G-CSF and CEP-701. Abstract 2935.Blood. 2002; 100(11) and 44th Annual Meeting of the American Society of Hematology. Philadelphia, PA, USA. Dec. 6-10, 2002.
Amico, et al. Differential response of human acute myeloid leukemia cells to gemtuzumab ozogamicin in vitro: role of Chk1 and Chk2 phosphorylation and caspase 3. Blood. Jun. 1, 2003;101(11):4589-97.
Kumar, et al. 2-methoxyestradiol blocks cell-cycle progression at G(2)/M phase and inhibits growth of human prostate cancer cells. Mol Carcinog. Jul. 2001;31(3):111-24.
Mack, et al. Detection of caspase-activation in intact lymphoid cells using standard caspase substrates and inhibitors. J Immunol Methods. Jul. 31, 2000;241(1-2):19-31.
U.S. Appl. No. 13/094,735, filed Apr. 26, 2011, Perez et al.
U.S. Appl. No. 13/094,737, filed Apr. 26, 2011, Perez et al.
U.S. Appl. No. 13/453,636, filed Apr. 23, 2012, Purvis, Jr.
U.S. Appl. No. 13/464,254, filed May 4, 2012, Moser et al.
U.S. Appl. No. 13/473,829, filed May 17, 2012, Fantl et al.
U.S. Appl. No. 13/544,053, filed Jul. 9, 2012, Soper et al.

(56) References Cited

OTHER PUBLICATIONS

Borbolla-Escoboza, et al. Induction of apoptosis and effect on CD20+ using rituximab on autologous peripheral blood stem cell harvests from patients with B cell lymphomas. Stem Cells Dev. Apr. 2004;13(2):193-6.
U.S. Appl. No. 13/566,991, filed Aug. 3, 2012, Rosen et al.
U.S. Appl. No. 13/580,660, filed Aug. 22, 2012, Hale et al.
U.S. Appl. No. 13/596,579, filed Aug. 28, 2012, Fantl et al.
U.S. Appl. No. 13/636,627, filed Sep. 21, 2012, Nolan et al.
U.S. Appl. No. 13/645,325, filed Oct. 2, 2012, Covey et al.
U.S. Appl. No. 13/672,287, filed Nov. 8, 2012, Fantl et al.
U.S. Appl. No. 13/673,213, filed Nov. 9, 2012, Purvis et al.
U.S. Appl. No. 13/750,700, filed Jan. 25, 2013, Longo.
Office action dated Feb. 9, 2012 for U.S. Appl. No. 12/229,476.
Office action dated Jun. 7, 2012 for U.S. Appl. No. 12/784,478.
Office action dated Aug. 23, 2011 for U.S. Appl. No. 12/229,476.
Office action dated Oct. 17, 2012 for U.S. Appl. No. 12/784,478.
U.S. Appl. No. 14/667,388, filed Mar. 24, 2015, Covey et al.
Chiorazzi, et al. Clinical and laboratory parameters that define clinically relevant B-CLL subgroups. Curr Top Microbiol Immunol. 2005;294:109-33.
Database Biosis [Online] Biosceinces Information Service, Philadelphia, PA, US Nov. 2007. Fantl, et al.: High level phosphatase activity revealed in chronic lymphocytic leukemia cells that use mutated immunoglobulin heavy chain variable region genes and lack high-level expression of the zeta-associated protein (ZAP-70) Database accession No. PREV200800216016.
Efremov, et al. Signaling pathways activated by antigen-receptor engagement in chronic lymphocytic leukemia B-cells. Autoimmun Rev. Dec. 2007;7(2):102-8. Epub Mar. 28, 2007.
European search report and search opinion dated Mar. 12, 2015 for Application No. 14189449.3.
Nedellec, et al. B cell response to surface IgM cross-linking identifies different prognostic groups of B-chronic lymphocytic leukemia patients. J Immunol. Mar. 15, 2005;174(6):3749-56.
U.S. Appl. No. 14/294,592, filed Jun. 3, 2014, Fantl et al.
U.S. Appl. No. 14/450,639, filed Aug. 4, 2014, Soper et al.
U.S. Appl. No. 14/525,013, filed Oct. 27, 2014, Hotson et al.
U.S. Appl. No. 14/572,317, filed Dec. 16, 2014, Fantl et al.
U.S. Appl. No. 14/574,277, filed Dec. 17, 2014, Fantl et al.
PCT/US2013/045273, Appln filed Jun. 11, 2013, Cesano et al.
PCT/US2013/068815, Appln filed Nov. 6, 2013, Hawtin et al.
PCT/US2013/071354, Appln filed Nov. 21, 2013, Cesano et al.
U.S. Appl. No. 13/801,420, filed Mar. 13, 2013, Cesano et al.
U.S. Appl. No. 13/821,539, filed Mar. 7, 2013, Longo.
U.S. Appl. No. 13/900,170, filed May 22, 2013, Fantl.
U.S. Appl. No. 13/913,029, filed Jun. 7, 2013, Fantl et al.
U.S. Appl. No. 13/958,285, filed Aug. 2, 2013, Fantl et al.
U.S. Appl. No. 14/011,715, filed Aug. 27, 2013, Ptacek et al.
U.S. Appl. No. 14/013,567, filed Aug. 29, 2013, Purvis Jr.
U.S. Appl. No. 14/014,110, filed Aug. 29, 2013, Moser et al.
U.S. Appl. No. 14/036,216, filed Sep. 25, 2013, Fantl et al.
U.S. Appl. No. 14/045,548, filed Oct. 3, 2013, Fantl et al.
U.S. Appl. No. 14/072,623, filed Nov. 5, 2013, Longo.
U.S. Appl. No. 14/073,692, filed Nov. 6, 2013, Hawtin et al.
U.S. Appl. No. 14/086,922, filed Nov. 21, 2013, Cesano et al.

Buchner, et al. Spleen tyrosine kinase is overexpressed and represents a potential therapeutic target in chronic lymphocytic leukemia. Cancer Res. Jul. 1, 2009;69(13):5424-32. doi: 10.1158/0008-5472.CAN-08-4252. Epub Jun. 23, 2009.
Burks, et al. IRS proteins and beta-cell function. Diabetes. 2001. S140-S145.
Contri, et al. Chronic lymphocytic leukemia B cells contain anomalous Lyn tyrosine kinase, a putative contribution to defective apoptosis. J Clin Invest. Feb. 2005;115(2):369-78.
Deglesne, et al. Survival response to B-cell receptor ligation is restricted to progressive chronic lymphocytic leukemia cells irrespective of Zap70 expression. Cancer Res. Jul. 15, 2006;66(14):7158-66.
Gobessi, et al. Inhibition of constitutive and BCR-induced Syk activation downregulates Mcl-1 and induces apoptosis in chronic lymphocytic leukemia B cells. Leukemia. Apr. 2009;23(4):686-97. doi: 10.1038/leu.2008.346. Epub Dec. 18, 2008.
Guarini, et al. BCR ligation induced by IgM stimulation results in gene expression and functional changes only in IgV H unmutated chronic lymphocytic leukemia (CLL) cells. Blood. Aug. 1, 2008;112(3):782-92. doi: 10.1182/blood-2007-12-127688. Epub May 16, 2008.
Hunter. Signaling—2000 and beyond. Cell. 2000. 100(1):113-27.
Kato, et al. Selective activation of STAT5 unveils its role in stem cell self-renewal in normal and leukemic hematopoiesis. J Exp Med. Jul. 4, 2005;202(1):169-79.
Kurosaki, et al. Role of the Syk autophosphorylation site and SH2 domains in B cell antigen receptor signaling. J Exp Med. Dec. 1, 1995;182(6):1815-23.
Li, et al. Cell-based assays for profiling activity and safety properties of cancer drugs. J Pharmacol Toxicol Methods. Nov.-Dec. 2006;54(3):313-9. Epub Mar. 27, 2006.
Luciano, et al. The p54 cleaved form of the tyrosine kinase Lyn generated by caspases during BCR-induced cell death in B lymphoma acts as a negative regulator of apoptosis. FASEB J. Apr. 2003;17(6):711-3. Epub Feb. 5, 2003.
Malhotra, et al. Molecular biology of protein kinase C signaling in cardiac myocytes. Mol Cell Biochem. 2001. 225(1-):97-107.
Motiwala, et al. Methylation and silencing of protein tyrosine phosphatase receptor type O in chronic lymphocytic leukemia. Clin Cancer Res. Jun. 1, 2007;13(11):3174-81.
Muzio, et al. Constitutive activation of distinct BCR-signaling pathways in a subset of CLL patients: a molecular signature of anergy. Blood. Jul. 1, 2008;112(1):188-95. doi: 10.1182/blood-2007-09-111344. Epub Feb. 21, 2008.
Office action dated Jul. 2, 2013 for JP Application No. 2010-521884.
Sattler, et al. Hematopoietic growth factors signal through the formation of reactive oxygen species. Blood. May 1, 1999;93(9):2928-35.
Takata, et al. A role for Bruton's tyrosine kinase in B cell antigen receptor-mediated activation of phospholipase C-gamma 2. J Exp Med. Jul. 1, 1996;184(1):31-40.
Xiao, et al. Tumor suppression by phospholipase C-beta3 via SHP-1-mediated dephosphorylation of Stat5. Cancer Cell. Aug. 4, 2009;16(2):161-71. doi: 10.1016/j.ccr.2009.05.018.
International search report and written opinion dated Mar. 6, 2014 for PCT/US2013/056914.

* cited by examiner

US 9,182,385 B2

METHODS FOR DIAGNOSIS, PROGNOSIS AND METHODS OF TREATMENT

CROSS-REFERENCE

This application is a Continuation Application which claims the benefit of U.S. application Ser. No. 12/229,476 filed Aug. 21, 2008; which claims the benefit of U.S. Provisional Application No. 60/957,160 filed Aug. 21, 2007 and U.S. Provisional Application No. 61/048,920 filed Apr. 29, 2008 and each of which is hereby expressly incorporated by reference in its entirety.

BACKGROUND OF THE INVENTION

Many conditions are characterized by disruptions in cellular pathways that lead, for example, to aberrant control of cellular processes, or to uncontrolled growth and proliferation of cells. These disruptions are often caused by changes in the activity of molecules participating in cellular pathways. For example, specific signaling pathway alterations have been described for many cancers. Despite the increasing evidence that disruption in cellular pathways mediate the detrimental transformation, the precise molecular events underlying these transformations have not been elucidated. As a result, therapeutics may not be effective in treating conditions involving cellular pathways that are not well understood. Thus, the successful diagnosis of a condition and use of therapies will require knowledge of the cellular events that are responsible for the condition pathology.

In addition, patients suffering from different conditions follow heterogeneous clinical courses. For instance, tremendous clinical variability among remissions is also observed in cancer patients, even those that occur after one course of therapy. Some leukemia patients survive for prolonged periods without definitive therapy, while others die rapidly despite aggressive treatment. Patients who are resistant to therapy have very short survival times, regardless of when the resistance occurs. While various staging systems have been developed to address this clinical heterogeneity, they cannot accurately predict whether an early or intermediate stage patient will experience an indolent or aggressive course of disease.

Accordingly, there is a need for a reliable indicator of an individual predicted disease course to help clinicians to identify those patients that will respond to treatment, patients that progress to a more advanced state of the disease and patients with emerging resistance to treatment.

SUMMARY OF THE INVENTION

Other objects, features and advantages of the methods and compositions described herein will become apparent from the following detailed description. It should be understood, however, that the detailed description and the specific examples, while indicating specific embodiments, are given by way of illustration only, since various changes and modifications within the spirit and scope of the invention will become apparent to those skilled in the art from this detailed description.

All publications, patents, and patent applications mentioned in this specification are herein incorporated by reference to the same extent as if each individual publication or patent application was specifically and individually indicated to be incorporated by reference.

As disclosed herein is a method for classifying a cell comprising contacting the cell with an inhibitor, determining the presence or absence of a change in activation level of an activatable element in the cell, and classifying the cell based on the presence or absence of the change in the activation level of the activatable element. In some embodiments the change in activation level of an activatable element is an increase in the activation level of an activatable element. In some embodiments the activatable element is a protein subject to phosphorylation or dephosphorylation.

In some embodiments of the methods, the invention provides a method for classifying a cell by contacting the cell with an inhibitor; determining the activation levels of a plurality of activatable elements in the cell; and classifying the cell based on the activation level. In some embodiments, the inhibitor is a kinase or phosphatase inhibitor, such as adaphostin, AG 490, AG 825, AG 957, AG 1024, aloisine, aloisine A, alsterpaullone, aminogenistein, API-2, apigenin, arctigenin, AY-22989, BAY 61-3606, bisindolylmaleimide IX, chelerythrine, 10-[4'-(N,N-Diethylamino)butyl]-2-chlorophenoxazine hydrochloride, dasatinib, 2-Dimethylamino-4,5,6,7-tetrabromo-1H-benzimidazole, 5,7-Dimethoxy-3-(4-pyridinyl)quinoline dihydrochloride, edelfosine, ellagic acid, enzastaurin, ER 27319 maleate, erlotinib, ET18OCH3, fasudil, flavopiridol, gefitinib, GW 5074, H-7, H-8, H-89, HA-100, HA-1004, HA-1077, HA-1100, hydroxyfasudil, indirubin-3'-oxime, 5-Iodotubercidin, kenpaullone, KN-62, KY12420, LFM-A13, lavendustin A, luteolin, LY-294002, LY294002, mallotoxin, ML-9, NSC-154020, NSC-226080, NSC-231634, NSC-664704, NSC-680410, NU6102, olomoucine, oxindole I, PD-153035, PD-98059, PD-169316, phloretin, phloridzin, piceatannol, picropodophyllin, PK1, PP1, PP2, purvalanol A, quercetin, R406, R788, rapamune, rapamycin, Ro 31-8220, roscovitine, rottlerin, SB202190, SB203580, sirolimus, sorafenib, SL327, SP600125, staurosporine, STI-571, SU-11274, SU1498, SU4312, SU6656, 4,5,6,7-Tetrabromotriazole, TG101348, Triciribine, Tyrphostin AG 490, Tyrphostin AG 825, Tyrphostin AG 957, Tyrphostin AG 1024, Tyrphostin SU1498, U0126, VX-509, VX-667, VX-680, W-7, wortmannin, XL-019, XL-147, XL-184, XL-228, XL-281, XL-518, XL-647, XL-765, XL-820, XL-844, XL-880, Y-27632, ZD-1839, ZM-252868, ZM-447439, $H_2O_2$, siRNA, miRNA, Cantharidin, (−)-p-Bromotetramisole, Microcystin LR, Sodium Orthovanadate, Sodium Pervanadate, Vanadyl sulfate, Sodium oxodiperoxo (1,10-phenanthroline)vanadate, bis(maltolato)oxovanadium (IV), Sodium Molybdate, Sodium Perm olybdate, Sodium Tartrate, Imidazole, Sodium Fluoride, β-Glycerophosphate, Sodium Pyrophosphate Decahydrate, Calyculin A, Discodermia calyx, bpV(phen), mpV(pic), DMHV, Cypermethrin, Dephostatin, Okadaic Acid, NIPP-1, N-(9,10-Dioxo-9,10-dihydro-phenanthren-2-yl)-2,2-dimethyl-propionamide, α-Bromo-4-hydroxyacetophenone, 4-Hydroxyphenacyl Br, α-Bromo-4-methoxyacetophenone, 4-Methoxyphenacyl Br, α-Bromo-4-(carboxymethoxy)acetophenone, 4-(Carboxymethoxy)phenacyl Br, and bis(4-Trifluoromethylsulfonamidophenyl)-1,4-diisopropylbenzene, phenyarsine oxide, Pyrrolidine Dithiocarbamate, or Aluminum fluoride. In some embodiments the phosphatase inhibitor is $H_2O_2$.

In some embodiments the cell is a hematopoietic-derived cell. In some embodiments, the hematopoietically derived cell is selected from the group consisting of pluripotent hematopoietic stem cells, B-lymphocyte lineage progenitor or derived cells, T-lymphocyte lineage progenitor or derived cells, NK cell lineage progenitor or derived cells, granulocyte lineage progenitor or derived cells, monocyte lineage progenitor or derived cells, megakaryocyte lineage progenitor or derived cells and erythroid lineage progenitor or derived cells. In some embodiments, the hematopoietic derived cell is a B-lymphocyte lineage progenitor and derived cell, e.g., an early pro-B cell, late pro-B cell, large pre-B cell, small pre-B cell, immature B cell, mature B cell, plasma cell and memory B cell, a CD5+ B cell, a CD38+ B cell, a B cell bearing a mutatated or non mutated heavy chain of the B cell receptor, or a B cell expressing Zap70.

In some embodiments, the classification includes classifying the cell as a cell that is correlated with a clinical outcome. In some embodiments, the clinical outcome is the prognosis and/or diagnosis of a condition. In some embodiments, the clinical outcome is the presence or absence of a neoplastic or a hematopoietic condition, such as Non-Hodgkin Lymphoma, Hodgkin or other lymphomas, acute or chronic leukemias, polycythemias, thrombocythemias, multiple myeloma or plasma cell disorders, e.g., amyloidosis and Waldenstrom's macroglobulinemia, myelodysplastic disorders, myeloproliferative disorders, myelofibrosis, or atypical immune lymphoproliferations. In some embodiments, the neoplastic or hematopoietic condition is non-B lineage derived, such as acute myeloid leukemia (AML), Chronic Myeloid Leukemia (CML), non-B cell acute lymphocytic leukemia (ALL), non-B cell lymphomas, myelodysplastic disorders, myeloproliferative disorders, myelofibrosis, polycythemias, thrombocythemias, or non-B atypical immune lymphoproliferations. In some embodiments, the neoplastic or hematopoietic condition is a B-Cell or B cell lineage derived disorder, such as Chronic Lymphocytic Leukemia (CLL), B lymphocyte lineage leukemia, B lymphocyte lineage lymphoma, Multiple Myeloma, acute lymphoblastic leukemia (ALL), B-cell pro-lymphocytic leukemia, precursor B lymphoblastic leukemia, hairy cell leukemia or plasma cell disorders, e.g., amyloidosis or Waldenstrom's macroglobulinemia, B cell lymphomas including but not limited to diffuse large B cell lymphoma, follicular lymphoma, mucosa associated lymphatic tissue lymphoma, small cell lymphocytic lymphoma and mantle cell lymphoma. In some embodiments, the condition is CLL. In some embodiments, the CLL is defined by a monoclonal B cell population that co-expresses CD5 with CD19 and CD23 or CD5 with CD20 and CD23 and by surface immunoglobulin expression.

In some embodiments, the clinical outcome is the staging or grading of a neoplastic or hematopoietic condition. Examples of staging in methods provided by the invention include aggressive, indolent, benign, refractory, Roman Numeral staging, TNM Staging, Rai staging, Binet staging, WHO classification, FAB classification, IPSS score, WPSS score, limited stage, extensive stage, staging according to cellular markers such as ZAP70 and CD38, occult, including information that may inform on time to progression, progression free survival, overall survival, or event-free survival.

In some embodiments of the methods of the invention, classifying the cell based on activation levels of activatable element includes classifying the cell as a cell that is correlated to a patient response to a treatment, such as complete response, partial response, nodular partial response, no response, progressive disease, stable disease, relapse or adverse reaction. The method may further comprise determining a method of treatment, e.g., chemotherapy, biological therapy, radiation therapy, bone marrow transplantation, Peripheral stem cell transplantation, umbilical cord blood transplantation, autologous stem cell transplantation, allogeneic stem cell transplantation, syngeneic stem cell transplantation, surgery, induction therapy, maintenance therapy, watchful waiting, or holistic/alternative therapy.

In some embodiments of the methods of the invention, the classifying of the cell based on activation level includes classifying the cell as a cell that is correlated with minimal residual disease or emerging resistance.

In some embodiments of the invention, the activation level of the plurality of activatable elements in the cell is selected from the group consisting of cleavage by extracellular or intracellular protease exposure, novel hetero-oligomer formation, glycosylation level, phosphorylation level, acetylation level, methylation level, biotinylation level, glutamylation level, glycylation level, hydroxylation level, isomerization level, prenylation level, myristoylation level, lipoylation level, phosphopantetheinylation level, sulfation level, ISGylation level, nitrosylation level, palmitoylation level, SUMOylation level, ubiquitination level, neddylation level, citrullination level, deamidation level, disulfide bond formation level, proteolytic cleavage level, translocation level, changes in protein turnover, multi-protein complex level, oxidation level, multi-lipid complex, and biochemical changes in cell membrane. In some embodiments, the activation level is a phosphorylation level. In some embodiments, the activatable element is selected from the group consisting of proteins, carbohydrates, lipids, nucleic acids and metabolites. In some embodiments, the activatable element is a protein. In some embodiments, the activatable element is a change in metabolic state, temperature, or local ion concentration. In embodiments where the activatable element is a protein, in some embodiments the protein is a protein subject to phosphorylation or dephosphorylation, such as kinases, phosphatases, adaptor/scaffold proteins, ubiquitination enzymes, adhesion molecules, contractile proteins, cytoskeletal proteins, heterotrimeric G proteins, small molecular weight GTPases, guanine nucleotide exchange factors, GTPase activating proteins, caspases and proteins involved in apoptosis (e.g. PARP), ion channels, molecular transporters, molecular chaperones, metabolic enzymes, vesicular transport proteins, hydroxylases, isomerases, transferases, deacetylases, methylases, demethylases, proteases, esterases, hydrolases, DNA binding proteins or transcription factors. In some embodiments, the protein is selected from the group consisting of PI3-Kinase (p85, p110a, p110b, p110d), Jak1, Jak2, SOCs, Rac, Rho, Cdc42, Ras-GAP, Vav, Tiam, Sos, Dbl, Nck, Gab, PRK, SHPT, and SHP2, SHIP1, SHIP2, sSHIP, PTEN, Shc, Grb2, PDK1, SGK, Akt1, Akt2, Akt3, TSC1,2, Rheb, mTor, 4EBP-1, p70S6Kinase, S6, LKB-1, AMPK, PFK, Acetyl-CoAa Carboxylase, DokS, Rafs, Mos, Tpl2, MEK1/2, MLK3, TAK, DLK, MKK3/6, MEKK1,4, MLK3, ASK1, MKK4/7, SAPK/JNK1,2,3, p38s, Erk1/2, Syk, Btk, BLNK, LAT, ZAP70, Lck, Cbl, SLP-76, PLCγ1, PLCγ2, STAT1, STAT 3, STAT 4, STAT 5, STAT 6, FAK, p130CAS, PAKs, LIMK1/2, Hsp90, Hsp70, Hsp27, SMADs, Rel-A (p65-NFKB), CREB, Histone H2B, HATs, HDACs, PKR, Rb, Cyclin D, Cyclin E, Cyclin A, Cyclin B, P16, p14Arf, p27KIP, p21CIP, Cdk4, Cdk6, Cdk7, Cdk1, Cdk2, Cdk9, Cdc25,A/B/C, Abl, E2F, FADD, TRADD, TRAF2, RIP, Myd88, BAD, Bcl-2, Mcl-1, Bcl-XL, Caspase 2, Caspase 3, Caspase 6, Caspase 7, Caspase 8, Caspase 9, PARP, IAPB, Smac, Fodrin, Actin, Src, Lyn, Fyn, Lck, NIK, IκB, p65 (RelA), IKKα, PKA, PKCα, PKCβ, PKCθ, PKCδ, CAMK, Elk, AFT, Myc, Egr-1, NFAT, ATF-2, Mdm2, p53, DNA-PK, Chk1, Chk2, ATM, ATR, β-catenin, CrkL, GSK3α, GSK3β, and FOXO. In some embodiments, the protein selected from the group consisting of Erk, Syk, Zap70, Lck, Btk, BLNK, Cbl, PLCγ2, Akt, RelA, p38, S6. In some embodiments the protein is S6.

In some embodiments, the protein is selected from the group consisting of HER receptors, PDGF receptors, Kit receptor, FGF receptors, Eph receptors, Trk receptors, IGF receptors, Insulin receptor, Met receptor, Ret, VEGF receptors, TIE1, TIE2, FAK, Jak1, Jak2, Jak3, Tyk2, Src, Lyn, Fyn, Lck, Fgr, Yes, Csk, Abl, Btk, ZAP70, Syk, IRAKs, cRaf, ARaf, BRAF, Mos, Lim kinase, ILK, Tpl, ALK, TGFIβ receptors, BMP receptors, MEKKs, ASK, MLKs, DLK, PAKs, Mek 1, Mek 2, MKK3/6, MKK4/7, ASK1, Cot, NIK, Bub, Myt 1, Weel, Casein kinases, PDK1, SGK1, SGK2, SGK3, Akt1, Akt2, Akt3, p90Rsks, p70S6Kinase, Prks, PKCs, PKAs, ROCK 1, ROCK 2, Auroras, CaMKs, MNKs, AMPKs, MELK, MARKs, Chk1, Chk2, LKB-1, MAP-KAPKs, Pim1, Pim2, Pim3, IKKs, Cdks, Jnks, Erks, IKKs, GSK3α, GSK3β, Cdks, CLKs, PKR, PI3-Kinase class 1, class 2, class 3, mTor, SAPK/JNK1,2,3, p38s, PKR, DNA-PK, ATM, ATR, Receptor protein tyrosine phosphatases (RPTPs), LAR phosphatase, CD45, Non receptor tyrosine phosphatases (NPRTPs), SHPs, MAP kinase phosphatases (MKPs), Dual Specificity phosphatases (DUSPs), CDC25 phosphatases, Low molecular weight tyrosine phosphatase, Eyes absent (EYA) tyrosine phosphatases, Slingshot phosphatases (SSH), serine phosphatases, PP2A, PP2B, PP2C, PP1, PP5, inositol phosphatases, PTEN, SHIPs, myotubularins, phosphoinositide kinases, phospholipases, prostaglandin synthases, 5-lipoxygenase, sphingosine kinases, sphingomyelinases, adaptor/scaffold proteins, Shc, Grb2, BLNK, LAT, B cell adaptor for PI3-kinase (BCAP), SLAP, Dok, KSR, MyD88, Crk, CrkL, GAD, Nck, Grb2 associated binder (GAB), Fas associated death domain (FADD), TRADD, TRAF2, RIP, T-Cell leukemia family, IL-2, IL-4, IL-8, IL-6, interferon γ, interferon α, suppressors of cytokine signaling (SOCs), Cbl, SCF ubiquitination ligase complex, APC/C, adhesion molecules, integrins, Immunoglobulin-like adhesion molecules, selectins, cadherins, catenins, focal adhesion kinase, p130CAS, fodrin, actin, paxillin, myosin, myosin binding proteins, tubulin, eg5/KSP, CENPs, β-adrenergic receptors, muscarinic receptors, adenylyl cyclase receptors, small molecular weight GTPases, H-Ras, K-Ras, N-Ras, Ran, Rac, Rho, Cdc42, Arfs, RABs, RHEB, Vav, Tiam, Sos, Dbl, PRK, TSC1,2, Ras-GAP, Arf-GAPs, Rho-GAPs, caspases, Caspase 2, Caspase 3, Caspase 6, Caspase 7, Caspase 8, Caspase 9, PARP, Bcl-2, Mcl-1, Bcl-XL, Bcl-w, Bcl-B, A1, Bax, Bak, Bok, Bik, Bad, Bid, Bim, Bmf, Hrk, Noxa, Puma, IAPB, XIAP, Smac, Cdk4, Cdk 6, Cdk 2, Cdk1, Cdk 7, Cyclin D, Cyclin E, Cyclin A, Cyclin B, Rb, p16, p14Arf, p27KIP, p21CIP, molecular chaperones, Hsp90s, Hsp70, Hsp27, metabolic enzymes, Acetyl-CoAa Carboxylase, ATP citrate lyase, nitric oxide synthase, caveolins, endosomal sorting complex required for transport (ESCRT) proteins, vesicular protein sorting (Vsps), hydroxylases, prolyl-hydroxylases PHD-1, 2 and 3, asparagine hydroxylase FIH transferases, Pin1 prolyl isomerase, topoisomerases, deacetylases, Histone deacetylases, sirtuins, histone acetylases, CBP/P300 family, MYST family, ATF2, DNA methyl transferases, Histone H3K4 demethylases, H3K27, JHDM2A, UTX, VHL, WT-1, p53, Hdm, PTEN, ubiquitin proteases, urokinase-type plasminogen activator (uPA) and uPA receptor (uPAR) system, cathepsins, metalloproteinases, esterases, hydrolases, separase, potassium channels, sodium channels, multi-drug resistance proteins, P-Gycoprotein, nucleoside transporters, Ets, Elk, SMADs, Rel-A (p65-NFKB), CREB, NFAT, ATF-2, AFT, Myc, Fos, Sp1, Egr-1, T-bet, β-catenin, HIFs, FOXOs, E2Fs, SRFs, TCFs, Egr-1, β-catenin, FOXO STAT1, STAT 3, STAT 4, STAT 5, STAT 6, p53, WT-1, HMGA, pS6, 4EPB-1, eIF4E-binding protein, RNA polymerase, initiation factors, elongation factors.

In some embodiments, the invention provides methods for determining the presence or absence of a condition in an individual by subjecting a cell from the individual to a modulator or an inhibitor, determining the activation level of an activatable element in the cell and determining the presence or absence of the condition based on the activation level. In some embodiments, the cell is a hematopoietic derived cell. In some embodiments, the hematopoietically derived cell is selected from the group consisting of pluripotent hematopoietic stem cells, B-lymphocyte lineage progenitor or derived cells, T-lymphocyte lineage progenitor or derived cells, NK cell lineage progenitor or derived cells, granulocyte lineage progenitor or derived cells, monocyte lineage progenitor or derived cells, megakaryocyte lineage progenitor or derived cells and erythroid lineage progenitor or derived cells. In some embodiments, the hematopoietic derived cell is a B-lymphocyte lineage progenitor and derived cell, e.g., an early pro-B cell, late pro-B cell, large pre-B cell, small pre-B cell, immature B cell, mature B cell, plasma cell and memory B cell, a CD5+ B cell, a CD38+ B cell, a B cell bearing a mutatated or non mutated heavy chain of the B cell receptor, or a B cell expressing Zap70. In some embodiments, the condition is a neoplastic or hematopoietic condition.

In some embodiments of the methods of the invention, the modulator to which the cell is subjected is an activator or an inhibitor. In some embodiments, the modulator is, e.g., a growth factor, cytokine, adhesion molecule modulator, hormone, small molecule, polynucleotide, antibodies, natural compounds, lactones, chemotherapeutic agents, immune modulator, carbohydrate, proteases, ions, reactive oxygen species, or radiation. In some embodiments, the modulator is a B cell receptor modulator, e.g., a B cell receptor activator such as a cross-linker of the B cell receptor complex or the B-cell co-receptor complex. In some embodiments, the cross-linker is an antibody, or molecular binding entity. In some embodiments, the cross-linker is an antibody, such as a multivalent antibody. In some embodiments, the antibody is a monovalent, bivalent, or multivalent antibody made more multivalent by attachment to a solid surface or tethered on a nanoparticle surface to increase the local valency of the epitope binding domain. In some embodiments, the cross-linker is a molecular binding entity, such as an entity that acts upon or binds the B cell receptor complex via carbohydrates or an epitope in the complex. In some embodiments, the molecular binding entity is a monovalent, bivalent, or multivalent binding entity that is made more multivalent by attachment to a solid surface or tethered on a nanoparticle surface to increase the local valency of the epitope binding domain. In some embodiments where the modulator is a B cell receptor modulator, e.g., a B cell receptor activator such as a cross-linker of the B cell receptor complex or the B-cell co-receptor complex, cross-linking includes binding of an antibody or molecular binding entity to the cell and then causing its crosslinking via interaction of the cell with a solid surface that causes crosslinking of the BCR complex via antibody or molecular binding entity. In some embodiments, the crosslinker is selected from the group consisting of F(ab)2 IgM, IgG, IgD, polyclonal BCR antibodies, monoclonal BCR antibodies, Fc receptor derived binding elements. The Ig may be derived from a species selected from the group consisting of mouse, goat, rabbit, pig, rat, horse, cow, shark, chicken, or llama. In some embodiments, the crosslinker is F(ab)2 IgM, Polyclonal IgM antibodies, Monoclonal IgM antibodies, Biotinylated F(ab)2 IgCM, Biotinylated Polyclonal IgM antibodies, Biotinylated Monoclonal IgM antibodies and/or a combination thereof.

In some embodiments, the inhibitor is a kinase or phosphatase inhibitor, such as adaphostin, AG 490, AG 825, AG 957, AG 1024, aloisine, aloisine A, alsterpaullone, aminogenistein, API-2, apigenin, arctigenin, AY-22989, BAY 61-3606, bisindolylmaleimide IX, chelerythrine, 10-[4'-(N, N-Diethylamino)butyl]-2-chlorophenoxazine hydrochloride, dasatinib, 2-Dimethylamino-4,5,6,7-tetrabromo-1H-benzimidazole, 5,7-Dimethoxy-3-(4-pyridinyl)quinoline dihydrochloride, edelfosine, ellagic acid, enzastaurin, ER 27319 maleate, erlotinib, ET18OCH3, fasudil, flavopiridol, gefitinib, GW 5074, H-7, H-8, H-89, HA-100, HA-1004, HA-1077, HA-1100, hydroxyfasudil, indirubin-3'-oxime, 5-Iodotubercidin, kenpaullone, KN-62, KY12420, LFM-A13, lavendustin A, luteolin, LY-294002, LY294002, mallotoxin, ML-9, NSC-154020, NSC-226080, NSC-231634, NSC-664704, NSC-680410, NU6102, olomoucine, oxindole I, PD-153035, PD-98059, PD-169316, phloretin, phloridzin, piceatannol, picropodophyllin, PK1, PP1, PP2, purvalanol A, quercetin, R406, R788, rapamune, rapamycin, Ro 31-8220, roscovitine, rottlerin, SB202190, SB203580, sirolimus, sorafenib, SL327, SP600125, staurosporine, STI-571, SU-11274, SU1498, SU4312, SU6656, 4,5,6,7-Tetrabromotriazole, TG101348, Triciribine, Tyrphostin AG 490, Tyrphostin AG 825, Tyrphostin AG 957, Tyrphostin AG 1024, Tyrphostin SU1498, U0126, VX-509, VX-667, VX-680, W-7, wortmannin, XL-019, XL-147, XL-184, XL-228, XL-281, XL-518, XL-647, XL-765, XL-820, XL-844, XL-880, Y-27632, ZD-1839, ZM-252868, ZM-447439, $H_2O_2$, siRNA, miRNA, Cantharidin, (−)-p-Bromotetramisole, Microcystin LR, Sodium Orthovanadate, Sodium Pervanadate, Vanadyl sulfate, Sodium oxodiperoxo(1,10-phenanthroline)vanadate, bis(maltolato)oxovanadium(IV), Sodium Molybdate, Sodium Perm olybdate, Sodium Tartrate, Imidazole, Sodium Fluoride, β-Glycerophosphate, Sodium Pyrophosphate Decahydrate, Calyculin A, Discodermia calyx, bpV(phen), mpV(pic), DMHV, Cypermethrin, Dephostatin, Okadaic Acid, NIPP-1, N-(9,10-Dioxo-9,10-dihydro-phenanthren-2-yl)-2,2-dimethyl-propionamide, α-Bromo-4-hydroxyacetophenone, 4-Hydroxyphenacyl Br, α-Bromo-4-methoxyacetophenone, 4-Methoxyphenacyl Br, α-Bromo-4-(carboxymethoxy)acetophenone, 4-(Carboxymethoxy)phenacyl Br, and bis(4-Trifluoromethylsulfonamidophenyl)-1,4-diisopropylbenzene, phenyarsine oxide, Pyrrolidine Dithiocarbamate, or Aluminum fluoride. In some embodiments the phosphatase inhibitor is $H_2O_2$.

In some embodiments of the methods of the invention, the cell is subjected to a B cell receptor activator and a phosphatase inhibitor or kinase inhibitor, such as $F(ab)_2IgM$ or biotinylated $F(ab)_2IgM$ and a phosphatase inhibitor (e.g. $H_2O_2$).

In some embodiments, the invention provides a method of determining a tonic signaling status of a cell by subjecting the cell to a modulator, determining the activation level of an activatable element that participates in a tonic signaling pathway in the cell, and determining the status of a tonic signaling pathway in the cell from the activation level. In some embodiments, a condition of an individual is determined based on tonic signaling status of a cell. In some embodiments, the condition is a neoplastic and/or hematopoietic condition. In some embodiments, the neoplastic or hematopoietic condition is selected from the group consisting of Non-Hodgkin Lymphoma, Hodgkin or other lymphomas, acute or chronic leukemias, polycythemias, thrombocythemias, multiple myeloma and plasma cell disorders, e.g., amyloidosis and Waldenstrom's macroglobulinemia, myelodysplastic disorders, myeloproliferative disorders, myelofibrosis, and atypical immune lymphoproliferations. In some embodiments, the neoplastic or hematopoietic condition is non-B lineage derived, such as acute myeloid leukemia (AML), Chronic Myeloid Leukemia (CML), non-B cell acute lymphocytic leukemia (ALL), non-B cell lymphomas, myelodysplastic disorders, myeloproliferative disorders, myelofibrosis, polycythemias, thrombocythemias, and non-B atypical immune lymphoproliferations. In some embodiments, the neoplastic or hematopoietic condition is a B-Cell or B cell lineage derived disorder such as B-Cell or B cell lineage derived disorder is selected from the group consisting of Chronic Lymphocytic Leukemia (CLL), B lymphocyte lineage leukemia, B lymphocyte lineage lymphoma, Multiple Myeloma, and plasma cell disorders, e.g., amyloidosis and Waldenstrom's macroglobulinemia. In some embodiments, the condition is CLL. In some embodiments, the CLL is defined by a monoclonal B cell population that co-expresses CD5 with CD19 and CD23 or CD5 with CD20 and CD23 and by surface immunoglobulin expression.

In some embodiments, the tonic signaling status of a cell is correlated with a clinical outcome such as prognosis or diagnosis of the condition. In some embodiments, the clinical outcome is the staging or grading of a neoplastic or hematopoietic condition, such as aggressive, indolent, benign, refractory, Roman Numeral staging, TNM Staging, Rai staging, Binet staging, WHO classification, FAB classification, IPSS score, WPSS score, limited stage, extensive stage, staging according to molecular markers such as ZAP70, the mutational status of the heavy chain of the B-cell receptor (IgVH) and CD38, occult, including information that may inform on time to progression, progression free survival, overall survival, or event-free survival.

In some embodiments, the correlation is determining the individual's response to a treatment, e.g., normal responder, hyper responder, poor responder, having emerging resistance, non-compliant, and adverse reaction.

In some embodiments, the correlation includes classifying the cell as minimal residual disease or emerging resistance. The correlation may further include determining a method of treatment, such as chemotherapy, biological therapy, radiation therapy, bone marrow transplantation, Peripheral stem cell transplantation, umbilical cord blood transplantation, autologous stem cell transplantation, allogeneic stem cell transplantation, syngeneic stem cell transplantation, surgery, induction therapy, maintenance therapy, or watchful waiting.

In some embodiments of this aspect, the invention provides a method of correlating an activation level of a B-lymphocyte lineage derived cell with a neoplastic or hematopoietic condition in an individual by subjecting the B-lymphocyte lineage derived cell from the individual to a modulator; determining the activation levels of a plurality of activatable elements that participate in a tonic signaling pathway in the B-lymphocyte lineage derived cell; and identifying a pattern of the activation levels of the plurality of activatable elements in the tonic signaling pathway in the cell that correlates with a clinical outcome, such as the prediction of outcome for a particular treatment, a prognosis or diagnosis of a cetain condition (e.g. a neoplastic condition). In some embodiments, the B-lymphocyte lineage progenitor or derived cell is selected from the group consisting of early pro-B cell, late pro-B cell, large pre-B cell, small pre-B cell, immature B cell, mature B cell, plasma cell and memory B cell, a CD5+B cell, a CD38+B cell, a B cell bearing a mutatated or non mutated heavy chain of the B cell receptor and a B cell expressing Zap70. In some embodiments, the correlation is determining a clinical outcome, such as prognosis or diagnosis of the condition.

In some embodiments of the methods of the invention, the modulator to which the cell is subjected is an activator or an inhibitor. In some embodiments, the modulator is, e.g., a growth factor, cytokine, adhesion molecule modulator, hormone, small molecule, polynucleotide, antibodies, natural compounds, lactones, chemotherapeutic agents, immune modulator, carbohydrate, proteases, ions, reactive oxygen species, or radiation. In some embodiments, the modulator is a B cell receptor modulator, e.g., a B cell receptor activator such as a cross-linker of the B cell receptor complex or the B-cell co-receptor complex. In some embodiments, the cross-linker is an antibody, or molecular binding entity. In some embodiments, the cross-linker is an antibody, such as a multivalent antibody. In some embodiments, the antibody is a monovalent, bivalent, or multivalent antibody made more multivalent by attachment to a solid surface or tethered on a nanoparticle surface to increase the local valency of the epitope binding domain. In some embodiments, the cross-linker is a molecular binding entity, such as an entity that acts upon or binds the B cell receptor complex via carbohydrates or an epitope in the complex. In some embodiments, the molecular binding entity is a monovalent, bivalent, or multivalent binding entity that is made more multivalent by attachment to a solid surface or tethered on a nanoparticle surface to increase the local valency of the epitope binding domain. In some embodiments where the modulator is a B cell receptor modulator, e.g., a B cell receptor activator such as a cross-linker of the B cell receptor complex or the B-cell co-receptor complex, cross-linking includes binding of an antibody or molecular binding entity to the cell and then causing its crosslinking via interaction of the cell with a solid surface that causes crosslinking of the BCR complex via antibody or molecular binding entity. In some embodiments, the crosslinker is selected from the group consisting of F(ab)2 IgM, IgG, IgD, polyclonal BCR antibodies, monoclonal BCR antibodies, Fc receptor derived binding elements and/or a combination thereof. The Ig may be derived from a species selected from the group consisting of mouse, goat, rabbit, pig, rat, horse, cow, shark, chicken, or llama. In some embodiments, the crosslinker is F(ab)2 IgM, Polyclonal IgM antibodies, Monoclonal IgM antibodies, Biotinylated F(ab)2 IgCM, Biotinylated Polyclonal IgM antibodies, Biotinylated Monoclonal IgM antibodies and/or a combination thereof.

In some embodiments of the methods of the invention, the modulator to which the cell is subjected is an inhibitor of a cellular factor or a plurality of factors that participates in a signaling cascade in the cell. In some embodiments, the inhibitor is a kinase or phosphatase inhibitor, such as adaphostin, AG 490, AG 825, AG 957, AG 1024, aloisine, aloisine A, alsterpaullone, aminogenistein, API-2, apigenin, arctigenin, AY-22989, BAY 61-3606, bisindolylmaleimide IX, chelerythrine, 10-[4'-(N,N-Diethylamino)butyl]-2-chlorophenoxazine hydrochloride, dasatinib, 2-Dimethylamino-4,5,6,7-tetrabromo-1H-benzimidazole, 5,7-Dimethoxy-3-(4-pyridinyl)quinoline dihydrochloride, edelfosine, ellagic acid, enzastaurin, ER 27319 maleate, erlotinib, ET18OCH3, fasudil, flavopiridol, gefitinib, GW 5074, H-7, H-8, H-89, HA-100, HA-1004, HA-1077, HA-1100, hydroxyfasudil, indirubin-3'-oxime, 5-Iodotubercidin, kenpaullone, KN-62, KY12420, LFM-A13, lavendustin A, luteolin, LY-294002, LY294002, mallotoxin, ML-9, NSC-154020, NSC-226080, NSC-231634, NSC-664704, NSC-680410, NU6102, olomoucine, oxindole I, PD-153035, PD-98059, PD-169316, phloretin, phloridzin, piceatannol, picropodophyllin, PK1, PP1, PP2, purvalanol A, quercetin, R406, R788, rapamune, rapamycin, Ro 31-8220, roscovitine, rottlerin, SB202190, SB203580, sirolimus, sorafenib, SL327, SP600125, staurosporine, STI-571, SU-11274, SU1498, SU4312, SU6656, 4,5,6,7-Tetrabromotriazole, TG101348, Triciribine, Tyrphostin AG 490, Tyrphostin AG 825, Tyrphostin AG 957, Tyrphostin AG 1024, Tyrphostin SU1498, U0126, VX-509, VX-667, VX-680, W-7, wortmannin, XL-019, XL-147, XL-184, XL-228, XL-281, XL-518, XL-647, XL-765, XL-820, XL-844, XL-880, Y-27632, ZD-1839, ZM-252868, ZM-447439, $H_2O_2$, siRNA, miRNA, Cantharidin, (−)-p-Bromotetramisole, Microcystin LR, Sodium Orthovanadate, Sodium Pervanadate, Vanadyl sulfate, Sodium oxodiperoxo (1,10-phenanthroline)vanadate, bis(maltolato)oxovanadium (IV), Sodium Molybdate, Sodium Perm olybdate, Sodium Tartrate, Imidazole, Sodium Fluoride, β-Glycerophosphate, Sodium Pyrophosphate Decahydrate, Calyculin A, Discodermia calyx, bpV(phen), mpV(pic), DMHV, Cypermethrin, Dephostatin, Okadaic Acid, NIPP-1, N-(9,10-Dioxo-9,10-dihydro-phenanthren-2-yl)-2,2-dimethyl-propionamide, α-Bromo-4-hydroxyacetophenone, 4-Hydroxyphenacyl Br, α-Bromo-4-methoxyacetophenone, 4-Methoxyphenacyl Br, α-Bromo-4-(carboxymethoxy)acetophenone, 4-(Carboxymethoxy)phenacyl Br, and bis(4-Trifluoromethylsulfonamidophenyl)-1,4-diisopropylbenzene, phenyarsine oxide, Pyrrolidine Dithiocarbamate, or Aluminum fluoride. In some embodiments the phosphatase inhibitor is $H_2O_2$.

In some embodiments of the methods of the invention, the cell is further subjected to a second modulator, e.g., the cell may be subjected to a B cell receptor activator and a phosphatase inhibitor, such as $F(ab)_2$IgM or biotinylated $F(ab)_2$IgM and a phosphatase inhibitor (e.g. $H_2O_2$).

In some embodiments of the invention, the activation level of the plurality of activatable elements in the cell is selected from the group consisting of cleavage by extracellular or intracellular protease exposure, novel hetero-oligomer formation, glycosylation level, phosphorylation level, acetylation level, methylation level, biotinylation level, glutamylation level, glycylation level, hydroxylation level, isomerization level, prenylation level, myristoylation level, lipoylation level, phosphopantetheinylation level, sulfation level, ISGylation level, nitrosylation level, palmitoylation level, SUMOylation level, ubiquitination level, neddylation level, citrullination level, deamidation level, disulfide bond formation level, proteolytic cleavage level, translocation level, changes in protein turnover, multi-protein complex level, oxidation level, multi-lipid complex, and biochemical changes in cell membrane. In some embodiments, the activation level is a phosphorylation level. In some embodiments, the activatable element is selected from the group consisting of proteins, carbohydrates, lipids, nucleic acids and metabolites. In some embodiments, the activatable element is a protein. In some embodiments, the activatable element is a change in metabolic state, temperature, or local ion concentration. In embodiments where the activatable element is a protein, in some embodiments the protein is a protein subject to phosphorylation or dephosphorylation, such as kinases, phosphatases, adaptor/scaffold proteins, ubiquitination enzymes, adhesion molecules, contractile proteins, cytoskeletal proteins, heterotrimeric G proteins, small molecular weight GTPases, guanine nucleotide exchange factors, GTPase activating proteins, caspases and proteins involved in apoptosis (e.g. PARP), ion channels, molecular transporters, molecular chaperones, metabolic enzymes, vesicular transport proteins, hydroxylases, isomerases, transferases, deacetylases, methylases, demethylases, proteases, esterases, hydrolases, DNA binding proteins or transcription factors. In some embodiments, the protein is selected from the group consisting of PI3-Kinase (p85, p110a, p110b, p110d), Jak1, Jak2, SOCs, Rac, Rho, Cdc42, Ras-GAP, Vav, Tiam, Sos, Dbl, Nck, Gab, PRK, SHPT, and SHP2, SHIP1, SHIP2, sSHIP, PTEN, Shc, Grb2, PDK1, SGK, Akt1, Akt2, Akt3, TSC1,2, Rheb, mTor, 4EBP-1, p70S6Kinase, S6, LKB-1, AMPK, PFK, Acetyl-CoAa Carboxylase, DokS, Rafs, Mos, Tpl2, MEK1/2, MLK3, TAK, DLK, MKK3/6, MEKK1,4, MLK3, ASK1, MKK4/7, SAPK/JNK1,2,3, p38s, Erk1/2, Syk, Btk, BLNK, LAT, ZAP70, Lck, Cbl, SLP-76, PLCγ$_1$, PLCγ$_2$, STAT1, STAT 3, STAT 4, STAT 5, STAT 6, FAK, p130CAS, PAKs, LIMK1/2, Hsp90, Hsp70, Hsp27, SMADs, Rel-A (p65-NFKB), CREB, Histone H2B, HATs, HDACs, PKR, Rb, Cyclin D, Cyclin E, Cyclin A, Cyclin B, P16, p14Arf, p27KIP, p21CIP, Cdk4, Cdk6, Cdk7, Cdk1, Cdk2, Cdk9, Cdc25,A/B/C, Abl, E2F, FADD, TRADD, TRAF2, RIP, Myd88, BAD, Bcl-2, Mcl-1, Bcl-XL, Caspase 2, Caspase 3, Caspase 6, Caspase 7, Caspase 8, Caspase 9, PARP, IAPB, Smac, Fodrin, Actin, Src, Lyn, Fyn, Lck, NIK, IκB, p65 (RelA), IKKα, PKA, PKCα, PKCβ, PKCθ, PKCδ, CAMK, Elk, AFT, Myc, Egr-1, NFAT, ATF-2, Mdm2, p53, DNA-PK, Chk1, Chk2, ATM, ATR, β-catenin, CrkL, GSK3α, GSK3β, and FOXO. In some embodiments, the protein selected from the group consisting of Erk, Syk, Zap70, Lck, Btk, BLNK, Cbl, PLCγ$_2$, Akt, RelA, p38, S6. In some embodiments the protein is S6.

In some embodiments, the protein is selected from the group consisting of HER receptors, PDGF receptors, Kit receptor, FGF receptors, Eph receptors, Trk receptors, IGF receptors, Insulin receptor, Met receptor, Ret, VEGF receptors, TIE1, TIE2, FAK, Jak1, Jak2, Jak3, Tyk2, Src, Lyn, Fyn, Lck, Fgr, Yes, Csk, Abl, Btk, ZAP70, Syk, IRAKs, cRaf, ARaf, BRAF, Mos, Lim kinase, ILK, Tpl, ALK, TGFβ receptors, BMP receptors, MEKKs, ASK, MLKs, DLK, PAKs, Mek 1, Mek 2, MKK3/6, MKK4/7, ASK1, Cot, NIK, Bub, Myt 1, Wee1, Casein kinases, PDK1, SGK1, SGK2, SGK3, Akt1, Akt2, Akt3, p90Rsks, p70S6Kinase, Prks, PKCs, PKAs, ROCK 1, ROCK 2, Auroras, CaMKs, MNKs, AMPKs, MELK, MARKs, Chk1, Chk2, LKB-1, MAPKAPKs, Pim 1, Pim2, Pim3, IKKs, Cdks, Jnks, Erks, IKKs, GSK3α, GSK3β, Cdks, CLKs, PKR, PI3-Kinase class 1, class 2, class 3, mTor, SAPK/JNK1,2,3, p38s, PKR, DNA-PK, ATM, ATR, Receptor protein tyrosine phosphatases (RPTPs), LAR phosphatase, CD45, Non receptor tyrosine phosphatases (NPRTPs), SHPs, MAP kinase phosphatases (MKPs), Dual Specificity phosphatases (DUSPs), CDC25 phosphatases, Low molecular weight tyrosine phosphatase, Eyes absent (EYA) tyrosine phosphatases, Slingshot phosphatases (SSH), serine phosphatases, PP2A, PP2B, PP2C, PP1, PP5, inositol phosphatases, PTEN, SHIPs, myotubularins, phosphoinositide kinases, phospholipases, prostaglandin synthases, 5-lipoxygenase, sphingosine kinases, sphingomyelinases, adaptor/scaffold proteins, Shc, Grb2, BLNK, LAT, B cell adaptor for PI3-kinase (BCAP), SLAP, Dok, KSR, MyD88, Crk, CrkL, GAD, Nck, Grb2 associated binder (GAB), Fas associated death domain (FADD), TRADD, TRAF2, RIP, T-Cell leukemia family, IL-2, IL-4, IL-8, IL-6, interferon γ, interferon α, suppressors of cytokine signaling (SOCs), Cbl, SCF ubiquitination ligase complex, APC/C, adhesion molecules, integrins, Immunoglobulin-like adhesion molecules, selectins, cadherins, catenins, focal adhesion kinase, p130CAS, fodrin, actin, paxillin, myosin, myosin binding proteins, tubulin, eg5/KSP, CENPs, β-adrenergic receptors, muscarinic receptors, adenylyl cyclase receptors, small molecular weight GTPases, H-Ras, K-Ras, N-Ras, Ran, Rac, Rho, Cdc42, Arfs, RABs, RHEB, Vav, Tiam, Sos, Dbl, PRK, TSC1,2, Ras-GAP, Arf-GAPs, Rho-GAPs, caspases, Caspase 2, Caspase 3, Caspase 6, Caspase 7, Caspase 8, Caspase 9, PARP, Bcl-2, Mcl-1, Bcl-XL, Bcl-w, Bcl-B, A1, Bax, Bak, Bok, Bik, Bad, Bid, Bim, Bmf, Hrk, Noxa, Puma, IAPB, XIAP, Smac, Cdk4, Cdk 6, Cdk 2, Cdk1, Cdk 7, Cyclin D, Cyclin E, Cyclin A, Cyclin B, Rb, p16, p14Arf, p27KIP, p21CIP, molecular chaperones, Hsp90s, Hsp70, Hsp27, metabolic enzymes, Acetyl-CoAa Carboxylase, ATP citrate lyase, nitric oxide synthase, caveolins, endosomal sorting complex required for transport (ESCRT) proteins, vesicular protein sorting (Vsps), hydroxylases, prolyl-hydroxylases PHD-1, 2 and 3, asparagine hydroxylase FIH transferases, Pin1 prolyl isomerase, topoisomerases, deacetylases, Histone deacetylases, sirtuins, histone acetylases, CBP/P300 family, MYST family, ATF2, DNA methyl transferases, Histone H3K4 demethylases, H3K27, JHDM2A, UTX, VHL, WT-1, p53, Hdm, PTEN, ubiquitin proteases, urokinase-type plasminogen activator (uPA) and uPA receptor (uPAR) system, cathepsins, metalloproteinases, esterases, hydrolases, separase, potassium channels, sodium channels, multi-drug resistance proteins, P-Gycoprotein, nucleoside transporters, Ets, Elk, SMADs, Rel-A (p65-NFKB), CREB, NFAT, ATF-2, AFT, Myc, Fos, Sp1, Egr-1, T-bet, β-catenin, HIFs, FOXOs, E2Fs, SRFs, TCFs, Egr-1, β-catenin, FOXO STAT1, STAT 3, STAT 4, STAT 5, STAT 6, p53, WT-1, HMGA, pS6, 4EPB-1, eIF4E-binding protein, RNA polymerase, initiation factors, elongation factors.

In addition to determining the activation level of an activatable protein, in some embodiments the methods for classifying a cell further comprise determining the level of an additional intracellular marker and/or a cell surface marker. In some embodiments the methods for classifying a cell comprise determining the level of an additional intracellular marker. In some embodiments the intracelluar marker is a captured intracellular cytokine. In some embodiments the methods for classifying a cell comprise determining the level of an additional cell surface marker. In some embodiments the cell surface marker is a cell surface ligand or receptor. In some embodiments the cell surface marker is a component of a B-cell receptor. In some embodiments the cell surface marker is CD45, CD5, CD19, CD20, CD22, CD23, CD27, CD37, CD40, CD52, CD79, CD38, CD96, major histocompatability antigen (MHC) Class1 or MHC Class 2.

In some embodiments the methods of the invention for prognosis, diagnosis, or determination of treatment further comprise determining the level of an additional serum marker. In some embodiments the serum marker comprises a protein. In some embodiments the serum marker is a cytokine, growth factor, chemokine, soluble receptor, small compound, or phamaceutical drug. In some embodiments the serum marker comprises a component or product of a pathogen or parasite. In some embodiment the serum marker is selected from a group consisting of beta-2-microglobulin, calcitonin, thymidine kinase and ferritin.

In some embodiments, the invention provides a method of correlating an activation level of B-lymphocyte lineage derived cells with a neoplastic or hematopoietic condition in an individual by subjecting the B-lymphocyte lineage derived cell from the individual to a modulator; determining the activation levels of a plurality of activatable elements in the B-lymphocyte lineage derived cell; and identifying a pattern of the activation levels of the plurality of activatable elements in the cell that correlates with the neoplastic condition. In some embodiments, the activatable element is selected from the group consisting of elements selected from the group consisting of Erk, Syk, Zap70, Lck, Btk, BLNK, Cbl, PLCγ$_2$, Akt, RelA, p38, S6. In some embodiments, the activatable element is selected from the group consisting of Cbl, PLCγ$_2$, and S6. In some embodiments, the activatable element is S6. In some embodiments, the B-lymphocyte lineage progenitor or derived cell is selected from the group consisting of early pro-B cell, late pro-B cell, large pre-B cell, small pre-B cell, immature B cell, mature B cell, plasma cell and memory B cell, a CD5+ B cell, a CD38+ B cell, a B cell bearing a mutatated or non mutated heavy chain of the B cell receptor, or a B cell expressing Zap70. In some embodiments, the invention provides methods for correlating and/or classifying an activation state of a CLL cell with a clinical outcome in an individual by subjecting the CLL cell from the individual to a modulator, where the CLL cell expresses a B-Cell receptor (BCR), determining the activation levels of a plurality of activatable elements, and identifying a pattern of the activation levels of the plurality of activatable elements to determine the presence or absence of an alteration in signaling proximal to the BCR, wherein the presence of the alteration is indicative of a clinical outcome.

In some embodiments the method comprises identifying a pattern of said activation levels of said pluralilty of activatable elements in said cell, wherein said pattern is correlated to a disease or condition.

In some embodiments, the correlation is determining a clinical outcome, such as prognosis or determination of treatment of the condition. In some embodiments, the neoplastic or hematopoietic condition is selected from the group consisting of Non-Hodgkin Lymphoma, Hodgkin or other lymphomas, acute or chronic leukemias, polycythemias, thrombocythemias, multiple myeloma and plasma cell disorders, such as amyloidosis and Waldenstrom's macroglobulinemia, myelodysplastic disorders, myeloproliferative disorders, myelofibrosis, or atypical immune lymphoproliferations. In some embodiments, the neoplastic or hematopoietic condition is non-B lineage derived, such as acute myeloid leukemia (AML), Chronic Myeloid Leukemia (CML), non-B cell acute lymphocytic leukemia (ALL), non-B cell lymphomas, myelodysplastic disorders, myeloproliferative disorders, myelofibrosis, polycythemias, thrombocythemias, and non-B atypical immune lymphoproliferations. In some embodiments, the neoplastic or hematopoietic condition is a B-Cell or B cell lineage derived disorder, such as B-Cell or B cell lineage derived disorder is selected from the group consisting of Chronic Lymphocytic Leukemia (CLL), B lymphocyte lineage leukemia, B lymphocyte lineage lymphoma, Multiple Myeloma, or plasma cell disorders, e.g., amyloidosis and Waldenstrom's macroglobulinemias. In some embodiments, the condition is CLL. In some embodiments the CLL is defined by a monoclonal B cell population that co-expresses CD5 with CD19 and CD23 or CD5 with CD20 and CD23 and dim surface immunoglobulin expression.

In some embodiments, the clinical outcome is the staging or grading of a neoplastic or hematopoietic condition, such as aggressive, indolent, benign, refractory, Roman Numeral staging, TNM Staging, Rai staging, Binet staging, WHO classification, FAB classification, IPSS score, WPSS score, limited stage, extensive stage, staging according to cellular markers such as ZAP70, IgV$_H$ mutational status and CD38, occult, including information that may inform on time to progression, progression free survival, overall survival, or event-free survival.

In some embodiments, the correlation is determining the individual's response to a specific treatment, e.g., normal responder, hyper responder, poor responder, having emerging resistance, non-compliant, and adverse reaction.

In some embodiments, the correlation includes classifying the cell as minimal residual disease or emerging resistance. The correlation may further include determining a method of treatment, such as chemotherapy, biological therapy, targeted therapy, radiation therapy, bone marrow transplantation, Peripheral stem cell transplantation, umbilical cord blood transplantation, autologous stem cell transplantation, allogeneic stem cell transplantation, syngeneic stem cell transplantation, surgery, induction therapy, maintenance therapy, or watchful waiting. In additional embodiments the correlation may further include determination of the appropriate dosage or timing of a given treatment.

In some embodiments of the methods of the invention, the modulator to which the cell is subjected is an activator or an inhibitor. In some embodiments, the modulator is, e.g., a growth factor, cytokine, adhesion molecule modulator, hormone, small molecule, polynucleotide, antibodies, natural compounds, lactones, chemotherapeutic agents, immune modulator, carbohydrate, proteases, ions, reactive oxygen species, or radiation. In some embodiments the modulator is an antibody e.g. anti-CD20 (Rituxan), anti-CD22 (epratuzumab), anti-CD23 (lumiliximab) or anti-CD52 (Alemtuzumab), that recognize antigens on the cell surface. In some embodiments, the modulator is a B cell receptor complex modulator, e.g., anti-CD20, which recognizes a component of the B cell receptor co-complex, or a B cell receptor activator such as a cross-linker of the B cell receptor complex or the B-cell co-receptor complex. In some embodiments, the cross-linker is an antibody, or molecular binding entity. In some embodiments, the cross-linker is an antibody, such as a multivalent antibody. In some embodiments, the antibody is a monovalent, bivalent, or multivalent antibody made more multivalent by attachment to a solid surface or tethered on a nanoparticle surface to increase the local valency of the epitope binding domain. In some embodiments, the cross-linker is a molecular binding entity, such as an entity that acts upon or binds the B cell receptor complex via carbohydrates or an epitope in the complex. In some embodiments, the molecular binding entity is a monovalent, bivalent, or multivalent binding entity that is made more multivalent by attachment to a solid surface or tethered on a nanoparticle surface to increase the local valency of the epitope binding domain. In some embodiments where the modulator is a B cell receptor modulator, e.g., a B cell receptor activator such as a cross-linker of the B cell receptor complex or the B-cell co-receptor complex, cross-linking includes binding of an antibody or molecular binding entity to the cell and then causing its crosslinking via interaction of the cell with a solid surface that causes crosslinking of the BCR complex via antibody or molecular binding entity. In some embodiments, the crosslinker is selected from the group consisting of F(ab)2 IgM, IgG, IgD, polyclonal BCR antibodies, monoclonal BCR antibodies, Fc receptor derived binding elements and/or a combination thereof. The Ig may be derived from a species selected from the group consisting of mouse, goat, rabbit, pig, rat, horse, cow, shark, chicken, or llama. In some embodiments, the crosslinker is F(ab)2 IgM, Polyclonal IgM antibodies, Monoclonal IgM antibodies, Biotinylated F(ab)2 IgCM, Biotinylated Polyclonal IgM antibodies, Biotinylated Monoclonal IgM antibodies and/or a combination thereof.

In some embodiments of the methods of the invention, the modulator to which the cell is subjected is an inhibitor of a cellular factor or a plurality of factors that participates in a signaling cascade in the cell. In some embodiments, the inhibitor is a kinase or phosphatase inhibitor, such as adaphostin, AG 490, AG 825, AG 957, AG 1024, aloisine, aloisine A, alsterpaullone, aminogenistein, API-2, apigenin, arctigenin, AY-22989, BAY 61-3606, bisindolylmaleimide IX, chelerythrine, 10-[4'-(N,N-Diethylamino)butyl]-2-chlorophenoxazine hydrochloride, dasatinib, 2-Dimethylamino-4,5,6,7-tetrabromo-1H-benzimidazole, 5,7-Dimethoxy-3-(4-pyridinyl)quinoline dihydrochloride, edelfosine, ellagic acid, enzastaurin, ER 27319 maleate, erlotinib, ET18OCH3, fasudil, flavopiridol, gefitinib, GW 5074, H-7, H-8, H-89, HA-100, HA-1004, HA-1077, HA-1100, hydroxyfasudil, indirubin-3'-oxime, 5-Iodotubercidin, kenpaullone, KN-62, KY12420, LFM-A13, lavendustin A, luteolin, LY-294002, LY294002, mallotoxin, ML-9, NSC-154020, NSC-226080, NSC-231634, NSC-664704, NSC-680410, NU6102, olomoucine, oxindole I, PD-153035, PD-98059, PD-169316, phloretin, phloridzin, piceatannol, picropodophyllin, PK1, PP1, PP2, purvalanol A, quercetin, R406, R788, rapamune, rapamycin, Ro 31-8220, roscovitine, rottlerin, SB202190, SB203580, sirolimus, sorafenib, SL327, SP600125, staurosporine, STI-571, SU-11274, SU1498, SU4312, SU6656, 4,5,6,7-Tetrabromotriazole, TG101348, Triciribine, Tyrphostin AG 490, Tyrphostin AG 825, Tyrphostin AG 957, Tyrphostin AG 1024, Tyrphostin SU1498, U0126, VX-509, VX-667, VX-680, W-7, wortmannin, XL-019, XL-147, XL-184, XL-228, XL-281, XL-518, XL-647, XL-765, XL-820, XL-844, XL-880, Y-27632, ZD-1839, ZM-252868, ZM-447439, $H_2O_2$, siRNA, miRNA, Cantharidin, (−)-p-Bromotetramisole, Microcystin LR, Sodium Orthovanadate, Sodium Pervanadate, Vanadyl sulfate, Sodium oxodiperoxo (1,10-phenanthroline)vanadate, bis(maltolato)oxovanadium (IV), Sodium Molybdate, Sodium Perm olybdate, Sodium Tartrate, Imidazole, Sodium Fluoride, β-Glycerophosphate, Sodium Pyrophosphate Decahydrate, Calyculin A, Discodermia calyx, bpV(phen), mpV(pic), DMHV, Cypermethrin, Dephostatin, Okadaic Acid, NIPP-1, N-(9,10-Dioxo-9,10-dihydro-phenanthren-2-yl)-2,2-dimethyl-propionamide, α-Bromo-4-hydroxyacetophenone, 4-Hydroxyphenacyl Br, α-Bromo-4-methoxyacetophenone, 4-Methoxyphenacyl Br, α-Bromo-4-(carboxymethoxy)acetophenone, 4-(Carboxymethoxy)phenacyl Br, and bis(4-Trifluoromethylsulfonamidophenyl)-1,4-diisopropylbenzene, phenyarsine oxide, Pyrrolidine Dithiocarbamate, or Aluminum fluoride. In some embodiments the phosphatase inhibitor is $H_2O_2$.

In some embodiments of the methods of the invention, the cell is further subjected to a second modulator, e.g., the cell may be subjected to a B cell receptor activator and a kinase inhibitor or a phosphatase inhibitor, such as F(ab)$_2$IgM or biotinylated F(ab)$_2$IgM and $H_2O_2$.

In some embodiments of the invention, the activation level of the activatable element in the cell is selected from the group consisting of cleavage by extracellular or intracellular protease exposure, novel hetero-oligomer formation, glycosylation level, phosphorylation level, acetylation level, methylation level, biotinylation level, glutamylation level, glycylation level, hydroxylation level, isomerization level, prenylation level, myristoylation level, lipoylation level, phosphopantetheinylation level, sulfation level, ISGylation level, nitrosylation level, palmitoylation level, SUMOylation level, ubiquitination level, neddylation level, citrullination level, deamidation level, disulfide bond formation level, proteolytic cleavage level, translocation level, changes in protein turnover, multi-protein complex level, oxidation level, multi-lipid complex, and biochemical changes in cell membrane. In some embodiments, the activation level is a phosphorylation level. In some embodiments, the activatable element is selected from the group consisting of proteins, carbohydrates, lipids, nucleic acids and metabolites. In some embodiments, the activatable element is a protein. In some embodiments, the activatable element is a change in metabolic state, temperature, or local ion concentration. In embodiments where the activatable element is a protein, in some embodiments the protein is a protein subject to phosphorylation or dephosphorylation, such as kinases, phosphatases, adaptor/scaffold proteins, ubiquitination enzymes, adhesion molecules, contractile proteins, cytoskeletal proteins, heterotrimeric G proteins, small molecular weight GTPases, guanine nucleotide exchange factors, GTPase activating proteins, caspases and proteins involved in apoptosis (e.g. PARP), ion channels, molecular transporters, molecular chaperones, metabolic enzymes, vesicular transport proteins, hydroxylases, isomerases, transferases, deacetylases, methylases, demethylases, proteases, esterases, hydrolases, DNA binding proteins or transcription factors.

In another aspect, the invention provides for methods for determining a phenotypic profile of a population of cells by exposing the population of cells to a plurality of modulators in separate cultures, where at least one of the modulators is an inhibitor, determining the presence or absence of an increase in activation level of an activatable element in the cell population from each of the separate culture and classifying the cell population based on the presence or absence of the increase in the activation of the activatable element from each of the separate culture. In some embodiments, the inhibitor is an inhibitor of a cellular factor or a plurality of factors that participates in a signaling cascade in the cell. In some embodiments, the inhibitor is a phosphatase or kinase inhibitor. Examples of kinase inhibitors include adaphostin, AG 490, AG 825, AG 957, AG 1024, aloisine, aloisine A, alsterpaullone, aminogenistein, API-2, apigenin, arctigenin, AY-22989, BAY 61-3606, bisindolylmaleimide IX, chelerythrine, 10-[4'-(N,N-Diethylamino)butyl]-2-chlorophenoxazine hydrochloride, dasatinib, 2-Dimethylamino-4,5,6, 7-tetrabromo-1H-benzimidazole, 5,7-Dimethoxy-3-(4-pyridinyl)quinoline dihydrochloride, edelfosine, ellagic acid, enzastaurin, ER 27319 maleate, erlotinib, ET18OCH3, fasudil, flavopiridol, gefitinib, GW 5074, H-7, H-8, H-89, HA-100, HA-1004, HA-1077, HA-1100, hydroxyfasudil, indirubin-3'-oxime, 5-Iodotubercidin, kenpaullone, KN-62, KY12420, LFM-A13, lavendustin A, luteolin, LY-294002, LY294002, mallotoxin, ML-9, NSC-154020, NSC-226080, NSC-231634, NSC-664704, NSC-680410, NU6102, olomoucine, oxindole I, PD-153035, PD-98059, PD 169316, phloretin, phloridzin, piceatannol, picropodophyllin, PK1, PP1, PP2, purvalanol A, quercetin, R406, R788, rapamune, rapamycin, Ro 31-8220, roscovitine, rottlerin, SB202190, SB203580, sirolimus, sorafenib, SL327, SP600125, staurosporine, STI-571, SU-11274, SU1498, SU4312, SU6656, 4,5,6,7-Tetrabromotriazole, TG101348, Triciribine, Tyrphostin AG 490, Tyrphostin AG 825, Tyrphostin AG 957, Tyrphostin AG 1024, Tyrphostin SU1498, U0126, VX-509, VX-667, VX-680, W-7, wortmannin, XL-019, XL-147, XL-184, XL-228, XL-281, XL-518, XL-647, XL-765, XL-820, XL-844, XL-880, Y-27632, ZD-1839, ZM-252868, ZM-447439, siRNA, miRNA Examples of phosphatase inhibitors include, but are not limited to $H_2O_2$, siRNA, miRNA, Cantharidin, (−)-p-Bromotetramisole, Microcystin LR, Sodium Orthovanadate, Sodium Pervanadate, Vanadyl sulfate, Sodium oxodiperoxo(1,10-phenanthroline)vanadate, bis(maltolato)oxovanadium(IV), Sodium Molybdate, Sodium Perm olybdate, Sodium Tartrate, Imidazole, Sodium Fluoride, β-Glycerophosphate, Sodium Pyrophosphate Decahydrate, Calyculin A, Discodermia calyx, bpV(phen), mpV(pic), DMHV, Cypermethrin, Dephostatin, Okadaic Acid, NIPP-1, N-(9,10-Dioxo-9,10-dihydro-phenanthren-2-yl)-2,2-dimethyl-propionamide, α-Bromo-4-hydroxyacetophenone, 4-Hydroxyphenacyl Br, α-Bromo-4-methoxyacetophenone, 4-Methoxyphenacyl Br, α-Bromo-4-(carboxymethoxy)acetophenone, 4-(Carboxymethoxy)phenacyl Br, and bis(4-Trifluoromethylsulfonamidophenyl)-1,4-diisopropylbenzene, phenyarsine oxide, Pyrrolidine Dithiocarbamate, and Aluminum fluoride. In some embodiments, the phosphatase inhibitor is $H_2O_2$.

In some embodiments, the modulator is an activator or an inhibitor. In some embodiments, the modulators are independently selected from the group consisting of growth factor, cytokine, adhesion molecule modulator, hormone, small molecule, polynucleotide, antibodies, natural compounds, lactones, chemotherapeutic agents, immune modulator, carbohydrate, proteases, ions, reactive oxygen species, and radiation. In some embodiments, at least one modulator is a B cell receptor modulator. In some embodiments, the B cell receptor modulator is a B cell receptor activator, such as Rituxan or a cross-linker of the B cell receptor complex or the B-cell co-receptor complex.

In some embodiments, the modulator is PMA, BAFF, April, SDF1a, SCF, CD40L, IGF-1, Imiquimod, polyCpG, fludarabine, cyclophosphamide, chlorambucil IL-7, IL-6, IL-10, IL-27, IL-4, IL-2, IL-3, thapsigargin and/or a combination thereof.

In some embodiments, the activatable element is a protein. In some embodiments, the protein is selected from the group consisting of Akt1, Akt2, Akt3, SAPK/JNK1,2,3, p38s, Erk1/2, Syk, ZAP70, Btk, BLNK, Lck, PLCγ, PLC1γ$_2$, STAT1, STAT 3, STAT 4, STAT 5, STAT 6, CREB, Lyn, p-S6, Cbl, NF-κB, GSK3β, CARMA/Bcl10 and Tcl-1.

In another aspect, the invention provides methods of classifying a cell population by contacting the cell population with at least one modulator, where the modulator is F(ab)2 IgM, Rituxan, Alemtuzumab, anti CD22 (epratuzumab), anti-CD23 (lumiliximab), Campath, $H_2O_2$, PMA, BAFF, April, SDF1a, CD40L, IGF-1, Imiquimod, polyCpG, fludarabine, cyclophosphamide, chlorambucil, IL-7, IL-6, IL-10, IL-27, IL-4, IL-2, IL-3, thapsigargin and/or a combination thereof, determining the presence or absence of an increase in activation level of an activatable element in the cell population, and classifying the cell population based on the presence or absence of the increase in the activation of the activatable element.

In some embodiments the cell population is a hematopoietic-derived cell population. In some embodiments, the hematopoietically derived cell population is selected from the group consisting of pluripotent hematopoietic stem cells, B-lymphocyte lineage progenitor or derived cells, T-lymphocyte lineage progenitor or derived cells, NK cell lineage progenitor or derived cells, granulocyte lineage progenitor or derived cells, monocyte lineage progenitor or derived cells, megakaryocyte lineage progenitor or derived cells and erythroid lineage progenitor or derived cells. In some embodiments, the hematopoietic derived cell population is a B-lymphocyte lineage progenitor and derived cell population, e.g., an early pro-B cell population, late pro-B cell population, large pre-B cell population, small pre-B cell population, immature B cell population, mature B cell population, plasma cell and memory B cell population, a CD5+ B cell population, a CD38+ B cell, a B cell bearing a mutatated or non mutated heavy chain of the B cell receptor, or a B cell population expressing Zap70.

In some embodiments, the classification includes classifying the cell population as a cell population that is correlated with a clinical outcome. In some embodiments, the clinical outcome is the predicted respose to a specific therapy, or the prognosis and/or diagnosis of a condition. In some embodiments, the clinical outcome is the presence or absence of a neoplastic or a hematopoietic condition, such as Non-Hodgkin Lymphoma, Hodgkin or other lymphomas, acute or chronic leukemias, polycythemias, thrombocythemias, multiple myeloma or plasma cell disorders, e.g., amyloidosis and Waldenstrom's macroglobulinemia, myelodysplastic disorders, myeloproliferative disorders, myelofibrosis, or atypical immune lymphoproliferations. In some embodiments, the neoplastic or hematopoietic condition is non-B lineage derived, such as acute myeloid leukemia (AML), Chronic Myeloid Leukemia (CML), non-B cell acute lymphocytic leukemia (ALL), non-B cell lymphomas, myelodysplastic disorders, myeloproliferative disorders, myelofibrosis, polycythemias, thrombocythemias, or non-B atypical immune lymphoproliferations. In some embodiments, the neoplastic or hematopoietic condition is a B-Cell or B cell lineage derived disorder, such as Chronic Lymphocytic Leukemia (CLL), B lymphocyte lineage leukemia, B lymphocyte lineage lymphoma, Multiple Myeloma, or plasma cell disorders, e.g., amyloidosis or Waldenstrom's macroglobulinemia. In some embodiments, the condition is CLL. In some embodiments, the CLL is defined by a monoclonal B cell population that co-expresses CD5 with CD19 and CD23 or CD5 with CD20 and CD23 and dim surface immunoglobulin expression.

In some embodiments, the clinical outcome is the staging or grading of a neoplastic or hematopoietic condition. Examples of staging in methods provided by the invention include aggressive, indolent, benign, refractory, Roman Numeral staging, TNM Staging, Rai staging, Binet staging, WHO classification, FAB classification, IPSS score, WPSS score, limited stage, extensive stage, staging according to cellular markers such as ZAP70, IgV$_H$ mutation status and CD38, occult, including information that may inform on time to progression, progression free survival, overall survival, or event-free survival.

In some embodiments of the methods of the invention, the classifying of the cell population based on activation level includes classifying the cell population as a cell population that is correlated to a patient response to a treatment, such as complete response, partial response, nodular partial response, no response, progressive disease, stable disease, relapse or adverse reaction. The method may further comprise determining a method of treatment, e.g., chemotherapy, biological therapy, targeted therapy, radiation therapy, bone marrow transplantation, Peripheral stem cell transplantation, umbilical cord blood transplantation, autologous stem cell transplantation, allogeneic stem cell transplantation, syngeneic stem cell transplantation, surgery, induction therapy, maintenance therapy, watchful waiting, or holistic/alternative therapy.

In some embodiments of the methods of the invention, the classifying of the cell population based on activation level includes classifying the cell population as a cell population that is correlated with minimal residual disease or emerging resistance.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

DETAILED DESCRIPTION OF THE INVENTION

Figure 1:
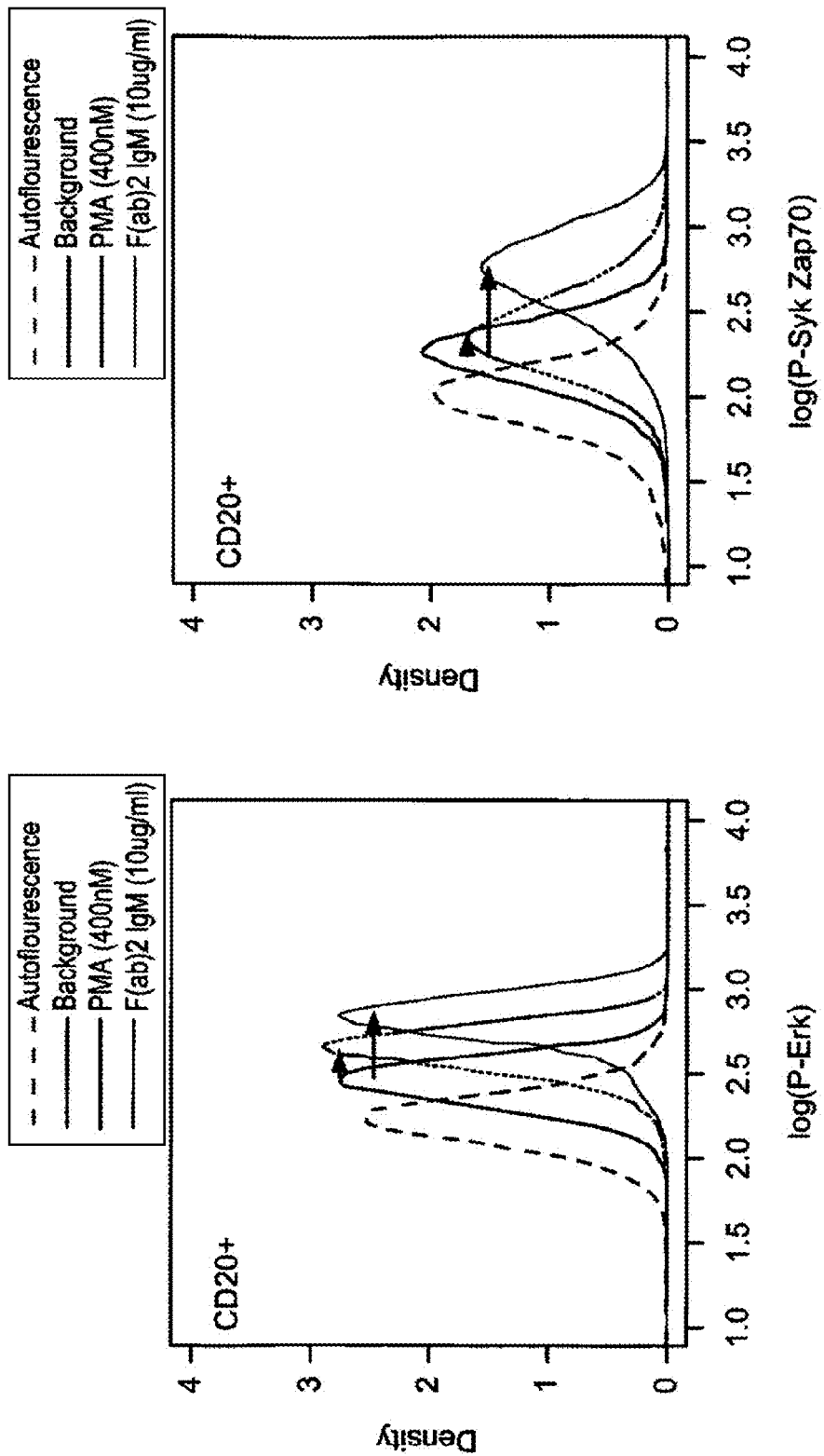
FIG. 1 depicts histograms showing the activation of p-Erk and p-Syk/pZap70 in Ramos cells following F(ab)$_2$IgM stimulation.

The present invention incorporates information disclosed in other applications and texts. The following patent and other publications are hereby incorporated by reference in their entireties: Haskell et al, Cancer Treatment, 5$^{th}$ Ed., W.B. Saunders and Co., 2001; Alberts et al., The Cell, 4$^{th}$ Ed., Garland Science, 2002; Vogelstein and Kinzler, The Genetic Basis of Human Cancer, 2d Ed., McGraw Hill, 2002; Michael, Biochemical Pathways, John Wiley and Sons, 1999; Weinberg, The Biology of Cancer, 2007; Immunobiology, Janeway et al. 7$^{th}$ Ed., Garland, and Leroith and Bondy, Growth Factors and Cytokines in Health and Disease, A Multi Volume Treatise, Volumes 1A and 1B, Growth Factors, 1996. Patents and applications that are also incorporated by reference include U.S. Pat. Nos. 7,381,535 and 7,393,656 and U.S. Ser. Nos. (USSN) 10/193,462; 11/655,785; 11/655,789; 11/655,821; 11/338,957, 61/048,886; 61/048,920; 61/048,657; 61/079,766; 61/155,362; 61/079,579; 61/079,537; 61/079,551; 61/087,555 and 61/085,789. Some commercial reagents, protocols, software and instruments that are useful in some embodiments of the present invention are available at the Becton Dickinson Website http://www.bdbiosciences.com/features/products/, and the Beckman Coulter website, http://www.beckmancoulter.com/Default.asp?bhfv=7. Relevant articles include High-content single-cell drug screening with phosphospecific flow cytometry, Krutzik et al., Nature Chemical Biology, 23 December (2007); Irish et al., FLt3 ligand Y591 duplication and Bcl-2 over expression are detected in acute myeloid leukemia cells with high levels of phosphorylated wild-type p53, Neoplasia, (2007), Irish et al. Mapping normal and cancer cell signaling networks: towards single-cell proteomics, Nature (2006) 6:146-155; and Irish et al., Single cell profiling of potentiated phospho-protein networks in cancer cells, Cell, (2004) 118, 1-20; Schulz, K. R., et al., Single-cell phospho-protein analysis by flow cytometry, Curr Protoc Immunol, (2007) 78:8 8.17.1-20; Krutzik, P. O., et al., Coordinate analysis of murine immune cell surface markers and intracellular phosphoproteins by flow cytometry, J. Immunol. (2005) 175(4):2357-65; Krutzik, P. O., et al., Characterization of the murine immunological signaling network with phosphospecific flow cytometry, J. Immunol. (2005) 175(4):2366-73; Shulz et al., Current Protocols in Immunology (2007) 78:8.17.1-20; Stelzer et al. Use of Multiparameter Flow Cytometry and Immunophenotyping for the Diagnosis and Classfication of Acute Myeloid Leukemia, Immunophenotyping, Wiley, 2000; and Krutzik, P. O. and Nolan, G. P., Intracellular phospho-protein staining techniques for flow cytometry: monitoring single cell signaling events, Cytometry A. (2003) 55(2):61-70; Hanahan D., Weinberg, The Hallmarks of Cancer, CELL (2000) 100:57-70; Krutzik et al, High content single cell drug screening with phophospospecific flow cytometry, Nat Chem. Biol. (2008) 4:132-42. Experimental and process protocols and other helpful information can be found at http:/proteomices.stanford.edu. The articles and other references cited below are also incorporated by reference in their entireties for all purposes.

Introduction

In some embodiments, this invention is directed to methods and compositions for diagnosis, prognosis and to methods of treatment. In some embodiments, the physiological status of cells present in a sample (e.g. clinical sample) is used, e.g., in diagnosis or prognosis of a condition, patient selection for therapy, to monitor treatment, modify therapeutic regimens, and to further optimize the selection of therapeutic agents; which may be administered as one or a combination of agents. Hence, therapeutic regimens can be individualized and tailored according to the data obtained prior to, and at different times over the course of treatment, thereby providing a regimen that is individually appropriate.

In some embodiments, the present invention is directed to methods for classifying a sample derived from an individual having or suspected of having a condition, e.g., a neoplastic or a hematopoietic condition. The invention allows for identification of prognostically and therapeutically relevant subgroups of conditions and prediction of the clinical course of an individual. The methods of the invention provide tools useful in the treatment of an individual afflicted with a condition, including but not limited to methods of choosing a therapy for an individual, methods of predicting response to a therapy for an individual, methods of determining the efficacy of a therapy in an individual, methods for assigning a risk group, methods of predicting an increased risk of relapse, methods of predicting an increased risk of developing secondary complications, and methods of determining the prognosis for an individual. The present invention provides methods that can serve as a prognostic indicator to predict the course of a condition, e.g. whether the course of a neoplastic or a hematopoietic condition in an individual will be aggressive or indolent, thereby aiding the clinician in managing the patient and evaluating the modality of treatment to be used.

In some embodiments, the invention is directed to methods for determining the activation level of one or more activatable elements in a cell upon treatment with one or more modulators. The activation of an activatable element in the cell upon treatment with one or more modulators can reveal operative pathways in a condition that can then be used, e.g., choose a therapy for an individual, predict response to a therapy for an individual, determine the efficacy of a therapy in an individual. In some embodiments the modulators may themselves be used directly within individuals as therapeutic agents. In some embodiments the activation of an activateable agent may be used as an indicator to predict course of the condition, identify risk group, predict an increased risk of developing secondary complications, and determine the prognosis for an individual.

In some embodiments, the invention is directed to methods for classifying a cell by contacting the cell with an inhibitor, determining the presence or absence of an increase in activation level of an activatable element in the cell, and classifying the cell based on the presence or absence of the increase in the activation of the activatable element. In some embodiments, the invention is directed to methods of determining the presence or absence of a condition in an individual by subjecting a cell from the individual to a modulator and an inhibitor, determining the activation level of an activatable element in the cell, and determining the presence or absence of the condition based on the activation level upon treatment with a modulator and an inhibitor.

In some embodiments, the invention is directed to methods for classifying a cell by contacting the cell with an inhibitor, determining the presence or absence of a change in activation level of an activatable element in the cell, and classifying the cell based on the presence or absence of the change in the activation of the activatable element. In some embodiments the change is an increase. In some embodiments the change is a decrease.

In some embodiments, the invention is directed to methods of determining tonic signaling status of a cell by subjecting the cell to a modulator, determining the activation level of an activatable element that participates in a tonic signaling pathway in the cell, and determining the status of a tonic signaling pathway in the cell from the activation level. Tonic signaling in a cell may have functional consequences, for instance, to maintain certain differentiated cellular properties or functions. In some embodiments of the invention, the status of a tonic signaling pathway is used to correlate the status to differences in populations.

In some embodiments, the invention is directed to methods of determining a phenotypic profile of a population of cells by exposing the population of cells in separate cultures to a plurality of modulators, wherein at least one of the modulators is an inhibitor, determining the presence or absence of an increase in activation level of an activatable element in the cell population from each of the separate culture and classifying the cell population based on the presence or absence of the increase in the activation of the activatable element from populations of cells in each separate culture.

In some embodiments, the invention is directed to methods of classifying a cell population by contacting the cell population with at least one modulator, where the modulator is F(ab)2 IgM, $H_2O_2$, PMA, BAFF, April, SDFla, CD40L, IGF-1, Imiquimod, polyCpG, IL-7, IL-6, IL-10, IL-27, IL-4, IL-2, IL-3, thapsigargin and/or a combination thereof, determining the presence or absence of an increase in activation level of an activatable element in the cell population, and classifying the cell population based on the presence or absence of the increase in the activation of the activatable element.

In some embodiments, the invention is directed to methods of correlating and/or classifying an activation state of a CLL cell with a clinical outcome in an individual by subjecting the CLL cell from the individual to a modulator, where the CLL cell expresses a B-Cell receptor (BCR), determining the activation levels of a plurality of activatable elements, and identifying a pattern of the activation levels of the plurality of activatable elements to determine the presence or absence of an alteration in signaling proximal to the BCR, where the presence of the alteration is indicative of a clinical outcome.

In some embodiments a method for classifying a cell comprises contacting the cell with an inhibitor, determining the presence or absence of a change in an activation level of at least one activatable element in said cell, and classifying said cell based on said presence or absence of said change in the activation level of said at least one activatable element. In some embodiments the change is an increase. In some embodiments the change is a decrease.

In some embodiments the method of classifying a cell further comprises determining the level of an intracellular marker, cell surface marker or any combination thereof. For example a cell may be classified by a change in activation level of an activatable element and also by the level of one or more cell surface markers. In addition a cell may be classified by a change in activation level of an activatable element and by the level of an intracellular marker. Combinations may also be used. Serum markers are also useful in methods of diagnosis, prognosis, determining treatments effects and/or choosing a treatment.

One or more cell surface markers may also be used in the method of the invention in addition to intracellular markers (e.g. phospho-proteins). In some embodiments, the method comprises determining the level of a plurality of cell surface markers. Cell surface markers may include any cell surface molecule that is detected by flow cytometry. In some embodiments the cell surface marker is a human leukocyte differentiation antigen. In some embodiments the human leukocyte differentiation antigen is selected from the list: CD1, CD2, CD3, CD4, CD5, CD8, CD10, CD14, CD19, CD20, CD22, CD23, CD40, CD52, CD100, CD280, CD281, CD282, CD283, CD284, and CD289. In some embodiments the human leukocyte differentiation antigen is selected from the list comprising CD1 though CD300. In some embodiments the cell surface marker is any cell surface receptor or ligand. Examples of cell surface ligands and receptors include, but are not limited to, members of the TNF superfamily, interleukins, hormones, neurotransmitters, interferons, growth factor, chemokines, integrins, toll receptor ligands, prostaglandins, or leukotriene families. Other examples of cell surface markers include, but are not limited to metalloproteases. In some embodiments the cell surface marker is membrane bound IgM. In some embodiments the cell surface marker is a B-cell receptor (BCR) or a component of a BCR. In some embodiments the marker is CD45, CD5, CD14, CD19, CD20, CD22, CD23, CD27, CD37, CD40, CD52, CD79, CD38, CD96, major histocompatability antigen (MHC) Class1 or MHC Class 2. In some embodiments the cell surface marker is membrane bound IgD. In some embodiments the cell surface marker is membrane bound IgG. In some embodiments, the method of classifying a cell comprises determining a level of at least one cell surface marker on said cell and an activation level of at least one activatable element on said cell. In some embodiments, the method of classifying a cell comprises determining the level of cell surface IgM on said cell. In some embodiments, the method comprises determining the level of cell surface IgD on said cell. In some embodiments, the method comprises determining the level of a BCR on said cell. In some embodiment the cell surface marker is associated with a diesease or conditions. In some embodiments the maker is CD38 or CD96. In some embodiments the marker is CD38 and the condition is leukemia. In some embodiments the marker is CD96 and the condition is leukemia.

One or more intracellular markers may be used in the method of the invention. The levels of these markers can be determined before they are secreted and are referred to as "captured". Examples of captured intracellular markers include, but are not limited to, TNF superfamily members, interleukins, hormones, neurotransmitters, interferons, growth factors, chemokines, integrins, prostaglandins, leukotrines and receptors for all of the above. Examples of intracellular markers also include, but are not limited to, metalloproteases. Examples of intracellular markers also include, but are not limited to, proteins involved in programmed cell death and proliferation. Examples of intracellular markers also include, but are not limited to viruses, pathogens, parasites and components or products thereof. In some embodiments, the method of classifying a cell further comprises determining the level of an intracellular pathogen or component of a pathogen. In some embodiments the intracellular pathogen is HIV. In some embodiments the intracellular pathogen is EBV. In some embodiments the intracellular component of a pathogen is a nucleic acid sequence derived from said pathogen. In some embodiments the intracellular component of a pathogen is a pathogen derived polypeptide.

The method of the invention may comprise determining the level of one or more serum markers. In some embodiments the serum marker is a marker of a condition. In some embodiments the serum marker is a marker of inflammation. In some embodiments the serum marker is a soluble cytokine, TNF superfamily member, interleukin, hormone, neurotransmitter, interferon, growth factor, chemokine, integrin, prostaglandin, leukotriene or any soluble receptor thereof. In some embodiments the serum marker is a marker of a specific disease or condition. In some embodiments the serum marker is a cancer marker. In some embodiments the serum marker is a leukemia marker. In some embodiments the serum marker is beta-2-microglobulin, calcitonin, CD20, CD23, CD52, IL6, IL2R, ICAM-1, CD14, IgG, thymidine kinase or ferritin. In some embodiments the serum marker is a pharmaceutical drug, pathogen, virus, parasite, small compound or toxin. Therefore, in some embodiments, the methods described herein are for diagnosis, prognosis or determining a method of treatment for a subject or patient. In some embodiments the methods comprise classifying a cell or population of cells. In certain embodiments, the methods of diagnosis, prognosis or determining a method of treatment comprise determining the level of at least one serum marker derived from the subject or patient. In some embodiments the serum marker is a cytokine, chemokine, soluble receptor, growth factor, antibody or binding protein. In some embodiments the serum marker is a pathogen. In some embodiments the serum marker is a pharmaceutical compound or drug.

The subject invention also provides kits for use in determining the physiological status of cells in a sample, the kit comprising one or more specific binding elements for signaling molecules, and may additionally comprise one or more therapeutic agents. The kit may further comprise a software package for data analysis of the physiological status, which may include reference profiles for comparison with the test profile.

Methods

In some embodiments, the invention provides methods, including methods to determine the physiological status of a cell, e.g., by determining the activation level of an activatable element upon contact with one or more modulators. In some embodiments, the invention provides methods, including methods to classify a cell according to the status of an activatable element in a cellular pathway. The information can be used in prognosis and diagnosis, including susceptibility to disease(s), status of a diseased state and response to changes, in the environment, such as the passage of time, treatment with drugs or other modalities. The physiological status of the cells provided in a sample (e.g. clinical sample) may be classified according to the-activation of cellular pathways of interest. The cells can also be classified as to their ability to respond to therapeutic agents and treatments.

One or more cells, or samples containing one or more cells, can be isolated from body samples, such as, but not limited to, smears, sputum, biopsies, secretions, cerebrospinal fluid, bile, blood, lymph fluid, urine and feces, a lavage of a tissue or organ (e.g. lung) or tissue which has been removed from organs, such as breast, lung, intestine, skin, cervix, prostate, and stomach. For example, a tissue sample can comprise a region of functionally related cells or adjacent cells. Such samples can comprise complex populations of cells, which can be assayed as a population, or separated into sub-populations. Such cellular and acellular samples can be separated by centrifugation, elutriation, density gradient separation, apheresis, affinity selection, panning, FACS, centrifugation with Hypaque, etc. By using antibodies specific for markers identified with particular cell types, a relatively homogeneous population of cells may be obtained. Alternatively, a heterogeneous cell population can be used. Cells can also be separated by using filters. For example, whole blood can also be applied to filters that are engineered to contain pore sizes that select for the desired cell type or class. Rare pathogenic cells can be filtered out of diluted, whole blood following the lysis of red blood cells by using filters with pore sizes between 5 to 10 µm, as disclosed in U.S. patent application Ser. No. 09/790,673. Other devices can separate tumor cells from the bloodstream, see Demirci U, Toner M., Direct etch method for microfluidic channel and nanoheight post-fabrication by picoliter droplets, Applied Physics Letters 2006; 88 (5), 053117; and Irimia D, Geba D, Toner M., Universal microfluidic gradient generator, Analytical Chemistry 2006; 78: 3472-3477. Once a sample is obtained, it can be used directly, frozen, or maintained in appropriate culture medium for short periods of time. Methods to isolate one or more cells for use according to the methods of this invention are performed according to standard techniques and protocols well-established in the art.

Suitable cells include those cell types associated in a wide variety of disease conditions, even while in a non-diseased state. Accordingly, suitable eukaryotic cell types include, but are not limited to, tumor cells of all types (e.g. melanoma, myeloid leukemia, carcinomas of the lung, breast, ovaries, colon, kidney, prostate, pancreas and testes), cardiomyocytes, dendritic cells, endothelial cells, epithelial cells, lymphocytes (T-cell and B cell), mast cells, eosinophils, vascular intimal cells, macrophages, natural killer cells, erythrocytes, hepatocytes, leukocytes including mononuclear leukocytes, stem cells such as haemopoetic, neural, skin, lung, kidney, liver and myocyte stem cells (for use in screening for differentiation and de-differentiation factors), osteoclasts, chondrocytes and other connective tissue cells, keratinocytes, melanocytes, liver cells, kidney cells, and adipocytes. Suitable cells also include primary disease state cells, such as primary tumor cells. Suitable cells also include known research cells, including, but not limited to, Jurkat T cells, NIH3T3 cells, CHO, COS, etc. See the ATCC cell line catalog, hereby expressly incorporated by reference.

In some embodiments, the cells are cultured post collection in a media suitable for revealing the activation level of an activatable element (e.g. RPMI, DMEM) in the presence, or absence, of serum such as fetal bovine serum, bovine serum, human serum, porcine serum, horse serum, or goat serum. When serum is present in the media it could be present at a level ranging from 0.0001% to 100%. In some embodiments serum is present in the media at a level ranging from 0.0001% to 90%. In some embodiments serum is present in the media at a level ranging from 0.01% to 30%. In some embodiments serum is present in the media at 1, 2, 3, 4, 5, 6, 7, 8, 9 or 10%. In some embodiments, serum is present in the media at any suitable level.

In some embodiments, the cell is a hematopoietic cell. Examples of hematopoietic cells include but are not limited to pluripotent hematopoietic stem cells, B-lymphocyte lineage progenitor or derived cells, T-lymphocyte lineage progenitor or derived cells, NK cell lineage progenitor or derived cells, granulocyte lineage progenitor or derived cells, monocyte lineage progenitor or derived cells, megakaryocyte lineage progenitor or derived cells and erythroid lineage progenitor or derived cells.

In some embodiments, the cells used in the present invention are taken from a patient. Cells used in the present invention can be purified from whole blood by any suitable method.

The term "patient" or "individual" as used herein includes humans as well as other mammals. The methods generally involve determining the status of an activatable element. The methods also involve determining the status of a plurality of activatable elements.

In some embodiments, the invention provides a method of classifying a cell by determining the presence or absence of a change in activation level of an activatable element in the cell upon treatment with one or more modulators, and classifying the cell based on the presence or absence of the change in the activation of the activatable element. In some embodiments the change is a decrease. In some embodiments the change is an increase. In some embodiments of the invention, the activation level of the activatable element is determined by contacting the cell with a binding element that is specific for an activation state of the activatable element. In some embodiments, a cell is classified according to the activation level of a plurality of activatable elements after the cell have been subjected to a modulator. In some embodiments of the invention, the activation levels of a plurality of activatable elements are determined by contacting a cell with a plurality of binding element, where each binding element is specific for an activation state of an activatable element.

The classification of a cell according to the status of an activatable element can comprise classifying the cell as a cell that is correlated with a clinical outcome. In some embodiments, the clinical outcome is the prognosis and/or diagnosis of a condition. In some embodiments, the clinical outcome is the presence or absence of a neoplastic or a hematopoietic condition such as Non-Hodgkin Lymphoma, Hodgkin or other lymphomas, acute or chronic leukemias, polycythemias, thrombocythemias, multiple myeloma or plasma cell disorders, e.g., amyloidosis and Waldenstrom's macroglobulinemia, myelodysplastic disorders, myeloproliferative disorders, myelofibrosis, or atypical immune lymphoproliferations. In some embodiments, the neoplastic or hematopoietic condition is non-B lineage derived, such as Acute myeloid leukemia (AML), Chronic Myeloid Leukemia (CML), non-B cell Acute lymphocytic leukemia (ALL), non-B cell lymphomas, myelodysplastic disorders, myeloproliferative disorders, myelofibrosis, polycythemias, thrombocythemias, or non-B atypical immune lymphoproliferations, Chronic Lymphocytic Leukemia (CLL), B lymphocyte lineage leukemia, B lymphocyte lineage lymphoma, Multiple Myeloma, or plasma cell disorders, e.g., amyloidosis or Waldenstrom's macroglobulinemia. In some embodiments, the clinical outcome is the presence or absence of a neoplastic or a hematopoietic condition, such as Chronic Lymphocytic Leukemia (CLL), B lymphocyte lineage leukemia, B lymphocyte lineage lymphoma, Multiple Myeloma, acute lymphoblastic leukemia (ALL), B-cell pro-lymphocytic leukemia, precursor B lymphoblastic leukemia, hairy cell leukemia or plasma cell disorders, e.g., amyloidosis or Waldenstrom's macroglobulinemia, B cell lymphomas including but not limited to diffuse large B cell lymphoma, follicular lymphoma, mucosa associated lymphatic tissue lymphoma, small cell lymphocytic lymphoma, mantle cell lymphoma and marginal zone lymphoma. In some embodiments, the condition is CLL. In some embodiments, the clinical outcome is the staging or grading of a neoplastic or hematopoietic condition. Examples of staging include, but are not limited to, aggressive, indolent, benign, refractory, Roman Numeral staging, TNM Staging, Rai staging, Binet staging, WHO classification, FAB classification, IPSS score, WPSS score, limited stage, extensive stage, staging according to cellular markers such as ZAP70 and CD38, occult, including information that may inform on time to progression, progression free survival, overall survival, or event-free survival.

The classification of a cell according to the status of an activatable element can comprise classifying a cell as a cell that is correlated to a patient response to a treatment. In some embodiments, the patient response is selected from the group consisting of complete response, partial response, nodular partial response, no response, progressive disease, stable disease and adverse reaction.

The classification of a cell according to the status of an activatable element can comprise classifying the cell as a cell that is correlated with minimal residual disease or emerging resistance.

The classification of a cell according to the status of an activatable element can comprise selecting a method of treatment. Example of methods of treatments include, but are not limited to, chemotherapy, biological therapy, radiation therapy, bone marrow transplantation, Peripheral stem cell transplantation, umbilical cord blood transplantation, autologous stem cell transplantation, allogeneic stem cell transplantation, syngeneic stem cell transplantation, surgery, induction therapy, maintenance therapy, watchful waiting, and holistic/alternative therapy.

Modulators include compounds or conditions capable of impacting cellular signaling networks. A modulator can be an activator or an inhibitor. Modulators can take the form of a wide variety of environmental inputs. Examples of modulators include but are not limited to growth factors, cytokines, chemokines, soluble receptors, Toll-like receptor ligands, pathogens, parasites, components of pathogens or parasites, adhesion molecule modulators, pharmaceutical compounds, drugs, hormones, small molecules, polynucleotides, antibodies, natural compounds, lactones, chemotherapeutic agents, immune modulators, carbohydrates, proteases, ions, reactive oxygen species, radiation, physical parameters such as heat, cold, UV radiation, peptides, and protein fragments, either alone or in the context of cells, cells themselves, viruses, and biological and non-biological complexes (e.g. beads, plates, viral envelopes, antigen presentation molecules such as major histocompatibility complex). Examples of modulators include, but are not limited to, F(ab)2 IgM, Rituxan, alemtuzumab, fludarabine, cyclophosphamide, chlorambucil, anti CD22 (epratuzumab), anti CD23 (lumiliximab), $H_2O_2$, PMA, BAFF, April, SDF1a, CD40L, IGF-1, Imiquimod, polyCpG, IL-7, IL-6, IL-10, IL-27, IL-4, IL-2, and IL-3. Additional modulators, inhibitors and activators are disclosed in U.S. 61/085,789 which is hereby incorporated by reference in its entirety.

In some embodiments, the modulator is an activator. In some embodiments the modulator is an inhibitor. In some embodiments, the invention provides methods for classifying a cell by contacting the cell with an inhibitor, determining the presence or absence of a change in activation level of an activatable element in the cell, and classifying the cell based on the presence or absence of the change in the activation of the activatable element. In some embodiments the change is a decrease. In some embodiments the change is an increase. In some embodiments, a cell is classified according to the activation level of a plurality of activatable elements after the cell have been subjected to an inhibitor. In some embodiments, the inhibitor is an inhibitor of a cellular factor or a plurality of factors that participates in a signaling cascade in the cell. In some embodiments, the inhibitor is a kinase or phosphatase inhibitor. Examples of kinase inhibitors include adaphostin, AG 490, AG 825, AG 957, AG 1024, aloisine, aloisine A, alsterpaullone, aminogenistein, API-2, apigenin, arctigenin, AY-22989, BAY 61-3606, bisindolylmaleimide IX, chelerythrine, 10-[4'-(N,N-Diethylamino)butyl]-2-chlorophenoxazine hydrochloride, dasatinib, 2-Dimethylamino-4,5,6,7-tetrabromo-1H-benzimidazole, 5,7-Dimethoxy-3-(4-pyridinyl)quinoline dihydrochloride, edelfosine, ellagic acid, enzastaurin, ER 27319 maleate, erlotinib, ET18OCH3, fasudil, flavopiridol, gefitinib, GW 5074, H-7, H-8, H-89, HA-100, HA-1004, HA-1077, HA-1100, hydroxyfasudil, indirubin-3'-oxime, 5-Iodotubercidin, kenpaullone, KN-62, KY12420, LFM-A13, lavendustin A, luteolin, LY-294002, LY294002, mallotoxin, ML-9, NSC-154020, NSC-226080, NSC-231634, NSC-664704, NSC-680410, NU6102, olomoucine, oxindole I, PD-153035, PD-98059, PD 169316, phloretin, phloridzin, piceatannol, picropodophyllin, PK1, PP1, PP2, purvalanol A, quercetin, R406, R788, rapamune, rapamycin, Ro 31-8220, roscovitine, rottlerin, SB202190, SB203580, sirolimus, sorafenib, SL327, SP600125, staurosporine, STI-571, SU-11274, SU1498, SU4312, SU6656, 4,5,6,7-Tetrabromotriazole, TG101348, Triciribine, Tyrphostin AG 490, Tyrphostin AG 825, Tyrphostin AG 957, Tyrphostin AG 1024, Tyrphostin SU1498, U0126, VX-509, VX-667, VX-680, W-7, wortmannin, XL-019, XL-147, XL-184, XL-228, XL-281, XL-518, XL-647, XL-765, XL-820, XL-844, XL-880, Y-27632, ZD-1839, ZM-252868, ZM-447439, Examples of phosphatase inhibitors include, but are not limited to $H_2O_2$, siRNA, miRNA, Cantharidin, (−)-p-Bromotetramisole, Microcystin LR, Sodium Orthovanadate, Sodium Pervanadate, Vanadyl sulfate, Sodium oxodiperoxo (1,10-phenanthroline)vanadate, bis(maltolato)oxovanadium (IV), Sodium Molybdate, Sodium Perm olybdate, Sodium Tartrate, Imidazole, Sodium Fluoride, β-Glycerophosphate, Sodium Pyrophosphate Decahydrate, Calyculin A, Discodermia calyx, bpV(phen), mpV(pic), DMHV, Cypermethrin, Dephostatin, Okadaic Acid, NIPP-1, N-(9,10-Dioxo-9,10-dihydro-phenanthren-2-yl)-2,2-dimethyl-propionamide, α-Bromo-4-hydroxyacetophenone, 4-Hydroxyphenacyl Br, α-Bromo-4-methoxyacetophenone, 4-Methoxyphenacyl Br, α-Bromo-4-(carboxymethoxy)acetophenone, 4-(Carboxymethoxy)phenacyl Br, and bis(4-Trifluoromethylsulfonamidophenyl)-1,4-diisopropylbenzene, phenyarsine oxide, Pyrrolidine Dithiocarbamate, and Aluminum fluoride. In some embodiments, the phosphatase inhibitor is $H_2O_2$.

In some embodiments, the methods of the invention provide methods for determining the presence or absence of a condition in an individual by subjecting a cell from the individual to a modulator and an inhibitor, determining the activation level of an activatable element in the cell, and determining the presence or absence of a condition based on the activation level. In some embodiments, the activation level of a plurality of activatable elements in the cell is determined. The inhibitor can be an inhibitor as described herein. In some embodiments, the inhibitor is a phosphatase inhibitor. In some embodiments, the inhibitor is $H_2O_2$. The modulator can be any modulator described herein. In some embodiments, the modulator is a B cell receptor modulator. In some embodiments, the B cell receptor modulator is a B cell receptor activator. An example of B cell receptor activator is a cross-linker of the B cell receptor complex or the B-cell co-receptor complex. In some embodiments, cross-linker is an antibody or molecular binding entity. In some embodiments, the cross-linker is an antibody. In some embodiments, the antibody is a multivalent antibody. In some embodiments, the antibody is a monovalent, bivalent, or multivalent antibody made more multivalent by attachment to a solid surface or tethered on a nanoparticle surface to increase the local valency of the epitope binding domain.

The cross-linker can be a molecular binding entity. In some embodiments, the molecular binding entity acts upon or binds the B cell receptor complex via carbohydrates or an epitope in the complex. In some embodiments, the molecular is a monovalent, bivalent, or multivalent is made more multivalent by attachment to a solid surface or tethered on a nanoparticle surface to increase the local valency of the epitope binding domain.

The cross-linking of the B cell receptor complex or the B-cell co-receptor complex can comprise binding of an antibody or molecular binding entity to the cell and then causing its crosslinking via interaction of the cell with a solid surface that causes crosslinking of the BCR complex via antibody or molecular binding entity.

The crosslinker can be F(ab)2 IgM, IgG, IgD, polyclonal BCR antibodies, monoclonal BCR antibodies, Fc receptor derived binding elements and/or a combination thereof. The Ig can be derived from a species selected from the group consisting of mouse, goat, rabbit, pig, rat, horse, cow, shark, chicken, llama or human. The Ig or binding element can be fully human or partially human and can be generated by any suitable method known in the art. In some embodiments, the crosslinker is F(ab)2 IgM, Polyclonal IgM antibodies, Monoclonal IgM antibodies, Biotinylated F(ab)2 IgCM, Biotinylated Polyclonal IgM antibodies, Biotinylated Monoclonal IgM antibodies and/or a combination thereof.

In some embodiments, the methods of the invention provides for the use of more than one modulator. In some embodiments, the methods of the invention utilize a B cell receptor activator and a phosphatase inhibitor. In some embodiments, the methods of the invention utilize F(ab)2IgM or biotinylated F(ab)2IgM and $H_2O_2$.

In some embodiments, the methods of the invention provides for methods of classifying a cell population by exposing the cell population in separate cultures to a plurality of modulators and determining the status of activatable elements in the cell populations. In some embodiments, the status of a plurality of activatable elements in the cell population is determined. In some embodiments, at least one of the modulators of the plurality of modulators is an inhibitor. The modulator can be any modulators described herein. In some embodiments, the modulator is selected from the group consisting of F(ab)2 IgM, $H_2O_2$, PMA, BAFF, April, SDFla, CD40L, IGF-1, Imiquimod, polyCpG, IL-7, IL-6, IL-10, IL-27, IL-4, IL-2, IL-3, thapsigargin and a combination thereof. In some embodiments of the invention, the status of an activatable element is determined by contacting the cell population with a binding element that is specific for an activation state of the activatable element. In some embodiments, the status of a plurality of activatable elements is determined by contacting the cell population with a plurality of binding elements, where each binding element is specific for an activation state of an activatable element.

In some embodiments, the methods of the invention provide for methods for classifying a cell population by contacting the cell population with at least one modulator, where the modulator is to F(ab)2 IgM, Rituxan, Alemtuzumab, anti CD22 (epratuzumab), anti-CD23 (lumiliximab), Campath, $H_2O_2$, PMA, BAFF, April, SDF1a, CD40L, IGF-1, Imiquimod, polyCpG, fludarabine, cyclophosphamide, chlorambucil, IL-7, IL-6, IL-10, IL-27, IL-4, IL-2, IL-3, thapsigargin and/or a combination thereof, and determining the status of an activatable element in the cell population. In some embodiments, the status of a plurality of activatable elements in the cell population is determined. In some embodiments of the invention, the status of an activatable element is determined by contacting the cell population with a binding element that is specific for an activation state of the activatable element. In some embodiments, the status of a plurality of activatable elements is determined by contacting the cell population with a plurality of binding elements, where each binding element is specific for an activation state of an activatable element.

In some embodiments, the methods of the invention provide for determining a phenotypic profile of a population of cells by exposing the population of cells in separate cultures to a plurality of modulators, wherein at least one of the modulators is an inhibitor, determining the presence or absence of a change in activation level of an activatable element in the cell population from each of the separate cultures and classifying the cell population based on the presence or absence of the change in the activation of the activatable element from each of the separate cultures. In some embodiments the change is a decrease. In some embodiments the change is an increase. In some embodiments, the modulator is selected from the group consisting of F(ab)2 IgM, Rituxan, Alemtuzumab, anti CD22 (epratuzumab), anti-CD23 (lumiliximab), Campath, $H_2O_2$, PMA, BAFF, April, SDFla, CD40L, IGF-1, Imiquimod, polyCpG, fludarabine, cyclophosphamide, chlorambucil, IL-7, IL-6, IL-10, IL-27, IL-4, IL-2, IL-3, thapsigargin and combination thereof. In some embodiments, the status of a plurality of activatable elements in the cell population is determined. In some embodiments, the phenotypic profile of a population of cells is used to classify the population as described herein. In some embodiments, the presence or absence of an increase in the activation level of an activatable element is determined by contacting the cell population with a binding element that is specific for an activation state of the activatable element. In some embodiments, the status of a plurality of activatable elements is determined by contacting the cell population with a plurality of binding elements, where each binding element is specific for an activation state of an activatable element.

In some embodiments, the invention provides a method for classifying a B-lymphocyte progenitor or derived cell as described herein by contacting the cell with a modulator, determining the presence or absence of a change in activation level of an activatable element in the cell, and classifying the cell based on the presence or absence of the change in the activation of the activatable element. In some embodiments the change is a decrease. In some embodiments the change is an increase. In some embodiments, the presence or absence of a change in the activation level of an activatable element is determined by contacting the cell with a binding element that is specific for an activation state of the activatable element. In some embodiments, a B-lymphocyte progenitor or derived cell is classified according to the activation level of a plurality of activatable elements after the cells have been subjected to a modulator. In some embodiments, the presence or absence of a change in the activation levels of a plurality of activatable elements is determined by contacting the cell population with a plurality of binding elements, where each binding elements is specific for an activation state of an activatable element. In some embodiments, the method for classifying a B-lymphocyte progenitor or derived cell further comprises determining the level of at least one cell-surface marker. In some embodiments, the method for classifying a B-lymphocyte progenitor or derived cell further comprises determining the level of at least one intracellular marker, for example a captured intracellular cytokine. In some embodiments, the B-lymphocyte progenitor or derived cell is associated with a condition such a neoplastic or hematopoetic condition. Thus, in some embodiments, the invention provides methods for classifying a B-lymphocyte progenitor or derived cell associated with a condition (e.g. neoplastic or hematopoetic condition) by contacting the cell with a modulator, determining the presence or absence of a change in activation level of one or more activatable elements in the cell, and classifying the cell based on the presence or absence of the change in the activation of the one or more activatable elements. In some embodiments the change is a decrease. In some embodiments the change is an increase.

In some embodiments, the invention provides methods for correlating and/or classifying an activation state of a CLL cell with a clinical outcome in an individual by subjecting the CLL cell from the individual to a modulator, wherein the CLL cell expresses B-Cell receptor (BCR), determining the activation levels of a plurality of activatable elements, and identifying a pattern of the activation levels of the plurality of activatable elements to determine the presence or absence of an alteration in signaling proximal to the BCR, wherein the presence of the alteration is indicative of a clinical outcome. In some embodiments, the activation levels of a plurality of activatable elements are determined by contacting the cell with a plurality of binding elements, where each binding element is specific for an activation state of an activatable element. The clinical outcome can be any clinical outcome described herein.

In some embodiments, the methods of the invention provide methods for determining tonic signaling status of a cell by subjecting the cell to a modulator, determining the activation level of an activatable element that participates in a tonic signaling pathway in the cell, and determining the status of a tonic signaling pathway in the cell from the activation level. In some embodiments, the status of a plurality of activatable elements in the cell population is determined. In some embodiments, the activation level of an activatable element is determined by contacting the cell with a binding element that is specific for an activation state of the activatable element. In some embodiments, the activation level of a plurality of activatable elements is determined by contacting the cell with a plurality of binding elements, where each binding element is specific for an activation state of an activatable element. In some embodiments, the tonic signaling is a cellular receptor tonic signaling. In some embodiments, the tonic signaling is a T-cell receptor (TCR) tonic signaling. In some embodiments, the tonic signaling is a BCR tonic signaling. In some embodiments, the tonic signaling status in the cell is used to classify the cell as described herein.

Patterns and profiles of one or more activatable elements are detected using the methods known in the art including those described herein. In some embodiments, patterns and profiles of activatable elements that are cellular components of a cellular pathway are detected using the methods described herein. In some embodiments, patterns and profiles of activatable elements that are cellular components of a signaling pathway are detected using the methods described herein. In some embodiments, patterns and profiles of activatable elements that are cellular components of a tonic signaling pathway are detected using the methods described herein. For example, patterns and profiles of one or more phosphorylated polypeptide are detected using methods known in art including those described herein.

In some embodiments of the methods described herein, cells (e.g. normal non-transformed cells) other than the cells associated with a condition (e.g. cancer cells) can be used to make clinical decisions. That is that cells, other than cells associated with a condition (e.g. cancer cells), are in fact reflective of the condition process. Normal cells (e.g. healthy cells or non-transformed cells) can be used, e.g., in assigning a risk group, predicting an increased risk of relapse, predicting an increased risk of developing secondary complications, choosing a therapy for an individual, predicting response to a therapy for an individual, determining the efficacy of a therapy in an individual, and/or determining the prognosis for an individual. That is that cells other than cells associated with a condition (e.g. cancer cells) are in fact reflective of the condition process. For instance, in the case of cancer, infiltrating immune cells can determine the outcome of the disease. In another aspect, a combination of information from a cancer cell plus responding immune cells in the blood of a cancer patient can be used for diagnosis or prognosis of the cancer.

Conditions

The methods of the invention are applicable to any condition in an individual involving, indicated by, and/or arising from, in whole or in part, altered physiological status in a cell. The term "physiological status" includes mechanical, physical, and biochemical functions in a cell. In some embodiments, the physiological status of a cell is determined by measuring characteristics of cellular components of a cellular pathway. Cellular pathways are well known in the art. In some embodiments the cellular pathway is a signaling pathway. Signaling pathways are also well known in the art (see, e.g., Hunter T., Cell (2000) 100(1): 113-27; Cell Signaling Technology, Inc., 2002 Catalogue, Pathway Diagrams pgs. 232-253). A condition involving or characterized by altered physiological status may be readily identified, for example, by determining the state in a cell of one or more activatable elements, as taught herein.

In certain embodiments of the invention, the condition is a neoplastic or hematopoietic condition. In some embodiments, the neoplastic or hematopoietic condition is selected from the group consisting of Non-Hodgkin Lymphoma, Hodgkin or other lymphomas, acute or chronic leukemias, polycythemias, thrombocythemias, multiple myeloma and plasma cell disorders, including amyloidosis and Waldenstrom's macroglobulinemia, myelodysplastic disorders, myeloproliferative disorders, myelofibrosis, and atypical immune lymphoproliferations.

In some embodiments, the neoplastic or hematopoietic condition is non-B lineage derived. Examples of non-B lineage derived neoplastic or hematopoietic condition include, but are not limited to, Acute myeloid leukemia (AML), Chronic Myeloid Leukemia (CML), non-B cell Acute lymphocytic leukemia (ALL), non-B cell lymphomas, myelodysplastic disorders, myeloproliferative disorders, myelofibrosis, polycythemias, thrombocythemias, and non-B atypical immune lymphoproliferations.

In some embodiments, the neoplastic or hematopoietic condition is a B-Cell or B cell lineage derived disorder. Examples of B-Cell or B cell lineage derived neoplastic or hematopoietic condition include but are not limited to Chronic Lymphocytic Leukemia (CLL), B lymphocyte lineage leukemia, B lymphocyte lineage lymphoma, Multiple Myeloma, and plasma cell disorders, including amyloidosis and Waldenstrom's macroglobulinemia.

In some embodiments, the condition is CLL. In some embodiments, CLL is defined by a monoclonal B cell population that co-expresses CD5 with CD19 and CD23 or CD5 with CD20 and CD23 and by surface immunoglobulin expression. In some embodiments, CLL is defined by a monoclonal B cell population that co-expresses CD5 with CD19 and CD23 or CD5 with CD20 and CD23 and dim surface immunoglobulin expression.

Other conditions within the scope of the present invention include, but are not limited to, cancers such as gliomas, lung cancer, colon cancer and prostate cancer. Specific signaling pathway alterations have been described for many cancers, including loss of PTEN and resulting activation of Akt signaling in prostate cancer (Whang Y E. Proc Natl Acad Sci USA Apr. 28, 1998;95(9):5246-50), increased IGF-1 expression in prostate cancer (Schaefer et al., Science Oct. 9, 1998, 282: 199a), EGFR over expression and resulting ERK activation in glioma cancer (Thomas C Y. Int J Cancer Mar. 10, 2003;104(1):19-27), expression of HER2 in breast cancers (Menard et al. Oncogene. Sep. 29 2003, 22(42):6570-8), and APC mutation and activated Wnt signaling in colon cancer (Bienz M. Curr Opin Genet Dev 1999 October, 9(5):595-603).

Diseases other than cancer involving altered physiological status are also encompassed by the present invention. For example, it has been shown that diabetes involves underlying signaling changes, namely resistance to insulin and failure to activate downstream signaling through IRS (Burks D J, White M F. Diabetes 2001 February; 50 Suppl 1:S140-5). Similarly, cardiovascular disease has been shown to involve hypertrophy of the cardiac cells involving multiple pathways such as the PKC family (Malhotra A. Mol Cell Biochem 2001 September; 225 (1-):97-107). Inflammatory diseases, such as rheumatoid arthritis, are known to involve the chemokine receptors and disrupted downstream signaling (D'Ambrosio D. J Immunol Methods 2003 February; 273 (1-2):3-13). The invention is not limited to diseases presently known to involve altered cellular function, but includes diseases subsequently shown to involve physiological alterations or anomalies.

In some embodiments, the present invention is directed to methods for classifying one or more cells in a sample derived from an individual having or suspected of having condition. In some embodiments, the invention allows for identification of prognostically and therapeutically relevant subgroups of the conditions and prediction of the clinical course of an individual. In some embodiments, the invention provides method of classifying a cell according to the activation level of one or more activatable element in a cell from an individual having or suspected of having condition. In some embodiments, the classification includes classifying the cell as a cell that is correlated with a clinical outcome. The clinical outcome can be the prognosis and/or diagnosis of a condition, and/or staging or grading of a condition. In some embodiments, the classifying of the cell includes classifying the cell as a cell that is correlated to a patient response to a treatment. In some embodiments, the classifying of the cell includes classifying the cell as a cell that is correlated with minimal residual disease or emerging resistance.

Activatable Elements

The methods and compositions of the invention may be employed to examine and profile the status of any activatable element in a cellular pathway, or collections of such activatable elements. Single or multiple distinct pathways may be profiled (sequentially or simultaneously), or subsets of activatable elements within a single pathway or across multiple pathways may be examined (again, sequentially or simultaneously).

As will be appreciated by those in the art, a wide variety of activation events can find use in the present invention. In general, the basic requirement is that the activation results in a change in the activatable protein that is detectable by some indication (termed an "activation state indicator"), preferably by altered binding of a labeled binding element or by changes in detectable biological activities (e.g., the activated state has an enzymatic activity which can be measured and compared to a lack of activity in the non-activated state). What is important is to differentiate, using detectable events or moieties, between two or more activation states (e.g. "off" and "on").

The activation state of an individual activatable element is either in the on or off state. As an illustrative example, and without intending to be limited to any theory, an individual phosphorylatable site on a protein can activate or deactivate the protein. The terms "on" and "off," when applied to an activatable element that is a part of a cellular constituent, are used here to describe the state of the activatable element, and not the overall state of the cellular constituent of which it is a part. Typically, a cell possesses a plurality of a particular protein or other constituent with a particular activatable element and this plurality of proteins or constituents usually has some proteins or constituents whose individual activatable element is in the on state and other proteins or constituents whose individual activatable element is in the off state. Since the activation state of each activatable element is measured through the use of a binding element that recognizes a specific activation state, only those activatable elements in the specific activation state recognized by the binding element, representing some fraction of the total number of activatable elements, will be bound by the binding element to generate a measurable signal. The measurable signal corresponding to the summation of individual activatable elements of a particular type that are activated in a single cell is the "activation level" for that activatable element in that cell.

Activation levels for a particular activatable element may vary among individual cells so that when a plurality of cells is analyzed, the activation levels follow a distribution. The distribution may be a normal distribution, also known as a Gaussian distribution, or it may be of another type. Different populations of cells may have different distributions of activation levels that can then serve to distinguish between the populations. In some embodiments, the basis for classifying cells is that the distribution of activation levels for one or more specific activatable elements will differ among different phenotypes. A certain activation level, or more typically a range of activation levels for one or more activatable elements seen in a cell or a population of cells, is indicative that that cell or population of cells belongs to a distinctive phenotype. Other measurements, such as cellular levels (e.g., expression levels) of biomolecules that may not contain activatable elements, may also be used to classify cells in addition to activation levels of activatable elements; it will be appreciated that these levels also will follow a distribution, similar to activatable elements. Thus, the activation level or levels of one or more activatable elements, optionally in conjunction with levels of one or more levels of biomolecules that may not contain activatable elements, of cell or a population of cells may be used to classify a cell or a population of cells into a class. Once the activation level of intracellular activatable elements of individual single cells is known they can be placed into one or more classes, e.g., a class that corresponds to a phenotype. A class encompasses a class of cells wherein every cell has the same or substantially the same known activation level, or range of activation levels, of one or more intracellular activatable elements. For example, if the activation levels of five intracellular activatable elements are analyzed, predefined classes that encompass one or more of the intracellular activatable elements can be constructed based on the activation level, or ranges of the activation levels, of each of these five elements. It is understood that activation levels can exist as a distribution and that an activation level of a particular element used to classify a cell may be a particular point on the distribution but more typically may be a portion of the distribution.

In addition to activation levels of intracellular activatable elements, expression levels of intracellular or extracellular biomolecues, e.g., proteins can be used alone or in combination with activation states of activatable elements to classify cells. Further, additional cellular elements, e.g., biomolecules or molecular complexes such as RNA, DNA, carbohydrates, metabolites, and the like, may be used in conjunction with activatable states or expression levels in the classification of cells encompassed here.

In some embodiments, other characteristics that affect the status of a cellular constituent may also be used to classify a cell. Examples include the translocation of biomolecules or changes in their turnover rates and the formation and disassociation of complexes of biomolecule. Such complexes can include multi-protein complexes, multi-lipid complexes, homo- or hetero-dimers or oligomers, and combinations thereof. Other characteristics include proteolytic cleavage, e.g. from exposure of a cell to an extracellular protease or from the intracellular proteolytic cleavage of a biomolecule.

Additional elements may also be used to classify a cell, such as the expression level of extracellular or intracellular markers, nuclear antigens, enzymatic activity, protein expression and localization, cell cycle analysis, chromosomal analysis, cell volume, and morphological characteristics like granularity and size of nucleus or other distinguishing characteristics. For example, B cells can be further subdivided based on the expression of cell surface markers such as CD45, CD5, CD19, CD20, CD22, CD23, CD27, CD37, CD40, CD52, CD79, CD38, CD96, major histocompatability antigen (MHC) Class 1 or MHC Class 2.

Alternatively, predefined classes of cells can be classified based upon shared characteristics that may include inclusion in one or more additional predefined class or the presence of extracellular and/or intracellular markers, a similar gene expression profile, mutational status, epigenetic silencing, nuclear antigens, enzymatic activity, protein expression and localization, cell cycle analysis, chromosomal analysis, cell volume, and morphological characteristics like granularity and size of nucleus or other distinguishing characteristics.

In some embodiments, the physiological status of one or more cells is determined by examining and profiling the activation level of one or more activatable elements in a cellular pathway. In some embodiments, a cell is classified according to the activation level of a plurality of activatable elements. In some embodiments, a hematopoietic cell is classified according to the activation levels of a plurality of activatable elements. In some embodiments, the activation level of one or more activatable elements of a hematopoietic cell is correlated with a condition. In some embodiments, the activation level of one or more activatable elements of a hematopoietic cell is correlated with a neoplastic or hematopoietic condition as described herein. Examples of hematopoietic cells include but are not limited to pluripotent hematopoietic stem cells, myeloid progenitors, B-lymphocyte lineage progenitor or derived cells, T-lymphocyte lineage progenitor or derived cells, NK cell lineage progenitor or derived cells, granulocyte lineage progenitor or derived cells, monocyte lineage progenitor or derived cells, megakaryocyte lineage progenitor or derived cells and erythroid lineage progenitor or derived cells. In some embodiments, the hematopoietic cell is a B-lymphocyte lineage progenitor or derived cell as described herein.

In some embodiments, the activation level of one or more activatable elements in single cells within the sample is determined. Cellular constituents that may include activatable elements include without limitation, proteins, carbohydrates, lipids, nucleic acids and metabolites. The activatable element may be a portion of the cellular constituent, for example, an amino acid residue in a protein that may undergo phosphorylation, or it may be the cellular constituent itself, for example, a protein that is activated by translocation from one part of the cell to another, change in conformation (due to, e.g., change in pH or ion concentration), by proteolytic cleavage, and the like. Upon activation, a change occurs to the activatable element, such as covalent modification of the activatable element (e.g., binding of a molecule or group to the activatable element, including but not limited to, phosphorylation, acetylation, methylation, ubiquitination) or a conformational change. Such changes generally contribute to changes in particular biological, biochemical, or physical properties of the cellular constituent that contains the activatable element. The state of the cellular constituent that contains the activatable element is determined to some degree, though not necessarily completely, by the state of activation of a particular activatable element of the cellular constituent. For example, a protein may have multiple activatable elements, and the particular activation states of these elements may overall determine the activation state of the protein; the state of a single activatable element is not necessarily determinative. Additional factors, such as the binding of other proteins, pH, ion concentration, interaction with other cellular constituents, and the like, can also affect the state of the cellular constituent.

In some embodiments, the activation levels of a plurality of intracellular activatable elements in single cells are determined. In some embodiments, at least about 2, 3, 4, 5, 6, 7, 8, 9, 10 or more than 10 intracellular activatable elements are determined.

Activation states of activatable elements may result from chemical additions or modifications of biomolecules and include biochemical processes such as glycosylation, phosphorylation, acetylation, methylation, biotinylation, glutamylation, glycylation, hydroxylation, isomerization, prenylation, myristoylation, lipoylation, phosphopantetheinylation, sulfation, ISGylation, nitrosylation, palmitoylation, SUMOylation, ubiquitination, neddylation, citrullination, amidation, and disulfide bond formation, disulfide bond reduction. Other possible chemical additions or modifications of biomolecules include the formation of protein carbonyls, direct modifications of protein side chains, such as o-tyrosine, chloro-, nitrotyrosine, and dityrosine, and protein adducts derived from reactions with carbohydrate and lipid derivatives. Other modifications may be non-covalent, such as binding of a ligand or binding of an allosteric modulator.

Examples of proteins that may include activatable elements include, but are not limited to kinases, phosphatases, lipid signaling molecules, adaptor/scaffold proteins, cytokines, cytokine regulators, ubiquitination enzymes, adhesion molecules, cytoskeletal/contractile proteins, heterotrimeric G proteins, small molecular weight GTPases, guanine nucleotide exchange factors, GTPase activating proteins, caspases, proteins involved in apoptosis (e.g. PARP), cell cycle regulators, molecular chaperones, metabolic enzymes, vesicular transport proteins, hydroxylases, isomerases, deacetylases, methylases, demethylases, tumor suppressor genes, proteases, ion channels, molecular transporters, transcription factors/DNA binding factors, regulators of transcription, and regulators of translation. Examples of activatable elements, activation states and methods of determining the activation level of activatable elements are described in US Publication Number 20060073474 entitled "Methods and compositions for detecting the activation state of multiple proteins in single cells" and U.S. Pat. No. 7,393,656 entitled "Methods and compositions for risk stratification" the content of which are incorporate here by reference.

In some embodiments, the protein is selected from the group consisting of HER receptors, PDGF receptors, Kit receptor, FGF receptors, Eph receptors, Trk receptors, IGF receptors, Insulin receptor, Met receptor, Ret, VEGF receptors, TIE1, TIE2, FAK, Jak1, Jak2, Jak3, Tyk2, Src, Lyn, Fyn, Lck, Fgr, Yes, Csk, Abl, Btk, ZAP70, Syk, IRAKs, cRaf, ARaf, BRAF, Mos, Lim kinase, ILK, Tpl, ALK, TGFβ receptors, BMP receptors, MEKKs, ASK, MLKs, DLK, PAKs, Mek 1, Mek 2, MKK3/6, MKK4/7, ASK1,Cot, NIK, Bub, Myt 1, Weel, Casein kinases, PDK1, SGK1, SGK2, SGK3, Akt1, Akt2, Akt3, p90Rsks, p70S6Kinase, Prks, PKCs, PKAs, ROCK 1, ROCK 2, Auroras, CaMKs, MNKs, AMPKs, MELK, MARKs, Chk1, Chk2, LKB-1, MAP-KAPKs, Pim1, Pim2, Pim3, IKKs, Cdks, Jnks, Erks, IKKs, GSK3α, GSK3β, Cdks, CLKs, PKR, PI3-Kinase class 1, class 2, class 3, mTor, SAPK/JNK1,2,3, p38s, PKR, DNA-PK, ATM, ATR, Receptor protein tyrosine phosphatases (RPTPs), LAR phosphatase, CD45, Non receptor tyrosine phosphatases (NPRTPs), SHPs, MAP kinase phosphatases (MKPs), Dual Specificity phosphatases (DUSPs), CDC25 phosphatases, Low molecular weight tyrosine phosphatase, Eyes absent (EYA) tyrosine phosphatases, Slingshot phosphatases (SSH), serine phosphatases, PP2A, PP2B, PP2C, PP1, PP5, inositol phosphatases, PTEN, SHIPs, myotubularins, phosphoinositide kinases, phospholipases, prostaglandin synthases, 5-lipoxygenase, sphingosine kinases, sphingomyelinases, adaptor/scaffold proteins, Shc, Grb2, BLNK, LAT, B cell adaptor for PI3-kinase (BCAP), SLAP, Dok, KSR, MyD88, Crk, CrkL, GAD, Nck, Grb2 associated binder (GAB), Fas associated death domain (FADD), TRADD, TRAF2, RIP, T-Cell leukemia family, IL-2, IL-4, IL-8, IL-6, interferon γ, interferon α, suppressors of cytokine signaling (SOCs), Cbl, SCF ubiquitination ligase complex, APC/C, adhesion molecules, integrins, Immunoglobulin-like adhesion molecules, selectins, cadherins, catenins, focal adhesion kinase, p130CAS, fodrin, actin, paxillin, myosin, myosin binding proteins, tubulin, eg5/KSP, CENPs, β-adrenergic receptors, muscarinic receptors, adenylyl cyclase receptors, small molecular weight GTPases, H-Ras, K-Ras, N-Ras, Ran, Rac, Rho, Cdc42, Arfs, RABs, RHEB, Vav, Tiam, Sos, Dbl, PRK, TSC1,2, Ras-GAP, Arf-GAPs, Rho-GAPs, caspases, Caspase 2, Caspase 3, Caspase 6, Caspase 7, Caspase 8, Caspase 9, PARP, Bcl-2, Mcl-1, Bcl-XL, Bcl-w, Bcl-B, A1, Bax, Bak, Bok, Bik, Bad, Bid, Bim, Bmf, Hrk, Noxa, Puma, IAPB, XIAP, Smac, Cdk4, Cdk 6, Cdk 2, Cdk1, Cdk 7, Cyclin D, Cyclin E, Cyclin A, Cyclin B, Rb, p16, p14Arf, p27KIP, p21CIP, molecular chaperones, Hsp90s, Hsp70, Hsp27, metabolic enzymes, Acetyl-CoAa Carboxylase, ATP citrate lyase, nitric oxide synthase, caveolins, endosomal sorting complex required for transport (ESCRT) proteins, vesicular protein sorting (Vsps), hydroxylases, prolyl-hydroxylases PHD-1, 2 and 3, asparagine hydroxylase FIH transferases, Pin1 prolyl isomerase, topoisomerases, deacetylases, Histone deacetylases, sirtuins, histone acetylases, CBP/P300 family, MYST family, ATF2, DNA methyl transferases, Histone H3K4 demethylases, H3K27, JHDM2A, UTX, VHL, WT-1, p53, Hdm, PTEN, ubiquitin proteases, urokinase-type plasminogen activator (uPA) and uPA receptor (uPAR) system, cathepsins, metalloproteinases, esterases, hydrolases, separase, potassium channels, sodium channels, multi-drug resistance proteins, P-Gycoprotein, nucleoside transporters, Ets, Elk, SMADs, Rel-A (p65-NFB), CREB, NFAT, ATF-2, AFT, Myc, Fos, Sp1, Egr-1, T-bet, β-catenin, HIFs, FOXOs, E2Fs, SRFs, TCFs, Egr-1, FOXO STAT1, STAT 3, STAT 4, STAT 5, STAT 6, p53, WT-1, HMGA, pS6, 4EPB-1, eIF4E-binding protein, RNA polymerase, initiation factors, elongation factors.

In some embodiments, the classification of a cell according to activation level of an activatable element, e.g., in a cellular pathway comprises classifying the cell as a cell that is correlated with a clinical outcome. In some embodiments, the clinical outcome is the prognosis and/or diagnosis of a condition. In some embodiments, the clinical outcome is the presence or absence of a neoplastic or a hematopoietic condition. In some embodiments, the clinical outcome is the staging or grading of a neoplastic or hematopoietic condition. Examples of staging include, but are not limited to, aggressive, indolent, benign, refractory, Roman Numeral staging, TNM Staging, Rai staging, Binet staging, WHO classification, FAB classification, IPSS score, WPSS score, limited stage, extensive stage, staging according to cellular markers such as ZAP70, $IgV_H$ mutational status and CD38, occult, including information that may inform on time to progression, progression free survival, overall survival, or event-free survival.

In some embodiments, methods and compositions are provided for the classification of a cell according to the activation level of an activatable element, e.g., in a cellular pathway wherein the classification comprises classifying a cell as a cell that is correlated to a patient response to a treatment. In some embodiments, the patient response is selected from the group consisting of complete response, partial response, nodular partial response, no response, progressive disease, stable disease and adverse reaction.

In some embodiments, methods and compositions are provided for the classification of a cell according to the activation level of an activatable element, e.g., in a cellular pathway wherein the classification comprises classifying the cell as a cell that is correlated with minimal residual disease or emerging resistance.

In some embodiments, methods and compositions are provided for the classification of a cell according to the activation level of an activatable element, e.g., in a cellular pathway wherein the classification comprises selecting a method of treatment. Example of methods of treatments include, but are not limited to, chemotherapy, biological therapy, radiation therapy, bone marrow transplantation, Peripheral stem cell transplantation, umbilical cord blood transplantation, autologous stem cell transplantation, allogeneic stem cell transplantation, syngeneic stem cell transplantation, surgery, induction therapy, maintenance therapy, and watchful waiting.

Generally, the methods of the invention involve determining the activation levels of an activatable element in a plurality of single cells in a sample.

A. Signaling Pathways

In some embodiments, the methods of the invention are employed to determine the status of an activatable element in a signaling pathway. In some embodiments, a cell is classified, as described herein, according to the activation level of one or more activatable elements in one or more signaling pathways. Signaling pathways and their members have been extensively described. See (Hunter T. Cell (2000) 100(1): 13-27). Exemplary signaling pathways include the following pathways and their members: The MAP kinase pathway including Ras, Raf, MEK, ERK and elk; the PI3K/Akt pathway including PI-3-kinase, PDK1, Akt and Bad; the NF-κB pathway including IKKs, IkB and NF-κB and the Wnt pathway including frizzled receptors, beta-catenin, APC and other co-factors and TCF (see Cell Signaling Technology, Inc. 2002 Catolog pages 231-279 and Hunter T., supra.). In some embodiments of the invention, the correlated activatable elements being assayed (or the signaling proteins being examined) are members of the MAP kinase, Akt, NFkB, WNT, STAT and/or PKC signaling pathways. The methods of the invention also comprise the methods, signaling pathways and signaling molecules disclosed in U.S. 61/085,789 which is hereby incorporated by reference in its entirety.

In some embodiments, the methods of the invention are employed to determine the status of a signaling protein in a signaling pathway known in the art including those described herein. Exemplary types of signaling proteins within the scope of the present invention include, but are not limited to, kinases, kinase substrates (i.e. phosphorylated substrates), phosphatases, phosphatase substrates, binding proteins (such as 14-3-3), receptor ligands and receptors (cell surface receptor tyrosine kinases and nuclear receptors)). Kinases and protein binding domains, for example, have been well described (see, e.g., Cell Signaling Technology, Inc., 2002 Catalogue "The Human Protein Kinases" and "Protein Interaction Domains" pgs. 254-279).

Exemplary signaling proteins include, but are not limited to, kinases, HER receptors, PDGF receptors, Kit receptor, FGF receptors, Eph receptors, Trk receptors, IGF receptors, Insulin receptor, Met receptor, Ret, VEGF receptors, TIE1, TIE2, FAK, Jak1, Jak2, Jak3, Tyk2, Src, Lyn, Fyn, Lck, Fgr, Yes, Csk, Abl, Btk, ZAP70, Syk, IRAKs, cRaf, ARaf, BRAF, Mos, Lim kinase, ILK, Tpl, ALK, TGFIβ receptors, BMP receptors, MEKKs, ASK, MLKs, DLK, PAKs, Mek 1, Mek 2, MKK3/6, MKK4/7, ASK1, Cot, NIK, Bub, Myt 1, Wee1, Casein kinases, PDK1, SGK1, SGK2, SGK3, Akt1, Akt2, Akt3, p90Rsks, p70S6Kinase, Prks, PKCs, PKAs, ROCK 1, ROCK 2, Auroras, CaMKs, MNKs, AMPKs, MELK, MARKs, Chk1, Chk2, LKB-1, MAPKAPKs, Pim1, Pim2, Pim3, IKKs, Cdks, Jnks, Erks, IKKs, GSK3α, GSK3β, Cdks, CLKs, PKR, PI3-Kinase class 1, class 2, class 3, mTor, SAPK/JNK1,2,3, p38s, PKR, DNA-PK, ATM, ATR, phosphatases, Receptor protein tyrosine phosphatases (RPTPs), LAR phosphatase, CD45, Non receptor tyrosine phosphatases (NPRTP5), SHPs, MAP kinase phosphatases (MKPs), Dual Specificity phosphatases (DUSPs), CDC25 phosphatases, low molecular weight tyrosine phosphatase, Eyes absent (EYA) tyrosine phosphatases, Slingshot phosphatases (SSH), serine phosphatases, PP2A, PP2B, PP2C, PP1, PP5, inositol phosphatases, PTEN, SHIPs, myotubularins, lipid signaling, phosphoinositide kinases, phospholipases, prostaglandin synthases, 5-lipoxygenase, sphingosine kinases, sphingomyelinases, adaptor/scaffold proteins, Shc, Grb2, BLNK, LAT, B cell adaptor for PI3-kinase (BCAP), SLAP, Dok, KSR, MyD88, Crk, CrkL, GAD, Nck, Grb2 associated binder (GAB), Fas associated death domain (FADD), TRADD, TRAF2, RIP, T-Cell leukemia family, cytokines, IL-2, IL-4, IL-8, IL-6, interferon γ, interferon α, cytokine regulators, suppressors of cytokine signaling (SOCs), ubiquitination enzymes, Cbl, SCF ubiquitination ligase complex, APC/C, adhesion molecules, integrins, Immunoglobulin-like adhesion molecules, selectins, cadherins, catenins, focal adhesion kinase, p130CAS, cytoskeletal/contractile proteins, fodrin, actin, paxillin, myosin, myosin binding proteins, tubulin, eg5/KSP, CENPs, heterotrimeric G proteins, β-adrenergic receptors, muscarinic receptors, adenylyl cyclase receptors, small molecular weight GTPases, H-Ras, K-Ras, N-Ras, Ran, Rac, Rho, Cdc42, Arfs, RABs, RHEB, guanine nucleotide exchange factors, Vav, Tiam, Sos, Dbl, PRK, TSC1,2, GTPase activating proteins, Ras-GAP, Arf-GAPs, Rho-GAPs, caspases, Caspase 2, Caspase 3, Caspase 6, Caspase 7, Caspase 8, Caspase 9, PARP, proteins involved in apoptosis, Bcl-2, Mcl-1, Bcl-XL, Bcl-w, Bcl-B, A1, Bax, Bak, Bok, Bik, Bad, Bid, Bim, Bmf, Hrk, Noxa, Puma, IAPB, XIAP, Smac, cell cycle regulators, Cdk4, Cdk 6, Cdk 2, Cdk1, Cdk 7, Cyclin D, Cyclin E, Cyclin A, Cyclin B, Rb, p16, p14Arf, p27KIP, p21CIP, molecular chaperones, Hsp90s, Hsp70, Hsp27, metabolic enzymes, Acetyl-CoAa Carboxylase, ATP citrate lyase, nitric oxide synthase, vesicular transport proteins, caveolins, endosomal sorting complex required for transport (ESCRT) proteins, vesicular protein sorting (Vsps), hydroxylases, prolyl-hydroxylases PHD-1, 2 and 3, asparagine hydroxylase FIH transferases, isomerases, Pin1 prolyl isomerase, topoisomerases, deacetylases, Histone deacetylases, sirtuins, acetylases, histone acetylases, CBP/P300 family, MYST family, ATF2, methylases, DNA methyl transferases, demethylases, Histone H3K4 demethylases, H3K27, JHDM2A, UTX, tumor suppressor genes, VHL, WT-1, p53, Hdm, PTEN, proteases, ubiquitin proteases, urokinase-type plasminogen activator (uPA) and uPA receptor (uPAR) system, cathepsins, metalloproteinases, esterases, hydrolases, separase, ion channels, potassium channels, sodium channels, molecular transporters, multi-drug resistance proteins, P-Gycoprotein, nucleoside transporters, transcription factors/DNA binding proteins, Ets, Elk, SMADs, Rel-A (p65-NFKB), CREB, NFAT, ATF-2, AFT, Myc, Fos, Sp1, Egr-1, T-bet, HIFs, FOXOs, E2Fs, SRFs, TCFs, Egr-1, β-catenin, FOXO STAT1, STAT 3, STAT 4, STAT 5, STAT 6, p53, WT-1, HMGA, regulators of translation, pS6, 4EPB-1, eIF4E-binding protein, regulators of transcription, RNA polymerase, initiation factors, and elongation factors.

In some embodiments the protein is selected from the group consisting of PI3-Kinase (p85, p110a, p110b, p110d), Jak1, Jak2, SOCs, Rac, Rho, Cdc42, Ras-GAP, Vav, Tiam, Sos, Dbl, Nck, Gab, PRK, SHPT, and SHP2, SHIP1, SHIP2, sSHIP, PTEN, Shc, Grb2, PDK1, SGK, Akt1, Akt2, Akt3, TSC1,2, Rheb, mTor, 4EBP-1, p70S6Kinase, S6, LKB-1, AMPK, PFK, Acetyl-CoAa Carboxylase, DokS, Rafs, Mos, Tpl2, MEK1/2, MLK3, TAK, DLK, MKK3/6, MEKK1,4, MLK3, ASK1, MKK4/7, SAPK/JNK1,2,3, p38s, Erk1/2, Syk, Btk, BLNK, LAT, ZAP70, Lck, Cbl, SLP-76, PLCγ$_1$, PLCγ$_2$, STAT1, STAT 3, STAT 4, STAT 5, STAT 6, FAK, p130CAS, PAKs, LIMK1/2, Hsp90, Hsp70, Hsp27, SMADs, Rel-A (p65-NFKB), CREB, Histone H$_2$B, HATs, HDACs, PKR, Rb, Cyclin D, Cyclin E, Cyclin A, Cyclin B, P16, p14Arf, p27KIP, p21CIP, Cdk4, Cdk6, Cdk7, Cdk1, Cdk2, Cdk9, Cdc25,A/B/C, Abl, E2F, FADD, TRADD, TRAF2, RIP, Myd88, BAD, Bcl-2, Mcl-1, Bcl-XL, Caspase 2, Caspase 3, Caspase 6, Caspase 7, Caspase 8, Caspase 9, PARP, IAPB, Smac, Fodrin, Actin, Src, Lyn, Fyn, Lck, NIK, IkB, p65(ReiA), IKKα, PKA, PKCα, PKCβ, PKCθ, PKCδ, CAMK, Elk, AFT, Myc, Egr-1, NFAT, ATF-2, Mdm2, p53, DNA-PK, Chk1, Chk2, ATM, ATR, β-catenin, CrkL, GSK3α, GSK3β, and FOXO.

MAP kinase pathway: In some embodiments, the methods of the invention are employed to determine the status of an activatable element in the MAP kinase pathway. Without intending to be limited to any theory, the MAP Kinase pathway is a signal transduction pathway that couples intracellular responses to the binding of growth factors to cell surface receptors. This pathway is very complex and includes many protein components. In many cell types, activation of this pathway promotes cell division.

Receptor-linked tyrosine kinases such as the epidermal growth factor receptor (EGFR) are activated by extracellular ligands. Binding of epidermal growth factor (EGF) to the EGFR activates the tyrosine kinase activity of the cytoplasmic domain of the receptor. The EGFR becomes phosphorylated on tyrosines. Docking proteins such as GRB2 contain SH2 domains that bind to the phosphotyrosines of the activated receptor. GRB2 binds to the guanine nucleotide exchange factor SOS by way of an SH3 domain of GRB2. When the GRB2-SOS complex docks to phosphorylated EGFR, SOS becomes activated. Activated SOS promotes the removal of GDP from Ras. Ras can then bind GTP and become active. Other small G proteins can be activated in a similar way, but are not discussed further here. Activated Ras activates the protein kinase activity of RAF kinase, a serine/threonine-selective protein kinase. RAF kinase phosphorylates and activates MEK, another serine/threonine kinase. MEK phosphorylates and activates mitogen-activated protein kinase (MAPK).

Technically, RAF, MEK and MAPK are all mitogen-activated kinases, as is MNK. MAPK was originally called "extracellular signal-regulated kinases" (ERKs) and microtubule-associated protein kinase (MAPK). One of the first proteins known to be phosphorylated by ERK was a microtubule-associated protein. Many additional targets for phosphorylation by MAPK have been found and the protein was re-named "mitogen-activated protein kinase" (MAPK). The series of kinases from RAF to MEK to MAPK is an example of a protein kinase cascade. Such series of kinases provide opportunities for feedback regulation and signal amplification. RAS is activated in a wide range of cancers (see Cell Signaling Technology, Inc. Catolog, supra. at pages 231-279 and Hunter T, supra. and references therein).

PI3K/Akt pathway: In some embodiments, the methods of the invention are employed to determine the status of an activatable element in a PI3K/Akt pathway. Without intending to be limited to any theory, the PI3K/Akt pathway plays a role in effecting alterations in abroad range of cellular functions in response to extracellular signals. A downstream effector of PI3K is the serine-threonine kinase Akt which in response to PI3K activation, phosphorylates and regulates the activity of a number of targets including kinases, transcription factors and other regulatory molecules. The serine/threonine kinase Akt functions intracellularly as a nodal point for a constellation of converging upstream signaling pathways, which involve stimulation of receptor tyrosine kinases such as IGF-1R, HER2/Neu, VEGF-R, PDGF-R), and an assembly of membrane-localized complexes of receptor-PI3K and activation of Akt through the second messenger PIP3. The integration of these intracellular signals at the level of Akt and its kinase activity, regulates the phosphorylation of its several downstream effectors, such as NF-B, mTOR, Forkhead, Bad, GSK-3 and MDM-2. These phosphorylation events, in turn, mediate the effects of Akt on cell growth, proliferation, protection from pro-apoptotic stimuli, and stimulation of neoangiogenesis. Akt and its upstream regulators are deregulated in a wide range of solid tumors and hematologic malignancies. The Akt pathway is the central cell survival pathway that is activated by such oncogenic events as over expression of an upstream receptor tyrosine kinase such as EGFR (ibid) or loss of an upstream regulatory protein such as PTEN (ibid).

NE-κB pathway: In some embodiments, the methods of the invention are employed to determine the status of an activatable element in a NF-κB pathway. Without intending to be limited to any theory, the NF-κB pathway is involved in regulating many aspects of cellular activity, in stress, injury and especially in pathways of the immune response. Some examples are the response to and induction of IL-2, the induction of TAP1 and MHC molecules by NF-κB, and many aspects of the inflammatory response, e.g. induction of IL-1 (alpha and beta), TNF-alpha and leukocyte adhesion molecules (E-selectin, VCAM-1 and ICAM-1). Moreover, NF-κB is involved in many aspects of cell growth, differentiation and proliferation via the induction of certain growth and transcription factors (e.g. c-myc, ras and p53). The NF-κB signal transduction pathway is misregulated in a variety of human cancers, especially those of lymphoid cell origin. Several human lymphoid cancer cells are reported to have mutations or amplifications of genes encoding NF-κB transcription factors. In most cancer cells NF-κB is constitutively active and resides in the nucleus. In some cases, this may be due to chronic stimulation of the IKK pathway, while in others the gene encoding IkBa may be defective. Such continuous nuclear NF-κB activity not only protects cancer cells from apoptotic cell death, but may even enhance their growth activity. Designing anti-tumor agents to block NF-κB activity or to increase their sensitivity to conventional chemotherapy may have great therapeutic value.

WNT pathway: In some embodiments, the methods of the invention are employed to determine the status of an activatable element in a WNT pathway. Without intending to be limited to any theory, the Wnt signaling pathway describes a complex network of proteins most well known for their roles in embryogenesis and cancer, but also involved in normal physiological processes in adult animals. The canonical Wnt pathway describes a series of events that occur when Wnt proteins bind to cell-surface receptors of the Frizzled family, causing the receptors to activate Dishevelled family proteins and ultimately resulting in a change in the amount of β-catenin that reaches the nucleus. Dishevelled (DSH) is a key component of a membrane-associated Wnt receptor complex which, when activated by Wnt binding, inhibits a second complex of proteins that includes axin, GSK-3, and the protein APC. The axin/GSK-3/APC complex normally promotes the proteolytic degradation of the β-catenin intracellular signaling molecule. After this "β-catenin destruction complex" is inhibited, a pool of cytoplasmic β-catenin stabilizes, and some β-catenin is able to enter the nucleus and interact with TCF/LEF family transcription factors to promote specific gene expression.

PKC pathway: In some embodiments, the methods of the invention are employed to determine the status of an activatable element in a PKC pathway. Without intending to be limited to any theory, PKC pathway is associated with cell proliferation, differentiation, and apoptosis. At least eleven closely related PKC isozymes have been reported that differ in their structure, biochemical properties, tissue distribution, subcellular localization, and substrate specificity. They are classified as conventional ($\alpha$, $\beta 1$, $\beta 2$, $\gamma$), novel ($\delta$, $\epsilon$, $\eta$, $\theta$, $\mu$), and atypical ($\zeta$, $\lambda$) isozymes. Conventional PKC isozymes are Ca2+-dependent, while novel and atypical isozymes do not require Ca2+ for their activation. All PKC isozymes, with the exception of $\zeta$ and $\lambda$, are activated by diacylglycerol (DAG). PKC isozymes negatively or positively regulate critical cell cycle transitions, including cell cycle entry and exit and the G1 and G2 checkpoints. Altered PKC activity has been linked with various types of malignancies. Higher levels of PKC and differential activation of various PKC isozymes have been reported in breast tumors, adenomatous pituitaries, thyroid cancer tissue, leukemic cells, and lung cancer cells. Down regulation of PKCα is reported in the majority of colon adenocarcinomas and in the early stages of intestinal carcinogenesis. Thus, PKC inhibitors have become important tools in the treatment of cancers. The involvement of PKC in the regulation of apoptosis adds another dimension to the effort to develop drugs that will specifically target PKC. PKC pathway activation is thought to also play a role in diseases such as cardiovascular disease and diabetes.

In some embodiments of the invention, the methods described herein are employed to determine the status of an activatable element in a signaling pathway. Methods and compositions are provided for the classification of a cell according to the status of an activatable element in a signaling pathway. The cell can be a hematopoietic cell. Examples of hematopoietic cells include but are not limited to pluripotent hematopoietic stem cells, B-lymphocyte lineage progenitor or derived cells, T-lymphocyte lineage progenitor or derived cells, NK cell lineage progenitor or derived cells, granulocyte lineage progenitor or derived cells, monocyte lineage progenitor or derived cells, megakaryocyte lineage progenitor or derived cells and erythroid lineage progenitor or derived cells.

In some embodiments, the classification of a cell according to the status of an activatable element in a signaling pathway comprises classifying the cell as a cell that is correlated with a clinical outcome. In some embodiments, the clinical outcome is the prognosis and/or diagnosis of a condition. In some embodiments, the clinical outcome is the presence or absence of a neoplastic or a hematopoietic condition. In some embodiments, the clinical outcome is the staging or grading of a neoplastic or hematopoietic condition. Examples of staging include, but are not limited to, aggressive, indolent, benign, refractory, Roman Numeral staging, TNM Staging, Rai staging, Binet staging, WHO classification, FAB classification, IPSS score, WPSS score, limited stage, extensive stage, staging according to cellular markers such as ZAP70, $IgV_H$ mutational status and CD38, occult, including information that may inform on time to progression, progression free survival, overall survival, or event-free survival.

In some embodiments, methods and compositions are provided for the classification of a cell according to the status of an activatable element in a signaling pathway wherein the classification comprises classifying a cell as a cell that is correlated to a patient response to a treatment. In some embodiments, the patient response is selected from the group consisting of complete response, partial response, nodular partial response, no response, progressive disease, stable disease and adverse reaction.

In some embodiments, methods and compositions are provided for the classification of a cell according to the status of an activatable element in a signaling pathway wherein the classification comprises classifying the cell as a cell that is correlated with minimal residual disease or emerging resistance.

In some embodiments, methods and compositions are provided for the classification of a cell according to the status of an activatable element in a signaling pathway wherein the classification comprises selecting a method of treatment. Example of methods of treatments include, but are not limited to, chemotherapy, biological therapy, radiation therapy, bone marrow transplantation, Peripheral stem cell transplantation, umbilical cord blood transplantation, autologous stem cell transplantation, allogeneic stem cell transplantation, syngeneic stem cell transplantation, surgery, induction therapy, maintenance therapy, watchful waiting, and holistic/alternative therapy.

The invention is not limited to presently elucidated signaling pathways and signal transduction proteins, and encompasses signaling pathways and proteins subsequently identified.

B. B-Cell Receptor Pathway

In some embodiments, the methods and compositions of the invention may be employed to examine and profile the status of any activatable element in B-Cell Receptor (BCR) signaling, or collections of such activatable elements in a B-lymphocyte lineage progenitor or derived cell. In some embodiments, the physiological status of one or more B-lymphocyte lineage progenitor or derived cell is determined by examining and profiling the status of one or more activatable element in BCR signaling. In some embodiments, a B-lymphocyte lineage progenitor or derived cell is classified, as described herein, according to the activation level of one or more activatable elements in BCR signaling. Examples of B-lymphocyte lineage derived cell include, but are not limited to, B-lymphocyte lineage early pro-B cell, late pro-B cell, large pre-B cell, small pre-B cell, immature B cell, mature B cell, plasma cell, memory B cell, a CD5+ B cell, a CD38+ B cell, a B cell bearing a mutatated or non mutated heavy chain of the B cell receptor and a B cell expressing Zap70. In some embodiments, the B-lymphocyte lineage progenitor or derived cell is a cell associated with a condition as described herein.

Without intending to be limited to any theory, BCR cross-linking triggers phosphorylation of tyrosines within the ITAM motif domains of Igα and Igβ by Src family member tyrosine kinases (e.g., Lyn, Lck, Blk, Fyn). The phosphorylated ITAMs of Igαβ recruit and enhance phosphorylation of Syk (directly) and Btk (via Syk). BCR cross-linking also brings together numerous regulator and adapter molecules (e.g., SLP-65/BLNK, Grb2, CD22, SHP-1) and compartmentalizes the BCR in lipid rafts with coreceptors CD19 and CD21. Following Syk and Btk activation, the enzymes phospholipase-Cγ2 (PLC $\gamma_2$) and PI3K propagate BCR signaling. PLC $\gamma_2$ activation generates calcium flux, inositol-1,4,5-triphosphate, and diacylglycerol, and results in activation of protein kinase C and NF-κB. Syk interacts with PLC $\gamma_2$ via adapters, whereas Btk can interact directly, and each is required for PLC $\gamma_2$ activity following BCR cross-linking Both Syk and Btk can activate PI3K following BCR cross-linking Activation of PI3K enables Akt-mediated survival signaling, and PI3K is required for BCR-mediated survival during B cell development. PLC $\gamma_2$ and PI3K also initiate kinase cascades that result in phosphorylation of the MAPK family proteins ERK1/2 and p38. Activation of the Ras-Raf-ERK1/2 signaling cascade is considered a central event in BCR signaling, and decreased Ras activation due to Ras-GRP1 and RasGRP3 loss in mouse impairs B cell proliferation. In contrast, p38 is a stress response protein that interacts with p53 and regulates cell cycle checkpoints. Differential activation of ERK1/2 and p38 might enable the BCR to drive diverse cellular outcomes, but the question arises whether a given B cell activates these two pathways simultaneously or favors one pathway depending on additional signaling context.

Efficient activation of BCR signaling depends on generation of $H_2O_2$ and inactivation of negative regulatory protein tyrosine phosphatases (PTPs). Following BCR cross-linking, recruitment and activation of calcium-dependent NADPH oxidases (NOX) proteins, such as NOX5, enables production of $H_2O_2$ and lowers the signaling threshold for the BCR. BCR-induced $H_2O_2$ transiently inactivates membrane proximal PTPs, including SHP-1, via reversible oxidation of the catalytic cysteine to sulfenic acid. Elegant work reconstituting the BCR signaling pathway in insect cells has suggested a model of redox feedback loops where $H_2O_2$ inactivates PTPs and enables amplification of early signaling events, such as Syk phosphorylation and ITAM binding. Recent work characterized endogenously generated H₂O₂ as the primary redox species generated by BCR signaling and indicated that NOX-dependent production of $H_2O_2$ was critical to initiate a wave of BCR signaling in mouse A20 B cells.

In some embodiments, the invention provides a method for classifying a B-lymphocyte lineage progenitor or derived cell upon treatment with a modulator and/or inhibitor. Examples of B-lymphocyte lineage progenitor or derived cells include, but are not limited to an early pro-B cell, late pro-B cell, large pre-B cell, small pre-B cell, immature B cell, mature B cell, plasma cell and memory B cell, a CD5+ B cell, a CD38+ B cell, a B cell bearing a mutatated or non mutated heavy chain of the B cell receptor, or a B cell expressing Zap70.

In some embodiments, the classification includes classifying the cell according to the status of an activatable element in a BCR pathway as a cell that is correlated with a clinical outcome. In some embodiments, the invention provides methods for classifying a B-lymphocyte lineage progenitor or derived cell based on an alteration in signaling proximal to the BCR. In some embodiments, the clinical outcome is the prognosis and/or diagnosis of a condition. In some embodiments, the clinical outcome is the presence or absence of a neoplastic or a hematopoietic condition, such as Chronic Lymphocytic Leukemia (CLL), B lymphocyte lineage leukemia, B lymphocyte lineage lymphoma, Multiple Myeloma, or plasma cell disorders, e.g., amyloidosis or Waldenstrom's macroglobulinemia. In some embodiments, the condition is CLL. In some embodiments, the invention provides methods for classifying a CLL cell based on an alteration in signaling proximal to the BCR. The presence of the alteration is indicative of a clinical outcome. In some embodiments CLL is defined by a monoclonal B cell population that co-expresses CD5 with CD19 and CD23 or CD5 with CD20 and CD23 and by surface immunoglobulin expression. In some embodiments, CLL is defined by a monoclonal B cell population that co-expresses CD5 with CD19 and CD23 or CD5 with CD20 and CD23 and dim surface immunoglobulin expression. Additional B-cell markers can be used to identify or classify a B-lymphocyte lineage progenitor or derived cell. Non-limiting examples of such markers include CD45, CD5, CD14, CD19, CD20, CD22, CD23, CD27, CD37, CD40, CD52, CD79, CD38, CD96, major histocompatability antigen (MHC) Class1 and MHC Class 2.

In some embodiments, the clinical outcome is the staging or grading of a neoplastic or hematopoietic condition. Examples of staging in methods provided by the invention include aggressive, indolent, benign, refractory, Roman Numeral staging, TNM Staging, Rai staging, Binet staging, WHO classification, FAB classification, IPSS score, WPSS score, limited stage, extensive stage, staging according to cellular markers such as ZAP70, $IgV_H$ mutational status and CD38, occult, including information that may inform on time to progression, progression free survival, overall survival, or event-free survival.

In some embodiments of the methods of the invention, the classifying of the B-lymphocyte lineage progenitor or derived cell based on activation level of an activatable element in BCR pathway includes classifying the cell as a cell that is correlated to a patient response to a treatment, such as complete response, partial response, nodular partial response, no response, progressive disease, stable disease, relapse or adverse reaction. The method may further comprise determining a method of treatment, e.g., chemotherapy, biological therapy, radiation therapy, bone marrow transplantation, Peripheral stem cell transplantation, umbilical cord blood transplantation, autologous stem cell transplantation, allogeneic stem cell transplantation, syngeneic stem cell transplantation, surgery, induction therapy, maintenance therapy, watchful waiting, or holistic/alternative therapy.

In some embodiments of the methods of the invention, the classifying of the B-lymphocyte lineage progenitor or derived cells based on activation of an activatable element in BCR pathway includes classifying the cell as a cell that is correlated with minimal residual disease or emerging resistance.

C. Tonic Signaling

In some embodiments, the methods and compositions of the invention may be employed to determine the status of a tonic signaling pathway in a cell. In some embodiments, the methods and compositions of the invention may be employed to examine and profile the status of any activatable element in a tonic signaling pathway, or collections of such activatable elements in a cell. In some embodiments, the physiological status of a cell is determined by examining and profiling the status of one or more activatable elements in a tonic signaling pathway. In some embodiments, a cell is classified, as described herein, according to the status of one or more activatable elements in a tonic signaling pathway. The term "tonic signaling" includes antigen-independent signaling, independent basal signaling and non-induced or ligand-independent signaling.

Without intending to be limited to any theory, recent evidence supports the notion that in most signal transduction systems regulated by cellular receptors some basal level of signaling occurs continuously in a ligand-independent manner, although the flux through such systems may vary considerably. The basal tone or the steady state level of signaling in unstimulated cells is the result of equilibrium of positive and negative regulators within a signaling pathway. Thus, the balanced actions of positive and negative regulators of signal transduction set the steady state equilibrium. Receptor stimulation then perturbs the equilibrium state in various ways to initiate cellular responses. The steady state level of signaling in the unstimulated state may itself have functional consequences, for instance, to maintain certain differentiated cellular properties or functions.

In some embodiments, the invention provides for methods of determining tonic signaling status of a cell. In some embodiments, the tonic signaling is a cellular receptor tonic signaling. In some embodiments, the tonic signaling is a BCR tonic signaling. Methods and compositions are provided for the classification of a cell according to the status of an activatable element in a tonic signaling pathway. The cell can be a hematopoietic cell. Examples of hematopoietic cells include but are not limited to pluripotent hematopoietic stem cells, B-lymphocyte lineage progenitor or derived cells, T-lymphocyte lineage progenitor or derived cells, NK cell lineage progenitor or derived cells, granulocyte lineage progenitor or derived cells, monocyte lineage progenitor or derived cells, megakaryocyte lineage progenitor or derived cells and erythroid lineage progenitor or derived cells.

In some embodiments, the classification of a cell according to the status of an activatable element in a tonic signaling pathway comprises classifying the cell as a cell that is correlated with a clinical outcome. In some embodiments, the clinical outcome is the prognosis and/or diagnosis of a condition. In some embodiments, the clinical outcome is the presence or absence of a neoplastic or a hematopoietic condition. Examples of neoplastic or hematopoietic conditions include, but are not limited to, such as Chronic Lymphocytic Leukemia (CLL), B lymphocyte lineage leukemia, B lymphocyte lineage lymphoma, Multiple Myeloma, or plasma cell disorders, e.g., amyloidosis or Waldenstrom's macroglobulinemia. In some embodiments, the condition is CLL. In some embodiments, CLL is defined by a monoclonal B cell population that co-expresses CD5 with CD19 and CD23 or CD5 with CD20 and CD23 and by surface immunoglobulin expression.

In some embodiments, the clinical outcome is the staging or grading of a neoplastic or hematopoietic condition. Examples of staging include, but are not limited to, aggressive, indolent, benign, refractory, Roman Numeral staging, TNM Staging, Rai staging, Binet staging, WHO classification, FAB classification, IPSS score, WPSS score, limited stage, extensive stage, staging according to cellular markers such as ZAP70, IgV$_H$ mutational status and CD38, including information that may inform on time to progression, progression free survival, overall survival, or event-free survival.

In some embodiments, the invention provides methods for classifying a CLL cell based on an alteration in signaling proximal to the BCR that is indicative of the presence of tonic signaling. The presence of the alteration is indicative of a clinical outcome, where the clinical outcome is as described herein.

In some embodiments, methods and compositions are provided for the classification of a cell according to the status of an activatable element in a tonic signaling pathway wherein the classification comprises classifying a cell as a cell that is correlated to a patient response to a treatment. In some embodiments, the patient response is selected from the group consisting of complete response, partial response, nodular partial response, no response, progressive disease, stable disease and adverse reaction.

In some embodiments, methods and compositions are provided for the classification of a cell according to the status of an activatable element in a tonic signaling pathway wherein the classification comprises classifying the cell as a cell that is correlated with minimal residual disease or emerging resistance.

In some embodiments, methods and compositions are provided for the classification of a cell according to the status of an activatable element in a tonic signaling pathway wherein the classification comprises selecting a method of treatment. Example of methods of treatments include, but are not limited to, chemotherapy, biological therapy, radiation therapy, bone marrow transplantation, Peripheral stem cell transplantation, umbilical cord blood transplantation, autologous stem cell transplantation, allogeneic stem cell transplantation, syngeneic stem cell transplantation, surgery, induction therapy, maintenance therapy, watchful waiting, and holistic/alternative therapy.

Binding Element

In some embodiments of the invention, the activation level of an activatable element is determined by contacting a cell with a binding element that is specific for an activation state of the activatable element. The term "Binding element" includes any molecule, e.g., peptide, nucleic acid, small organic molecule which is capable of detecting an activation state of an activatable element over another activation state of the activatable element.

In some embodiments, the binding element is a peptide, polypeptide, oligopeptide or a protein. The peptide, polypeptide, oligopeptide or protein may be made up of naturally occurring amino acids and peptide bonds, or synthetic peptidomimetic structures. Thus "amino acid", or "peptide residue", as used herein include both naturally occurring and synthetic amino acids. For example, homo-phenylalanine, citrulline and noreleucine are considered amino acids for the purposes of the invention. The side chains may be in either the (R) or the (S) configuration. In some embodiments, the amino acids are in the (S) or L-configuration. If non-naturally occurring side chains are used, non-amino acid substituents may be used, for example to prevent or retard in vivo degradation. Proteins including non-naturally occurring amino acids may be synthesized or in some cases, made recombinantly; see van Hest et al., FEBS Lett 428:(1-2) 68-70 May 22, 1998 and Tang et al., Abstr. Pap Am. Chem. S218: U138 Part 2 Aug. 22, 1999, both of which are expressly incorporated by reference herein.

Methods of the present invention may be used to detect any particular activatable element in a sample that is antigenically detectable and antigenically distinguishable from other activatable element which is present in the sample. For example, as demonstrated (see, e.g., the Examples) and described herein, the activation state-specific antibodies of the present invention can be used in the present methods to identify distinct signaling cascades of a subset or subpopulation of complex cell populations; and the ordering of protein activation (e.g., kinase activation) in potential signaling hierarchies. Hence, in some embodiments the expression and phosphorylation of one or more polypeptides are detected and quantified using methods of the present invention. In some embodiments, the expression and phosphorylation of one or more polypeptides that are cellular components of a cellular pathway are detected and quantified using methods of the present invention. As used herein, the term "activation state-specific antibody" or "activation state antibody" or grammatical equivalents thereof, refer to an antibody that specifically binds to a corresponding and specific antigen. Preferably, the corresponding and specific antigen is a specific form of an activatable element. Also preferably, the binding of the activation state-specific antibody is indicative of a specific activation state of a specific activatable element.

In some embodiments, the binding element is an antibody. In some embodiment, the binding element is an activation state-specific antibody. In some embodiment, the binding element is an phospho-specific antibody.

The term "antibody" includes full length antibodies and antibody fragments, and may refer to a natural antibody from any organism, an engineered antibody, or an antibody generated recombinantly for experimental, therapeutic, or other purposes as further defined below. Examples of antibody fragments, as are known in the art, such as Fab, Fab', F(ab')2, Fv, scFv, or other antigen-binding subsequences of antibodies, either produced by the modification of whole antibodies or those synthesized de novo using recombinant DNA technologies. The term "antibody" comprises monoclonal and polyclonal antibodies. Antibodies can be antagonists, agonists, neutralizing, inhibitory, or stimulatory.

The antibodies of the present invention may be nonhuman, chimeric, humanized, or fully human. For a description of the concepts of chimeric and humanized antibodies see Clark et al., 2000 and references cited therein (Clark, (2000) Immunol. Today 21:397-402). Chimeric antibodies comprise the variable region of a nonhuman antibody, for example VH and VL domains of mouse or rat origin, operably linked to the constant region of a human antibody (see for example U.S. Pat. No. 4,816,567). In some embodiments, the antibodies of the present invention are humanized. By "humanized" antibody as used herein is meant an antibody comprising a human framework region (FR) and one or more complementarity determining regions (CDR's) from a non-human (usually mouse or rat) antibody. The non-human antibody providing the CDR's is called the "donor" and the human immunoglobulin providing the framework is called the "acceptor". Humanization relies principally on the grafting of donor CDRs onto acceptor (human) VL and VH frameworks (Winter U.S. Pat. No. 5,225,539). This strategy is referred to as "CDR grafting". "Backmutation" of selected acceptor framework residues to the corresponding donor residues is often required to regain affinity that is lost in the initial grafted construct (U.S. Pat. Nos. 5,530,101; 5,585,089; 5,693,761; 5,693,762; 6,180,370; 5,859,205; 5,821,337; 6,054,297; 6,407,213). The humanized antibody optimally also will comprise at least a portion of an immunoglobulin constant region, typically that of a human immunoglobulin, and thus will typically comprise a human Fc region. Methods for humanizing non-human antibodies are well known in the art, and can be essentially performed following the method of Winter and co-workers (Jones et al., 1986, Nature 321:522-525; Riechmann et al., 1988, Nature 332:323-329; Verhoeyen et al., 1988, Science, 239:1534-1536). Additional examples of humanized murine monoclonal antibodies are also known in the art, for example antibodies binding human protein C(O'Connor et al., 1998, Protein Eng 11:321-8), interleukin 2 receptor (Queen et al., 1989, Proc Natl Acad Sci, USA 86:10029-33), and human epidermal growth factor receptor 2 (Carter et al., 1992, Proc Natl. Acad Sci USA 89:4285-9). In an alternate embodiment, the antibodies of the present invention may be fully human, that is the sequences of the antibodies are completely or substantially human. A number of methods are known in the art for generating fully human antibodies, including the use of transgenic mice (Bruggemann et al., 1997, Curr Opin Biotechnol 8:455-458) or human antibody libraries coupled with selection methods (Griffiths et al., 1998, Curr Opin Biotechnol 9:102-108).

Specifically included within the definition of "antibody" are aglycosylated antibodies. By "aglycosylated antibody" as used herein is meant an antibody that lacks carbohydrate attached at position 297 of the Fc region, wherein numbering is according to the EU system as in Kabat. The aglycosylated antibody may be a deglycosylated antibody, which is an antibody for which the Fc carbohydrate has been removed, for example chemically or enzymatically. Alternatively, the aglycosylated antibody may be a nonglycosylated or unglycosylated antibody, that is an antibody that was expressed without Fc carbohydrate, for example by mutation of one or residues that encode the glycosylation pattern or by expression in an organism that does not attach carbohydrates to proteins, for example bacteria.

As pointed out above, activation state specific antibodies can be used to detect kinase activity, however additional means for determining kinase activation are provided by the present invention. For example, substrates that are specifically recognized by protein kinases and phosphorylated thereby are known. Antibodies that specifically bind to such phosphorylated substrates but do not bind to such non-phosphorylated substrates (phospho-substrate antibodies) may be used to determine the presence of activated kinase in a sample.

In a further embodiment, an element activation profile is determined using a multiplicity of activation state antibodies that have been immobilized. Antibodies may be non-diffusibly bound to an insoluble support having isolated sample-receiving areas (e.g. a microtiter plate, an array, etc.). The insoluble supports may be made of any composition to which the compositions can be bound, is readily separated from soluble material, and is otherwise compatible with the overall method of screening. The surface of such supports may be solid or porous and of any convenient shape. Examples of suitable insoluble supports include microtiter plates, arrays, membranes, and beads. These are typically made of glass, plastic (e.g., polystyrene), polysaccharides, nylon or nitrocellulose, Teflon™, etc. Microtiter plates and arrays are especially convenient because a large number of assays can be carried out simultaneously, using small amounts of reagents and samples. In some cases magnetic beads and the like are included.

The particular manner of binding of the composition is not crucial so long as it is compatible with the reagents and overall methods of the invention, maintains the activity of the composition and is non-diffusible. Methods of binding include the use of antibodies (which do not sterically block either the ligand binding site or activation sequence when the protein is bound to the support), direct binding to "sticky" or ionic supports, chemical cross-linking, the synthesis of the antibody on the surface, etc. Following binding of the antibody, excess unbound material is removed by washing. The sample receiving areas may then be blocked through incubation with bovine serum albumin (BSA), casein or other innocuous protein or other moiety.

The antigenicity of an activated isoform of an activatable element is distinguishable from the antigenicity of non-activated isoform of an activatable element or from the antigenicity of an isoform of a different activation state. In some embodiments, an activated isoform of an element possesses an epitope that is absent in a non-activated isoform of an element, or vice versa. In some embodiments, this difference is due to covalent addition of moieties to an element, such as phosphate moieties, or due to a structural change in an element, as through protein cleavage, or due to an otherwise induced conformational change in an element which causes the element to present the same sequence in an antigenically distinguishable way. In some embodiments, such a conformational change causes an activated isoform of an element to present at least one epitope that is not present in a non-activated isoform, or to not present at least one epitope that is presented by a non-activated isoform of the element. In some embodiments, the epitopes for the distinguishing antibodies are centered around the active site of the element, although as is known in the art, conformational changes in one area of an element may cause alterations in different areas of the element as well.

Many antibodies, many of which are commercially available (for example, see Cell Signaling Technology, www.cellsignal.com, Millipore, eBioscience, Caltag, Santa Cruz Biotech, Abcam, BD Biosciences, Sigma and Anaspec) the contents which are incorporated herein by reference) have been produced which specifically bind to the phosphorylated isoform of a protein but do not specifically bind to a non-phosphorylated isoform of a protein. Many such antibodies have been produced for the study of signal transducing proteins which are reversibly phosphorylated. Particularly, many such antibodies have been produced which specifically bind to phosphorylated, activated isoforms of protein. Examples of proteins that can be analyzed with the methods described herein include, but are not limited to, kinases, HER receptors, PDGF receptors, Kit receptor, FGF receptors, Eph receptors, Trk receptors, IGF receptors, Insulin receptor, Met receptor, Ret, VEGF receptors, TIE1, TIE2, FAK, Jak1, Jak2, Jak3, Tyk2, Src, Lyn, Fyn, Lck, Fgr, Yes, Csk, Abl, Btk, ZAP70, Syk, IRAKs, cRaf, ARaf, BRAF, Mos, Lim kinase, ILK, Tpl, ALK, TGFβ receptors, BMP receptors, MEKKs, ASK, MLKs, DLK, PAKs, Mek 1, Mek 2, MKK3/6, MKK4/7, ASK1, Cot, NIK, Bub, Myt 1, Wee1, Casein kinases, PDK1, SGK1, SGK2, SGK3, Akt1, Akt2, Akt3, p90Rsks, p70S6Kinase, Prks, PKCs, PKAs, ROCK 1, ROCK 2, Auroras, CaMKs, MNKs, AMPKs, MELK, MARKs, Chk1, Chk2, LKB-1, MAPKAPKs, Pim1, Pim2, Pim3, IKKs, Cdks, Jnks, Erks, IKKs, GSK3α, GSK3β, Cdks, CLKs, PKR, PI3-Kinase class 1, class 2, class 3, mTor, SAPK/JNK1,2,3, p38s, PKR, DNA-PK, ATM, ATR, phosphatases, Receptor protein tyrosine phosphatases (RPTPs), LAR phosphatase, CD45, Non receptor tyrosine phosphatases (NPRTPs), SHPs, MAP kinase phosphatases (MKPs), Dual Specificity phosphatases (DUSPs), CDC25 phosphatases, Low molecular weight tyrosine phosphatase, Eyes absent (EYA) tyrosine phosphatases, Slingshot phosphatases (SSH), serine phosphatases, PP2A, PP2B, PP2C, PP1, PP5, inositol phosphatases, PTEN, SHIPs, myotubularins, lipid signaling, phosphoinositide kinases, phospholipases, prostaglandin synthases, 5-lipoxygenase, sphingosine kinases, sphingomyelinases, adaptor/scaffold proteins, Shc, Grb2, BLNK, LAT, B cell adaptor for PI3-kinase (BCAP), SLAP, Dok, KSR, MyD88, Crk, CrkL, GAD, Nck, Grb2 associated binder (GAB), Fas associated death domain (FADD), TRADD, TRAF2, RIP, T-Cell leukemia family, cytokines, IL-2, IL-4, IL-8, IL-6, interferon γ, interferon α, cytokine regulators, suppressors of cytokine signaling (SOCs), ubiquitination enzymes, Cbl, SCF ubiquitination ligase complex, APC/C, adhesion molecules, integrins, Immunoglobulin-like adhesion molecules, selectins, cadherins, catenins, focal adhesion kinase, p130CAS, cytoskeletal/contractile proteins, fodrin, actin, paxillin, myosin, myosin binding proteins, tubulin, eg5/KSP, CENPs, heterotrimeric G proteins, β-adrenergic receptors, muscarinic receptors, adenylyl cyclase receptors, small molecular weight GTPases, H-Ras, K-Ras, N-Ras, Ran, Rac, Rho, Cdc42, Arfs, RABs, RHEB, guanine nucleotide exchange factors, Vav, Tiam, Sos, Dbl, PRK, TSC1,2, GTPase activating proteins, Ras-GAP, Arf-GAPs, Rho-GAPs, caspases, Caspase 2, Caspase 3, Caspase 6, Caspase 7, Caspase 8, Caspase 9, PARP, proteins involved in apoptosis, Bcl-2, Mcl-1, Bcl-XL, Bcl-w, Bcl-B, A1, Bax, Bak, Bok, Bik, Bad, Bid, Bim, Bmf, Hrk, Noxa, Puma, IAPB, XIAP, Smac, cell cycle regulators, Cdk4, Cdk 6, Cdk 2, Cdk1, Cdk 7, Cyclin D, Cyclin E, Cyclin A, Cyclin B, Rb, p16, p14Arf, p27KIP, p21CIP, molecular chaperones, Hsp90s, Hsp70, Hsp27, metabolic enzymes, Acetyl-CoAa Carboxylase, ATP citrate lyase, nitric oxide synthase, vesicular transport proteins, caveolins, endosomal sorting complex required for transport (ESCRT) proteins, vesicular protein sorting (Vsps), hydroxylases, prolyl-hydroxylases PHD-1, 2 and 3, asparagine hydroxylase FIH transferases, isomerases, Pin1 prolyl isomerase, topoisomerases, deacetylases, Histone deacetylases, sirtuins, acetylases, histone acetylases, CBP/P300 family, MYST family, ATF2, methylases, DNA methyl transferases, demethylases, Histone H3K4 demethylases, H3K27, JHDM2A, UTX, tumor suppressor genes, VHL, WT-1, p53, Hdm, PTEN, proteases, ubiquitin proteases, urokinase-type plasminogen activator (uPA) and uPA receptor (uPAR) system, cathepsins, metalloproteinases, esterases, hydrolases, separase, ion channels, potassium channels, sodium channels, molecular transporters, multi-drug resistance proteins, P-Gycoprotein, nucleoside transporters, transcription factors/DNA binding proteins, Ets, Elk, SMADs, Rel-A (p65-NFB), CREB, NFAT, ATF-2, AFT, Myc, Fos, Sp1, Egr-1, T-bet, β-catenin, HIFs, FOXOs, E2Fs, SRFs, TCFs, Egr-1, β-☐catenin, FOXO STAT1, STAT 3, STAT 4, STAT 5, STAT 6, p53, WT-1, HMGA, regulators of translation, pS6, 4EPB-1, eIF4E-binding protein, regulators of transcription, RNA polymerase, initiation factors, elongation factors. In some embodiments, the protein is S6.

In some embodiments, an epitope-recognizing fragment of an activation state antibody rather than the whole antibody is used. In some embodiments, the epitope-recognizing fragment is immobilized. In some embodiments, the antibody light chain that recognizes an epitope is used. A recombinant nucleic acid encoding a light chain gene product that recognizes an epitope may be used to produce such an antibody fragment by recombinant means well known in the art.

Non-activation state antibodies may also be used in the present invention. In some embodiments, non-activation state antibodies bind to epitopes in both activated and non-activated forms of an element. Such antibodies may be used to determine the amount of non-activated plus activated element in a sample. In some embodiments, non-activation state antibodies bind to epitopes present in non-activated forms of an element but absent in activated forms of an element. Such antibodies may be used to determine the amount of non-activated element in a sample. Both types of non-activation state antibodies may be used to determine if a change in the amount of activation state element, for example from samples before and after treatment with a candidate bioactive agent as described herein, coincide with changes in the amount of non-activation state element. For example, such antibodies can be used to determine whether an increase in activated element is due to activation of non-activation state element, or due to increased expression of the element, or both.

In some embodiments, antibodies are immobilized using beads analogous to those known and used for standardization in flow cytometry. Attachment of a multiplicity of activation state specific antibodies to beads may be done by methods known in the art and/or described herein. Such conjugated beads may be contacted with sample, preferably cell extract, under conditions that allow for a multiplicity of activated elements, if present, to bind to the multiplicity of immobilized antibodies. A second multiplicity of antibodies comprising non-activation state antibodies which are uniquely labeled may be added to the immobilized activation state specific antibody-activated element complex and the beads may be sorted by FACS on the basis of the presence of each label, wherein the presence of label indicates binding of corresponding second antibody and the presence of corresponding activated element.

In alternative embodiments of the instant invention, aromatic amino acids of protein binding elements may be replaced with D- or L-naphylalanine, D- or L-phenylglycine, D- or L-2-thieneylalanine, D- or L-1-, 2-, 3- or 4-pyreneylalanine, D- or L-3-thieneylalanine, D- or L-(2-pyridinyl)-alanine, D- or L-(3-pyridinyl)-alanine, D- or L-(2-pyrazinyl)-alanine, D- or L-(4-isopropyl)-phenylglycine, D-(trifluoromethyl)-phenylglycine, D-(trifluoromethyl)-phenylalanine, D-p-fluorophenylalanine, D- or L-p-biphenylphenylalanine, D- or L-p-methoxybiphenylphenylalanine, D- or L-2-indole(alkyl)alanines, and D- or L-alkylalanines where alkyl may be substituted or unsubstituted methyl, ethyl, propyl, hexyl, butyl, pentyl, isopropyl, iso-butyl, sec-isotyl, iso-pentyl, and non-acidic amino acids of C1-C20.

Acidic amino acids can be substituted with non-carboxylate amino acids while maintaining a negative charge, and derivatives or analogs thereof, such as the non-limiting examples of (phosphono)alanine, glycine, leucine, isoleucine, threonine, or serine; or sulfated (e.g., —SO3H) threonine, serine, or tyrosine.

Other substitutions may include non-natural hydroxylated amino acids may made by combining "alkyl" with any natural amino acid. The term "alkyl" as used herein refers to a branched or unbranched saturated hydrocarbon group of 1 to 24 carbon atoms, such as methyl, ethyl, n-propyl, isoptopyl, n-butyl, isobutyl, t-butyl, octyl, decyl, tetradecyl, hexadecyl, eicosyl, tetracisyl and the like. Alkyl includes heteroalkyl, with atoms of nitrogen, oxygen and sulfur. In some embodiments, alkyl groups herein contain 1 to 12 carbon atoms. Basic amino acids may be substituted with alkyl groups at any position of the naturally occurring amino acids lysine, arginine, ornithine, citrulline, or (guanidino)-acetic acid, or other (guanidino)alkyl-acetic acids, where "alkyl" is define as above. Nitrile derivatives (e.g., containing the CN-moiety in place of COOH) may also be substituted for asparagine or glutamine, and methionine sulfoxide may be substituted for methionine. Methods of preparation of such peptide derivatives are well known to one skilled in the art.

In addition, any amide linkage in any of the polypeptides may be replaced by a ketomethylene moiety. Such derivatives are expected to have the property of increased stability to degradation by enzymes, and therefore possess advantages for the formulation of compounds which may have increased in vivo half lives, as administered by oral, intravenous, intramuscular, intraperitoneal, topical, rectal, intraocular, or other routes.

Additional amino acid modifications of amino acids of variant polypeptides of to the present invention may include the following: Cysteinyl residues may be reacted with alphahaloacetates (and corresponding amines), such as 2-chloroacetic acid or chloroacetamide, to give carboxymethyl or carboxyamidomethyl derivatives. Cysteinyl residues may also be derivatized by reaction with compounds such as bromotrifluoroacetone, alpha-bromo-beta-(5-imidozoyl)propionic acid, chloroacetyl phosphate, N-alkylmaleimides, 3-nitro-2-pyridyl disulfide, methyl 2-pyridyl disulfide, p-chloromercuribenzoate, 2-chloromercuri-4-nitrophenol, or chloro-7-nitrobenzo-2-oxa-1,3-diazole.

Histidyl residues may be derivatized by reaction with compounds such as diethylprocarbonate e.g., at pH 5.5-7.0 because this agent is relatively specific for the histidyl side chain, and para-bromophenacyl bromide may also be used; e.g., where the reaction is preferably performed in 0.1M sodium cacodylate at pH 6.0.

Lysinyl and amino terminal residues may be reacted with compounds such as succinic or other carboxylic acid anhydrides. Derivatization with these agents is expected to have the effect of reversing the charge of the lysinyl residues.

Other suitable reagents for derivatizing alpha-amino-containing residues include compounds such as imidoesters, e.g., as methyl picolinimidate; pyridoxal phosphate; pyridoxal; chloroborohydride; trinitrobenzenesulfonic acid; O-methylisourea; 2,4 pentanedione; and transaminase-catalyzed reaction with glyoxylate. Arginyl residues may be modified by reaction with one or several conventional reagents, among them phenylglyoxal, 2,3-butanedione, 1,2-cyclohexanedione, and ninhydrin according to known method steps. Derivatization of arginine residues requires that the reaction be performed in alkaline conditions because of the high pKa of the guanidine functional group. Furthermore, these reagents may react with the groups of lysine as well as the arginine epsilon-amino group. The specific modification of tyrosyl residues per se is well known, such as for introducing spectral labels into tyrosyl residues by reaction with aromatic diazonium compounds or tetranitromethane.

N-acetylimidizol and tetranitromethane may be used to form O-acetyl tyrosyl species and 3-nitro derivatives, respectively. Carboxyl side groups (aspartyl or glutamyl) may be selectively modified by reaction with carbodiimides (R'—N—C—N—R') such as 1-cyclohexyl-3-(2-morpholiny-1-(4-ethyl) carbodiimide or 1-ethyl-3-(4-azonia-4,4-dimethylpentyl) carbodiimide. Furthermore aspartyl and glutamyl residues may be converted to asparaginyl and glutaminyl residues by reaction with ammonium ions.

Glutaminyl and asparaginyl residues may be frequently deamidated to the corresponding glutamyl and aspartyl residues. Alternatively, these residues may be deamidated under mildly acidic conditions. Either form of these residues falls within the scope of the present invention.

In some embodiments, the activation state-specific binding element is a peptide comprising a recognition structure that binds to a target structure on an activatable protein. A variety of recognition structures are well known in the art and can be made using methods known in the art, including by phage display libraries (see e.g., Gururaja et al. (2000) Chem. Biol. 7:515-27; Houimel et al., (2001) Eur. J. Immunol. 31:3535-45; Cochran et al. (2001) J. Am. Chem. Soc. 123:625-32; Houimel et al. (2001) Int. J. Cancer 92:748-55, each incorporated herein by reference). Further, fluorophores can be attached to such antibodies for use in the methods of the present invention.

A variety of recognitions structures are known in the art (e.g., Cochran et al., (2001) J. Am. Chem. Soc. 123:625-32; Boer et al., (2002) Blood 100:467-73, each expressly incorporated herein by reference)) and can be produced using methods known in the art (see e.g., Boer et al., (2002) Blood 100:467-73; Gualillo et al., (2002) Mol. Cell. Endocrinol. 190:83-9, each expressly incorporated herein by reference)), including for example combinatorial chemistry methods for producing recognition structures such as polymers with affinity for a target structure on an activatable protein (see e.g., Barn et al., (2001) J. Comb. Chem. 3:534-41; Ju et al., (1999) Biotechnol. 64:232-9, each expressly incorporated herein by reference). In another embodiment, the activation state-specific antibody is a protein that only binds to an isoform of a specific activatable protein that is phosphorylated and does not bind to the isoform of this activatable protein when it is not phosphorylated or non-phosphorylated. In another embodiment the activation state-specific antibody is a protein that only binds to an isoform of an activatable protein that is intracellular and not extracellular, or vice versa. In a some embodiment, the recognition structure is an anti-laminin single-chain antibody fragment (scFv) (see e.g., Sanz et al., (2002) Gene Therapy 9:1049-53; Tse et al., (2002) J. Mol. Biol. 317:85-94, each expressly incorporated herein by reference).

In some embodiments the binding element is a nucleic acid. The term "nucleic acid" include nucleic acid analogs, for example, phosphoramide (Beaucage et al., (1993) Tetrahedron 49(10):1925 and references therein; Letsinger, J. (1970) Org. Chem. 35:3800; Sprinzl et al., (1977) Eur. J. Biochem. 81:579; Letsinger et al., (1986) Nucl. Acids Res. 14:3487; Sawai et al, (1984) Chem. Lett. 805, Letsinger et al., (1988) J. Am. Chem. Soc. 110:4470; and Pauwels et al., (1986) Chemica Scripta 26:141-9), phosphorothioate (Mag et al., (1991) Nucleic Acids Res. 19:1437; and U.S. Pat. No. 5,644,048), phosphorodithioate (Briu et al., (1989) J. Am. Chem. Soc. 111:2321, O-methylphosphoroamidite linkages (see Eckstein, Oligonucleotides and Analogues: A Practical Approach, Oxford University Press), and peptide nucleic acid backbones and linkages (see Egholm, (1992) J. Am. Chem. Soc. 114:1895; Meier et al., (1992) Chem. Int. Ed. Engl. 31:1008; Nielsen, (1993) Nature, 365:566; Carlsson et al., (1996) Nature 380:207, all of which are incorporated by reference). Other analog nucleic acids include those with positive backbones (Denpcy et al., (1995) Proc. Natl. Acad. Sci. USA 92:6097; non-ionic backbones (U.S. Pat. Nos. 5,386,023, 5,637,684, 5,602,240, 5,216,141 and 4,469,863; Kiedrowshi et al., Angew. Chem. Intl. Ed. English 30:423 (1991); Letsinger et al., (1988) J. Am. Chem. Soc. 110:4470; Letsinger et al., (1994) Nucleoside & Nucleotide 13:1597; Chapters 2 and 3, ASC Symposium Series 580, "Carbohydrate Modifications in Antisense Research", Ed.Y. S. Sanghui and P. Dan Cook; Mesmaeker et al., (1994) Bioorganic &

Medicinal Chem. Lett. 4:395; Jeffs et al., (1994) J. Biomolecular NMR 34:17; Tetrahedron Lett. 37:743 (1996)) and non-ribose backbones, including those described in U.S. Pat. Nos. 5,235,033 and 5,034,506, and Chapters 6 and 7, ASC Symposium Series 580, "Carbohydrate Modifications in Antisense Research", Ed. Y. S. Sanghui and P. Dan Cook. Nucleic acids containing one or more carbocyclic sugars are also included within the definition of nucleic acids (see Jenkins et al., (1995) Chem. Soc. Rev. pp 169-176). Several nucleic acid analogs are described in Rawls, C & E News Jun. 2, 1997 page 35. All of these references are hereby expressly incorporated by reference. These modifications of the ribose-phosphate backbone may be done to facilitate the addition of additional moieties such as labels, or to increase the stability and half-life of such molecules in physiological environments.

As will be appreciated by those in the art, all of these nucleic acid analogs may find use in the present invention. In addition, mixtures of naturally occurring nucleic acids and analogs can be made. Alternatively, mixtures of different nucleic acid analogs, and mixtures of naturally occurring nucleic acids and analogs may be made. In some embodiments, peptide nucleic acids (PNA) which includes peptide nucleic acid analogs are used. These backbones are substantially non-ionic under neutral conditions, in contrast to the highly charged phosphodiester backbone of naturally occurring nucleic acids.

The nucleic acids may be single stranded or double stranded, as specified, or contain portions of both double stranded or single stranded sequence. The nucleic acid may be DNA, both genomic and cDNA, RNA or a hybrid, where the nucleic acid contains any combination of deoxyribo- and ribo-nucleotides, and any combination of bases, including uracil, adenine, thymine, cytosine, guanine, inosine, xathanine hypoxathanine, isocytosine, isoguanine, etc.

In some embodiments, the binding element is a synthetic compound. Any numbers of techniques are available for the random and directed synthesis of a wide variety of organic compounds and biomolecules, including expression of randomized oligonucleotides. See for example WO 94/24314, hereby expressly incorporated by reference, which discusses methods for generating new compounds, including random chemistry methods as well as enzymatic methods.

Alternatively, some embodiments utilize natural compounds, as binding elements, in the form of bacterial, fungal, plant and animal extracts that are available or readily produced.

Additionally, natural or synthetically produced compounds are readily modified through conventional chemical, physical and biochemical means. Known pharmacological agents may be subjected to directed or random chemical modifications, including enzymatic modifications, to produce binding elements that may be used in the instant invention.

In some embodiment the binding element is a small organic compound. Binding elements can be synthesized from a series of substrates that can be chemically modified. "Chemically modified" herein includes traditional chemical reactions as well as enzymatic reactions. These substrates generally include, but are not limited to, alkyl groups (including alkanes, alkenes, alkynes and heteroalkyl), aryl groups (including arenes and heteroaryl), alcohols, ethers, amines, aldehydes, ketones, acids, esters, amides, cyclic compounds, heterocyclic compounds (including purines, pyrimidines, benzodiazepins, beta-lactams, tetracylines, cephalosporins, and carbohydrates), steroids (including estrogens, androgens, cortisone, ecodysone, etc.), alkaloids (including ergots, vinca, curare, pyrollizdine, and mitomycines), organometallic compounds, hetero-atom bearing compounds, amino acids, and nucleosides. Chemical (including enzymatic) reactions may be done on the moieties to form new substrates or binding elements that can then be used in the present invention.

In some embodiments the binding element is a carbohydrate. As used herein the term carbohydrate is meant to include any compound with the general formula $(CH_2O)_n$. Examples of carbohydrates are di-, tri- and oligosaccharides, as well polysaccharides such as glycogen, cellulose, and starches.

In some embodiments the binding element is a lipid. As used herein the term lipid herein is meant to include any water insoluble organic molecule that is soluble in nonpolar organic solvents. Examples of lipids are steroids, such as cholesterol, and phospholipids such as sphingomeylin.

Examples of activatable elements, activation states and methods of determining the activation level of activatable elements are described in US publication number 20060073474 entitled "Methods and compositions for detecting the activation state of multiple proteins in single cells" and US publication number 20050112700 entitled "Methods and compositions for risk stratification" the content of which are incorporate here by reference.

A. Labels

The methods and compositions of the instant invention provide binding elements comprising a label or tag. By label is meant a molecule that can be directly (i.e., a primary label) or indirectly (i.e., a secondary label) detected; for example a label can be visualized and/or measured or otherwise identified so that its presence or absence can be known. A compound can be directly or indirectly conjugated to a label which provides a detectable signal, e.g. radioisotopes, fluorescers, enzymes, antibodies, particles such as magnetic particles, chemiluminescers, or specific binding molecules, etc. Specific binding molecules include pairs, such as biotin and streptavidin, digoxin and antidigoxin etc. Examples of labels include, but are not limited to, optical fluorescent and chromogenic dyes including labels, label enzymes and radioisotopes.

In some embodiments, one or more binding elements are uniquely label. Using the example of two activation state specific antibodies, by "uniquely labeled" is meant that a first activation state antibody recognizing a first activated element comprises a first label, and second activation state antibody recognizing a second activated element comprises a second label, wherein the first and second labels are detectable and distinguishable, making the first antibody and the second antibody uniquely labeled.

In general, labels fall into four classes: a) isotopic labels, which may be radioactive or heavy isotopes; b) magnetic, electrical, thermal labels; c) colored, optical labels including luminescent, phosphorous and fluorescent dyes or moieties; and d) binding partners. Labels can also include enzymes (horseradish peroxidase, etc.) and magnetic particles. In some embodiments, the detection label is a primary label. A primary label is one that can be directly detected, such as a fluorophore.

Labels include optical labels such as fluorescent dyes or moieties. Fluorophores can be either "small molecule" fluors, or proteinaceous fluors (e.g. green fluorescent proteins and all variants thereof).

Suitable fluorescent labels include, but are not limited to, fluorescein, rhodamine, tetramethylrhodamine, eosin, erythrosin, coumarin, methyl-coumarins, pyrene, Malacite green, stilbene, Lucifer Yellow, Cascade Blue™, Texas Red, IAEDANS, EDANS, BODIPY FL, LC Red 640, Cy 5, Cy 5.5, LC Red 705 and Oregon green. Suitable optical dyes are described in the 1996 Molecular Probes Handbook by Richard P. Haugland, hereby expressly incorporated by reference. Suitable fluorescent labels also include, but are not limited to, green fluorescent protein (GFP; Chalfie, et al., Science 263 (5148):802-805 (Feb. 11, 1994); and EGFP; Clontech—Genbank Accession Number U55762), blue fluorescent protein (BFP; 1. Quantum Biotechnologies, Inc. 1801 de Maisonneuve Blvd. West, 8th Floor, Montreal (Quebec) Canada H3H 1J9; 2. Stauber, R. H. Biotechniques 24(3):462-471 (1998); 3. Heim, R. and Tsien, R. Y. Curr. Biol. 6:178-182 (1996)), enhanced yellow fluorescent protein (EYFP; 1. Clontech Laboratories, Inc., 1020 East Meadow Circle, Palo Alto, Calif. 94303), luciferase (Ichiki, et al., J. Immunol. 150(12): 5408-5417 (1993)), .beta.-galactosidase (Nolan, et al., Proc Natl Acad Sci USA 85(8):2603-2607 (April 1988)) and Renilla WO 92/15673; WO 95/07463; WO 98/14605; WO 98/26277; WO 99/49019; U.S. Pat. Nos. 5,292,658; 5,418,155; 5,683,888; 5,741,668; 5,777,079; 5,804,387; 5,874,304; 5,876,995; and 5,925,558). All of the above-cited references are expressly incorporated herein by reference.

In some embodiments, labels for use in the present invention include: Alexa-Fluor dyes (Alexa Fluor 350, Alexa Fluor 430, Alexa Fluor 488, Alexa Fluor 546, Alexa Fluor 568, Alexa Fluor 594, Alexa Fluor 633, Alexa Fluor 660, Alexa Fluor 680), Cascade Blue, Cascade Yellow and R-phycoerythrin (PE) (Molecular Probes) (Eugene, Oreg.), FITC, Rhodamine, and Texas Red (Pierce, Rockford, Ill.), Cy5, Cy5.5, Cy7 (Amersham Life Science, Pittsburgh, Pa.). Tandem conjugate protocols for Cy5PE, Cy5.5PE, Cy7PE, Cy5.5APC, Cy7APC are known in the art. Quantitation of fluorescent probe conjugation may be assessed to determine degree of labeling and protocols including dye spectral properties are also well known in the art. In some embodiments the fluorescent label is conjugated to an aminodextran linker which is conjugated to a binding element or antibody. Additional labels listed in and are available through the on-line and hard copy catalogues of BD Biosciences, Beckman Coulter, AnaSpec, Invitrogen, Cell Signaling Technology, Millipore, eBioscience, Caltag, Santa Cruz Biotech, Abcam and Sigma, the contents of which are incorporated herein by reference.

In some embodiments, the fluorescent label is a GFP and, more preferably, a Renilla, Ptilosarcus, or Aequorea species of GFP.

In some embodiments, a secondary detectable label is used. A secondary label is one that is indirectly detected; for example, a secondary label can bind or react with a primary label for detection, can act on an additional product to generate a primary label (e.g. enzymes), etc. Secondary labels include, but are not limited to, one of a binding partner pair; chemically modifiable moieties; nuclease inhibitors, enzymes such as horseradish peroxidase, alkaline phosphatases, luciferases, etc.

In some embodiments, the secondary label is a binding partner pair. For example, the label may be a hapten or antigen, which will bind its binding partner. For example, suitable binding partner pairs include, but are not limited to: antigens (such as proteins (including peptides) and small molecules) and antibodies (including fragments thereof (FAbs, etc.)); proteins and small molecules, including biotin/streptavidin; enzymes and substrates or inhibitors; other protein-protein interacting pairs; receptor-ligands; and carbohydrates and their binding partners. Nucleic acid-nucleic acid binding proteins pairs are also useful. Binding partner pairs include, but are not limited to, biotin (or imino-biotin) and streptavidin, digeoxinin and Abs, and Prolinx™ reagents.

In some embodiments, the binding partner pair comprises an antigen and an antibody that will specifically bind to the antigen. By "specifically bind" herein is meant that the partners bind with specificity sufficient to differentiate between the pair and other components or contaminants of the system. The binding should be sufficient to remain bound under the conditions of the assay, including wash steps to remove non-specific binding. In some embodiments, the dissociation constants of the pair will be less than about $10^{-4}$ to $10^{-9}$ $M^{-1}$, with less than about $10^{-5}$ to $10^{-9}$ $M^{-1}$ being preferred and less than about $10^{-7}$ to $10^{-9}$ $M^{-1}$ being particularly preferred.

In some embodiment, the secondary label is a chemically modifiable moiety. In this embodiment, labels comprising reactive functional groups are incorporated into the molecule to be labeled. The functional group can then be subsequently labeled (e.g. either before or after the assay) with a primary label. Suitable functional groups include, but are not limited to, amino groups, carboxy groups, maleimide groups, oxo groups and thiol groups, with amino groups and thiol groups being particularly preferred. For example, primary labels containing amino groups can be attached to secondary labels comprising amino groups, for example using linkers as are known in the art; for example, homo-or hetero-bifunctional linkers are well known (see 1994 Pierce Chemical Company catalog, technical section on cross-linkers, pages 155-200, incorporated herein by reference).

In some embodiments, multiple fluorescent labels are employed in the methods and compositions of the present invention. In some embodiments, each lable is distinct and distinguishable from other labels.

As will be appreciated in the art antibody-label conjugation may be performed using standard procedures or by using protein-protein/protein-dye cross-linking kits from Molecular Probes (Eugene, Oreg.).

In some embodiments, labeled antibodies are used for functional analysis of activatable proteins in cells. In performing such analysis several areas of the experiment are considered: (1) identification of the proper combination of antibody cocktails for the stains (2), identification of the sequential procedure for the staining using the antigens (i.e., the activatable protein) and antibody clones of interest, and (3) thorough evaluation of cell culture conditions' effect on cell stimulation. Antigen clone selection is of particular importance for surface antigens of human cells, as different antibody clones yield different result and do not stain similarly in different protocols. Selection of cell types and optimization of culture conditions is also a critical component in detecting differences. For example, some cell lines have the ability to adapt to culture conditions and can yield heterogeneous responses.

In some embodiments, activation state-specific antibodies are labeled with quantum dots as disclosed by Chattopadhyay, P. K. et al. Quantum dot semiconductor nanocrystals for immunophenotyping by polychromatic flow cytometry. Nat. Med. 12, 972-977 (2006). Quantum dot labels are commercially available through Invitrogen, http://probes.invitrogen.com/products/qdot/.

Quantum dot labeled antibodies can be used alone or they can be employed in conjunction with organic fluorochrome-conjugated antibodies to increase the total number of labels available. As the number of labeled antibodies increase so does the ability for subtyping known cell populations. Additionally, activation state-specific antibodies can be labeled using chelated or caged lanthanides as disclosed by Erkki, J. et al. Lanthanide chelates as new fluorochrome labels for cytochemistry. J. Histochemistry Cytochemistry, 36:1449-1451, 1988, and U.S. Pat. No. 7,018,850, entitled Salicylamide-Lanthanide Complexes for Use as Luminescent Markers. Other methods of detecting fluorescence may also be used, e.g., Quantum dot methods (see, e.g., Goldman et al., J. Am. Chem. Soc. (2002) 124:6378-82; Pathak et al. J. Am. Chem. Soc. (2001) 123:4103-4; and Remade et al., Proc. Natl. Sci. USA (2000) 18:553-8, each expressly incorporated herein by reference) as well as confocal microscopy.

In some embodiments, the activatable elements are labeled with tags suitable for Inductively Coupled Plasma Mass Spectrometer (ICP-MS) as disclosed in Tanner et al. Spectrochimica Acta Part B: Atomic Spectroscopy, 2007 March; 62(3):188-195; Ornatsky et al, mRNA Detection in Leukemia Cell lines by Novel Metal-Tagged in situ Hybridization using Inductively Coupled Plasma Mass Spectometry, Translational Oncogenomics (2006):1, 1-9; Ornatsky et al, Multiple Cellular Antigen Detection by ICP-MS, J. 1 mm. Methods 308 (2006) 68-76; and Lou et al., Polymer-Based Elemental Tags for Sensitive Bioassays, Angew. Chem. Int. Ed., (2007) 46, 6111-6114.

Alternatively, detection systems based on FRET, discussed in detail below, may be used. FRET finds use in the instant invention, for example, in detecting activation states that involve clustering or multimerization wherein the proximity of two FRET labels is altered due to activation. In some embodiments, at least two fluorescent labels are used which are members of a fluorescence resonance energy transfer (FRET) pair.

FRET is phenomenon known in the art wherein excitation of one fluorescent dye is transferred to another without emission of a photon. A FRET pair consists of a donor fluorophore and an acceptor fluorophore. The fluorescence emission spectrum of the donor and the fluorescence absorption spectrum of the acceptor must overlap, and the two molecules must be in close proximity. The distance between donor and acceptor at which 50% of donors are deactivated (transfer energy to the acceptor) is defined by the Forster radius (Ro), which is typically 10-100 Å. Changes in the fluorescence emission spectrum comprising FRET pairs can be detected, indicating changes in the number of that are in close proximity (i.e., within 100 521 of each other). This will typically result from the binding or dissociation of two molecules, one of which is labeled with a FRET donor and the other of which is labeled with a FRET acceptor, wherein such binding brings the FRET pair in close proximity. Binding of such molecules will result in an increased fluorescence emission of the acceptor and/or quenching of the fluorescence emission of the donor.

FRET pairs (donor/acceptor) useful in the invention include, but are not limited to, EDANS/fluorescein, IAEDANS/fluorescein, fluorescein/tetramethylrhodamine, fluorescein/LC Red 640, fluorescein/Cy 5, fluorescein/Cy 5.5 and fluorescein/LC Red 705.

In some embodiments when FRET is used, a fluorescent donor molecule and a non-fluorescent acceptor molecule ("quencher") may be employed. In this application, fluorescent emission of the donor will increase when quencher is displaced from close proximity to the donor and fluorescent emission will decrease when the quencher is brought into close proximity to the donor. Useful quenchers include, but are not limited to, TAMRA, DABCYL, QSY 7 and QSY 33. Useful fluorescent donor/quencher pairs include, but are not limited to EDANS/DABCYL, Texas Red/DABCYL, BODIPY/DABCYL, Lucifer yellow/DABCYL, coumarin/DABCYL and fluorescein/QSY 7 dye.

The skilled artisan will appreciate that FRET and fluorescence quenching allow for monitoring of binding of labeled molecules over time, providing continuous information regarding the time course of binding reactions.

Preferably, changes in the degree of FRET are determined as a function of the change in the ratio of the amount of fluorescence from the donor and acceptor moieties, a process referred to as "ratioing." Changes in the absolute amount of substrate, excitation intensity, and turbidity or other background absorbances in the sample at the excitation wavelength affect the intensities of fluorescence from both the donor and acceptor approximately in parallel. Therefore the ratio of the two emission intensities is a more robust and preferred measure of cleavage than either intensity alone.

The ratio-metric fluorescent reporter system described herein has significant advantages over existing reporters for protein integration analysis, as it allows sensitive detection and isolation of both expressing and non-expressing single living cells. In some embodiments, the assay system uses a non-toxic, non-polar fluorescent substrate that is easily loaded and then trapped intracellularly. Modification of the fluorescent substrate by a cognate protein yields a fluorescent emission shift as substrate is converted to product. Because the reporter readout is ratiometric it is unique among reporter protein assays in that it controls for variables such as the amount of substrate loaded into individual cells. The stable, easily detected, intracellular readout eliminates the need for establishing clonal cell lines prior to expression analysis. This system and other analogous flow sorting systems can be used to isolate cells having a particular receptor element clustering and/or activation profile from pools of millions of viable cells.

The methods and composition of the present invention may also make use of label enzymes. By label enzyme is meant an enzyme that may be reacted in the presence of a label enzyme substrate that produces a detectable product. Suitable label enzymes for use in the present invention include but are not limited to, horseradish peroxidase, alkaline phosphatase and glucose oxidase. Methods for the use of such substrates are well known in the art. The presence of the label enzyme is generally revealed through the enzyme's catalysis of a reaction with a label enzyme substrate, producing an identifiable product. Such products may be opaque, such as the reaction of horseradish peroxidase with tetramethyl benzedine, and may have a variety of colors. Other label enzyme substrates, such as Luminol (available from Pierce Chemical Co.), have been developed that produce fluorescent reaction products. Methods for identifying label enzymes with label enzyme substrates are well known in the art and many commercial kits are available. Examples and methods for the use of various label enzymes are described in Savage et al., Previews 247:6-9 (1998), Young, J. Virol. Methods 24:227-236 (1989), which are each hereby incorporated by reference in their entirety.

By radioisotope is meant any radioactive molecule. Suitable radioisotopes for use in the invention include, but are not limited to $^{14}C$, $^{3}H$, $^{32}P$, $^{33}P$, $^{35}S$, $^{125}I$, and $^{131}I$. The use of radioisotopes as labels is well known in the art.

As mentioned, labels may be indirectly detected, that is, the tag is a partner of a binding pair. By "partner of a binding pair" is meant one of a first and a second moiety, wherein the first and the second moiety have a specific binding affinity for each other. Suitable binding pairs for use in the invention include, but are not limited to, antigens/antibodies (for example, digoxigenin/anti-digoxigenin, dinitrophenyl (DNP)/anti-DNP, dansyl-X-anti-dansyl, Fluorescein/anti-fluorescein, lucifer yellow/anti-lucifer yellow, and rhodamine anti-rhodamine), biotin/avidin (or biotin/streptavidin) and calmodulin binding protein (CBP)/calmodulin. Other suitable binding pairs include polypeptides such as the FLAG-peptide [Hopp et al., BioTechnology, 6:1204-1210 (1988)]; the KT3 epitope peptide [Martin et al., Science, 255: 192-194 (1992)]; tubulin epitope peptide [Skinner et al., J. Biol. Chem., 266:

15163-15166 (1991)]; and the T7 gene 10 protein peptide tag [Lutz-Freyermuth et al., Proc. Natl. Acad. Sci. USA, 87:6393-6397 (1990)] and the antibodies each thereto. As will be appreciated by those in the art, binding pair partners may be used in applications other than for labeling, as is described herein.

As will be appreciated by those in the art, a partner of one binding pair may also be a partner of another binding pair. For example, an antigen (first moiety) may bind to a first antibody (second moiety) that may, in turn, be an antigen for a second antibody (third moiety). It will be further appreciated that such a circumstance allows indirect binding of a first moiety and a third moiety via an intermediary second moiety that is a binding pair partner to each.

As will be appreciated by those in the art, a partner of a binding pair may comprise a label, as described above. It will further be appreciated that this allows for a tag to be indirectly labeled upon the binding of a binding partner comprising a label. Attaching a label to a tag that is a partner of a binding pair, as just described, is referred to herein as "indirect labeling".

By "surface substrate binding molecule" or "attachment tag" and grammatical equivalents thereof is meant a molecule have binding affinity for a specific surface substrate, which substrate is generally a member of a binding pair applied, incorporated or otherwise attached to a surface. Suitable surface substrate binding molecules and their surface substrates include, but are not limited to poly-histidine (poly-his) or poly-histidine-glycine (poly-his-gly) tags and Nickel substrate; the Glutathione-S Transferase tag and its antibody substrate (available from Pierce Chemical); the flu HA tag polypeptide and its antibody 12CA5 substrate [Field et al., Mol. Cell. Biol., 8:2159-2165 (1988)]; the c-myc tag and the 8F9, 3C7, 6E10, G4, B7 and 9E10 antibody substrates thereto [Evan et al., Molecular and Cellular Biology, 5:3610-3616 (1985)]; and the Herpes Simplex virus glycoprotein D (gD) tag and its antibody substrate [Paborsky et al., Protein Engineering, 3(6):547-553 (1990)]. In general, surface binding substrate molecules useful in the present invention include, but are not limited to, polyhistidine structures (His-tags) that bind nickel substrates, antigens that bind to surface substrates comprising antibody, haptens that bind to avidin substrate (e.g., biotin) and CBP that binds to surface substrate comprising calmodulin.

Production of antibody-embedded substrates is well known; see Slinkin et al., Bioconj. Chem., 2:342-348 (1991); Torchilin et al., supra; Trubetskoy et al., Bioconj. Chem. 3:323-327 (1992); King et al., Cancer Res. 54:6176-6185 (1994); and Wilbur et al., Bioconjugate Chem. 5:220-235 (1994) (all of which are hereby expressly incorporated by reference), and attachment of or production of proteins with antigens is described above. Calmodulin-embedded substrates are commercially available, and production of proteins with CBP is described in Simcox et al., Strategies 8:40-43 (1995), which is hereby incorporated by reference in its entirety.

As will be appreciated by those in the art, tag-components of the invention can be made in various ways, depending largely upon the form of the tag. Components of the invention and tags are preferably attached by a covalent bond.

The production of tag-polypeptides by recombinant means when the tag is also a polypeptide is described below. Production of tag-labeled proteins is well known in the art and kits for such production are commercially available (for example, from Kodak and Sigma). Examples of tag labeled proteins include, but are not limited to, a Flag-polypeptide and His-polypeptide. Methods for the production and use of tag-labeled proteins are found, for example, in Winston et al., Genes and Devel. 13:270-283 (1999), incorporated herein in its entirety, as well as product handbooks provided with the above-mentioned kits.

Biotinylation of target molecules and substrates is well known, for example, a large number of biotinylation agents are known, including amine-reactive and thiol-reactive agents, for the biotinylation of proteins, nucleic acids, carbohydrates, carboxylic acids; see chapter 4, Molecular Probes Catalog, Haugland, 6th Ed. 1996, hereby incorporated by reference. A biotinylated substrate can be attached to a biotinylated component via avidin or streptavidin. Similarly, a large number of haptenylation reagents are also known (Id.).

Methods for labeling of proteins with radioisotopes are known in the art. For example, such methods are found in Ohta et al., (1999) Molec. Cell 3:535-541, which is hereby incorporated by reference in its entirety.

Production of proteins having tags by recombinant means is well known, and kits for producing such proteins are commercially available. For example, such a kit and its use are described in the QIAexpress Handbook from Qiagen by Joanne Crowe et al., hereby expressly incorporated by reference.

The functionalization of labels with chemically reactive groups such as thiols, amines, carboxyls, etc. is generally known in the art. In some embodiments, the tag is functionalized to facilitate covalent attachment. The covalent attachment of the tag may be either direct or via a linker. In one embodiment, the linker is a relatively short coupling moiety, which is used to attach the molecules. A coupling moiety may be synthesized directly onto a component of the invention and contains at least one functional group to facilitate attachment of the tag. Alternatively, the coupling moiety may have at least two functional groups, which are used to attach a functionalized component to a functionalized tag, for example. In an additional embodiment, the linker is a polymer. In this embodiment, covalent attachment is accomplished either directly, or through the use of coupling moieties from the component or tag to the polymer. In some embodiments, the covalent attachment is direct, that is, no linker is used. In this embodiment, the component preferably contains a functional group such as a carboxylic acid that is used for direct attachment to the functionalized tag. It should be understood that the component and tag may be attached in a variety of ways, including those listed above. In some embodiments, the tag is attached to the amino or carboxy terminus of the polypeptide. As will be appreciated by those in the art, the above description of the covalent attachment of a label applies to the attachment of virtually any two molecules of the present disclosure.

In some embodiments, the tag is functionalized to facilitate covalent attachment, as is generally outlined above. Thus, a wide variety of tags are commercially available which contain functional groups, including, but not limited to, isothiocyanate groups, amino groups, haloacetyl groups, maleimides, succinimidyl esters, and sulfonyl halides, all of which may be used to covalently attach the tag to a second molecule, as is described herein. The choice of the functional group of the tag will depend on the site of attachment to either a linker, as outlined above or a component of the invention. Thus, for example, for direct linkage to a carboxylic acid group of a protein, amino modified or hydrazine modified tags will be used for coupling via carbodiimide chemistry, for example using 1-ethyl-3-(3-dimethylaminopropyl)-carbodiimi-de (EDAC) as is known in the art (see Set 9 and Set 11 of the Molecular Probes Catalog, supra; see also the Pierce 1994 Catalog and Handbook, pages T-155 to T-200, both of which are hereby incorporated by reference). In one embodiment, the carbodiimide is first attached to the tag, such as is commercially available for many of the tags described herein.

Alternative Activation State Indicators

An alternative activation state indicator useful with the instant invention is one that allows for the detection of activation by indicating the result of such activation. For example, phosphorylation of a substrate can be used to detect the activation of the kinase responsible for phosphorylating that substrate. Similarly, cleavage of a substrate can be used as an indicator of the activation of a protease responsible for such cleavage. Methods are well known in the art that allow coupling of such indications to detectable signals, such as the labels and tags described above in connection with binding elements. For example, cleavage of a substrate can result in the removal of a quenching moiety and thus allowing for a detectable signal being produced from a previously quenched label.

Modulators

In some embodiments, the methods and composition utilize a modulator. A modulator can be an activator, an inhibitor or a compound capable of impacting a cellular pathway. Modulators can take the form of environmental cues and inputs.

Modulation can be performed in a variety of environments. In some embodiments, cells are exposed to a modulator immediately after collection. In some embodiments where there is a mixed population of cells, purification of cells is performed after modulation. In some embodiments, whole blood is collected to which a modulator is added. In some embodiments, cells are modulated after processing for single cells or purified fractions of single cells. As an illustrative example, whole blood can be collected and processed for an enriched fraction of lymphocytes that is then exposed to a modulator. Modulation can include exposing cells to more than one modulator. For instance, in some embodiments, cells are exposed to at least 2, 3, 4, 5, 6, 7, 8, 9, or 10 modulators.

In some embodiments, cells are cultured post collection in a suitable media before exposure to a modulator. In some embodiments, the media is a growth media. In some embodiments, the growth media is a complex media that may include serum. In some embodiments, the growth media comprises serum. In some embodiments, the serum is selected from the group consisting of fetal bovine serum, bovine serum, human serum, porcine serum, horse serum, and goat serum. In some embodiments, the serum level ranges from 0.0001% to 30%. In some embodiments any suitable amount of serum is used. In some embodiments, the growth media is a chemically defined minimal media and is without serum. In some embodiments, cells are cultured in a differentiating media.

Modulators include chemical and biological entities, and physical or environmental stimuli. Modulators can act extracellularly or intracellularly. Chemical and biological modulators include growth factors, cytokines, neurotransmitters, adhesion molecules, hormones, small molecules, inorganic compounds, polynucleotides, antibodies, natural compounds, lectins, lactones, chemotherapeutic agents, biological response modifiers, carbohydrate, proteases and free radicals. Modulators include complex and undefined biologic compositions that may comprise cellular or botanical extracts, cellular or glandular secretions, physiologic fluids such as serum, amniotic fluid, or venom. Physical and environmental stimuli include electromagnetic, ultraviolet, infrared or particulate radiation, redox potential and pH, the presence or absences of nutrients, changes in temperature, changes in oxygen partial pressure, changes in ion concentrations and the application of oxidative stress. Modulators can be endogenous or exogenous and may produce different effects depending on the concentration and duration of exposure to the single cells or whether they are used in combination or sequentially with other modulators. Modulators can act directly on the activatable elements or indirectly through the interaction with one or more intermediary biomolecule. Indirect modulation includes alterations of gene expression wherein the expressed gene product is the activatable element or is a modulator of the activatable element.

In some embodiments, modulators produce different activation states depending on the concentration of the modulator, duration of exposure or whether they are used in combination or sequentially with other modulators.

In some embodiments the modulator is selected from the group consisting of growth factor, cytokine, adhesion molecule modulator, drugs, hormone, small molecule, polynucleotide, antibodies, natural compounds, lactones, chemotherapeutic agents, immune modulator, carbohydrate, proteases, ions, reactive oxygen species, peptides, and protein fragments, either alone or in the context of cells, cells themselves, viruses, and biological and non-biological complexes (e.g. beads, plates, viral envelopes, antigen presentation molecules such as major histocompatibility complex). In some embodiments, the modulator is a physical stimuli such as heat, cold, UV radiation, and radiation. Examples of modulators, include but are not limited to, F(ab)2 IgM, Rituxan, Alemtuzumab, anti CD22 (epratuzumab), anti-CD23 (lumiliximab), Campath, $H_2O_2$, PMA, BAFF, April, SDFla, CD40L, IGF-1, Imiquimod, polyCpG, fludarabine, cyclophosphamide, chlorambucil, IL-7, IL-6, IL-10, IL-27, IL-4, IL-2, IL-3, and thapsigargin.

In some embodiments, the modulator is an activator. In some embodiments the modulator is an inhibitor. In some embodiments, cells are exposed to one or more modulator. In some embodiments, cells are exposed to at least 2, 3, 4, 5, 6, 7, 8, 9, or 10 modulators. In some embodiments, cells are exposed to at least two modulators, wherein one modulator is an activator and one modulator is an inhibitor. In some embodiments, cells are exposed to at least 2, 3, 4, 5, 6, 7, 8, 9, or 10 modulators, where at least one of the modulators is an inhibitor.

In some embodiments, the modulator is a B cell receptor modulator. In some embodiments, the B cell receptor modulator is a B cell receptor activator. An example of B cell receptor activator is a cross-linker of the B cell receptor complex or the B-cell co-receptor complex. In some embodiments, cross-linker is an antibody or molecular binding entity. In some embodiments, the cross-linker is an antibody. In some embodiments, the antibody is a multivalent antibody. In some embodiments, the antibody is a monovalent, bivalent, or multivalent antibody made more multivalent by attachment to a solid surface or tethered on a nanoparticle surface to increase the local valency of the epitope binding domain.

In some embodiments, the cross-linker is a molecular binding entity. In some embodiments, the molecular binding entity acts upon or binds the B cell receptor complex via carbohydrates or an epitope in the complex. In some embodiments, the molecular is a monovalent, bivalent, or multivalent is made more multivalent by attachment to a solid surface or tethered on a nanoparticle surface to increase the local valency of the epitope binding domain.

In some embodiments, the cross-linking of the B cell receptor complex or the B-cell co-receptor complex comprises binding of an antibody or molecular binding entity to the cell and then causing its crosslinking via interaction of the cell with a solid surface that causes crosslinking of the BCR complex via antibody or molecular binding entity.

In some embodiments, the crosslinker is F(ab)2 IgM, IgG, IgD, polyclonal BCR antibodies, monoclonal BCR antibodies, Fc receptor derived binding elements and/or a combination thereof. The Ig can be derived from a species selected from the group consisting of mouse, goat, rabbit, pig, rat, horse, cow, shark, chicken, or llama. In some embodiments, the crosslinker is F(ab)2 IgM, Polyclonal IgM antibodies, Monoclonal IgM antibodies, Biotinylated F(ab)2 IgCM, Biotinylated Polyclonal IgM antibodies, Biotinylated Monoclonal IgM antibodies and/or combination thereof.

In some embodiments, the inhibitor is an inhibitor of a cellular factor or a plurality of factors that participates in a cellular pathway (e.g. signaling cascade) in the cell. In some embodiments, the inhibitor is a kinase or phosphatase inhibitor. Examples of kinase inhibitors include adaphostin, AG 490, AG 825, AG 957, AG 1024, aloisine, aloisine A, alsterpaullone, aminogenistein, API-2, apigenin, arctigenin, AY-22989, BAY 61-3606, bisindolylmaleimide IX, chelerythrine, 10-[4'-(N,N-Diethylamino)butyl]-2-chlorophenoxazine hydrochloride, dasatinib, 2-Dimethylamino-4,5,6,7-tetrabromo-1H-benzimidazole, 5,7-Dimethoxy-3-(4-pyridinyl)quinoline dihydrochloride, edelfosine, ellagic acid, enzastaurin, ER 27319 maleate, erlotinib, ET18OCH3, fasudil, flavopiridol, gefitinib, GW 5074, H-7, H-8, H-89, HA-100, HA-1004, HA-1077, HA-1100, hydroxyfasudil, indirubin-3'-oxime, 5-Iodotubercidin, kenpaullone, KN-62, KY12420, LFM-A13, lavendustin A, luteolin, LY-294002, LY294002, mallotoxin, ML-9, NSC-154020, NSC-226080, NSC-231634, NSC-664704, NSC-680410, NU6102, olomoucine, oxindole I, PD-153035, PD-98059, PD 169316, phloretin, phloridzin, piceatannol, picropodophyllin, PK1, PP1, PP2, purvalanol A, quercetin, R406, R788, rapamune, rapamycin, Ro 31-8220, roscovitine, rottlerin, SB202190, SB203580, sirolimus, sorafenib, SL327, SP600125, staurosporine, STI-571, SU-11274, SU1498, SU4312, SU6656, 4,5,6,7-Tetrabromotriazole, TG101348, Triciribine, Tyrphostin AG 490, Tyrphostin AG 825, Tyrphostin AG 957, Tyrphostin AG 1024, Tyrphostin SU1498, U0126, VX-509, VX-667, VX-680, W-7, wortmannin, XL-019, XL-147, XL-184, XL-228, XL-281, XL-518, XL-647, XL-765, XL-820, XL-844, XL-880, Y-27632, ZD-1839, ZM-252868, ZM-447439, siRNA, miRNA Examples of phosphatase inhibitors include, but are not limited to $H_2O_2$, siRNA, miRNA, Cantharidin, (−)-p-Bromotetramisole, Microcystin LR, Sodium Orthovanadate, Sodium Pervanadate, Vanadyl sulfate, Sodium oxodiperoxo(1,10-phenanthroline)vanadate, bis(maltolato)oxovanadium(IV), Sodium Molybdate, Sodium Perm olybdate, Sodium Tartrate, Imidazole, Sodium Fluoride, β-Glycerophosphate, Sodium Pyrophosphate Decahydrate, Calyculin A, Discodermia calyx, bpV(phen), mpV(pic), DMHV, Cypermethrin, Dephostatin, Okadaic Acid, NIPP-1, N-(9,10-Dioxo-9,10-dihydro-phenanthren-2-yl)-2,2-dimethyl-propionamide, α-Bromo-4-hydroxyacetophenone, 4-Hydroxyphenacyl Br, α-Bromo-4-methoxyacetophenone, 4-Methoxyphenacyl Br, α-Bromo-4-(carboxymethoxy)acetophenone, 4-(Carboxymethoxy)phenacyl Br, and bis(4-Trifluoromethylsulfonamidophenyl)-1,4-diisopropylbenzene, phenyarsine oxide, Pyrrolidine Dithiocarbamate, and Aluminum fluoride. In some embodiments, the phosphatase inhibitor is $H_2O_2$.

In some embodiments $H_2O_2$ is administered as an inhibitor. In some embodiments $H_2O_2$ is administered at between 0.01 and 50 mM. In some embodiments $H_2O_2$ is administered at between 0.1 and 10 mM. In some embodiments $H_2O_2$ is administered at between 1 and 10 mM. In some embodiments $H_2O_2$ is administered at between 1 and 5 mM. In some embodiments $H_2O_2$ is administered at 0.5, 1, 1.5, 2, 2.5, 3, 3.5, 4, 4.5, 5, 5.5, 6, 6.5, 7, 7.5, 8, 8.5, 9, 9.5 or 10 mM. In certain embodiments, $H_2O_2$ is administered at 3.0 mM. In certain embodiments, $H_2O_2$ is administered at 3.3 mM. In some embodiments the duration of exposure of $H_2O_2$ is between 0.01 and 360 minutes. In some embodiments the duration of exposure of $H_2O_2$ is between 0.1 and 240 minutes. In some embodiments the duration of exposure of $H_2O_2$ is between 0.5 and 180 minutes. In some embodiments the duration of exposure of $H_2O_2$ is between 0 and 120 minutes. In some embodiments the duration of exposure to $H_2O_2$ is between 5 and 15 minutes. In some embodiments the duration of exposure of $H_2O_2$ is 1, 2, 3, 4, 5, 10, 15, 20, 25, 30, 35, 40, 45, 50, 55, 60, 70, 80, 90, 100, 110, 120, 140, 160 or 180 minutes. In some embodiments the duration of exposure of $H_2O_2$ is 10 minutes. In some embodiments $H_2O_2$ is administered as an inhibitor with at least one other modulator. In some embodiments $H_2O_2$ is administered as an inhibitor with F(ab)2 IgM or any suitable BCR agonist. In some embodiments $H_2O_2$ is administered before administration of F(ab)2 IgM. In some embodiments $H_2O_2$ is administered simultaneously with F(ab)2 IgM. In some embodiments $H_2O_2$ is administered after F(ab)2 IgM.

In some embodiments, the activation level of an activatable element in a cell is determined after contacting the cell with at least 2, 3, 4, 5, 6, 7, 8, 9, or 10 modulators. In some embodiments, the activation level of an activatable element in a cell is determined after contacting the cell with at least 2, 3, 4, 5, 6, 7, 8, 9, or 10 modulators where at least one of the modulators is an inhibitor. In some embodiments, the activation level of an activatable element in a cell is determined after contacting the cell with an inhibitor and a modulator, where the modulator can be an inhibitor or an activator. In some embodiments, the activation level of an activatable element in a cell is determined after contacting the cell with an inhibitor and an activator. In some embodiments, the activation level of an activatable element in a cell is determined after contacting the cell with two or more modulators.

In some embodiments, a phenotypic profile of a population of cells is determined by measuring the activation level of an activatable element when the population of cells is exposed to a plurality of modulators in separate cultures. In some embodiments, the modulators include F(ab)2 IgM, Rituxan, Alemtuzumab, anti CD22 (epratuzumab), anti-CD23 (lumiliximab), Campath, $H_2O_2$, PMA, BAFF, April, SDF1a, CD40L, IGF-1, Imiquimod, polyCpG, fludarabine, cyclophosphamide, chlorambucil, IL-7, IL-6, IL-10, IL-27, IL-4, IL-2, IL-3, thapsigardin and/or a combination thereof. For instance a population of cells can be exposed to one or more, all or a combination of the following combination of modulators: (i) F(ab)2 IgM; (ii) Rituxan,; (iii) Campath; (iv) $H_2O_2$; (v) PMA; (vi) BAFF; (vii) April; (viii) SDF1a; (ix) CD40L; (x) IGF-1; (xi) Imiquimod; (xii) polyCpG; (xiii) fludarabine; (xiv) cyclophosphamide;(xv) chlorambucil; IL-7; (xvi) IL-6; (xvii)IL-10; (xviii) IL-27; (xx) IL-4; (xx) IL-2; (xxi) IL-3; (xxii) Alemtuzumab, (xxiii) anti CD22 (epratuzumab), (xxiv) anti-CD23 (lumiliximab), (xxv) thapsigargin; and (xxvi) F(ab)2 IgM and $H_2O_2$. In some embodiments, the phenotypic profile of the population of cells is used to classify the population as described herein.

Detection

In practicing the methods of this invention, the detection of the status of the one or more activatable elements can be carried out by a person, such as a technician in the laboratory. Alternatively, the detection of the status of the one or more activatable elements can be carried out using automated systems. In either case, the detection of the status of the one or more activatable elements for use according to the methods of this invention is performed according to standard techniques and protocols well-established in the art.

One or more activatable elements can be detected and/or quantified by any method that detect and/or quantitates the presence of the activatable element of interest. Such methods may include radioimmunoassay (RIA) or enzyme linked immunoabsorbance assay (ELISA), immunohistochemistry, immunofluorescent histochemistry with or without confocal microscopy, reversed phase assays, homogeneous enzyme immunoassays, and related non-enzymatic techniques, Western blots, whole cell staining, immunoelectronmicroscopy, nucleic acid amplification, gene array, protein array, mass spectrometry, patch clamp, 2-dimensional gel electrophoresis, differential display gel electrophoresis, microsphere-based multiplex protein assays, label-free cellular assays and flow cytometry, etc. U.S. Pat. No. 4,568,649 describes ligand detection systems, which employ scintillation counting. These techniques are particularly useful for modified protein parameters. Cell readouts for proteins and other cell determinants can be obtained using fluorescent or otherwise tagged reporter molecules. Flow cytometry methods are useful for measuring intracellular parameters.

In some embodiments, the present invention provides methods for determining an activatable element's activation profile for a single cell. The methods may comprise analyzing cells by flow cytometry on the basis of the activation level of at least two activatable elements. Binding elements (e.g. activation state-specific antibodies) are used to analyze cells on the basis of activatable element activation level, and can be detected as described below. Alternatively, non-binding elements systems as described above can be used in any system described herein.

When using fluorescent labeled components in the methods and compositions of the present invention, it will recognized that different types of fluorescent monitoring systems, e.g., Cytometric measurement device systems, can be used to practice the invention. In some embodiments, flow cytometric systems are used or systems dedicated to high throughput screening, e.g. 96 well or greater microtiter plates. Methods of performing assays on fluorescent materials are well known in the art and are described in, e.g., Lakowicz, J. R., Principles of Fluorescence Spectroscopy, New York: Plenum Press (1983); Herman, B., Resonance energy transfer microscopy, in: Fluorescence Microscopy of Living Cells in Culture, Part B, Methods in Cell Biology, vol. 30, ed. Taylor, D. L. & Wang, Y.-L., San Diego: Academic Press (1989), pp. 219-243; Turro, N.J., Modern Molecular Photochemistry, Menlo Park: Benjamin/Cummings Publishing Col, Inc. (1978), pp. 296-361.

Fluorescence in a sample can be measured using a fluorimeter. In general, excitation radiation, from an excitation source having a first wavelength, passes through excitation optics. The excitation optics cause the excitation radiation to excite the sample. In response, fluorescent proteins in the sample emit radiation that has a wavelength that is different from the excitation wavelength. Collection optics then collect the emission from the sample. The device can include a temperature controller to maintain the sample at a specific temperature while it is being scanned. According to one embodiment, a multi-axis translation stage moves a microtiter plate holding a plurality of samples in order to position different wells to be exposed. The multi-axis translation stage, temperature controller, auto-focusing feature, and electronics associated with imaging and data collection can be managed by an appropriately programmed digital computer. The computer also can transform the data collected during the assay into another format for presentation. In general, known robotic systems and components can be used.

Other methods of detecting fluorescence may also be used, e.g., Quantum dot methods (see, e.g., Goldman et al., J. Am. Chem. Soc. (2002) 124:6378-82; Pathak et al. J. Am. Chem. Soc. (2001) 123:4103-4; and Remade et al., Proc. Natl. Sci. USA (2000) 18:553-8, each expressly incorporated herein by reference) as well as confocal microscopy. In general, flow cytometry involves the passage of individual cells through the path of a laser beam. The scattering the beam and excitation of any fluorescent molecules attached to, or found within, the cell is detected by photomultiplier tubes to create a readable output, e.g. size, granularity, or fluorescent intensity.

The detecting, sorting, or isolating step of the methods of the present invention can entail fluorescence-activated cell sorting (FACS) techniques, where FACS is used to select cells from the population containing a particular surface marker, or the selection step can entail the use of magnetically responsive particles as retrievable supports for target cell capture and/or background removal. A variety of FACS systems are known in the art and can be used in the methods of the invention (see e.g., WO99/54494, filed Apr. 16, 1999; U.S. Ser. No. 20010006787, filed Jul. 5, 2001, each expressly incorporated herein by reference).

In some embodiments, a FACS cell sorter (e.g. a FACS-Vantage™ Cell Sorter, Becton Dickinson Immunocytometry Systems, San Jose, Calif.) is used to sort and collect cells based on their activation profile (positive cells) in the presence or absence of a change in activation level in an activatable element in response to a modulator. In some embodiments the change is a decrease. In some embodiments the change is an increase.

In some embodiments, the cells are first contacted with fluorescent-labeled activation state-specific binding elements (e.g. antibodies) directed against specific activation state of specific activatable elements. In such an embodiment, the amount of bound binding element on each cell can be measured by passing droplets containing the cells through the cell sorter. By imparting an electromagnetic charge to droplets containing the positive cells, the cells can be separated from other cells. The positively selected cells can then be harvested in sterile collection vessels. These cell-sorting procedures are described in detail, for example, in the FACSVantage™ Training Manual, with particular reference to sections 3-11 to 3-28 and 10-1 to 10-17, which is hereby incorporated by reference in its entirety.

In another embodiment, positive cells can be sorted using magnetic separation of cells based on the presence of an isoform of an activatable element. In such separation techniques, cells to be positively selected are first contacted with specific binding element (e.g., an antibody or reagent that binds an isoform of an activatable element). The cells are then contacted with retrievable particles (e.g., magnetically responsive particles) that are coupled with a reagent that binds the specific element. The cell-binding element-particle complex can then be physically separated from non-positive or non-labeled cells, for example, using a magnetic field. When using magnetically responsive particles, the positive or labeled cells can be retained in a container using a magnetic filed while the negative cells are removed. These and similar separation procedures are described, for example, in the Baxter Immunotherapy Isolex training manual which is hereby incorporated in its entirety.

In some embodiments, methods for the determination of a receptor element activation state profile for a single cell are provided. The methods comprise providing a population of cells and analyze the population of cells by flow cytometry.

Preferably, cells are analyzed on the basis of the activation level of at least two activatable elements. In some embodiments, a multiplicity of activatable element activation-state antibodies is used to simultaneously determine the activation level of a multiplicity of elements.

In some embodiment, cell analysis by flow cytometry on the basis of the activation level of at least two elements is combined with a determination of other flow cytometry readable outputs, such as the presence of surface markers, granularity and cell size to provide a correlation between the activation level of a multiplicity of elements and other cell qualities measurable by flow cytometry for single cells.

As will be appreciated, the present invention also provides for the ordering of element clustering events in signal transduction. Particularly, the present invention allows the artisan to construct an element clustering and activation hierarchy based on the correlation of levels of clustering and activation of a multiplicity of elements within single cells. Ordering can be accomplished by comparing the activation level of a cell or cell population with a control at a single time point, or by comparing cells at multiple time points to observe subpopulations arising out of the others.

The present invention provides a valuable method of determining the presence of cellular subsets within cellular populations. Ideally, signal transduction pathways are evaluated in homogeneous cell populations to ensure that variances in signaling between cells do not qualitatively nor quantitatively mask signal transduction events and alterations therein. As the ultimate homogeneous system is the single cell, the present invention allows the individual evaluation of cells to allow true differences to be identified in a significant way.

Thus, the invention provides methods of distinguishing cellular subsets within a larger cellular population. As outlined herein, these cellular subsets often exhibit altered biological characteristics (e.g. activation levels, altered response to modulators) as compared to other subsets within the population. For example, as outlined herein, the methods of the invention allow the identification of subsets of cells from a population such as primary cell populations, e.g. peripheral blood mononuclear cells that exhibit altered responses (e.g. response associated with presence of a condition) as compared to other subsets. In addition, this type of evaluation distinguishes between different activation states, altered responses to modulators, cell lineages, cell differentiation states, etc.

As will be appreciated, these methods provide for the identification of distinct signaling cascades for both artificial and stimulatory conditions in complex cell populations, such a peripheral blood mononuclear cells, or naive and memory lymphocytes.

When necessary, cells are dispersed into a single cell suspension (e.g. by enzymatic digestion with a suitable protease, collagenase, dispase, etc; and the like). An appropriate solution is used for dispersion or suspension. Such solution will generally be a balanced salt solution, e.g. normal saline, PBS, Hanks balanced salt solution, etc., conveniently supplemented with fetal calf serum or other naturally occurring factors, in conjunction with an acceptable buffer at low concentration, generally from 5-25 mM. Convenient buffers include HEPES1 phosphate buffers, lactate buffers, etc. The cells may be fixed, e.g. with 3% paraformaldehyde, and are usually permeabilized, e.g. with ice cold methanol; HEPES-buffered PBS containing 0.1% saponin, 3% BSA; covering for 2 min in acetone at −200 C; and the like as known in the art and according to the methods described herein.

In some embodiments, one or more cells are contained in a well of a 96 well plate or other commercially available multi-well plate. In an alternate embodiment, the reaction mixture or cells are in a cytometric measurement device. Other multi-well plates useful in the present invention include, but are not limited to 384 well plates and 1536 well plates. Still other vessels for containing the reaction mixture or cells and useful in the present invention will be apparent to the skilled artisan.

The addition of the components of the assay for detecting the activation level or activity of an activatable element, or modulation of such activation level or activity, may be sequential or in a predetermined order or grouping under conditions appropriate for the activity that is assayed for. Such conditions are described here and known in the art. Moreover, further guidance is provided below (see, e.g., in the Examples).

In some embodiments, the activation level of an activatable element is measured using Inductively Coupled Plasma Mass Spectrometer (ICP-MS). A binding element that has been labeled with a specific element binds to the activatable element. When the cell is introduced into the ICP, it is atomized and ionized. The elemental composition of the cell, including the labeled binding element that is bound to the activatable element, is measured. The presence and intensity of the signals corresponding to the labels on the binding element indicates the level of the activatable element on that cell (Tanner et al. Spectrochimica Acta Part B: Atomic Spectroscopy, (2007), 62(3):188-195.).

As will be appreciated by one of skill in the art, the instant methods and compositions find use in a variety of other assay formats in addition to flow cytometry analysis. For example, a chip analogous to a DNA chip can be used in the methods of the present invention. Arrayers and methods for spotting nucleic acid to a chip in a prefigured array are known. In addition, protein chips and methods for synthesis are known. These methods and materials may be adapted for the purpose of affixing activation state binding elements to a chip in a prefigured array. In some embodiments, such a chip comprises a multiplicity of element activation state binding elements, and is used to determine an element activation state profile for elements present on the surface of a cell.

In some embodiments, a chip comprises a multiplicity of the "second set binding elements," in this case generally unlabeled. Such a chip is contacted with sample, preferably cell extract, and a second multiplicity of binding elements comprising element activation state specific binding elements is used in the sandwich assay to simultaneously determine the presence of a multiplicity of activated elements in sample. Preferably, each of the multiplicity of activation state-specific binding elements is uniquely labeled to facilitate detection.

In some embodiments confocal microscopy can be used to detect activation profiles for individual cells. Confocal microscopy relies on the serial collection of light from spatially filtered individual specimen points, which is then electronically processed to render a magnified image of the specimen. The signal processing involved confocal microscopy has the additional capability of detecting labeled binding elements within single cells, accordingly in this embodiment the cells can be labeled with one or more binding elements. In some embodiments the binding elements used in connection with confocal microscopy are antibodies conjugated to fluorescent labels, however other binding elements, such as other proteins or nucleic acids are also possible.

In some embodiments, the methods and compositions of the instant invention can be used in conjunction with an "In-Cell Western Assay." In such an assay, cells are initially grown in standard tissue culture flasks using standard tissue culture techniques. Once grown to optimum confluency, the growth media is removed and cells are washed and trypsinized. The cells can then be counted and volumes sufficient to transfer the appropriate number of cells are aliquoted into microwell plates (e.g., Nunc™ 96 Microwell™ plates). The individual wells are then grown to optimum confluency in complete media whereupon the media is replaced with serum-free media. At this point controls are untouched, but experimental wells are incubated with a modulator, e.g. EGF. After incubation with the modulator cells are fixed and stained with labeled antibodies to the activation elements being investigated. Once the cells are labeled, the plates can be scanned using an imager such as the Odyssey Imager (LiCor, Lincoln Nebr.) using techniques described in the Odyssey Operator's Manual v1.2., which is hereby incorporated in its entirety. Data obtained by scanning of the multi-well plate can be analyzed and activation profiles determined as described below.

In some embodiments, the detecting is by high pressure liquid chromatography (HPLC), for example, reverse phase HPLC, and in a further aspect, the detecting is by mass spectrometry.

These instruments can fit in a sterile laminar flow or fume hood, or are enclosed, self-contained systems, for cell culture growth and transformation in multi-well plates or tubes and for hazardous operations. The living cells may be grown under controlled growth conditions, with controls for temperature, humidity, and gas for time series of the live cell assays. Automated transformation of cells and automated colony pickers may facilitate rapid screening of desired cells.

Flow cytometry or capillary electrophoresis formats can be used for individual capture of magnetic and other beads, particles, cells, and organisms.

Flexible hardware and software allow instrument adaptability for multiple applications. The software program modules allow creation, modification, and running of methods. The system diagnostic modules allow instrument alignment, correct connections, and motor operations. Customized tools, labware, and liquid, particle, cell and organism transfer patterns allow different applications to be performed. Databases allow method and parameter storage. Robotic and computer interfaces allow communication between instruments.

In some embodiment, the methods of the invention include the use of liquid handling components. The liquid handling systems can include robotic systems comprising any number of components. In addition, any or all of the steps outlined herein may be automated; thus, for example, the systems may be completely or partially automated.

As will be appreciated by those in the art, there are a wide variety of components which can be used, including, but not limited to, one or more robotic arms; plate handlers for the positioning of microplates; automated lid or cap handlers to remove and replace lids for wells on non-cross contamination plates; tip assemblies for sample distribution with disposable tips; washable tip assemblies for sample distribution; 96 well loading blocks; cooled reagent racks; microtiter plate pipette positions (optionally cooled); stacking towers for plates and tips; and computer systems.

Fully robotic or microfluidic systems include automated liquid-, particle-, cell- and organism-handling including high throughput pipetting to perform all steps of screening applications. This includes liquid, particle, cell, and organism manipulations such as aspiration, dispensing, mixing, diluting, washing, accurate volumetric transfers; retrieving, and discarding of pipet tips; and repetitive pipetting of identical volumes for multiple deliveries from a single sample aspiration. These manipulations are cross-contamination-free liquid, particle, cell, and organism transfers. This instrument performs automated replication of microplate samples to filters, membranes, and/or daughter plates, high-density transfers, full-plate serial dilutions, and high capacity operation. Additional examples of automation, automated sample collection and analysis are disclosed in U.S. 61/048,657 which is hereby incorporated by reference in its entirety.

In some embodiments, chemically derivatized particles, plates, cartridges, tubes, magnetic particles, or other solid phase matrix with specificity to the assay components are used. The binding surfaces of microplates, tubes or any solid phase matrices include non-polar surfaces, highly polar surfaces, modified dextran coating to promote covalent binding, antibody coating, affinity media to bind fusion proteins or peptides, surface-fixed proteins such as recombinant protein A or G, nucleotide resins or coatings, and other affinity matrix are useful in this invention.

In some embodiments, platforms for multi-well plates, multi-tubes, holders, cartridges, minitubes, deep-well plates, microfuge tubes, cryovials, square well plates, filters, chips, optic fibers, beads, and other solid-phase matrices or platform with various volumes are accommodated on an upgradeable modular platform for additional capacity. This modular platform includes a variable speed orbital shaker, and multi-position work decks for source samples, sample and reagent dilution, assay plates, sample and reagent reservoirs, pipette tips, and an active wash station. In some embodiments, the methods of the invention include the use of a plate reader.

In some embodiments, thermocycler and thermoregulating systems are used for stabilizing the temperature of heat exchangers such as controlled blocks or platforms to provide accurate temperature control of incubating samples from 0° C. to 100° C.

In some embodiments, interchangeable pipet heads (single or multi-channel) with single or multiple magnetic probes, affinity probes, or pipetters robotically manipulate the liquid, particles, cells, and organisms. Multi-well or multi-tube magnetic separators or platforms manipulate liquid, particles, cells, and organisms in single or multiple sample formats.

In some embodiments, the instrumentation will include a detector, which can be a wide variety of different detectors, depending on the labels and assay. In some embodiments, useful detectors include a microscope(s) with multiple channels of fluorescence; plate readers to provide fluorescent, ultraviolet and visible spectrophotometric detection with single and dual wavelength endpoint and kinetics capability, fluorescence resonance energy transfer (FRET), luminescence, quenching, two-photon excitation, and intensity redistribution; CCD cameras to capture and transform data and images into quantifiable formats; and a computer workstation.

In some embodiments, the robotic apparatus includes a central processing unit which communicates with a memory and a set of input/output devices (e.g., keyboard, mouse, monitor, printer, etc.) through a bus. Again, as outlined below, this may be in addition to or in place of the CPU for the multiplexing devices of the invention. The general interaction between a central processing unit, a memory, input/output devices, and a bus is known in the art. Thus, a variety of different procedures, depending on the experiments to be run, are stored in the CPU memory.

These robotic fluid handling systems can utilize any number of different reagents, including buffers, reagents, samples, washes, assay components such as label probes, etc.

Analysis

Advances in flow cytometry have enabled the individual cell enumeration of up to thirteen simultaneous parameters (De Rosa et al., 2001) and are moving towards the study of genomic and proteomic data subsets (Krutzik and Nolan, 2003; Perez and Nolan, 2002). Likewise, advances in other techniques (e.g. microarrays) allow for the identification of multiple activatable elements. As the number of parameters, epitopes, and samples have increased, the complexity of experiments and the challenges of data analysis have grown rapidly. An additional layer of data complexity has been added by the development of stimulation panels which enable the study of activatable elements under a growing set of experimental conditions. Methods for the analysis of multiple parameters are well known in the art. In some embodiments flow cytometry applications require software for different phases of operation and analysis, see 61/079,579; 61/079,551; 61/079,537; 61/087,555; 61/085,789 which are hereby incorporated by reference in their entireties.

In some embodiments where flow cytometry is used, flow cytometry experiments are arrayed and the results are approximated as fold changes using a heat map to facilitate evaluation. Generally speaking, arrayed flow cytometry experiments simplify multidimensional flow cytometry data based on experimental design and observed differences between flow cytometry samples. One common way of comparing changes in a set of flow cytometry samples is to overlay histograms of one parameter on the same plot. Arrayed flow cytometry experiments ideally contain a reference sample against which experimental samples are compared. This reference sample is placed in the first position of the array, and subsequent experimental samples follow the control in the sequence. Reference samples can include normal and/or cells associated with a condition (e.g. tumor cells).

In some embodiments where flow cytometry is used, prior to analyzing of data the populations of interest and the method for characterizing these populations are determined. For instance, there are at least two general ways of identifying populations for data analysis: (i) "Outside-in" comparison of Parameter sets for individual samples or subset (e.g., patients in a trial). In this more common case, cell populations are homogenous or lineage gated in such a way as to create distinct sets considered to be homogenous for targets of interest. An example of sample-level comparison would be the identification of signaling profiles in tumor cells of a patient and correlation of these profiles with non-random distribution of clinical responses. This is considered an outside-in approach because the population of interest is pre-defined prior to the mapping and comparison of its profile to other populations. (ii) "Inside-out" comparison of Parameters at the level of individual cells in a heterogeneous population. An example of this would be the signal transduction state mapping of mixed hematopoietic cells under certain conditions and subsequent comparison of computationally identified cell clusters with lineage specific markers. This could be considered an inside-out approach to single cell studies as it does not presume the existence of specific populations prior to classification. A major drawback of this approach is that it creates populations which, at least initially, require multiple transient markers to enumerate and may never be accessible with a single cell surface epitope. As a result, the biological significance of such populations can be difficult to determine. The main advantage of this unconventional approach is the unbiased tracking of cell populations without drawing potentially arbitrary distinctions between lineages or cell types.

Each of these techniques capitalizes on the ability of flow cytometry to deliver large amounts of multiparameter data at the single cell level. For cells associated with a condition (e.g. neoplastic or hematopoetic condition), a third "meta-level" of data exists because cells associated with a condition (e.g. cancer cells) are generally treated as a single entity and classified according to historical techniques. These techniques have included organ or tissue of origin, degree of differentiation, proliferation index, metastatic spread, and genetic or metabolic data regarding the patient.

In some embodiments, the present invention uses variance mapping techniques for mapping condition signaling space. These methods represent a significant advance in the study of condition biology because it enables comparison of conditions independent of a putative normal control. Traditional differential state analysis methods (e.g., DNA microarrays, subtractive Northern blotting) generally rely on the comparison of cells associated with a condition from each patient sample with a normal control, generally adjacent and theoretically untransformed tissue. Alternatively, they rely on multiple clusterings and re-clusterings to group and then further stratify patient samples according to phenotype. In contrast, variance mapping of condition states compares condition samples first with themselves and then against the parent condition population. As a result, activation states with the most diversity among conditions provide the core parameters in the differential state analysis. Given a pool of diverse conditions, this technique allows a researcher to identify the molecular events that underlie differential condition pathology (e.g., cancer responses to chemotherapy), as opposed to differences between conditions and a proposed normal control.

In some embodiments, when variance mapping is used to profile the signaling space of patient samples, conditions whose signaling response to modulators is similar are grouped together, regardless of tissue or cell type of origin. Similarly, two conditions (e.g. two tumors) that are thought to be relatively alike based on lineage markers or tissue of origin could have vastly different abilities to interpret environmental stimuli and would be profiled in two different groups.

When groups of signaling profiles have been identified it is frequently useful to determine whether other factors, such as clinical responses, presence of gene mutations, and protein expression levels, are non-randomly distributed within the groups. If experiments or literature suggest such a hypothesis in an arrayed flow cytometry experiment, it can be judged with simple statistical tests, such as the Student's t-test and the $X^2$ test. Similarly, if two variable factors within the experiment are thought to be related, the $r^2$ correlation coefficient from a linear regression is used to represent the degree of this relationship.

Examples of analysis for activatable elements are described in US publication number 20060073474 entitled "Methods and compositions for detecting the activation state of multiple proteins in single cells" and US publication number 20050112700 entitled "Methods and compositions for risk stratification" and U.S. 61/085,789 the contents of which are incorporate here by reference.

Figure 26:
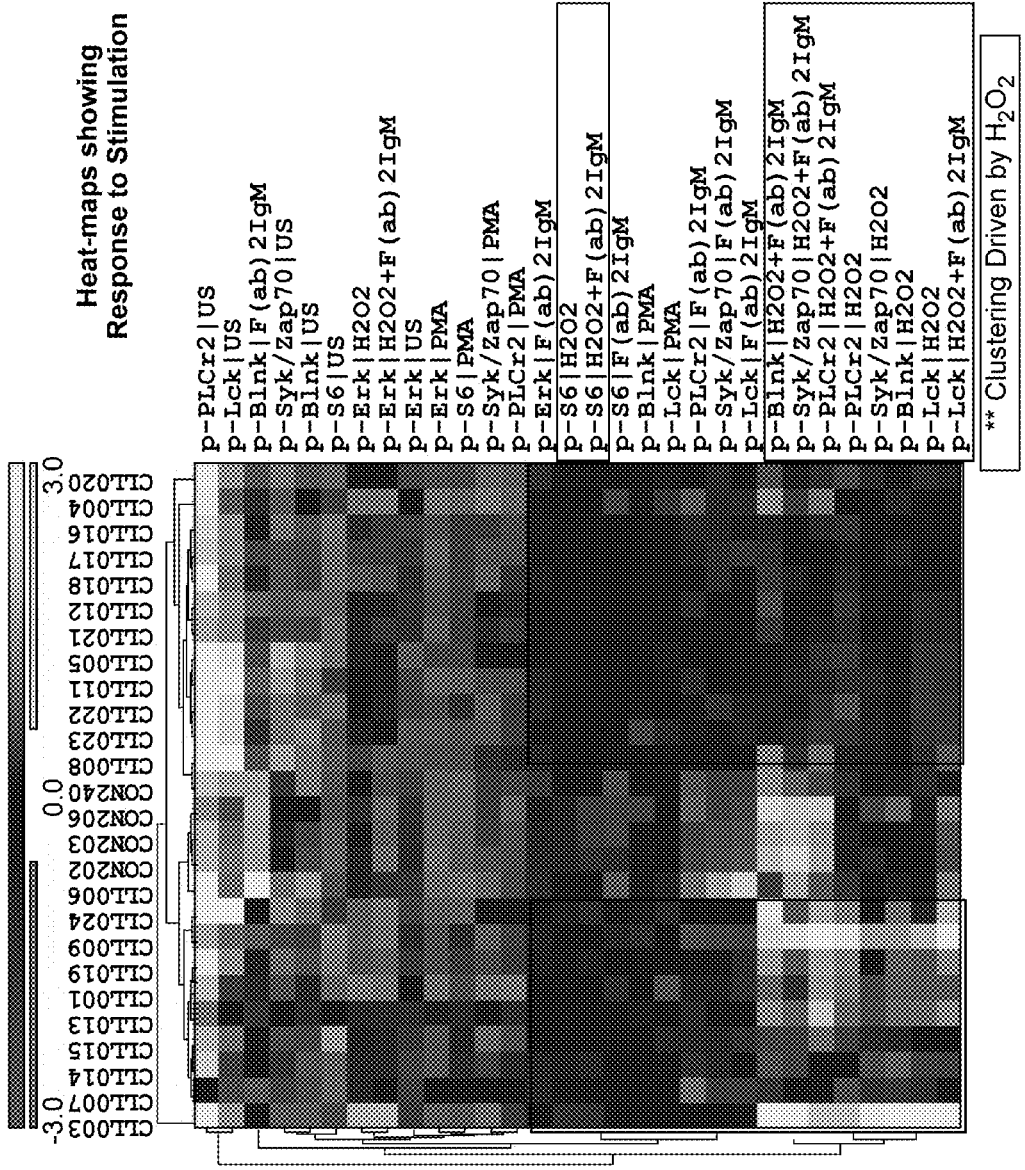
FIG. 26 depicts a heat-map showing intracellular responses of CLL patient peripheral blood samples to BCR and/or H$_2$O$_2$ stimulation. CLL indicates that the sample was taken from a patient diagnosed with CLL. CON indicates that the sample was taken from a healthy subject. The patient sample numbers are indicated at the top of the heat map and each column represents a single patient. The shaded squares within the column represent a phospho-protein node. The different shades represent the degree of phosphorylation of each node (see scale at top of figure). Bright white (located to the far right of the scale) represents the greatest increase (i.e. +3.0 Log Change). Black (located in the center of the scale) indicates little or no change and dark grey (located to the far left of the scale) represents the greatest decrease in phosphorylation status (i.e. −3.0 Log Change). These levels of phosphorylation are derived from an equation which calculates the log10-fold increase, or decrease, in median fluorescence intensity (MFI), of a stimulated sample divided by the MFI of an unstimulated sample. The rows of the heatmap indicate the identity of the phospho-protein that was analyzed. For example, the label "p-Blnk/H$_2$O$_2$/F(ab)2 IgM" indicates that the phosphorylation status of phosphorylated BLNK was measured in response to hydrogen peroxide (H$_2$O$_2$) and the Fab fragment that recognizes IgM (F(ab)2 IgM). "US" indicates that the sample was unstimulated.
Figure 27:
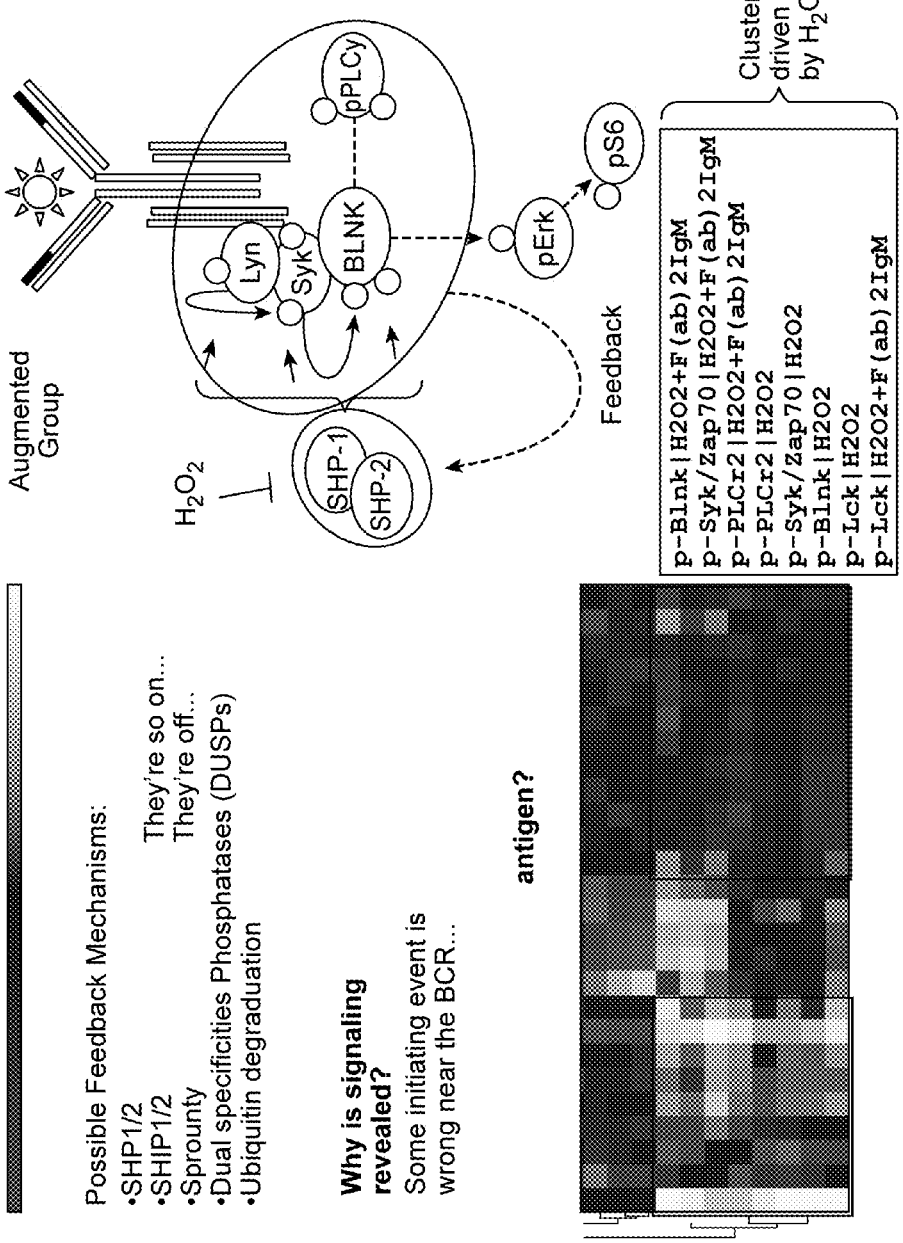
FIG. 27 depicts the lower portion of the heat map shown in FIG. 26. White framed boxes show 2 distinct clusters of CLL patient samples in which signaling increases in response to H$_2$O$_2$ treatment (left hand side) or signaling decreases in response to H$_2$O$_2$ treatment (righthand side).
Figure 28:
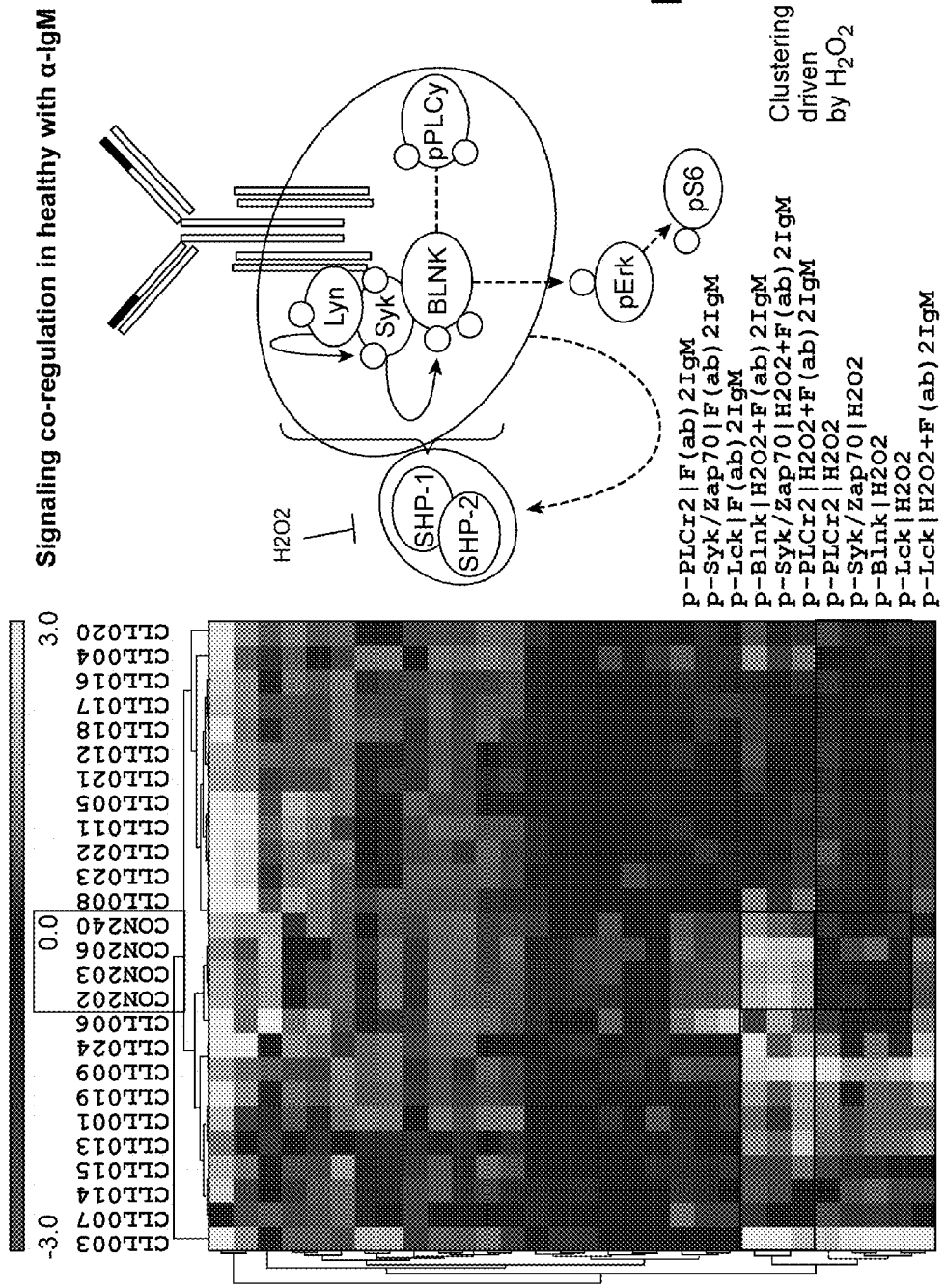
FIG. 28 depicts the lower portion of the heat map shown in FIG. 26 further illustrating the two patient clusters, 10/22 patients (top left white framed box) and 11/22 patients (bottom right white framed box), that are distinguished by H$_2$O$_2$ treatment. The cartoon on the right of the figure depicts the B cell receptor signaling pathway.

CLL serves as an example of the methods of the invention. The data shown in FIGS. 26, 27 and 28 is a heat map comparing the activation states of multiple activatable elements in 22 CLL patients and 4 control patients. This data demonstrates that B-cells from various CLL patients display distinguishable patterns of activatable elements as visualized by a heat map. An inhibitor or inhibitor plus another modulator further define additional patterns of activatable elements that allow identification, classification and grouping of cryptic or aberrant hematopoetic populations (i.e. patient clustering). In FIGS. 26, 27 & 28 patient samples are indicated at the top of the heat map. Each column represents a single patient. CLL indicates that the sample was obtained from a patient diagnosed with CLL. CON indicates that the sample was obtained from a control patient. The heat map legend is indicated at the top of the figure and uses a shaded scale based on the log 10-fold increase, or decrease, in mean fluorescence intensity (MFI), relative to the unstimulated control (0 min).

The heat map defines the activation state of various activatable elements by denoting a change, or lack thereof, in the level of an activatable element revealed by the presence of an inhibitor and/or additional modulator. Thus, the heat map can define the presence or absence of an increase in the activation level of a plurality of activatable elements in a cell upon contacting said cell with an inhibitor or a modulator. Labels to the right of the heat map indicate the activatable element detected, e.g. a phospho-protein. Labels to the right also indicate the modulator or inhibitor treatment for that row. "US" indicates unstimulated or untreated. FIG. 28 illustrates a pattern of activation levels of a plurality of activatable elements in a cell. FIG. 28 further illustrates the identification of patient clustering groups (i.e. clustering groups). A patient clustering group is comprised of samples from patients that display similar or distinct patterns of activation levels in one or more activatable elements in response to one or more modulators (e.g., an inhibitor, or an inhibitor and another modulator). FIG. 28 illustrates a clustering group comprised of samples from patients in which the activation levels of p-PLCγ$_2$, p-SyK/Zap-70, p-BLNK and p-Lck are similar in response to the same stimulus. Some patient clustering groups are revealed upon modulation or treatment with an inhibitor as illustrated by the boxed regions. Treatment with H$_2$O$_2$ reveals a patient clustering group defined by the levels of p-PLCγ$_2$, p-SyK/Zap-70, p-BLNK and p-Lck (FIG. 28, bottom right boxed area) that are similar to those of the four control patients (FIG. 28, bottom center box). Treatment with H$_2$O$_2$ further reveals a patient clustering group that is distinct from the controls (FIG. 28, 9 patients to the left of bottom boxed area). Modulation with H$_2$O$_2$ and BCR crosslinking defines another patient clustering group comprised of samples from patients that display the activation levels of p-BLNK, p-Syk and p-PLCγ$_2$ (FIG. 28, top left boxed area) that are similar to the control patients (top center box). In addition, modulation with H$_2$O$_2$ and BCR crosslinking further reveals another clustering group distinct from the controls (10 patients to the right of top boxed area).

Thus, also provided herein is a method of deriving a classification. Deriving a classification involves defining a clustering group. A clustering group is defined by determining the activation state of a plurality of activatable elements from a plurality of cells wherein each cell is derived from an individual with a known conditions and/or known clinical outcome. A clustering group may define a pattern that associated with a known condition or known clinical outcome. Any suitable activatable element can be used wherein the activation level of said activatable element provides useful information regarding a known condition or clinical outcome of a patient. A cell derived from a patient with an unknown condition and/or unknown clinical outcome may be classified depending upon which clustering group it is identified with. This can further lead to diagnosis, prognosis, and/or evaluation or choice of treatment for the patient.

Kits

In some embodiments the invention provides kits. Kits provided by the invention may comprise one or more of the state-specific binding element described herein, such as phospho-specific antibodies. In some embodiments, the kit comprises one or more of the phospho-specific antibodies specific for the proteins selected from the group consisting of PI3-Kinase (p85, p110a, p110b, p110d), Jak1, Jak2, SOCs, Rac, Rho, Cdc42, Ras-GAP, Vav, Tiam, Sos, Dbl, Nck, Gab, PRK, SHPT, and SHP2, SHIP1, SHIP2, sSHIP, PTEN, Shc, Grb2, PDK1, SGK, Akt1, Akt2, Akt3, TSC1,2, Rheb, mTor, 4EBP-1, p70S6Kinase, S6, LKB-1, AMPK, PFK, Acetyl-CoAa Carboxylase, DokS, Rafs, Mos, Tpl2, MEK1/2, MLK3, TAK, DLK, MKK3/6, MEKK1,4, MLK3, ASK1, MKK4/7, SAPK/JNK1,2,3, p38s, Erk1/2, Syk, Btk, BLNK, LAT, ZAP70, Lck, Cbl, SLP-76, PLCγ$_1$, PLCγ$_2$, STAT1, STAT 3, STAT 4, STAT 5, STAT 6, FAK, p130CAS, PAKs, LIMK1/2, Hsp90, Hsp70, Hsp27, SMADs, Rel-A (p65-NFKB), CREB, Histone H2B, HATs, HDACs, PKR, Rb, Cyclin D, Cyclin E, Cyclin A, Cyclin B, P16, p14Arf, p27KIP, p21CIP, Cdk4, Cdk6, Cdk7, Cdk1, Cdk2, Cdk9, Cdc25,A/B/C, Abl, E2F, FADD, TRADD, TRAF2, RIP, Myd88, BAD, Bcl-2, Mcl-1, Bcl-XL, Caspase 2, Caspase 3, Caspase 6, Caspase 7, Caspase 8, Caspase 9, PARP, IAPB, Smac, Fodrin, Actin, Src, Lyn, Fyn, Lck, NIK, IKB, p65(RelA), IKKα, PKA, PKCα, PKCβ, PKCθ, PKCδ, CAMK, Elk, AFT, Myc, Egr-1, NFAT, ATF-2, Mdm2, p53, DNA-PK, Chk1, Chk2, ATM, ATR, β-catenin, CrkL, GSK3α, GSK3β, and FOXO. In some embodiments, the kit comprises one or more of the phospho-specific antibodies specific for the proteins selected from the group consisting of Erk, Syk, Zap70, Lck, Btk, BLNK, Cbl, PLCγ$_2$, Akt, RelA, p38, S6. In some embodiments, the kit comprises one or more of the phospho-specific antibodies specific for the proteins selected from the group consisting of Akt1, Akt2, Akt3, SAPK/JNK1,2,3, p38s, Erk1/2, Syk, ZAP70, Btk, BLNK, Lck, PLCγ, PLC1γ$_2$, STAT1, STAT 3, STAT 4, STAT 5, STAT 6, CREB, Lyn, p-S6, Cbl, NF-κB, GSK3β, CARMA/Bcl10 and Tcl-1.

Kits provided by the invention may comprise one or more of the modulators described herein. In some embodiments, the kit comprises one or more modulators selected from the group consisting of F(ab)2 IgM, H$_2$O$_2$, PMA, BAFF, April, SDF1a, CD40L, IGF-1, Imiquimod, polyCpG, IL-7, IL-6, IL-10, IL-27, IL-4, IL-2, IL-3, thapsigargin and a combination thereof.

The state-specific binding element of the invention can be conjugated to a solid support and to detectable groups directly or indirectly. The reagents may also include ancillary agents such as buffering agents and stabilizing agents, e.g., polysaccharides and the like. The kit may further include, where necessary, other members of the signal-producing system of which system the detectable group is a member (e.g., enzyme substrates), agents for reducing background interference in a test, control reagents, apparatus for conducting a test, and the like. The kit may be packaged in any suitable manner, typically with all elements in a single container along with a sheet of printed instructions for carrying out the test.

Such kits enable the detection of activatable elements by sensitive cellular assay methods, such as IHC and flow cytometry, which are suitable for the clinical detection, prognosis, and screening of cells and tissue from patients, such as leukemia patients, having a disease involving altered pathway signaling.

Such kits may additionally comprise one or more therapeutic agents. The kit may further comprise a software package for data analysis of the physiological status, which may include reference profiles for comparison with the test profile.

Such kits may also include information, such as scientific literature references, package insert materials, clinical trial results, and/or summaries of these and the like, which indicate or establish the activities and/or advantages of the composition, and/or which describe dosing, administration, side effects, drug interactions, or other information useful to the health care provider. Such kits may also include instructions to access a database such as described in U.S. Ser. No. 61/087,555 for selecting an antibody specific for the pathway of interest. Such information may be based on the results of various studies, for example, studies using experimental animals involving in vivo models and studies based on human clinical trials. Kits described herein can be provided, marketed and/or promoted to health providers, including physicians, nurses, pharmacists, formulary officials, and the like. Kits may also, in some embodiments, be marketed directly to the consumer.

The following examples serve to more fully describe the manner of using the above-described invention, as well as to set forth the best modes contemplated for carrying out various aspects of the invention. It is understood that these examples in no way serve to limit the true scope of this invention, but rather are presented for illustrative purposes. All references cited herein are expressly incorporated by reference in their entirety.

EXAMPLES

Example 1

Signaling Pathways in CLL Samples

Signals propagated through the B cell receptor (BCR) guide the maturation and survival of B cells and might factor in the pathogenesis and progression of chronic lymphocytic leukemia (CLL). In this example, BCR signaling in CLL cells was investigated at the single-cell level using multiparametric flow cytometry. Concurrent analysis was performed using fluorochrome-conjugated antibodies specific for B-cell surface antigens and a panel of antibodies recognizing specific phospho-peptide epitopes within a selected group of intracellular signaling proteins. CLL samples from patients (N=6) showed weak or minimal signaling activity at p72SYK/p70ZAP, Erk1/2, B-Cell linker protein (BLNK) and phospholipase-C$\gamma$-2, (PLC$\gamma_2$) when stimulated only at the BCR with anti-$\mu$ crosslinking, whereas a robust signal was observed in a control Ramos B cell line. The low-level signaling in CLL cells could be accounted for by either a defect in activation of a key protein required for signaling, or by enhanced inhibition mediated by phosphatases such as SHIP-1, SHIP-2, SHP-1, or SHP-2. To determine whether phosphatases were preventing or dampening BCR activation in CLL samples, CLL cells were treated with hydrogen peroxide ($H_2O_2$), a physiologic phosphatase inhibitor generated during BCR signaling that has been used previously to reveal dysregulated BCR signaling in follicular lymphoma (Sing et al., (2005) Cell; Reth (2002) Nat. Immunol.; Irish et al., (2006) Blood. $H_2O_2$ treatment of CLL cells induced high-levels of phosphorylated p72SYK/p70ZAP, ERK1/2, BLNK, and PLC$\gamma_2$, in some patients independent of surface F(ab)2anti-$\mu$ ligation. In contrast, other CLL-B cells were significantly less responsive to this treatment, even in the presence of F(ab)2anti-$\mu$. Exposure of blood B cells from healthy donors to $H_2O_2$ failed to elicit a substantial increase in phosphorylation of these same intracellular signaling proteins. These studies reveal a previously unrecognized, constitutive high-level phosphatase activity in some CLL cells possibly contributing to the attenuated signaling observed in these cells following surface IgM ligation.

Analysis of Signaling Pathways in CLL Cells

Ramos cells were maintained and cultured using methods known in the art. Cells from CLL patients were obtained using methods known in the art.

BCR cross-linking and preparation for staining: Cells were thawed at 37° C. in a water bath until partially thawed (~50%). Cells were thawed into 5% FBS/RPMI at room temperature. The cell suspension was added drop-wise into media. Cells were centrifuged at 900 RPM for 10 minutes with no brake. The supernatants were decanted and pellets resuspended in 25 milliliters (ml) of media. Cells were re-centrifuged at 900 RPM for 10 minutes, decanted again and resuspended in 5 ml of 1% FBS/RPMI. Cells were counted with a hemocytometer using trypan blue staining. The concentration of the cells was adjusted as necessary to reduce crowding. Cells were incubated at 37° C. for 2 hours. The final cell concentration, including additives and reagents (e.g. stimulant, Fab fragment, $H_2O_2$, aqua, etc.) was 1.6 million/ml. Cells were aliquoted into wells. F(ab)2IgM alone, 3.3 mM $H_2O_2$ alone or F(ab)2IgM and $H_2O_2$ ($H_2O_2$ added within 30 seconds of F(ab)2IgM) were added to the appropriate tubes and mixed by vortexing the samples. Cells were incubated with the different treatments for 15 minutes, unless a time course was performed. If a time course was performed, the cells were incubated with the different treatments for 5, 10, 30, 60, or 120 minutes. After incubation, the cells were fixed with 1.6% paraformaldehyde for 5 minutes at room temperature in the dark. Cells were then washed with 0.1% BSA/PBS (2 ml) and centrifuged at 2000 RPM for 5 minutes. The supernatant were decanted and pellet resuspended in 1 ml of 100% MeOH (methanol).

Staining: Tubes were washed with 2 ml of 0.4% BSA PBS (ice cold) and centrifuged at 2000 RPM for 10 minutes at 4° C. Cells were washed twice. Then cells were stained with fluorescent conjugated antibodies specific for CD20, CD3, CD4, CD8, CD5, p-Erk, p-BLNK, p-syk/Zap70, for 25 min. at RT. Cells were placed into 80 wells making a total of 2 plates. The cocktail mix used for the staining is described below:
  a. Cocktail
     (i) CD3 pac blue=160 µl
     (ii) CD4 APC=80 µl
     (iii) CD8 PE Cy7=80 µl
     (iv) CD5 PE Cy5=400 µl
     (v) CD20 PerCP Cy5.5=800 µl
     (vi) p-Erk=800 µl
     (vii) p-BLNK=800 µl
     (viii) p-Syk/ZAP70=800 µl
  b. Total antibody volume in the cocktail mix was 3920 µl. PBS was added to bring the total volume to 8.0 ml. Each well received 100 µl of this cocktail mix.

Analysis by Flow Cytometry: Between 10,000 and 100,000 un-gated events were collected for each sample on the BD LSR II flow cytometry machine. The fluorescent anti-bodies directed to extra-cellular markers (i.e. CD3, CD4, CD8, CD5 and CD20) were used to mark the cells and a hierarchical gating strategy was used to identify the B-Cells and mature B-Cell population among the recorded events as described below:
  a. Forward and side scatter were first used to gate the Lymphocyte (Lymph) population.
  b. This "Lymph" population was then displayed on the CD20 and CD3 axes to gate for high CD3 expressing cells (CD3+) and high CD20 expressing cells (CD20+).
  c. The "CD20+" population was further gated to identify the mature B-Cell (high CD5 expressing cells—CD5+) population by displaying them on the CD20 and CD5 axes.
  d. All the recorded events were also marked by the following intra-cellular markers p-Erk, p-Syk/Zap70, and p-BLNK.

A probability density estimate of $\log_{10}$ of the fluorescence intensity value of each of the intra-cellular markers was computed for the cells in the CD20+ and CD5+ using the kernel density estimation function on the R-Statistics package (http://www.r-project.org/). The probability density estimates provided were then plotted to visualize the change in the phopho-levels of the various markers from the base-line.

Figure 2:
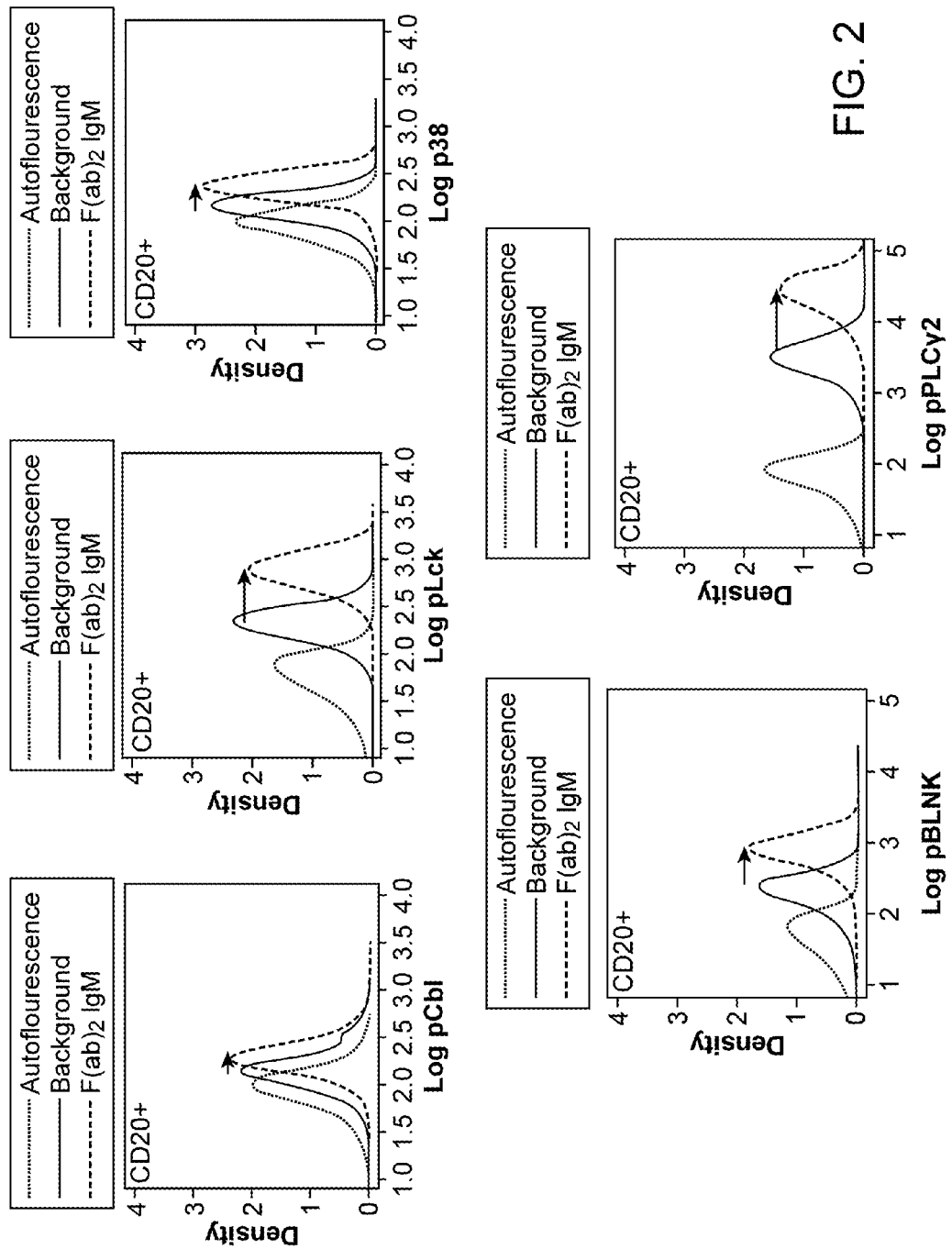
FIG. 2 depicts histograms showing the phosphorylation of BLNK, Cbl, PLCγ$_2$, Lck, and p38 in Ramos Cell lines following treatment with F(ab)$_2$IgM.

Results: FIG. 1 shows that both F(ab)$_2$ IgM and PMA activates p-Erk and p-Syk/pZap70 in Ramos cells. The large dashed line on the histograms represent the level of fluorescence of unstimulated and unstained cells referred herein after as autofluorescence. The thick solid line represents the level of fluorescence of unstimulated and stained cells referred hereinafter as background. After both stimulation with PMA (dotted line) and F(ab)$_2$ IgM (thin solid line) the p-Erk and p-Syk fluorescence is above the autofluorescence and background signal indicating activation of those proteins upon stimulation. FIG. 2 shows that F(ab)$_2$ IgM (dotted line) also activates pBLNK, pCbl, pPLCγ$_2$, pLck, p38 in Ramos cells. Ramos cells (Ramos cell lines) are used as positive control throughout the experiments performed herein.

Figure 3:
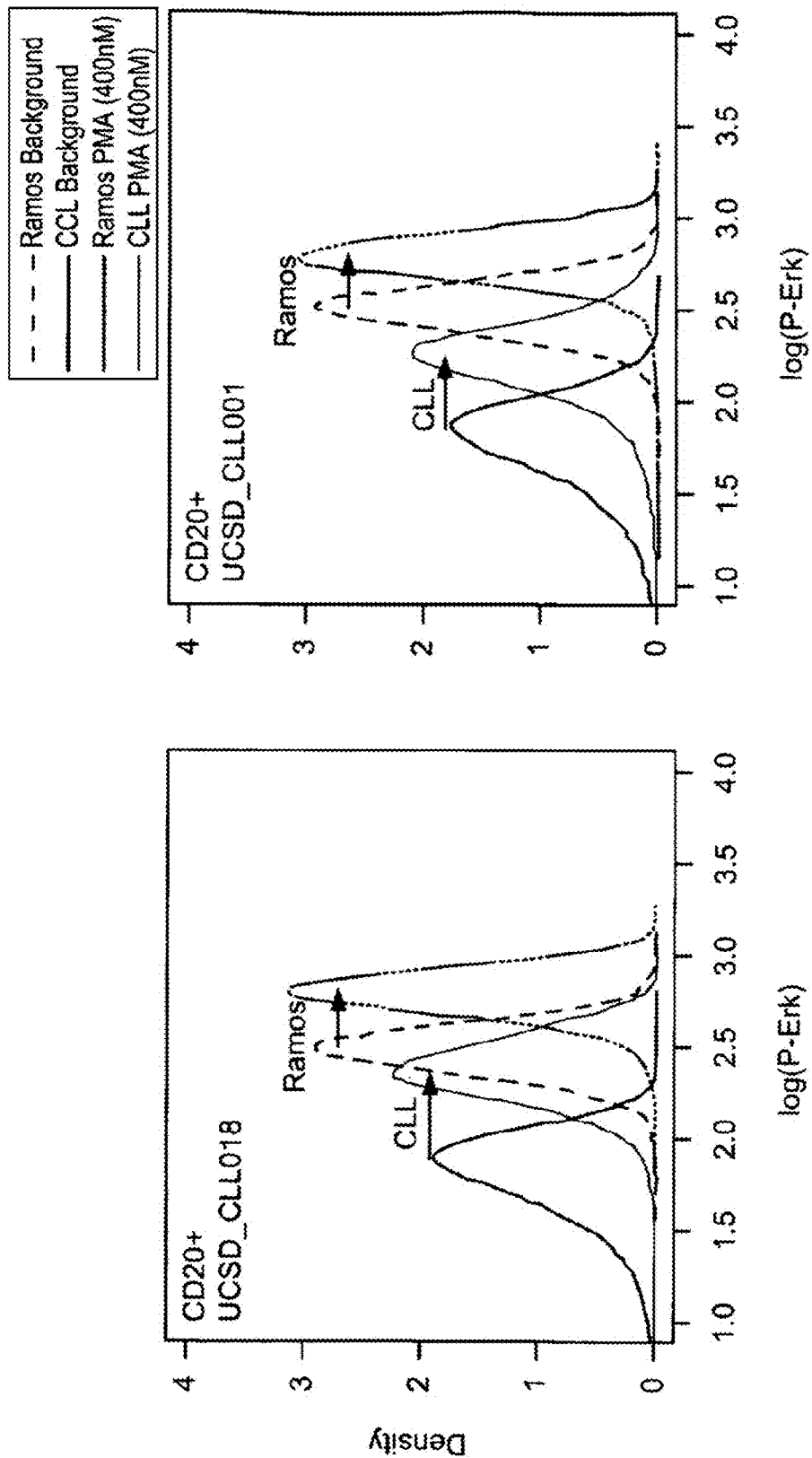
FIG. 3 depicts histograms showing increased phosphorylation of Erk in Pheresed CLL Samples and in the Ramos cell lines following PMA activation.
Figure 4:
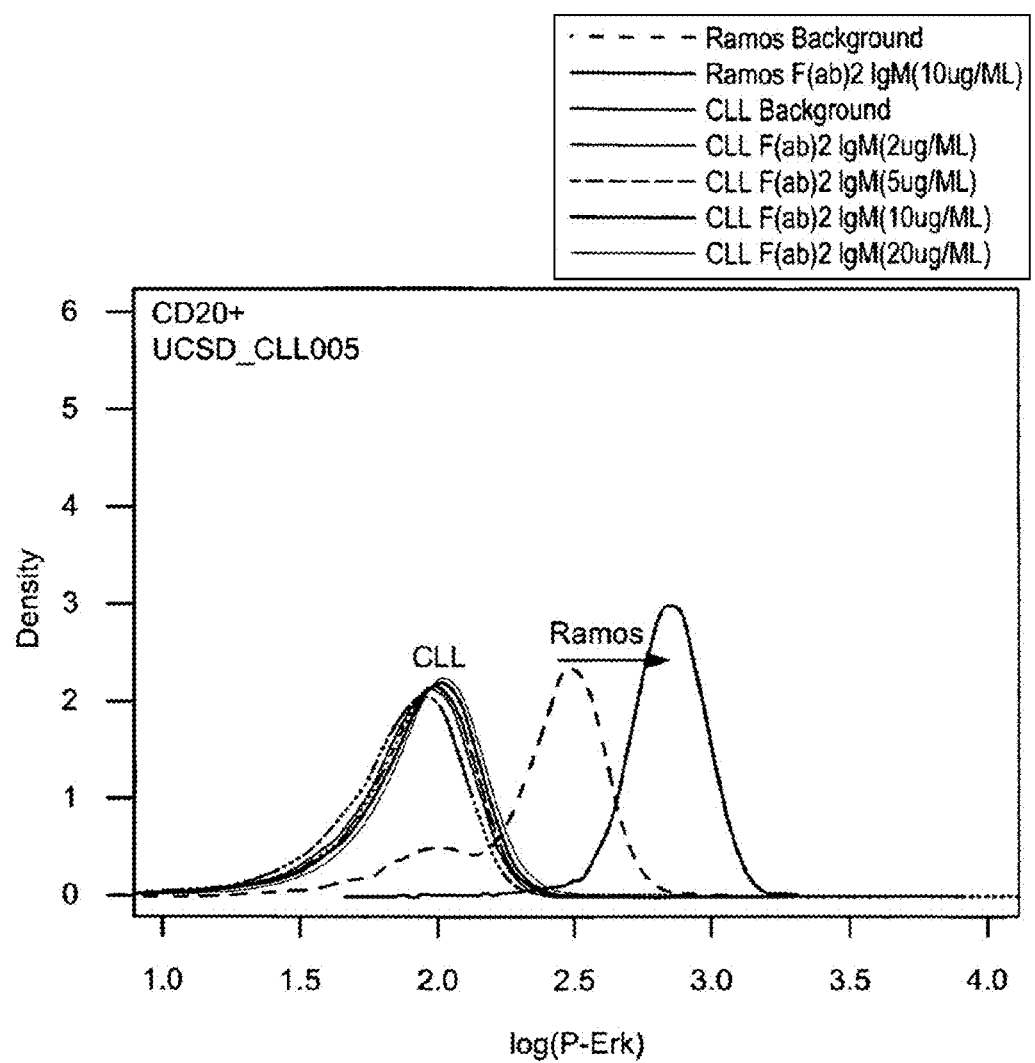
FIG. 4 depicts a histogram showing the activation of Erk in Pheresed CLL Samples and Ramos cells following activation with increasing amounts of F(ab)$_2$IgM for 15 Min.

Cells from CLL patients were analyzed. FIG. 3 shows that PMA (thin solid line) activates Erk in pheresed CLL samples. However, increasing amounts of amounts of F(ab)$_2$IgM for 15 min minimally activated signaling in CLL samples (FIG. 4).

Figure 5:
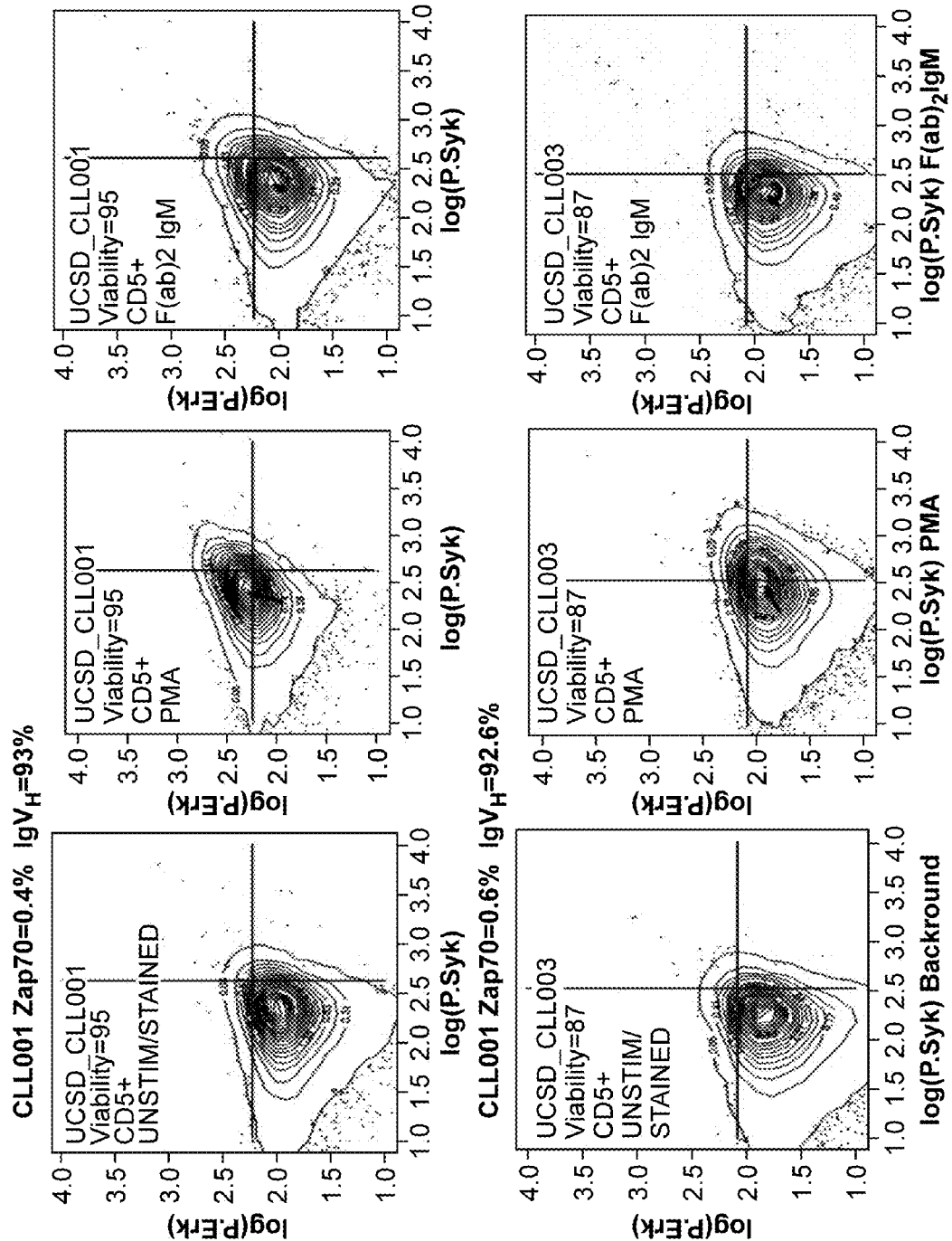
FIG. 5 depicts contour plots showing increased phosphorylation of Erk and Syk/Zap 70 in CLL Samples following treatment with PMA or F(ab)$_2$IgM.

CLL samples were divided into populations with low and high frequency of ZAP70. Zap70 can be a prognostic indicator used for CLL. However the clinical implications of CLL samples that contain ZAP70 are unclear. CLL samples show modest p-Erk (y-axis) and p-Syk (x-axis) phosphorylation when activated with PMA (FIG. 5). These cells show weak activation when activated with F(ab)$_2$IgM as shown in FIG. 5.

Figure 6:
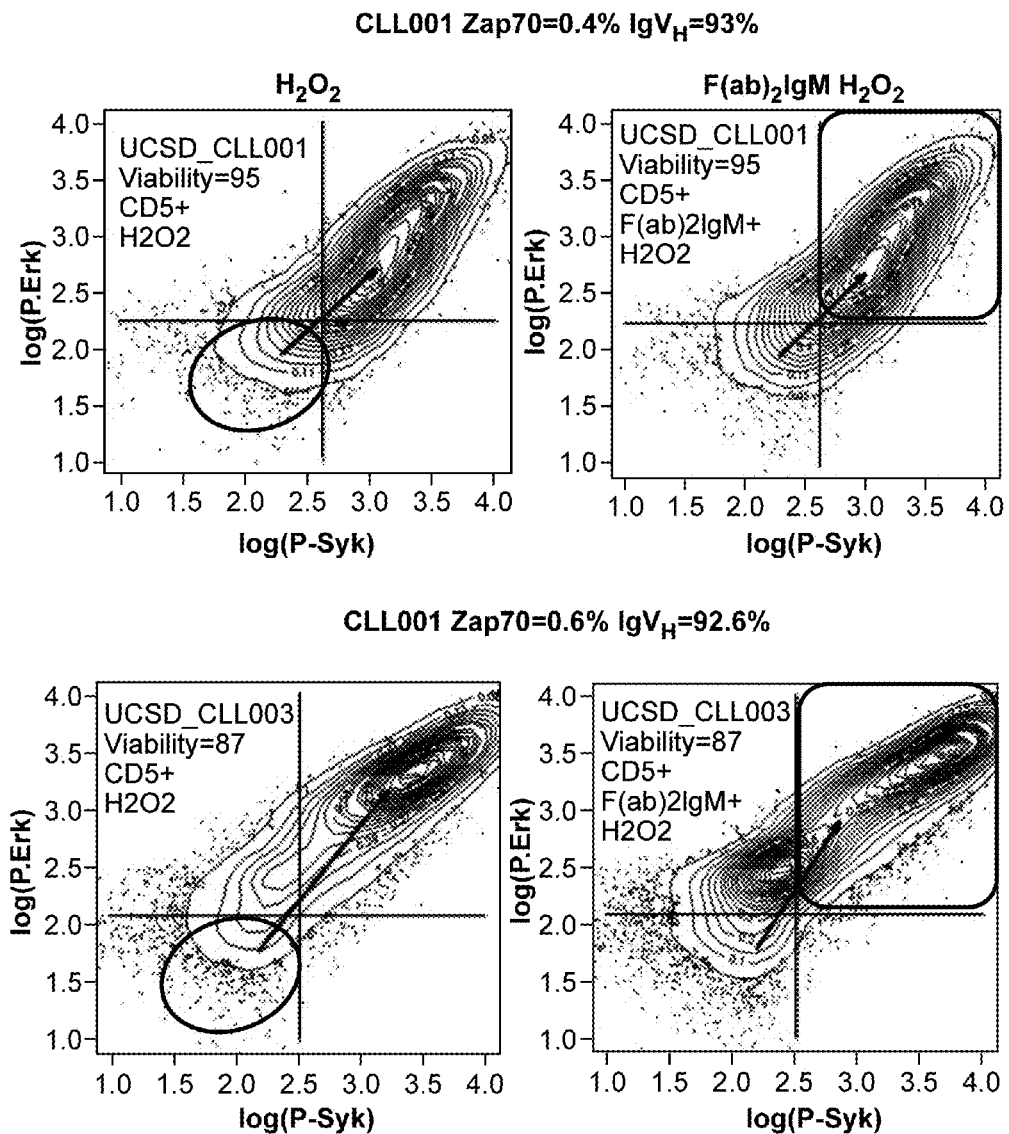
FIG. 6 depicts contour plots showing phosphorylation of Erk and Syk/Zap70 in CLL samples following treatment with H$_2$O$_2$ alone or in combination with F(ab)$_2$IgM.
Figure 7:
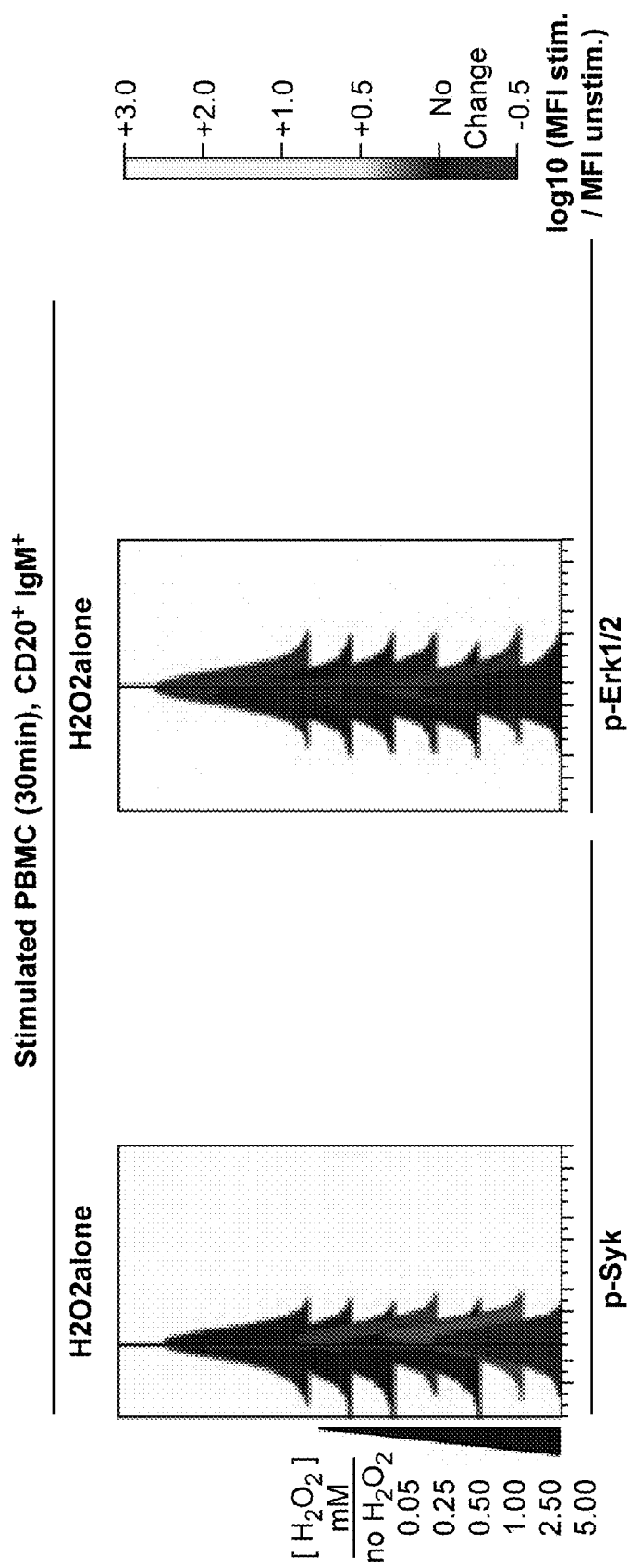
FIG. 7 depicts histograms showing the phosphorylation of Erk and Syk/Zap70 in healthy B cells following treatment with H$_2$O$_2$.
Figure 8:
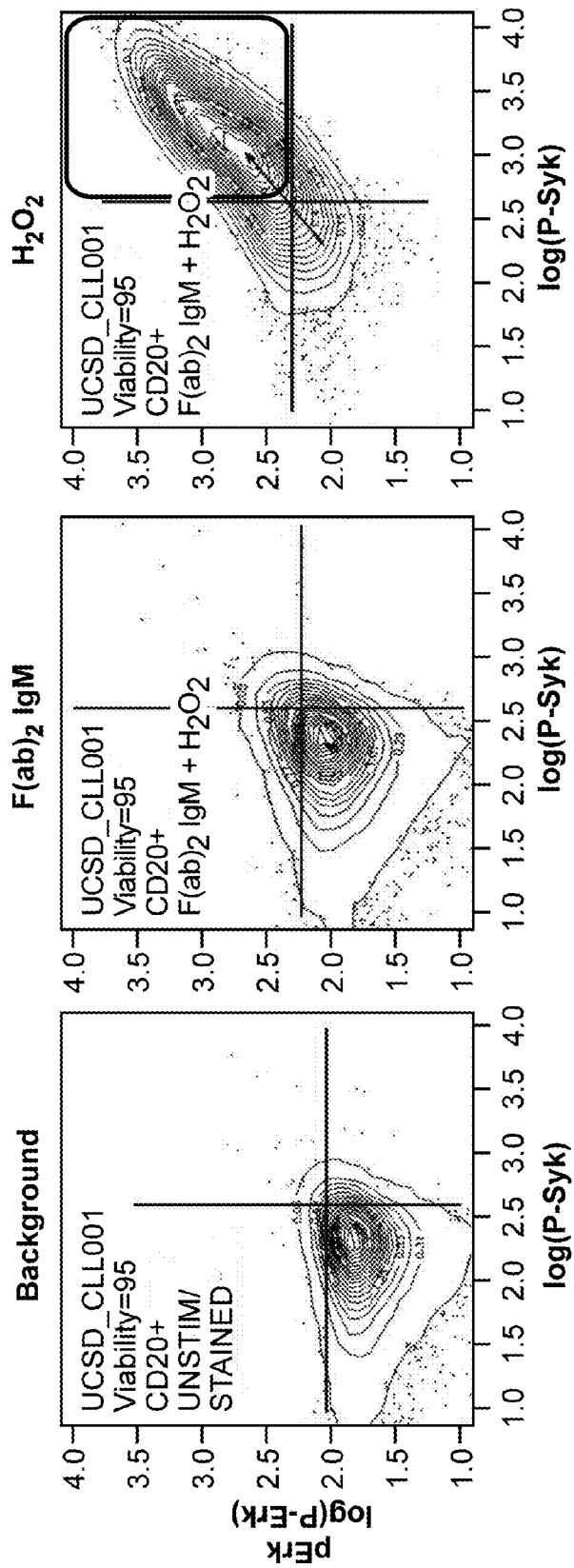
FIG. 8 depicts contour plots showing the phosphorylation of Erk and Syk/Zap70 in CLL cells upon treatment with H$_2$O$_2$ and F(ab)$_2$IgM.

CLL samples were treated with H$_2$O$_2$ or in combination with F(ab)$_2$IgM. H$_2$O$_2$ is a known inhibitor of phosphatases. Inhibition of phosphatases activates Erk and Syk as shown in FIG. 6. Without intending to be limited to any theory, inhibition of phosphatases reveals strong tonic BCR signaling. This tonic signaling is not apparent by F(ab)$_2$IgM alone (FIG. 4-5). F(ab)$_2$IgM and H$_2$O$_2$ reveals different kinetics subpopulation (heterogeneity) differences between CLL patients (FIG. 6). In contrast, in normal B cells H$_2$O$_2$ blocks phosphatases, but is incapable of activating post BCR by itself (FIG. 7). Without meaning to be limited to any theory, these results suggest that these CLLs have alterations in signaling proximal to the BCR. In CLL H$_2$O$_2$ reveals an underlying signaling event, possibly a tonic signaling, that can drive signaling events downstream of BCR (such as Syk and Erk) as shown in FIG. 8.

Figure 9:
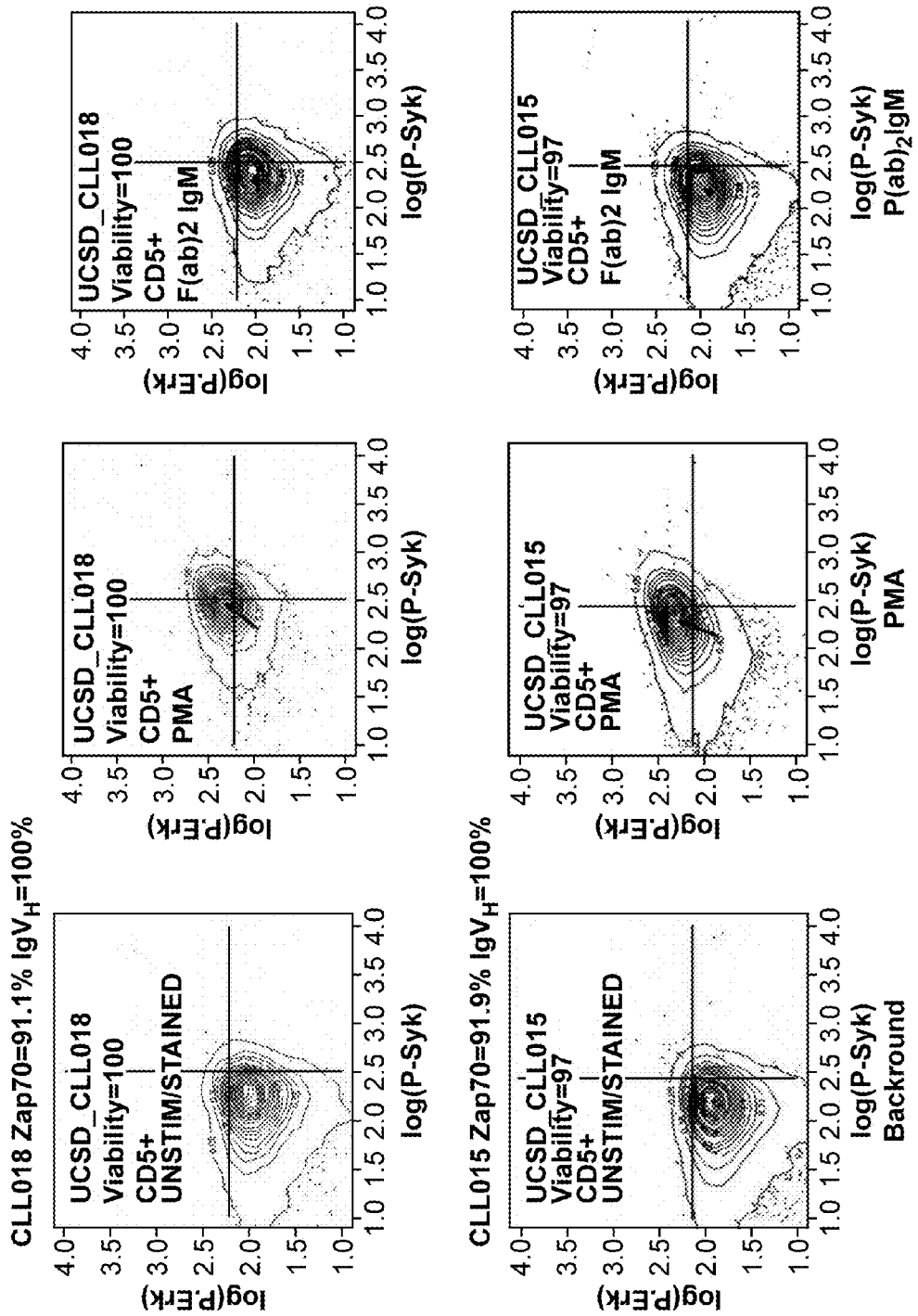
FIG. 9 depicts contour plots showing Erk and Syk in CLL samples following activation with PMA or F(ab)$_2$IgM.
Figure 10:
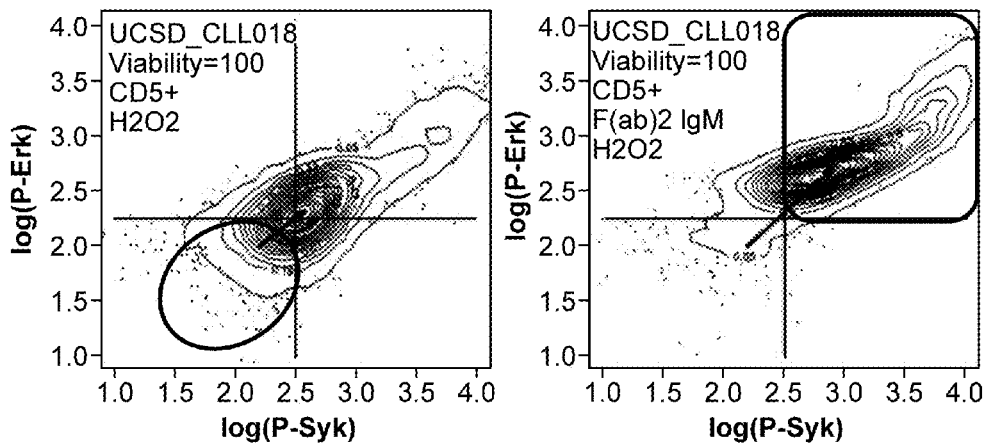
FIG. 10 depicts contour plots showing the phosphorylation of Erk and Syk/Zap70 following treatment with H$_2$O$_2$ alone or in combination with F(ab)$_2$IgM.
Figure 10:
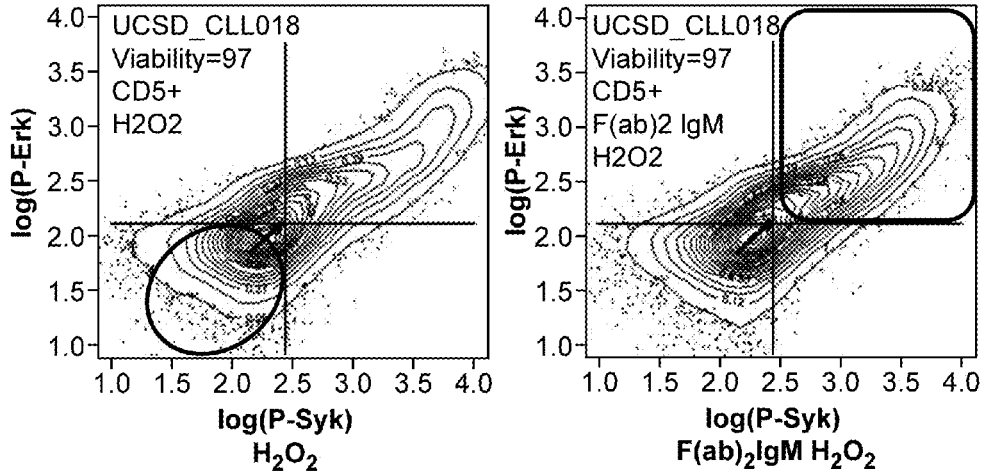
Figure 11:
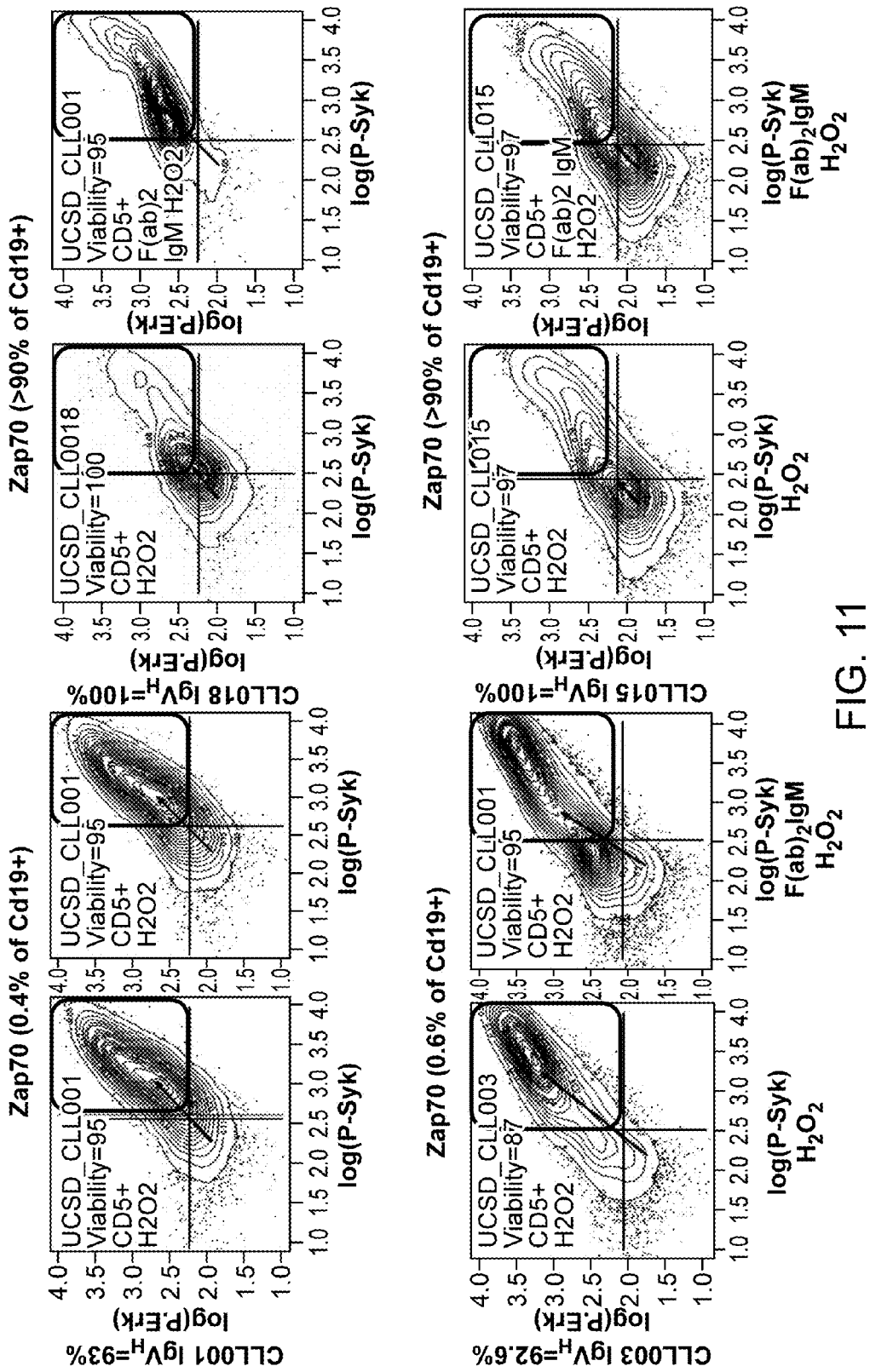
FIG. 11 depicts contour plots comparing CLL samples with low and high Frequency ZAP70 the phosphorylation or Erk and Syk/Zap70 following treatment with H$_2$O$_2$ alone or in combination with F(ab)$_2$IgM.

Other CLL samples show modest and weak Erk and Syk phosphorylation when activated with PMA and F(ab)$_2$IgM, respectively (FIG. 9). When these CLL samples are treated with H$_2$O$_2$, inhibition of phosphatases does not reveal strong tonic BCR signaling (FIG. 10). Treatment with F(ab)$_2$IgM and H$_2$O$_2$ reveals: (i) different kinetics (ii) subpopulation heterogeneity and (iii) differences between CLL patients as shown in FIG. 10.

Kinetics of Signaling in CLL Specimens

Cells were prepared and stained as described above.

Figure 12:
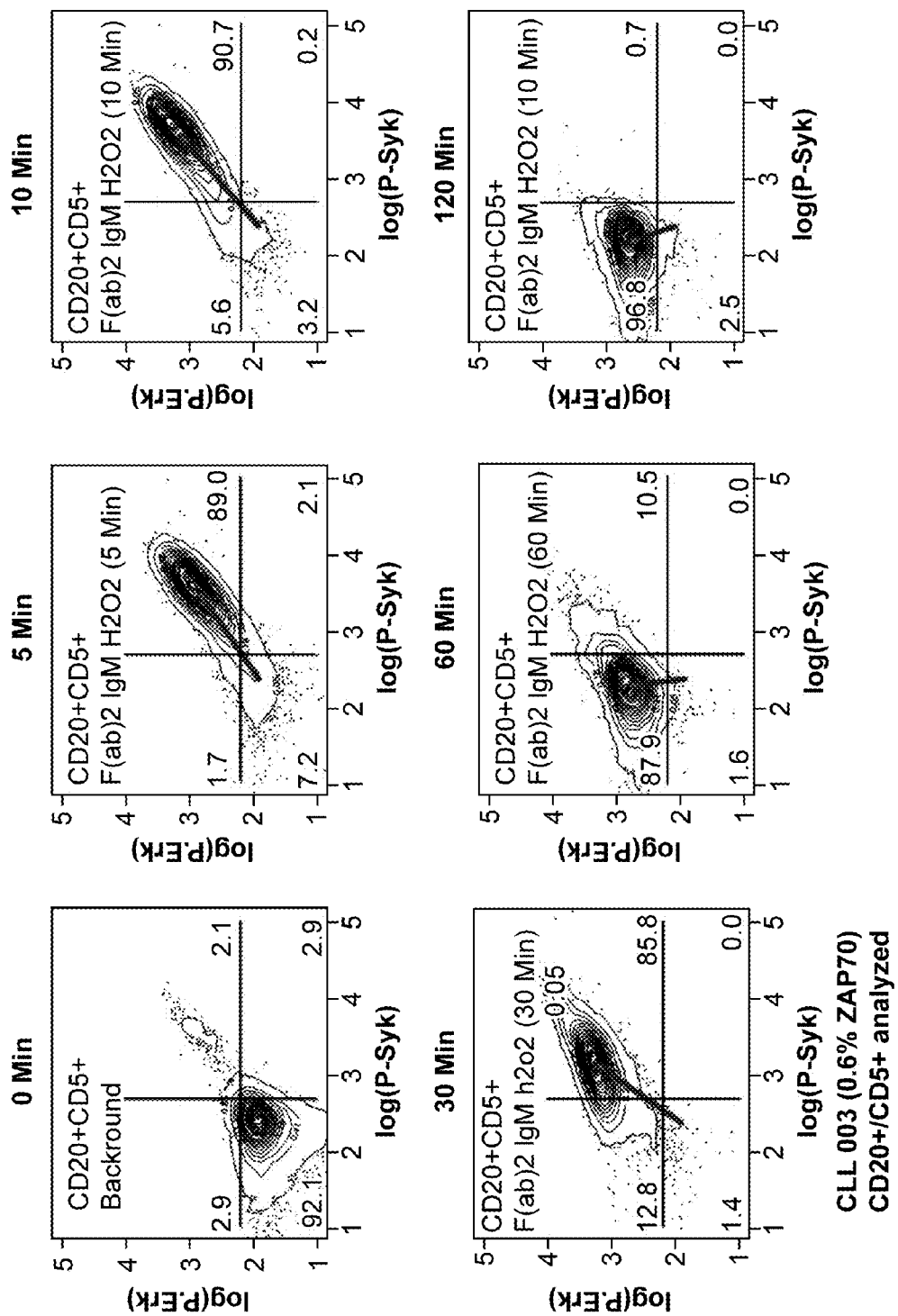
FIG. 12 depicts contour plots showing Syk/Zap70 and Erk phosphorylation after treatment F(ab)$_2$IgM and H$_2$O$_2$ at different times in CLL samples.

FIG. 12 shows different kinetics of Syk and Erk phosphorylation by F(ab)$_2$IgM and H$_2$O$_2$. Peak phosphorylation of Syk and BLNK occurred after 5 min of activation, whereas peak phosphorylation of Erk after 30 min.

Figure 13:
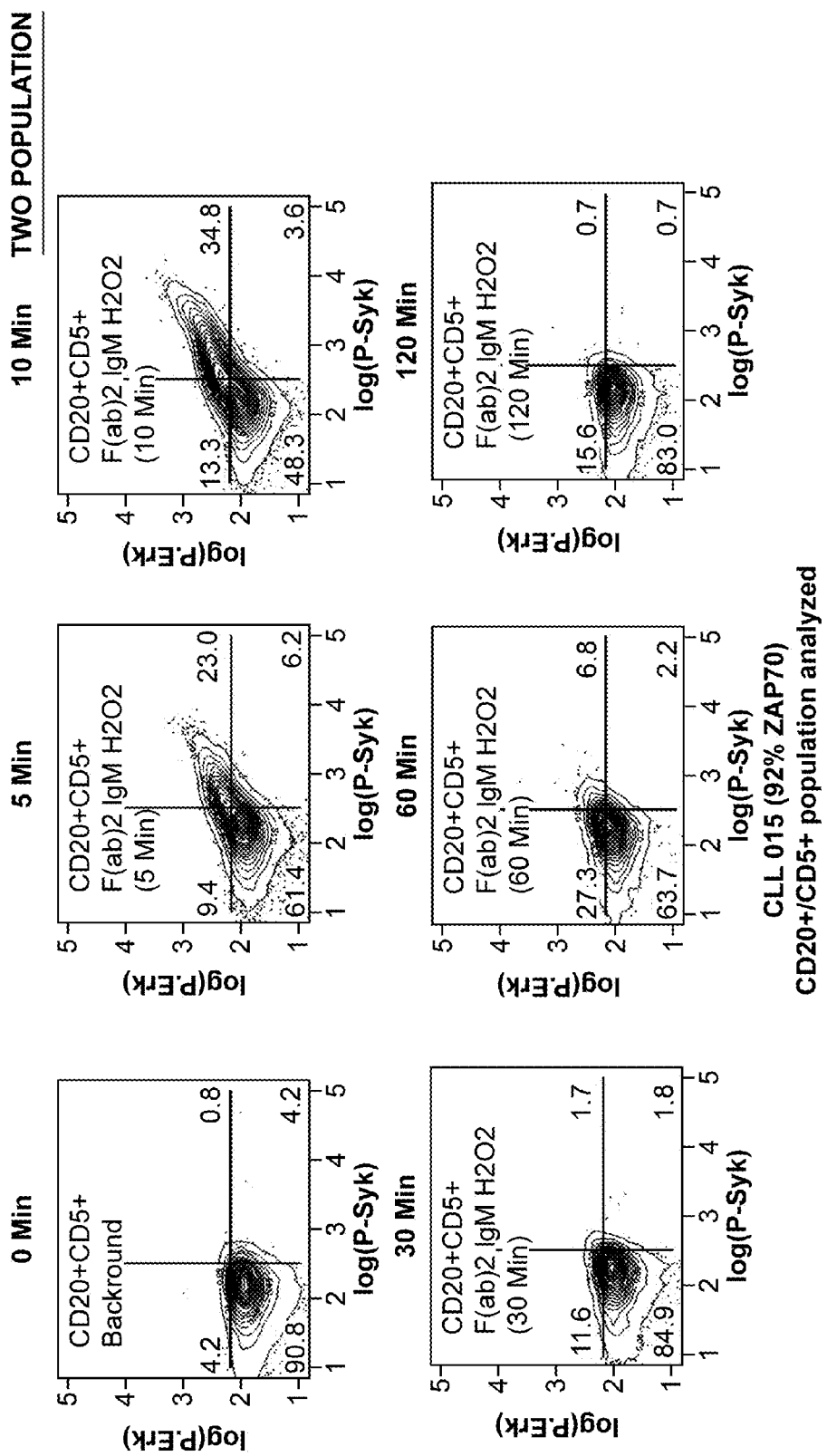
FIG. 13 depicts contour plots showing Syk/Zap70 and Erk phosphorylation after treatment with F(ab)$_2$IgM and H$_2$O$_2$ in CLL samples.
Figure 14:
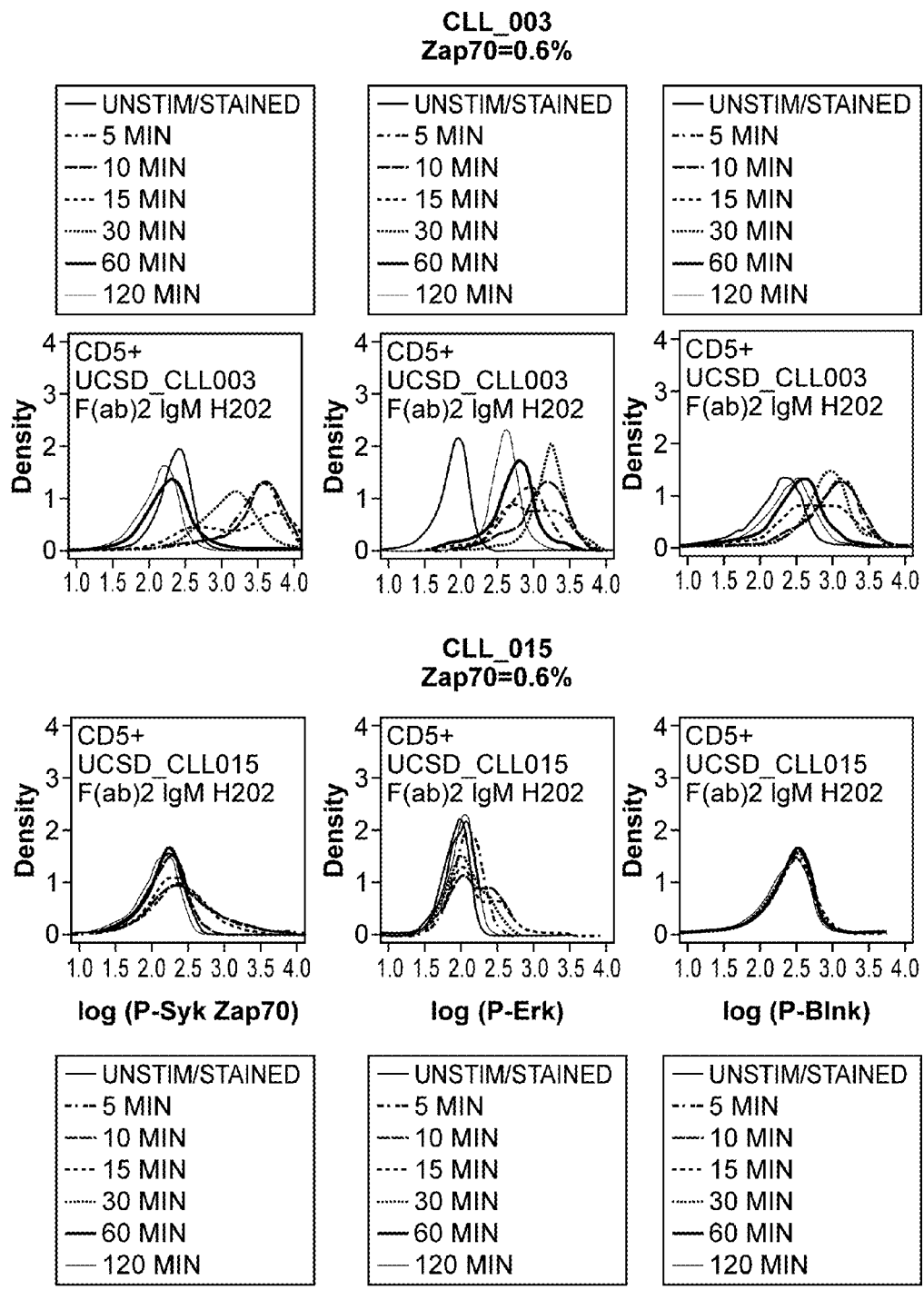
FIG. 14 depicts histograms showing the kinetics of signaling mediated by F(ab)$_2$IgM and H$_2$O$_2$ in CLL.
Figure 21:
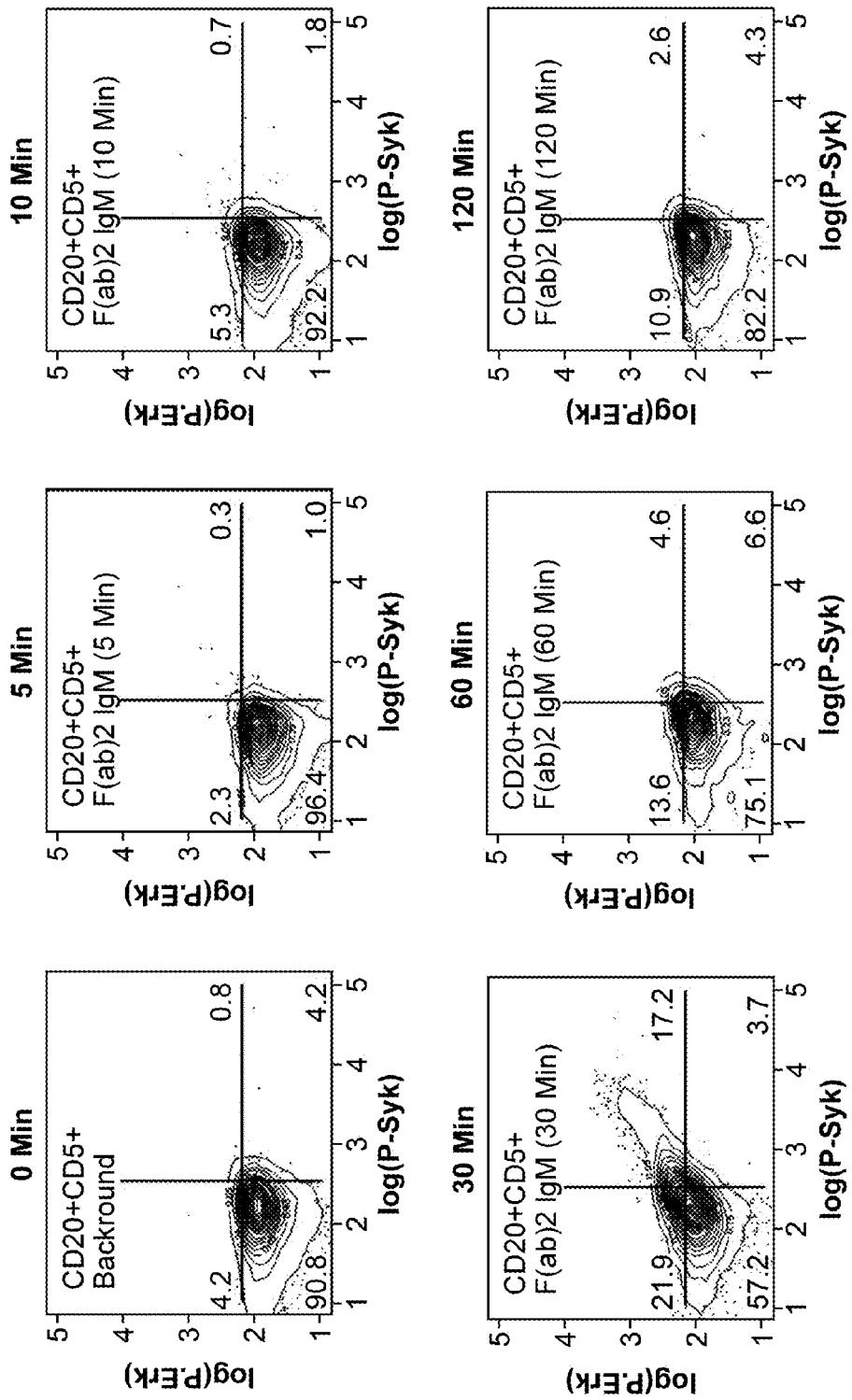
FIG. 21 depicts contour plots showing the phosphorylation of Syk/Zap 70 and Erk by F(ab)$_2$IgM alone over time.
Figure 22:
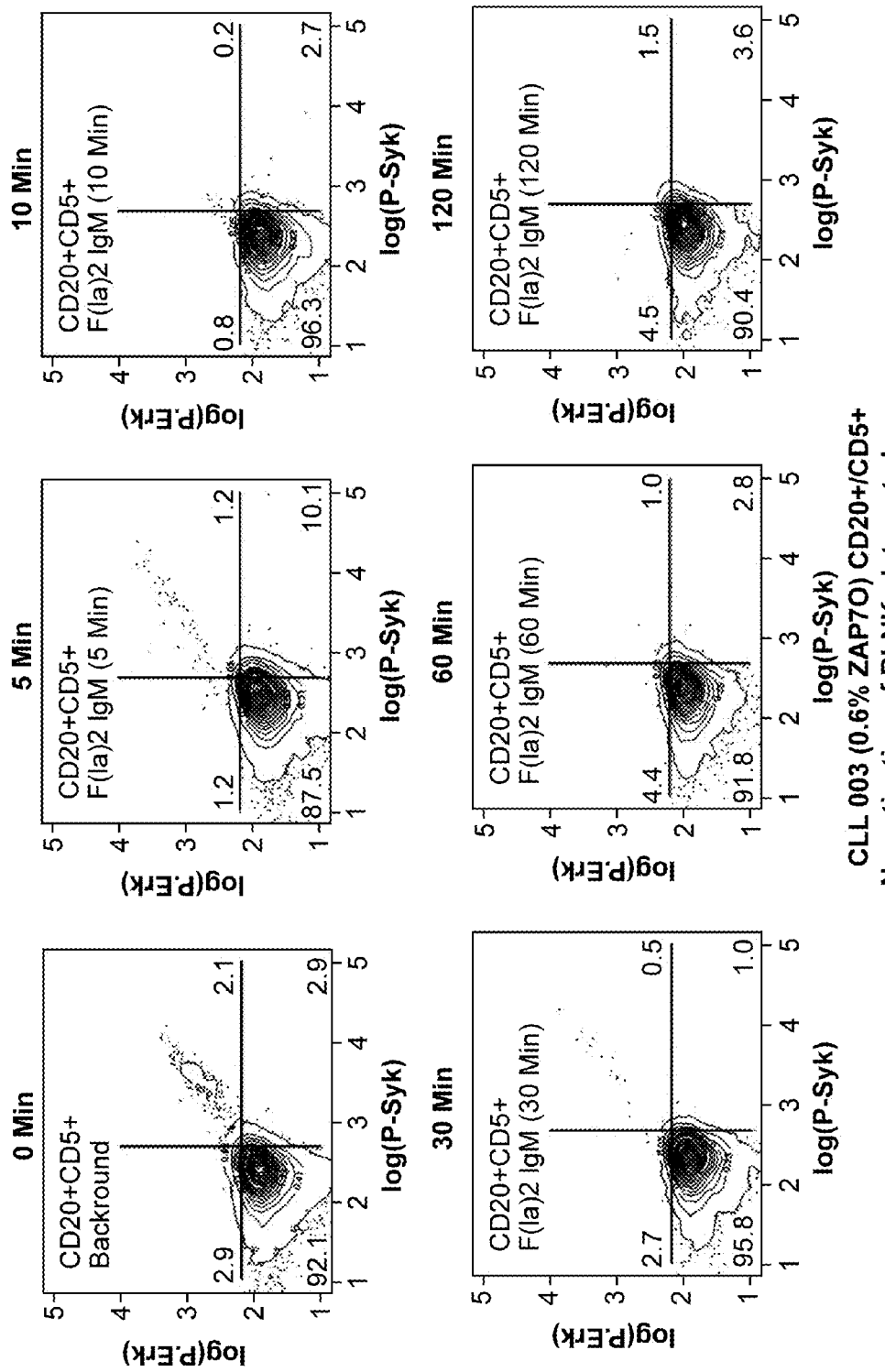
FIG. 22 depicts contour plots showing the phosphorylation of Syk/Zap 70 and Erk in response to F(ab)$_2$IgM alone over time.
Figure 23:
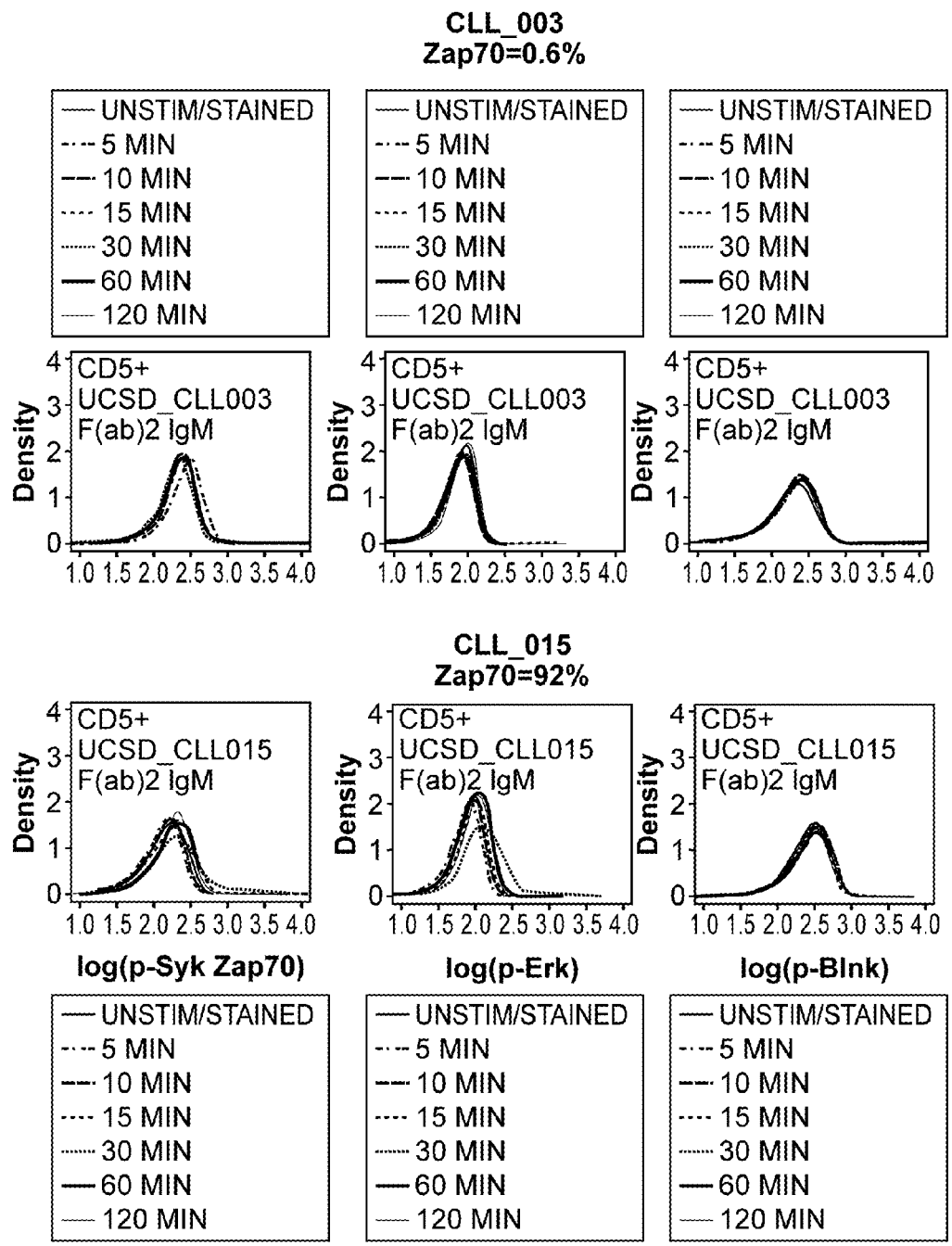
FIG. 23 depicts histograms showing phosphorylation of Syk, Erk and BLNK in response to F(ab)$_2$IgM over time in the CD20+/CD5+ population of CLL samples.

FIG. 13 shows moderate activation of Syk/Zap70 and Erk by F(ab)$_2$IgM and H$_2$O$_2$. FIG. 14 shows the kinetics of signaling by F(ab)$_2$IgM and H$_2$O$_2$. FIG. 21 shows minimal activation of Syk/Zap70 and Erk by F(ab)2IgM alone over time. FIG. 22 shows minimal activation of Syk/Zap70 and Erk in response to F(ab)2IgM alone over time. FIG. 23 shows an F(ab)2 time course of CD20+/CD5+ population, without H$_2$O$_2$.

Figure 15:
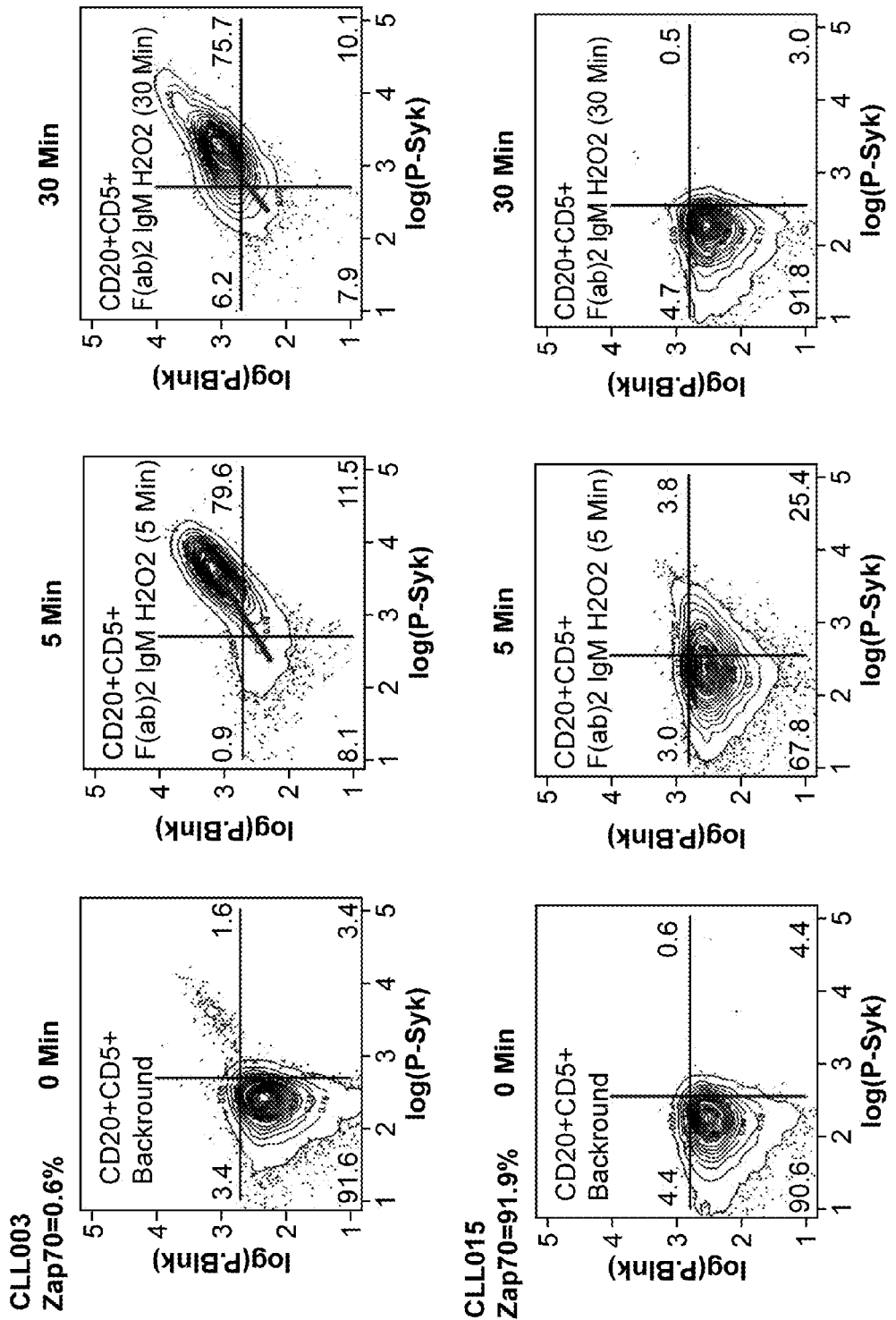
FIG. 15 depicts contour plots showing the influence of % ZAP70 on BLNK phosphorylation following treatment with H$_2$O$_2$ alone or in combination with F(ab)$_2$IgM.
Figure 16:
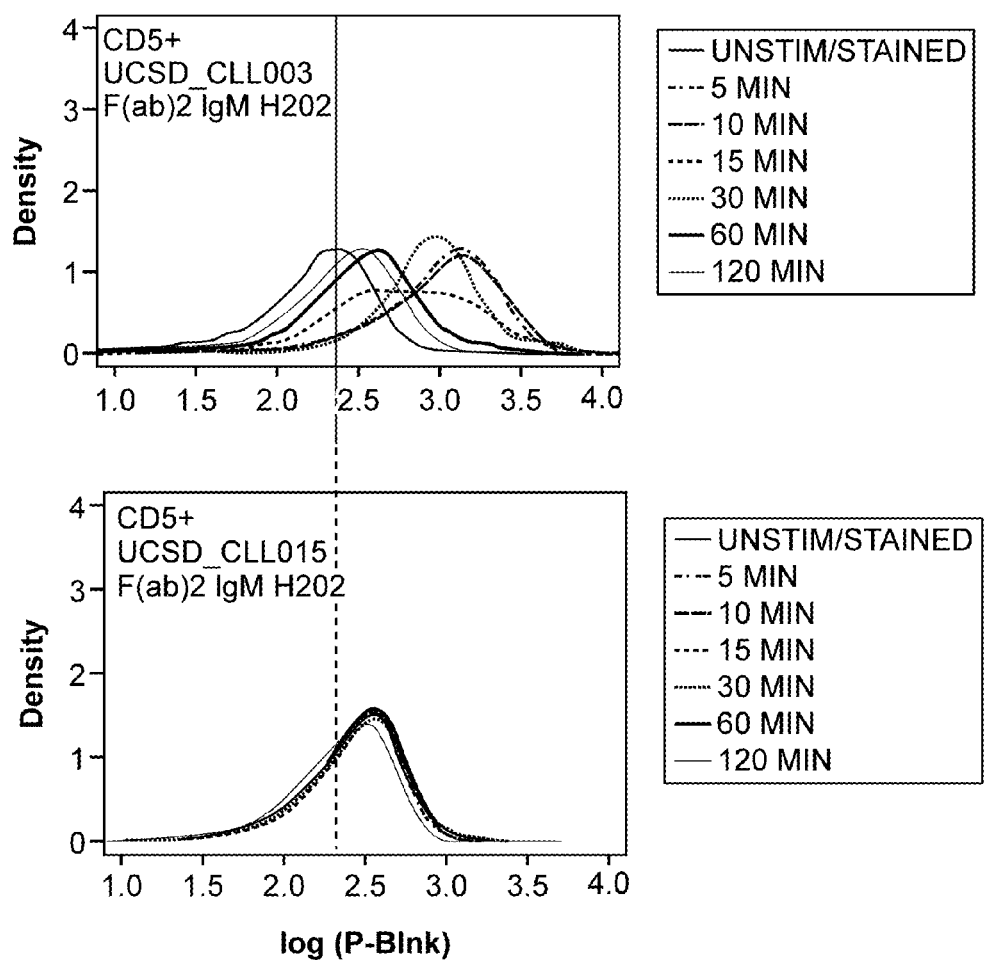
FIG. 16 depicts histograms showing the influence of ZAP70 status on BLNK phosphorylation.
Figure 17:
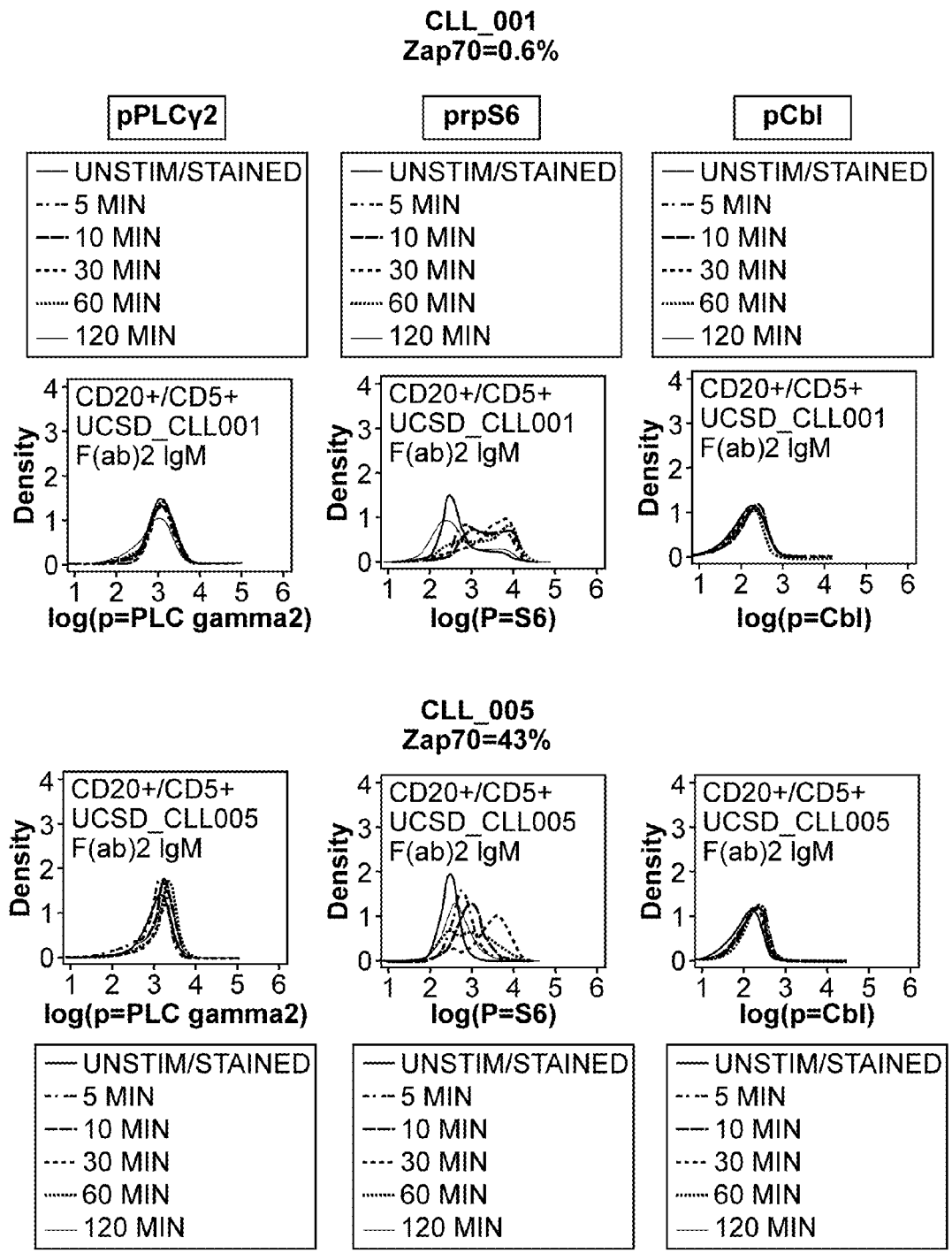
FIG. 17 depicts histograms showing the kinetics of phosphorylation of pPLCγ$_2$, prpS6, and pCbl after B-Cell Receptor crosslinking by F(ab)$_2$IgM Alone in CD20+/CD5+ population of CLL samples.
Figure 18:
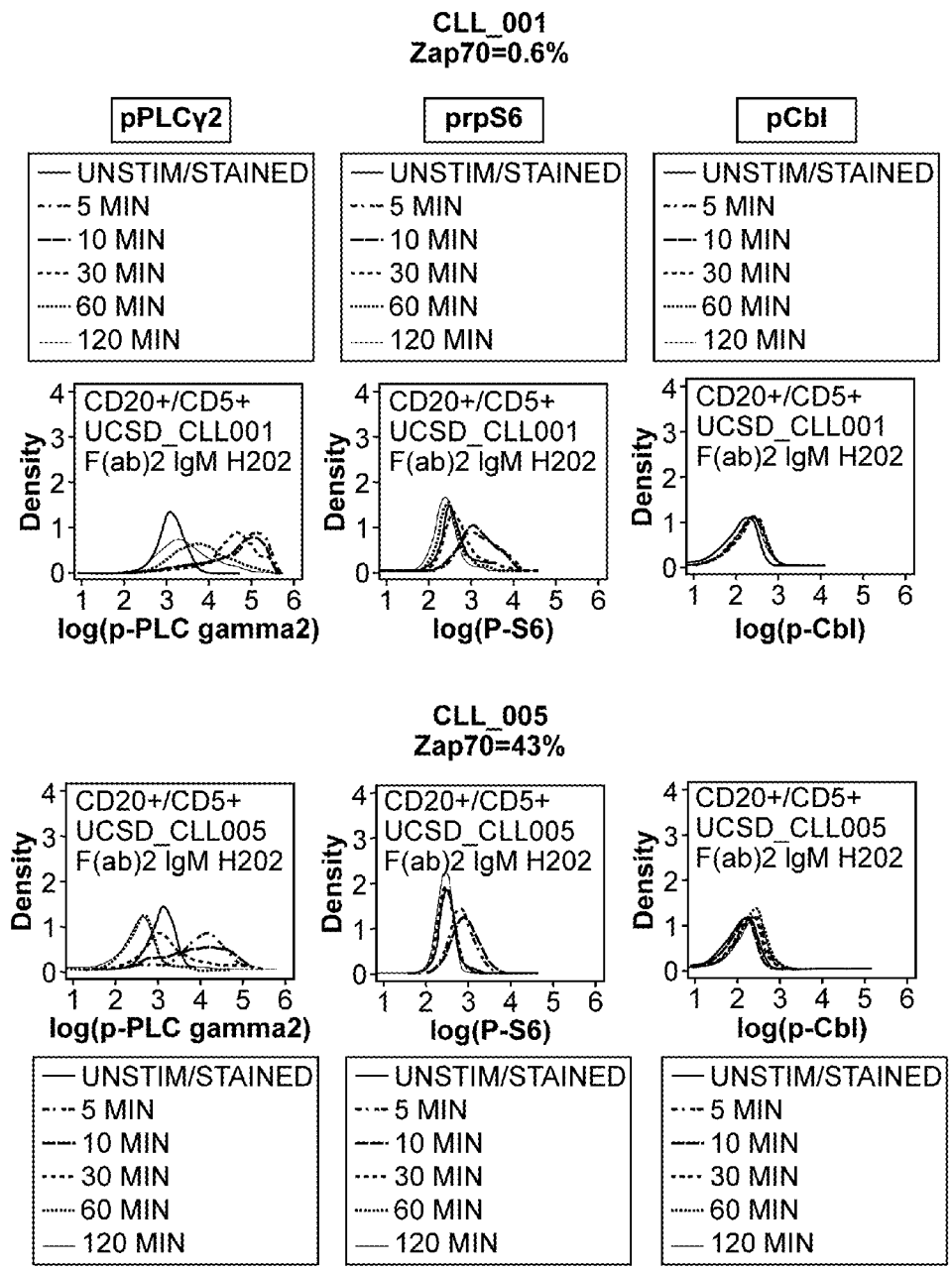
FIG. 18 depicts histograms showing the kinetics of phosphorylation of pPLCγ$_2$, prpS6, and pCbl after B-Cell Receptor crosslinking by F(ab)$_2$IgM and H$_2$O$_2$ in CD20+/CD5+ population in CLL samples.
Figure 19:
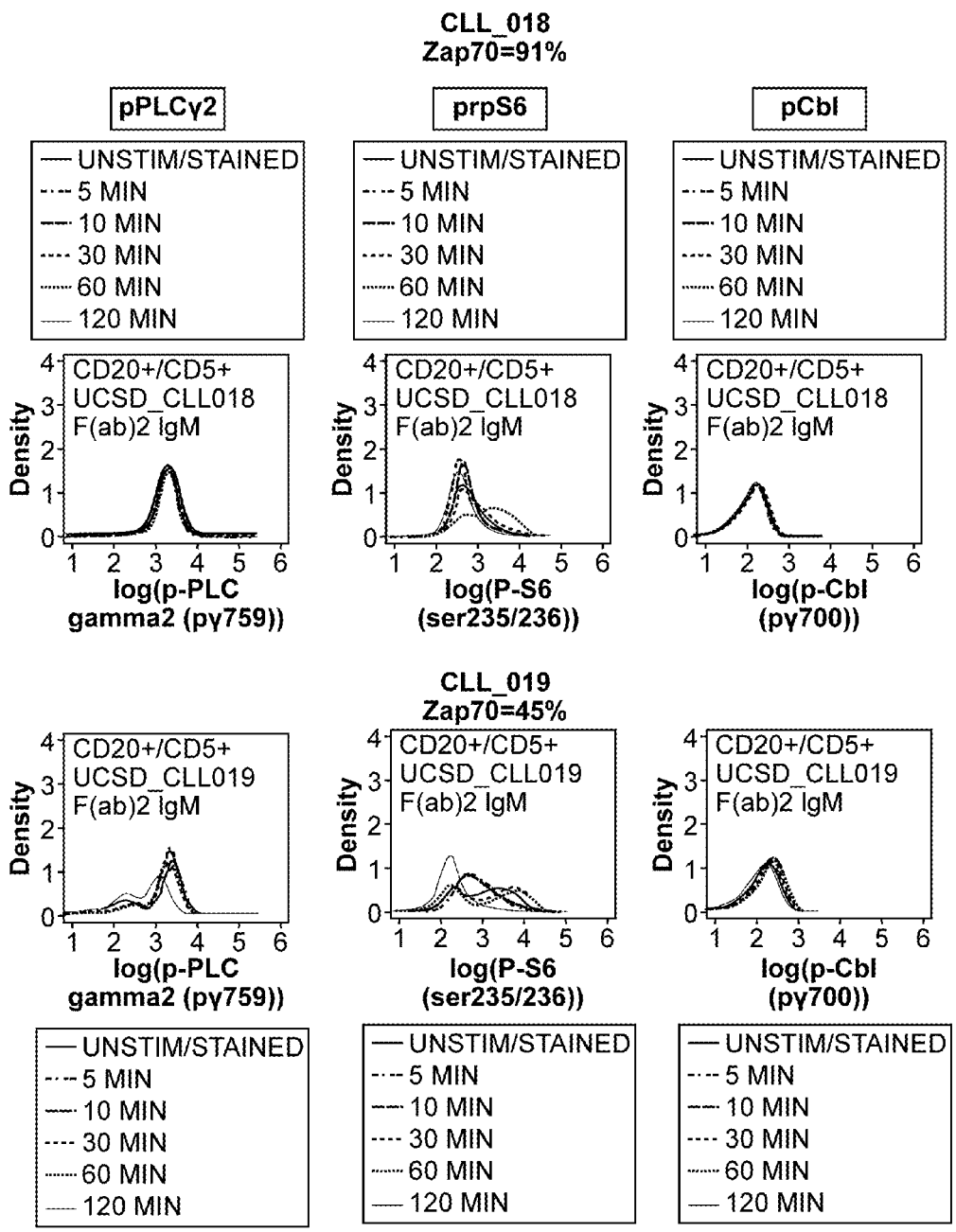
FIG. 19 depicts histograms showing the kinetics of phosphorylation of pPLCγ$_2$, prpS6, and pCbl after B-Cell Receptor crosslinking by F(ab)$_2$IgM Alone in CD20+/CD5+ population in CLL samples.
Figure 20:
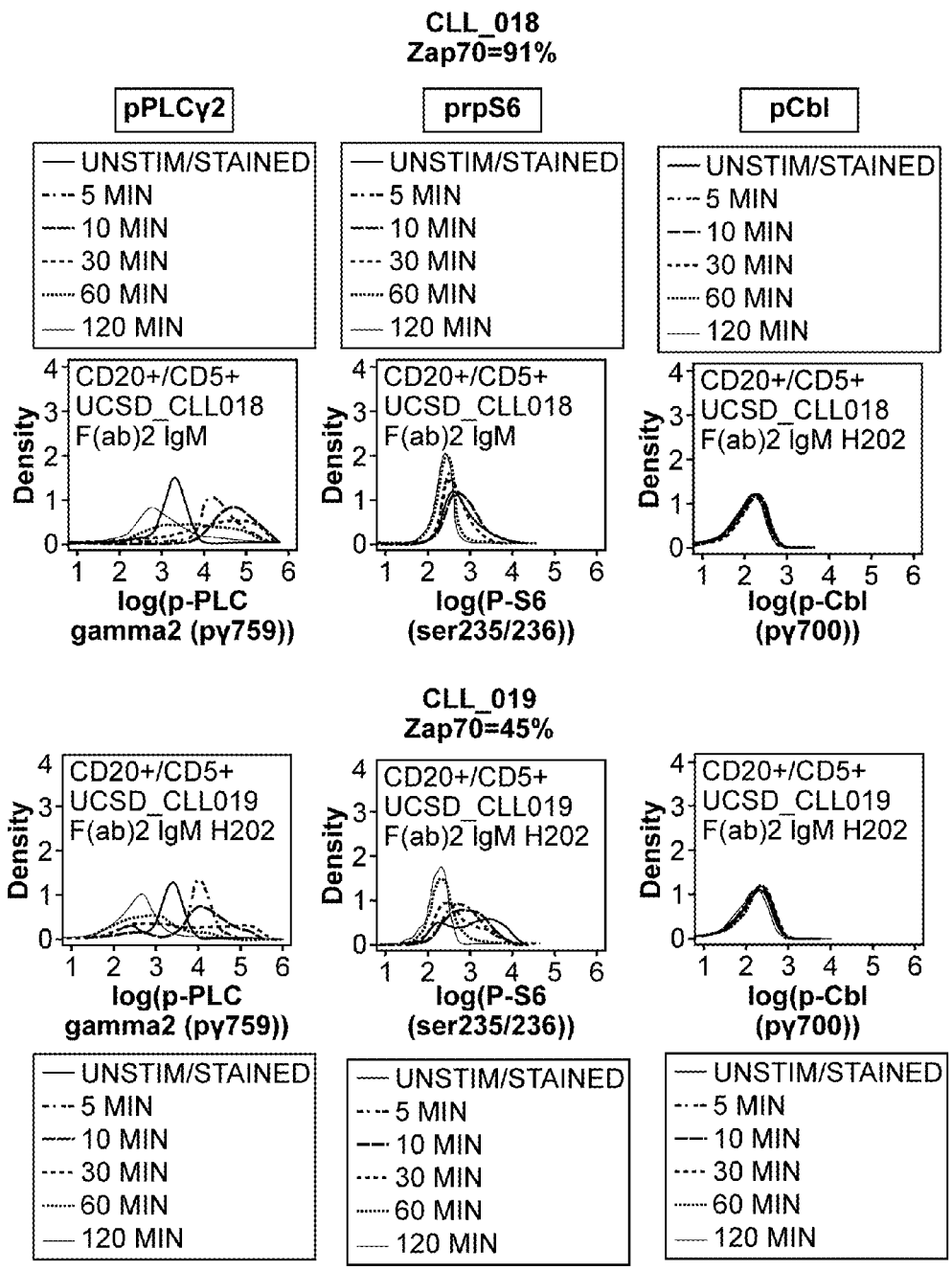
FIG. 20 depicts histograms showing the kinetics of phosphorylation of pPLCγ$_2$, prpS6, and pCbl after B-Cell Receptor crosslinking by F(ab)$_2$IgM and H$_2$O$_2$ in CD20+/CD5+ population in CLL samples.

FIGS. 15 and 16 show different levels of BLNK phosphorylation in response to an external stimulus in cells with different levels of ZAP70.

Figure 24:
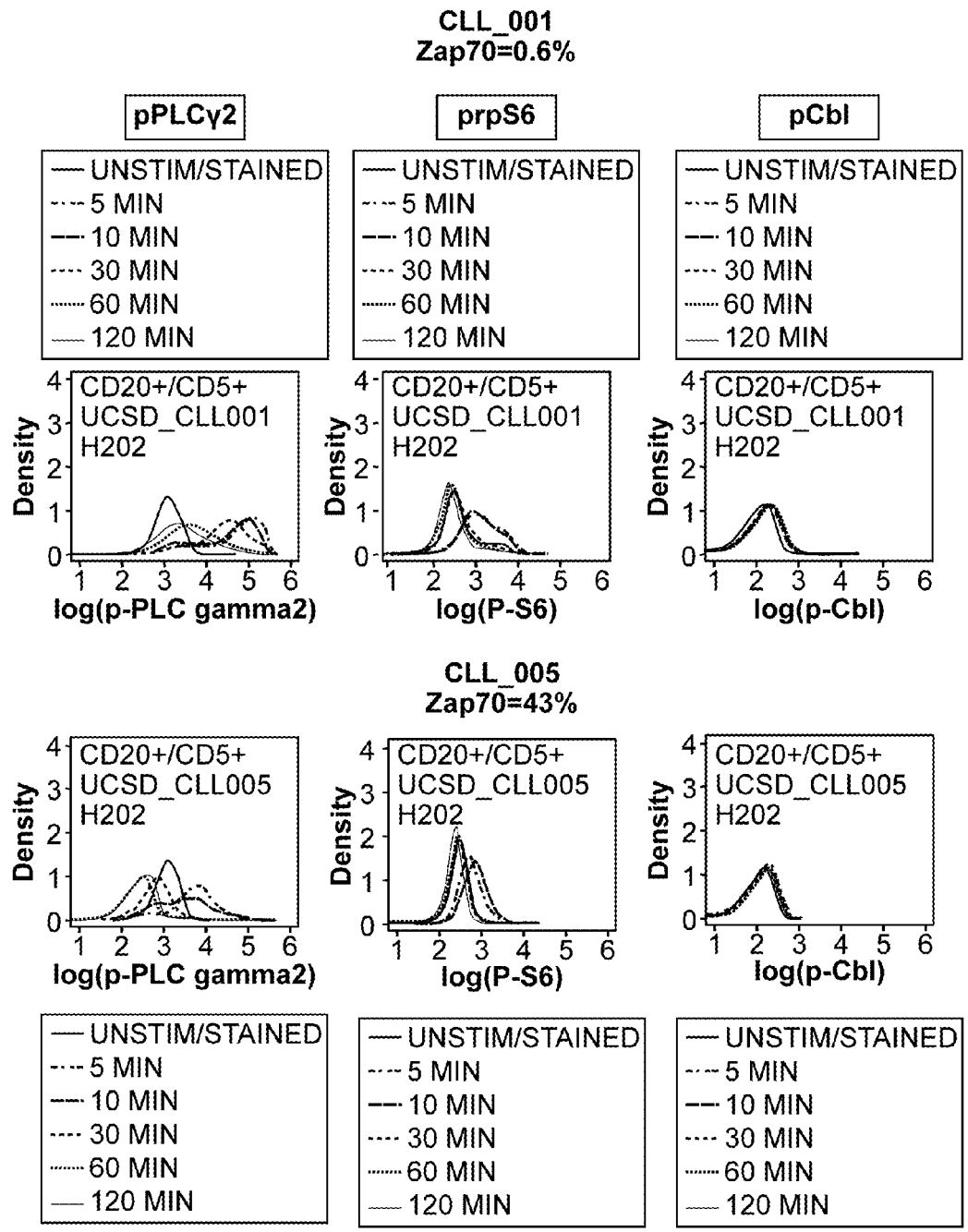
FIG. 24 depicts histograms showing the kinetics of phosphorylation of pPLCγ$_2$, prpS6, and pCbl after H$_2$O$_2$ treatment in CD20+/CD5+ population of CLL samples.
Figure 25:
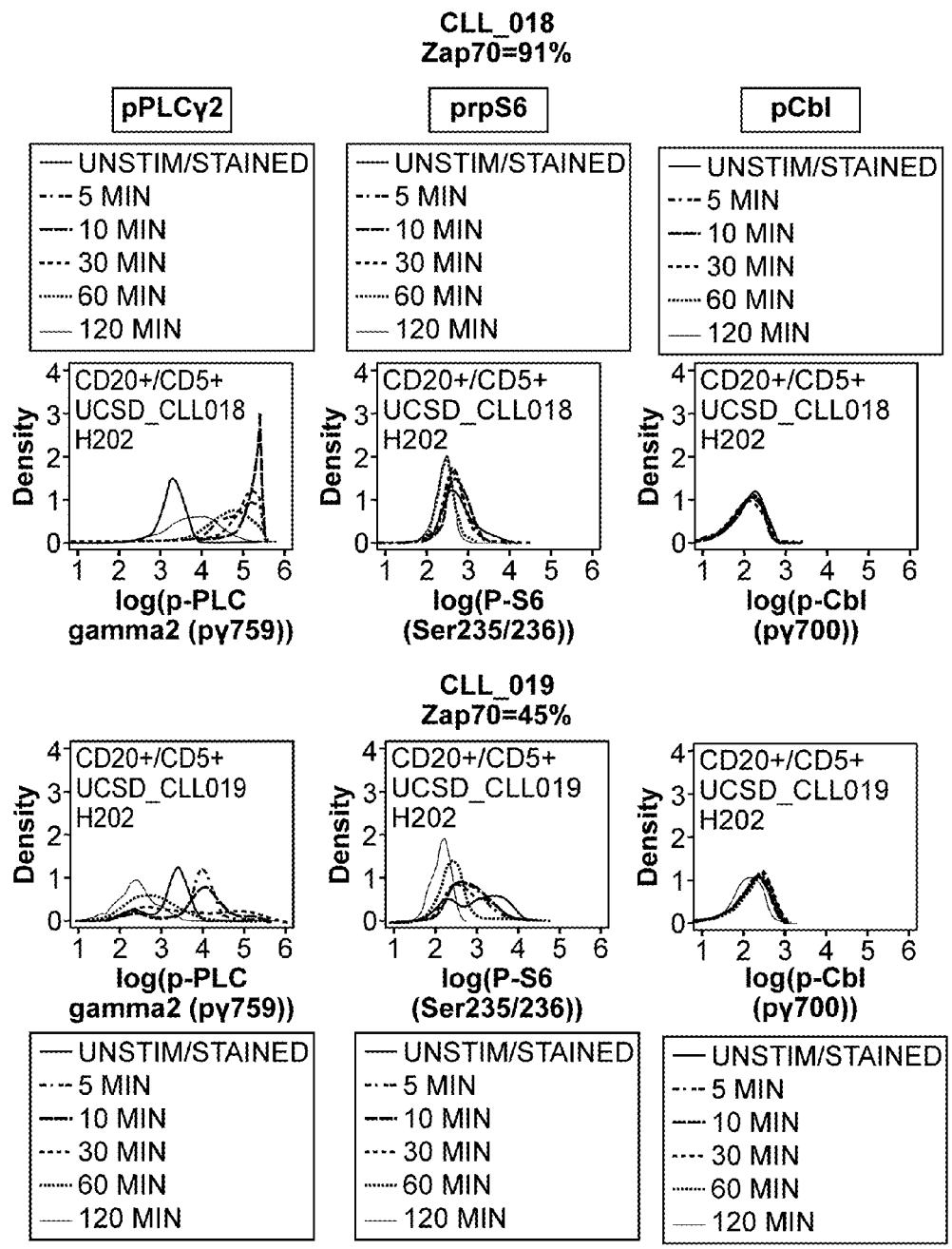
FIG. 25 depicts histograms showing the kinetics of phosphorylation of pPLCγ$_2$, prpS6, and pCbl after H$_2$O$_2$ treatment in CD20+/CD5+ population of CLL Samples.

FIGS. 17-21 show the kinetics of phosphorylation of PLCγ$_2$, S6 and Cbl in the CD20+/CD5+ cell population of CLL samples in response to B cell receptor crosslinking with and without peroxide. FIG. 24 shows the kinetics of H$_2$O$_2$ treatment in CD20+/CD5+ population of CLL samples. FIG. 25 shows the kinetics of H$_2$O$_2$ treatment in CD20+/CD5+ population of CLL samples. These results show that F(ab)$_2$IgM, alone mediates an increase in the phosphorylation of rpS6, in contrast to previously evaluated signaling molecules. H$_2$O$_2$ alone or in combination with F(ab)$_2$IgM attenuates this phosphorylation. PLCγ$_2$ phosphorylation increased in response to H$_2$O$_2$ alone or to the combination with F(ab)$_2$IgM. Cbl has a minimal response to all treatments. Without being limited to any theory, these results suggest that a separate pathway emanates from the BCR that regulates prpS6 and is distinct from the pathway(s) that regulate Erk, Syk/Zap, BLNK and PLCγ$_2$ with a distinct negative feedback loop In summary, these results show that for CLL patient samples PMA's activation of p-Erk is comparable in all patients regardless of ZAP70 expression and F(ab)$_2$IgM alone did not activate signaling. In two out of six CLL specimens two subpopulations of cells with distinct signaling profiles were observed. Finally, the kinetics of activation is different for Syk/ZAP70, BLNK and Erk.

Example 2

CLL Patients Display Distinguishable Patterns

Isolation, storage, thawing, and equilibration of primary cells. PBMC were isolated using density gradient separation (Ficoll-Paque Plus; Amersham Biosciences). In some embodiments, PBMC were pelleted by low-speed centrifugation, resuspended in medium composed of 90% FCS (Hy-Clone)+10% DMSO (Sigma-Aldrich), frozen slowly in the vapor phase of liquid nitrogen in multiple cryotubes, and stored in liquid nitrogen. For signaling analysis of frozen samples, an individual cryotube was thawed into 5 ml of RMPI+1% serum, counted, pelleted, and resuspended at 3.3× 10$^6$ cells/ml. Thawed PBMC were allowed to rest at 37° C. in a CO$_2$ incubator for 2 h before stimulation.

Modulation

At least half an hour before stimulation, 300 μA of medium containing 1×10$^6$ PBMC was aliquoted into flow cytometry tubes (Falcon 2052; BD Biosciences) and allowed to rest at 37° C. in a CO$_2$ incubator. Cross-linking of B cell receptors was achieved using goat polyclonal anti-IgM and anti-IgG F(ab')$_2$ (BioSource International). When used, H$_2$O$_2$ was at 3.3 mM final concentration and was added as 2 μl of a 500-mM stock solution immediately after BCR cross-linking During signaling, cells were kept in a 37° C. CO$_2$ incubator to allow signal transduction and phosphorylation. Signaling was stopped after 10 min. by fixing the cells. To determine basal levels of phosphorylation, unstimulated cells were maintained in parallel with stimulated cells and fixed at time zero. For fixation, paraformaldehyde (Electron Microscopy Services) was added to each tube of cells to a final concentration of 1.4%. Cells were fixed for 5 min at room temperature, pelleted, permeabilized by resuspension in 2 ml of methanol for 10 min, and stored at 4° C. until being stained for flow cytometry.

Flow Cytometry

Paraformaldehyde-fixed, methanol-permeabilized cells were rehydrated by addition of 2 ml of PBS, gentle resuspension, and then centrifugation. The cells were washed and stained as in Example I except phosphospecific alexa (Ax) dye Ax488 and Ax647 (Molecular Probes) or R-PE-conjugated Abs were also used. Staining cocktails comprised fluor conjugated antibodies specific for p-ERK1/2(T202/Y204), and p-Syk(Y352)/Zap70(Y319), p-Lck/p-Lyn, p-BLNK, p-PLCγ$_2$ (PLCr2) or p-S6. Detection, selection and gating of cell subsets was as described in Example I. Heat maps were generated using MeV (MultiExperiment Viewer) software (FIGS. 26, 27 & 28).

Results

The data shown in FIGS. 26, 27 and 28 demonstrate that B-cells from various CLL patients display distinguishable patterns of activatable elements as visualized by a heat map. Modulators of phosphorylation further define additional patterns of activatable elements that allow identification, classification and grouping of cryptic or aberrant hematopoetic populations. In FIGS. 26, 27 and 28 patient samples are indicated at the top of the heat map. Each column represents a single patient. CLL indicates that the sample was obtained from a patient diagnosed with CLL. CON indicates that the sample was obtained from a control patient. The heat map legend is indicated at the top of the figure and uses a shaded scale based on the log10-fold increase, or decrease, in mean fluorescence intensity (MFI), relative to the unstimulated control (0 min). Labels to the right of the histogram indicate the phospho-protein stained and the modulator treatment for that row. "US" indicates unstimulated. FIG. 28 illustrates the identification of several patient clustering groups comprised of similar or distinct levels of p-PLCγ$_2$, p-SyK/Zap-70, p-BLNK and p-Lck. Some patient clusterings become apparant upon modulation as illustrated by the boxed regions.

In FIG. 28, treatment with H$_2$O$_2$ reveals a patient clustering defined by the levels of p-PLCγ$_2$, p-SyK/Zap-70, p-BLNK and p-Lck (bottom right boxed area) that are similar to those of the four control patients (bottom center box). Treatment with H$_2$O$_2$ further reveals a patient clustering that is distinct from the controls (9 patients to the left of bottom boxed area). Modulation with H$_2$O$_2$ and BCR crosslinking defines another patient clustering comprised of levels of p-BLNK, p-Syk and p-PLCγ$_2$ (top left boxed area) that are similar to the control patients (top center box) and an abberant population of responders (10 patients to the right of top boxed area).

Example 3

Evaluation of Apoptosis Pathways in CLL Patient Samples

Current therapeutic approaches for CLL involve fludarabine-based regimens combined with monoclonal antibodies such as rituximab. Fludarabine, a purine analog, inhibits DNA synthesis by interfering with ribonucleotide reductase and DNA polymerase. Rituximab is a chimeric CD20 specific antibody and has mechanistically been shown to bind complement, induce antibody-dependent cellular cytotoxicity (ADCC) and, in some situations, rituximab binding to CD20 inhibits proliferation and induces cellular apoptosis (for a discussion of apoptosis see U.S. Ser. No. 61/085,789).

Cellular apoptosis in response to therapeutic agents, including but not limited to, DNA damaging agents such as Fludarabine or biological agents such as Rituximab, can be measured by multiparameter flow cytometry using fluorophore-conjugated antibodies that recognize intracellular protein components or nodes of the apoptotic machinery. Such nodes may include, but are not limited to, Caspase 3, Caspase 8, Cytochrome C, Poly ADP ribose polymerase (PARP), Bcl-2, Bcl-X, p-Chk2, p-BAD. Further information may be gathered by treating cells with a pan-caspase inhibitor Benzyloxycarbonyl-Val-Ala-Asp (OMe) fluoromethylketone (Z-VAD.FMK) in order to reveal caspase-dependent and/or independent pathways. The profile of how the apoptotic proteins respond to treatment with a therapeutic agent can be used to inform clinical decisions.

Experimental Procedure for Measuring Response to Apoptosis of Samples Treated with Fludarabine and Rituximab.

Cells are thawed at 37° C. in water bath until partially thawed (~50%) and are then added to RPMI/1% FBS at room temperature. Cells are centrifuged at 900 RPM for 10 minutes, the supernatants are decanted and pellets are resuspended in 25 milliliters of media. This step is repeated. An aliquot of cells is counted with a hemocytometer using trypan blue staining Cells are resuspended in RPMI/1% or 10%/FBS at the desired concentration. After an incubation at 37° C. for 2 hr., cells are aliquoted at a concentration of 1×10$^6$ cells per well of a 96-well plate. Cells are incubated with Fludarabine (at concentrations of 0-50 μM), Rituximab (at concentrations from 0-500 μM) and/or Staurosporine, alone or in combinations, in the absence or presence of ZVAD for various times. Post-incubation with drug, cells are processed for staining with cocktails of fluorochrome conjugated antibodies including CD3, CD5, CD19, CD20, CD3, CD5, CD19, CD20 (extracellular markers) and fluorochrome conjugated antibodies to the nodes/markers of apoptosis described above. Cells are analyzed by flow cytometry. The details of cell processing and flow cytometry analysis are given in U.S. Ser. No. 61/085, 789.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

The invention claimed is:

1. A method of determining a status of a B-cell receptor signaling pathway in a primary chronic lymphoid leukemia (CLL) cell comprising:

contacting said CLL cell with a B-cell receptor modulator which is selected from the group consisting of Rituxan, a cross-linker of a B-cell receptor complex, a B-cell co-receptor complex, F(ab)2 IgM, IgG, IgD, polyclonal BCR antibodies, monoclonal BCR antibodies, Fc receptor derived binding elements and/or combinations thereof;

determining an activation level of an activatable element in a B-cell receptor signaling pathway in said CLL cell on a single cell basis, said activatable element comprising p-Erk ½; and determining the status of the B-cell receptor signaling pathway in said CLL cell from said activation level of p-Erk ½.

2. The method of claim 1, wherein the B-cell receptor modulator is F(ab)2 IgM.

3. The method of claim 1, wherein the activation level of said activatable element is compared to a normal cell contacted with said modulator.

4. The method of claim 1, further comprising contacting said cell with a kinase or phosphatase inhibitor.

5. The method of claim 1, further comprising determining an activation level of a plurality of activatable elements.

6. The method of claim 4, wherein said kinase or phosphatase inhibitor is selected from the group consisting of adaphostin, aloisine A, alsterpaullone, aminogenistein, API-2, apigenin, arctigenin, AY-22989, BAY 61-3606, bisindolylmaleimide IX, chelerythrine, 10-[4'-(N,N-Diethylamino)butyl]-2-chlorophenoxazine hydrochloride, dasatinib, 2-Dimethylamino-4,5,6,7-tetrabromo-1H-benzimidazole, 5,7-Dimethoxy-3-(4-pyridinyl)quinoline dihydrochloride, edelfosine, ellagic acid, enzastaurin, ER 27319 maleate, erlotinib, ET18OCH3, fasudil, flavopiridol, gefitinib, GW 5074, H-7, H-8, H -89, HA-100, HA-1004, HA-1077, HA-1100, hydroxyfasudil, indirubin-3'-oxime, 5-Iodotubercidin, kenpaullone, KN-62, KY12420, LFM-A13, lavendustin A, luteolin, LY -294002, LY294002, mallotoxin, ML-9, NSC-154020, NSC-226080, NSC-231634, NSC -664704, NSC-680410, NU6102, olomoucine, oxindole I, PD-153035, PD-98059, PD-169316, phloretin, phloridzin, piceatannol, picropodophyllin, PKI, PP1, PP2, purvalanol A, quercetin, R406, R788, rapamune, rapamycin, Ro 31-8220, roscovitine, rottlerin, SB202190, SB203580, sirolimus, sorafenib, SL327, SP600125, staurosporine, STI-571, SU-11274, SU4312, SU6656, 4,5,6,7-Tetrabromotriazole, TG101348, Triciribine, Tyrphostin AG 490, Tyrphostin AG 825, Tyrphostin AG 957, Tyrphostin AG 1024, Tyrphostin SU1498, U0126, VX-509, VX-667, VX -680, W-7, wortmannin, XL-019, XL-147, XL-184, XL-228, XL-281, XL-518, XL-647, XL -765, XL-820, XL-844, XL-880, Y-27632, ZD-1839, ZM-252868, ZM-447439, $H_2O_2$, siRNA, miRNA, Cantharidin, (–)-p-Bromotetramisole, Microcystin LR, Sodium Orthovanadate, Sodium Pervanadate, Vanadyl sulfate, Sodium oxodiperoxo(1,10-phenanthroline)vanadate, bis(maltolato)oxovanadium(IV), Sodium Molybdate, Sodium Permolybdate, Sodium Tartrate, Imidazole, Sodium Fluoride, β-Glycerophosphate, Sodium Pyrophosphate Decahydrate, Calyculin A, Discodermia calyx, bpV(phen), mpV(pic), DMHV, Cypermethrin, Dephostatin, Okadaic Acid, NIPP-1, N-(9,10-Dioxo-9,10-dihydro-phenanthren-2-yl)-2,2-dimethyl -propionamide, α-Bromo-4-hydroxyacetophenone, 4-Hydroxyphenacyl Br, α-Bromo -4-methoxyacetophenone, 4-Methoxyphenacyl Br, α-Bromo-4-(carboxymethoxy)acetophenone, 4-(Carboxymethoxy)phenacyl Br, bis(4-Trifluoromethylsulfonamidophenyl)-1,4-diisopropylbenzene, phenyarsine oxide, Pyrrolidine Dithiocarbamate, and aluminum fluoride.

7. The method of claim 1, wherein the activation level is selected from the group consisting of glycosylation level, phosphorylation level, acetylation level, methylation level, biotinylation level, glutamylation level, glycylation level, hydroxylation level, isomerization level, prenylation level, myristoylation level, lipoylation level, phosphopantetheinylation level, sulfation level, ISGylation level, nitrosylation level, palmitoylation level, SUMOylation level, ubiquitination level, neddylation level, citrullination level, deamidation level, disulfide bond formation level, proteolytic cleavage level, translocation level, changes in protein turnover, multiprotein complex level, oxidation level, multi-lipid complex level, and biochemical changes in cell membrane.

8. The method of claim 1, wherein said activatable element further comprises a protein selected from the group consisting of Akt1, Akt2, Akt3, SAPK/JNK1,2,3, p38s, Syk, ZAP70, Btk, BLNK, Lck, PLCγ, PLC1γ$_2$, STAT1, STAT 3, STAT 4, STAT 5, STAT 6, CREB, Lyn, p-S6, Cbl, NF-κB, GSK3β, CARMA/Bc110 and Tcl-1.

9. The method of claim 4, wherein the kinase or phosphatase inhibitor is R788.

10. A method of determining a status of a B-cell receptor signaling pathway of a primary CLL cell, comprising:
   subjecting said CLL cell to a first modulator comprising $H_2O_2$;
   subjecting the cell to at least a second modulator comprising F(ab)2 IgM;
   determining an activation level of a phosphorylated protein, on a single cell basis, that participates in a B-cell receptor signaling pathway in said cell, said phosphorylated protein comprising p-Erk ½; and
   determining the status of the B-cell receptor signaling pathway in said CLL cell from said activation level of p-Erk ½.

11. A method of determining a status of a B-cell receptor signaling pathway in a primary CLL cell comprising:
   contacting the CLL cell with a modulator which is a B-cell receptor crosslinker selected from the group consisting of F(ab)2 IgM, IgG, IgD, polyclonal BCR antibodies, or monoclonal BCR antibodies, and Fc receptor derived binding elements;
   determining an activation level of an activatable element, on a single cell basis, that participates in a tonic signaling pathway and a B-cell receptor signaling pathway in said CLL cell, said activatable element comprising p-Erk ½; and
   determining the status of the B-cell receptor signaling pathway in said CLL cell from said activation level of p-Erk ½.

12. The method of claim 11, wherein the B-cell receptor crosslinker comprises F(ab)2 IgM.

13. The method of claim 11, further comprising providing a kinase or phosphatase inhibitor.

14. The method of claim 13, wherein the kinase or phosphatase inhibitor comprises R788.

15. The method of claim 1 further comprising detecting a surface marker on the cell.

16. The method of claim 15 wherein the cell surface marker is selected from the group consisting of CD45, CD5, CD19, CD20, CD22, CD23, CD27, CD37, CD40, CD52, CD79, CD38, CD96, major histocompatability antigen (MHC) Classl, MHC Class 2, and combinations thereof.

17. The method of claim 1 wherein the activation level of the activatable element is determined by a method comprising:
   (i) contacting the cell with a detectable binding element that specifically binds to the activated form of the activatable element; and
   (ii) detecting the binding element.

18. The method of claim 17 wherein the detecting is performed using a flow cytometer or a mass spectrometer.

* * * * *